(12) United States Patent
Yang et al.

(10) Patent No.: US 8,168,861 B2
(45) Date of Patent: May 1, 2012

(54) COMPOSITIONS AND METHODS FOR INCREASING CELLULOSE PRODUCTION

(75) Inventors: Zhenbiao Yang, Riverside, CA (US); Stephen Karr, Camarillo, CA (US)

(73) Assignee: The Regents of the University of California, Oakland, CA (US)

( * ) Notice: Subject to any disclaimer, the term of this patent is extended or adjusted under 35 U.S.C. 154(b) by 12 days.

(21) Appl. No.: 12/624,690

(22) Filed: Nov. 24, 2009

(65) Prior Publication Data

US 2010/0146672 A1    Jun. 10, 2010

Related U.S. Application Data

(60) Provisional application No. 61/117,309, filed on Nov. 24, 2008.

(51) Int. Cl.
*A01H 5/00* (2006.01)
*C12N 15/82* (2006.01)
(52) U.S. Cl. ........ 800/284; 435/419; 435/468; 536/23.6
(58) Field of Classification Search ........... 800/284, 800/278
See application file for complete search history.

(56) References Cited

U.S. PATENT DOCUMENTS

| 7,674,951 B1 * | 3/2010 | Joshi .............................. 800/287 |
| 2005/0223428 A1 | 10/2005 | Torii et al. |
| 2008/0057093 A1 | 3/2008 | Wan et al. |
| 2010/0146669 A1 | 6/2010 | Yang et al. |
| 2010/0170006 A1 | 7/2010 | Yang et al. |

FOREIGN PATENT DOCUMENTS

| WO | 2007138070 A2 | 12/2007 |
| WO | 2008074116 A1 | 6/2008 |
| WO | 2010060096 A2 | 5/2010 |
| WO | 2010060099 A2 | 5/2010 |
| WO | 2010080589 A2 | 7/2010 |

OTHER PUBLICATIONS

Eyüboglu et al (BMC Plant Biology, 2007, 7-16).*
Desprez et al, Plant Physiology, Feb. 2002, vol. 128 pp. 482-490.*
Baharlou, Simin, International Preliminary Report on Patentability and Written Opinion, Date of Issuance of Report: May 24, 2011, International Application No. PCT/US2009/065766.
Joo, Noh Eun, International Search Report and Written Opinion, Date of Issuance of Report: Sep. 27, 2010, International Application No. PCT/US2009/068682.
Kim, Jun Kyung. International Search Report and Written Opinion, Date of Mailing of Report: Aug. 5, 2010 International Application No. PCT/US2009/065766.
Kim, Yun-Kyung. International Search Report and Written Opinion, Date of Mailing of Report: Jul. 8, 2010 International Application No. PCT/US2009/065777.
Lindner, Nora. International Preliminary Report on Patentability and Written opinion, Date of Issuance of Report: May 24, 2011, International Application No. PCT/US2009/065777.
Lindner, Nora. International Preliminary Report on Patentability and Written Opinion, Date of Issuance of Report: Jun. 21, 2011, International Application No. PCT/US2009/068682.
Oh et al., "Recombiant brassinosteroid insensitive 1 receptor-like kinase autophophorylates on serine and threonine residues and phosphorylates a conserved peptide motif in vitro", Plant Physiology, Oct. 2000, pp. 751-765, vol. 124.
Shiu et al., "Plant receptor-like kinase gene family: diversity, function, and signaling", Sci. STKE, Dec. 18, 2001, pp. 1-13, vol. 113.
Shpak et al., "Dominant-negative receptor incovers reduncancy in the *Arabidopsis* ERECTA leucine-rich repeat receptor-like kinase signaling pathway that regulates organ shape", The Plant Cell, May 2003, pp. 1095-1110, vol. 15.
Tanaka, Masaru et al. "Analysis of genes developmentally regulated during storage root formation of sweet potato", Journal of Plant Physiology, Jan. 12, vol. 162, Issue 1, pp. 91-102, Published 2005.
Wei, Tang et al. "Increasing cellulose production and transgenic plant growth in forest tree species", Journal of Forestry Research, Mar. 2005, vol. 16, Issue 1, pp. 67-72.
Verica, J.A. et al. "The cell wall-associated kinase (*WAK*) and *WAK*-like kinase gene family", Plant Physiol., 2002, vol. 129, pp. 455-459.
Verica, J. A. et al. "Tissue-specific and developmentally regulated expression of a cluster of tandemly arrayed cell wall-associated kinase-like kinase genes in *Arabidopsis*", Plant Physiol. , 2003, vol. 133, pp. 1732-1746.
Wagner, T. A. et al., "Wall-associated kinases are expressed throughout plant development and are required for cell expansion", The Plant Cell, 2001, vol. 13, pp. 303-318.
Xuewen, H. et al., "Involvement of a cell wall-associated kinase. *WAKL4*, in *Arabidpsis* mineral responses", Plant Physiol., 2005, vol. 139, pp. 1704-1716.

* cited by examiner

*Primary Examiner* — Anne Grunberg
*Assistant Examiner* — Lee Visone
(74) *Attorney, Agent, or Firm* — Joseph R. Baker, Jr.; Gavrilovich, Dodd & Lindsey, LLP

(57) ABSTRACT

This disclosure relates to methods and compositions for genetically altering cellulose biosynthesis.

12 Claims, 16 Drawing Sheets

A

*SRF 6 (At1g53730)*

*SRF 7 (At3g14350)*

```
SRF1A' RKCLRKREDSEQLSKPHLTSEYGKAREGSRSNASMLPPSNTFNKDKEAKPKERVGGALKLQGGAERSVGSK---SKQESHEIDMDNAMDLMHPSSIPP      433
SRF1A  RKCLRKREDSEQLSKPHLTSEYGRAREGSRSNASMLPPSNTFNKDKEARPKERVGGASKLHGGAERSVGSE---SKQESHEIDMNGNAMDLMHPSSIPP      433
SRF1B  RKCLRKREDSEQLSKPHLTSEYGRAREGSRSNASMLPPSNTFNKGEISYLDFFTFRFQESHMPVFSSSMKF--KQKTRRLDQKRE                   420
SRF3   PKCARRREHANRVFKPHQVGADRGSRENALENGTPVLPPPGRSEKVQREPFKKAGEEPKVLHDIERLRRPAPISRQESQDIDFSMLPPPPPPPPPPPPP     437
SUB    RCCRSKIYNRYYSGARKDLQRPYFNKPPSQPTPTMGKVSREPMVKPFDGYGAGDRKYGYPMPQRAEESRRAMPPTSYYNKDVNTPQKPLQQP           455
SRF4   RRKNSNDSSHFFDDEKG--TNRSKPLFTPQSS--------QMLQFDNMEEFKNQKTVDSNTSLETKPSVKRTSSVSFKNSPTFHLIPSTQV             381
SRF5   ALVSKKKSSLSPHFIDEDNSHHTPKFKSLTSHGSA-----QELRVDFGNDYKDGKSGDSGDE------NIHRIGSKGLKHYVSSRVMSFTDT            372
SRF6   FLFRKKSKRSSPMDIEKTDN----QPFTLASNDFH-ENNSIQSSSVETKKLDTSLSINLRPPIDRNKSFDDEDST--RKPIAVKKSTVV               396
SRF7   KRKRSKRSSSTDIEKTDNNINQPIILASNDFHQENKSVQNPPLVETKKLDTSLSMNLRPPPSERHKSFDDDDSTMRKPIVAKKAAVV                  312
SRF8   CLHKKRKVRGSTRASQRSLP----------------LSGTPEVQEQRVKSVASVADLKSSPAEKVTVDRVMKNGSISRIRS---                    376
SRF2   RMNHRRAQNLAAIHRSMNNSIAYSL-------PVSTGREYPVATEDNPQIKRFQPPPAPQLRHLPSPVRIDKSARRKSFSAT                       393
Consensus .................................................k......................
       |————————— JM —————————|
                +
```

```
         |——————— I ———————|                    |——————— II ——————|         |———— III ————|
                                                    *  **            *
SRF1A' IKRVIAKANEPAEAASLKKT----SSKSHGPLIAVKFFTVASLQQFTNFSLENLIGTMLIGSVYRAELPGQLIAVKKLDKKSPNHEEGKFMELVNNE      528
SRF1A  IKRVIAKATEPAEAASLKRT----TSKSHGPLTAVKFFTVASLQQFTNSFHENLIGTMLIGSVYRAELPGGKLFAVRKLEKKSPNHEEGKFLELVNNE     528
SRF3   PPPLDEKVTVMPILSPERPVKKTSPVKRLPLTSVKHYSHASLQQYTESFAQENLIGSSVYRARLPNGKLRHQEFLAVKKQLSNTINRTQSDGEFLNLVSNV    535
SUB    FPPGLNSSSSATVHFHASLQQYTNFESENLIGESIGNVYRAELRHQEFLAVKKFLAVKGLSNTINRTQSDGEFLNLVSNV                        547
SRF4   SQDSPDTRGVKAFSHADLQNTPSCFSPNFHLIGESTIGRVYKAKFQDGRKFAVKFEDSSLIGKGNPEEESHIVSSE                            465
SRF5   RTTS---TRSAVEFELSDLQSPATANFSPGNLLIGECTFGRVYRAKYSEGRTLAVKKIDSTLFDSGKSEGITPIVMSL                          454
SRF6   V-------------------PSNVRLVSMADIQIATGSFSFSVDNLLIGECTFGRVYRAEFDEGKVIAVKKIDSSALPHGMTDDFFIEMVSKI           466
SRF7   V-------------------PSNVNTYHVSDLQVATNSESVDNLLIGECTFGRVYRAQFEDGKVIAVKKIDSSALPTDTADDFTELVSKI              469
SRF8   ----------PITASQYHVSSLQVAFNSEAEQLALNCFSEENLLIGEEPLGSVYRAKLPGQFAVMRNIPMSSLSLHEEEQFTEVLQTA                 445
SRF2   ----------CQYPSFAKLFSAEFLALNCFSEENLLIGEEPLGSVYRAKLPGQFAVMRNIPMSSLSLHEEEQFTEVLQTA                         465
Consensus .........f..a..lq..tnl.es.enl.ieg....g.vyra....gk...avkkid.....avkkid.
```

XI
               *
SRF1A'     AKSISLSREADVISRCVQSEPEFRPLMSEVVQDLSDMIQREHRRNDSNGDNQYTRRR
SRF1A      AKSISLSREADVISRCVQSEPEYRPLMSEVVQDLSDMIQREHRRNDSNGDNQYTGRR
SRF3       AKSISLSREADIISRCVQSEPEFRPLMSEVVQDLLDMIRERHGSGDSTAD
SUB        MKSISLSREADIISRSIQMEPGERPHISEHVQDLQHMI
SRF4       PESVSSEADINSICVMTEPGLRPHVSNMMEALKRIV
SRF5       PKSISLSREADIIALCVQMEPEFRPMSEVVEALVRMVQRSSMKLKDDLSSSYRAHDDYDY
SRF6       VKSISLSREADVIALCVQPEPEERPMSEVVQALVIVQRANMSKRTVGVDPSQRAGSADTTSDYM
SRF7       VKSISLSREADVIALCVQMEPEFRPMSEVVQALVIVQRANMSKRTVGVGSGSSGVNDYM
SRF8       AKSISLSREADIIALCIQPEFRPMSRVVQQLVRIVQRASVVKRRSSDDTGFSYRTPEHEHVDISF
SRF2       SRVASQYADIISLCIQPAEKEFRPNSEIVEATALIQKQNKEASSVADKTDPFSKFCSTRTRFISSPTFSYLSS
Consensus  .kslS..fADlisl.cvg..EpefRpmSevMg.L....gl..........................
```

FIGURE 11B (cont'd)

Consensus key
```
* - single, fully conserved residue
: - conservation of strong groups
. - conservation of weak groups
  - no consensus
```

```
AtSRF6    -------MRENWAVVALFTLCIVGFELRFIHGATDASDTSALNTLFSGMHSPAQLTQWTA
AtSRF7    -------MTENRVVLALLILCIVGFEPSFIHGATDSSDTSALNIMFSSMNSPGQLSQWTA
Grape     ----------------------------------------MFSSLNSPSQLAKWSS
Zea mays  ------------------------DPNDLNVLNTLFTSLNSPGQLTGWQA
Rice      MGRADAPWLPLLLLCSSCCFCIWPQKQILVAADTDPNDVTVLNTLFTSLNSPGQLKGWQA
                                                  :*:..::**.**  * :

AtSRF6    AAGDPCGQNWRGVTCSGSRVTQIKLSGLELSGTLGGYMLDKLTSLTELDLSSNNLGG--D
AtSRF7    SGGDPCGQNWKGITCSGSRVTQIKLPSLGLSGSLG-FMLDKLTSVTEFDMSNNNLGG--D
Grape     NGGDPCGESWQGITCKGSRVTEIELSGLRLTGSMG-YQLTSLTSVVNLDISNNNLGN--Q
Zea mays  NGGDPCGQSWKGITCSGSGVTKIQLPNLSLTGNLA-YNMNNLGSLVELDMSQNNLGGGGQ
Rice      SGGDPCGQSWQGITCSGSSVTAIKLPSLGLSGNLA-YNMNTMGSLIEIDMSQNNLGGGQQ
           .*****:.*:*.**.** **  *:*...* *:*.:.  :  .:  *: ::*:*.****. :

AtSRF6    LPYQFPPN-LQRLNLANNQFTGAASYSLSQITPLKYLNLGHNQFKGQIAIDFSKLDSLTT
AtSRF7    LPYQLPPN-LERLNLANNQFTGSAQYSISMMAPLKYLNLAHNQLK-QLAIDFTKLTSLSI
Grape     IPYQLPPN-LQRLNLAGNGFNGGIPYSISLMISLKYLNISHNQLQGQLGDMFSQLSSLTT
Zea mays  VQYNLPNMKLEKLNLAGNQFGGNLPYSISTMPNLKYLNLHNQLQGNISDVFSNLYSLSE
Rice      IQYNLPTNKLERLNLAGNQFTGNLPYSIFSMSNLKYLNLHNQLQGNITDVFSSLYSLTT
            : *::*   *::****.* * *   **:  : *****: ***:: ::   *:.* **:

AtSRF6    LDFSFNSFTNSLPATFSSLTSLKSLYLQNNQFSGTVDVLAGLPLETLNIANNDFTGWIPS
AtSRF7    LDLSSNAFIGSLPNTCSSLTSAKSIYLQNNQFSGTIDILATLPLENLNIANNRFTGWIPD
Grape     LDFSLNSLTGDLPESFSSLSSITTMFLQNNQFTGSINVLASLPLETLNVANNHFTGWIPE
Zea mays  LDLSFNSLTGDLPQSFTGLSSLKKVYLQNNQFTGNINVLANLPLETLNVANNHFTGWIPS
Rice      LDLSFNSLAGDLPQGFTSLSSLKKLYLQNNQFTGYINVLANLPLDDLNVANNHFTGWIPS
          **:* *:: ..**    :.*:*  ..::*******:* :::**  ***: **:*** ******.

AtSRF6    SLKGIT-LIKDGNSFNTGPAPPPPPGTPPIR-GSPSRKSGGRESRSSDESTRNGDSKKSG
AtSRF7    SLKGIN-LQKDGNLLNSGPAPPPPPGTPPISKSSPTPKSGNRGNRSNGDSSNSKDSSKSG
Grape     SLKNIN-LQKDGNSWSSGPAPPPPPGTPPVSRTPPKHKSGGNDGPSGG---GGGSGGKSG
Zea mays  QLKKINSLQTDGNSWSTGPAPPPPPYTAPPPPPNHWNADGSSSSSSSSG--------GRSG
Rice      QLKKINNLQTDGNSWSNGPAPPPPPYSAPPPPNRPNSPGQNNGGSSSG--------GSSG
           .** *. * .***  ..********:.*    .  . *..           **

AtSRF6    IGAGAIAGIIISLLVVTALLVAFFLFRRKKSKRSSPMDIEKTD---NQPFTLASNDFH-E
AtSRF7    LGAGGVAGIVISLIVVTA-VIAFFLIKRKRSKRSSSTDIEKTDNNINQPIILASNDFHQE
Grape     IGGGGIAGIVISILVIGA-IITFFLVKR-RSRRPS-MDVEKHD---DQPFAPLASKEVQE
Zea mays  IGGGGVAGIIISLLVVGS-VVAFLVIKRRKRKAAMKEHFEQH-----QPFTSFPSNEVKD
Rice      IGGGGVAGIIISLLVVGA-VVAFFVIRRRKRRAALEEHFEQH-----QPFTSFPSNEVKD
          :*.*.:***:**::*: :  :::*:..:*  :  . ..*:     **:    ...  :

AtSRF6    NNSIQSSSSVETKKLDTSLSINLRPPP-IDRNKSFDDEDS-TRKPIAVKKSTVVVPSNVR
AtSRF7    NKSVQNPPLVETKKLDTSLSMNLRPPP-SERHKSFDDDDSTMRKPIVAKKAAVVVPSNVN
Grape     MKSIQASSTINTKTYEPSASINLRPPP-IDRHKSFDEED-LPKKPIITKKAN-TAPINAI
Zea mays  MKPVCEATTVDIESLASPASVNLKPPPKIERNKSFDDDDDFSNKLVAKKSN--ITPINAT
Rice      MKPIEESTTIDVESLPSPASFSLKPPPKIERHKSFDDDD-LSNKPVLKKTN--VAPIKAT
           ::  .. ::  :.   .. *..:***  :*:****::*    .*  :  *.    .* :.

AtSRF6    LYSVADLQIATGSFSVDNLLGEGTFGRVYRAEFDDGKVLAVKKIDSSALPHGMTDDFIEM
AtSRF7    TYTVSDLQVATNSFSVDNLLGEGTFGRVYRAQFEDGKVLAVKKIDSSALPTDTADDFTEI
Grape     SYSIADLQMATGSFSVENLIGEGSFGRVYQAQFDDGKVVAVKKIDSSALPDQFSEDFTEI
Zea mays  VYSVADLQMATDSFSFDNLVGEGTFGRVYRAQFNDGKVLAIKKLDSTVMPFQSSDDFAEL
Rice      VYSVADLQMATESFSMDNLVGEGTFGRVYRAQFTGGKVLAVKKLDSTVMPFHSSDDFAEL
          *:::.**:** *** .:**.***:*****:*:*  ***:*:**:**:*  .  :** *:
```

FIGURE 11C

```
AtSRF6      VSKIANLDHPNVTKLVGYCAEHGQHLVVYEFHKNGSLHDFLHLSEEESKALVWNSRVKIA
AtSRF7      VSKIAHLDHENVTKLDGYCSEHGQHLVVYEFHRNGSLHDFLHLAEEESKPLIWNPRVKIA
Grape       VSNISQLHHPNVTELVGYCSEHGQHLLVYEFHKNGSLHDFLHLSDEYSKPLTWNTRVKIA
Zea mays    VSNISKLHHPNLNELVGYCMEHGQHLLVYDFHRNGSLHDLLHLSDEYSKPLSWNTRIKIA
Rice        VSDISKLHHPNLNELVGYCMEHGQHLLVYDFHRNGSLHDLLHLSDEYSKPLSWNSRVKIA
            **.*::*.* *:..:* *** ******:**:**:******:***::* **.* **.*:***

AtSRF6      LGTARALEYLHEVCSPSIVDKNIKSANILLDSELNPHLSDSGLASFLPTANELLNQTD-E
AtSRF7      LGTARALEYLHEVCSPSIVHKNIKSANILLDSELNPHLSDSGLASFLPTANELLNQND-E
Grape       LGTARALEYLHEVCSPSIVHKNFKSANILLDTELNPHLTDCGLASFIPNADQVLNHNAGS
Zea mays    LGSARALEYLHEICSPSIIHKNFKSSNILLDSEFNPHLSDAGLASFIPDAEFQAAEQS-A
Rice        LGSARALEYLHEICSPSIIHKNFKSSNLLLDSEFNPHLSDAGLASFISDAEFQAAQQS-A
            **:*********:*****:.**:**:*:***:*:****:*.*****:. *:    .

AtSRF6      GYSAPEVSMSGQYSLKSDIYSFGVVMLELLTGRKPFDSSTRSRSEQSLVRWATPQLHDID
AtSRF7      GYSAPETSMSGQYSLKSDVYSFGVVMLELLTGRKPFDS-TRSRSEQSLVRWATPQLHDID
Grape       GYSAPEVAMSGQYTLKSDVYSFGVVMLELLSGRKPFDS-SRSRSEQSLVRWATPQLHDID
Zea mays    GYTAPEVDMTGQYTFKSDVYSFGVVMLELLTGRRPFDS-SRPRSEQSLVRWATPQLHDID
Rice        GCTAPEVDMTGQYTLKSDVYSFGVVMLELLTGRRPFDS-TRPRSEQSLVRWATPQLHDID
            *  :***. *:***::***:*************:**:.****  :*.*****************

AtSRF6      ALAKMVDPALKGLYPVKSLSRFADVIALCVQPEPEFRPPMSEVVQALVVLVQRANMSKRT
AtSRF7      ALGKMVDPALKGLYPVKSLSRFADVIALCVQPEPEFRPPMSEVVQALVVLVQRANMSKRT
Grape       ALAKMVDPALKGLYPVKSLSRFADVIALCVQPEPEFRPPMSEVVQALVRLVQRANMSKRT
Zea mays    ALDRMVDPALKGLYPAKSLSRFADVLALCVQPEPEFRPPMSEVVQALVRLVQRANMTKRM
Rice        ALDRMVDPALKGLYPAKSLSRFADVLALCVQPEPEFRPPMSEVVQALVRLVQRANMTKRM
            ** :**********.*********:***********************.*******:**

AtSRF6             VGVDPSQRA-GSADTTSDYM-
AtSRF7             VGVG----S-GSSGVN-DYM-
Vitis vinifera    ISNEQGASPRGDNPDTQDHTS
Zea mays          LDGDTS-RR--PDDLDQDFI-
Oriza sativa      LDGDTSSRR--TDDQEQDFI-
                   :.              *.

Sequence type explicitly set to Protein
Sequence format is Pearson
Sequence 1: Zea mays            684 aa
Sequence 2: Oriza sativa        718 aa
Sequence 3: Vitis vinifera      679 aa
Sequence 4: AtSRF6              720 aa
Sequence 5: AtSRF7              717 aa
Start of Pairwise alignments Aligning...
Sequences (1:2) Aligned. Score:  86
Sequences (1:3) Aligned. Score:  65
Sequences (1:4) Aligned. Score:  60
Sequences (1:5) Aligned. Score:  60
Sequences (2:3) Aligned. Score:  65
Sequences (2:4) Aligned. Score:  59
Sequences (2:5) Aligned. Score:  58
Sequences (3:4) Aligned. Score:  67
Sequences (3:5) Aligned. Score:  66
Sequences (4:5) Aligned. Score:  78

Alignment Score 28400
```

FIGURE 11D

COMPOSITIONS AND METHODS FOR INCREASING CELLULOSE PRODUCTION

CROSS REFERENCE TO RELATED APPLICATIONS

This application claims priority under 35 U.S.C. §119 from Provisional Application Ser. No. 61/117,309, filed Nov. 24, 2008, the disclosure of which is incorporated herein by reference.

STATEMENT REGARDING FEDERALLY SPONSORED RESEARCH

The invention was supported by a grant no. DE-FG02-04ER15555 from U.S. Department of Energy. The government has certain rights in the invention.

TECHNICAL FIELD

This disclosure relates to methods and compositions for genetically altering cellulose biosynthesis.

BACKGROUND

Cellulose is a major building block of plant cell walls and provides mechanical strength and rigidity. Wood contains 30 to 50% cellulose, 20 to 30% lignin and 20 to 30% hemicellulose (Higuchi, 1997).

Production of increased amounts of cellulose in transgenic plants would improve the mechanical strength properties of juvenile wood formed in normal plants. This would be a great benefit to industry because juvenile wood is generally undesirable for solid wood applications because it has inferior mechanical properties.

Since many of society's fiber, chemical and energy demands are met through the industrial-scale production of cellulose from wood, genetic engineering of the cellulose biosynthesis machinery in plants could produce, for example, higher pulp yields. This would allow greater returns on investment by pulp and paper industries and provide increased cellulosic materials for biofuel production and fermentation processes.

SUMMARY

The disclosure shows that loss-of-function mutations of SRF6 (At1g53730) and SRF7 (At3g14350) (srf6-1 and srf7-1) reduced cellulose synthase A (CesA) gene expression, had reduced hypocotyl elongation in the dark similar to the CesA6 mutant PROCUSTE1 (prc1-1, At5g64740) and had reduced cellulose deposition as observed by Fourier Transform Infrared (FT-IR) microspectroscopy. Other insertional mutants of SRF7 (srf7-2 and srf7-3), which truncate the C-terminus, showed an increase in CesA gene expression that may be caused by the elimination of an auto-inhibitory region and thus generates a constitutively active mutant. Full-length overexpression of SRF7 (35S:SRF7) exhibited increased CesA gene expression and also had increased glycosidic bonds and carbohydrate bonds indicative of increased cellulose. This increase in cellulose production without a deleterious increase in pectin would be of great interest to bioenergy producers interested in cellulolytic ethanol production.

The disclosure provides a recombinant plant cell comprising a heterologous polynucleotide resulting in overexpression of an SRF-6, SRF-7 or homologs thereof, wherein the recombinant host cell comprises increased cellulose production compared to a wild-type cell. In one embodiment, the recombinant host cell comprises increased cellulose synthase expression (e.g., a CesA). In one embodiment, the heterologous polynucleotide comprises a heterologous regulatory element that increases expression of an SRF-6, SRF-7 or homolog thereof. In another embodiment, the heterologous polynucleotide comprises an expression vector comprising SRF-6, SRF-7 or homolog thereof.

The disclosure also provides use of the recombinant host cell in the production of a plant or tree comprising increased cellulose content compared to a wild-type plant or tree.

The disclosure also provides a method of producing a transgenic plant comprising growing the plant cell into a plant.

The disclosure provides a transgenic plant, wherein the plant comprises overexpression of an SRF-6, SRF-7 or homolog thereof, wherein the plant comprises increased cellulose production compared to a wild-type plant. In one embodiment, the plant comprises a tree.

The disclosure also provides an isolated polynucleotide encoding a polypeptide lacking all or a fragment of the extracellular domain of an SRF-6 polypeptide. In one embodiment, the polynucleotide comprises a sequence of SEQ ID NO:53.

The disclosure provides an isolated polynucleotide encoding a polypeptide lacking all or a fragment of the extracellular domain of an SRF-7 polypeptide (e.g., SEQ ID NO:54).

The disclosure also provides an isolated polynucleotide encoding a polypeptide lacking all or a fragment of the C-terminal domain of an SRF-6 polypeptide or SRF-7 polypeptide.

The disclosure provides polypeptides encoded by the polynucleotide above, vectors comprising such polynucleotides and host cells transformed with such polynucleotides and vectors.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 11A-E show an alignment of SRFs and a relationship diagram (an SRF-6 (SEQ ID NO:2) and -7 (SEQ ID NO:4) are shows in FIGS. 11A-B along with SFR1A'-SEQ ID NO:6; SRF1A-SEQ ID NO:8; SRF3-SEQ ID NO:16; SRF2-SEQ ID NO:14; SRF4-SEQ ID NO:18; SRF5-SEQ ID NO:20; SRF8-SEQ ID NO:26; SUB-SEQ ID NO:51). SRFs-6 and -7 and related homologs are shows in FIGS. 11C-D, SEQ ID NO:6, 8, 10, 12, 14, 16, 18, and 20).

DETAILED DESCRIPTION

Figure 1:
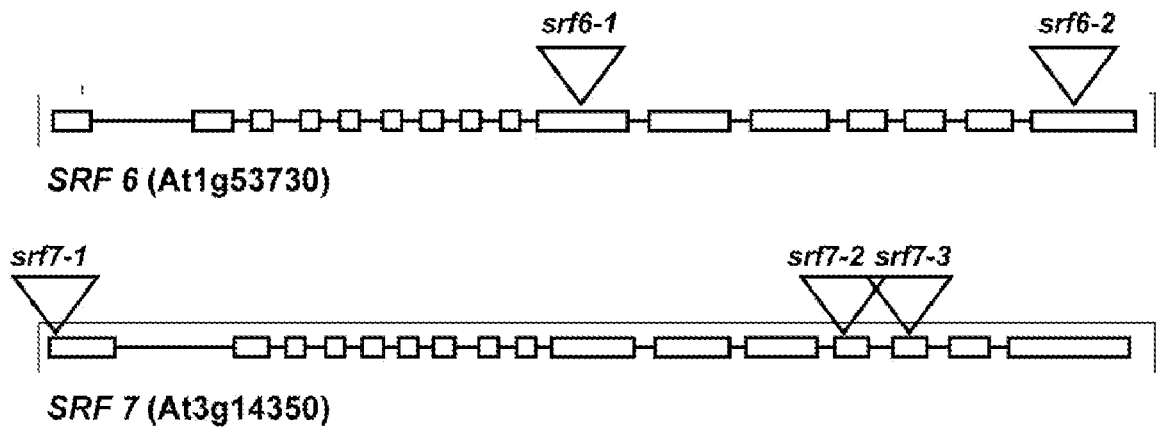
FIG. 1A-B shows A) Gene structure of SRF6 and SRF7 and location of insertional mutations. B) Quantitative analysis of dark-grown hypocotyl growth of SRF knockouts and overexpression mutants. Hypocotyl lengths of SRF knockout, overexpression and combinatorial mutants compared to cellulose synthesis mutants, mur10-2 and prc1-1 and the wild type. Error bars represent the standard deviation and are combined from 3 independent experiments. Student's t-test: $*=p<0.05$ and $+=p<0.01$.
Figure 1:
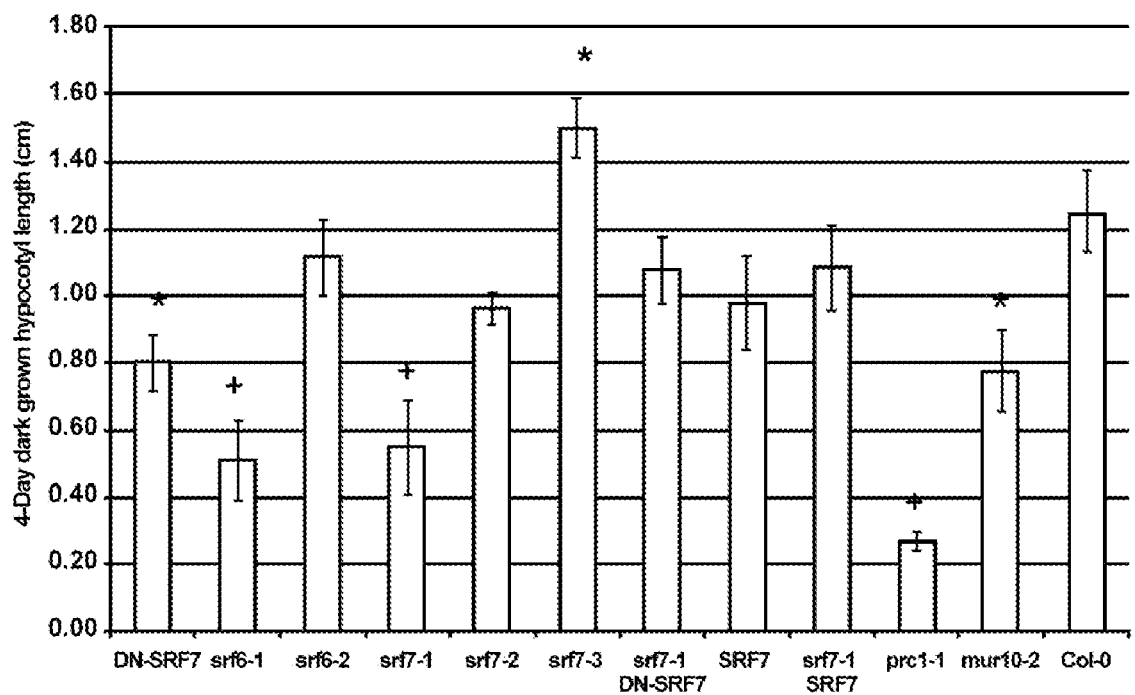

As used herein and in the appended claims, the singular forms "a," "and," and "the" include plural referents unless the context clearly dictates otherwise. Thus, for example, reference to "a probe" includes a plurality of such probes and reference to "the primer" includes reference to one or more primers and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of:"

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Plant biomass represents a useful and valuable resource as a fermentation substrate for highly valuable organic fuels and chemicals. Plant biomass generally consists of about 25% lignin and about 75% carbohydrate polymers including cellulose and hemicellulose. The latter represents one fifth to one half of the total carbohydrates in the biomass. Cellulose is a heteropolymer of hexose and pentose sugars, with glucose and xylose as two major constituents.

Cellulose synthesis is a critical process in plants for both the structural integrity of the developing cell and also for the overall structure and rigidity of the plant. The mechanisms underlying the synthesis of cellulose are becoming clearer but the regulation of this important process remains unknown.

Cellulose is the most abundant biopolymer on earth. It is an integral component of the plant cell wall and is responsible for most of the rigidity and strength of the cell. Cellulose is currently being investigated as a new fuel source. Because of its chemical structure, a polymer of β-linked glucose residues, cellulose would make an excellent feedstock for ethanol production, which may relieve some of the pressure of dwindling fossil fuel sources. One of the current limitations to cellulolytic ethanol production, ethanol produced from the conversion of cellulose to simple sugars that are then fermented, is a supply of cellulose dense organic matter that is also low in pectins and lignins. These two components of the plant cell wall act as additional "glues" that bind the cellulose together forming a stronger cell wall (Bonnetta et al., 2002). But these act as contaminants in ethanol production and reduce the yield of cellulose from plant tissue. One way to avoid this is to engineer plants that produced less lignin and pectins. The disclosure also provides a method to produce more cellulose per cell. The polynucleotides of the disclosure that produce more cellulose are from a superfamily of genes called receptor-like kinases (RLKs). The superfamily of RLKs consists of over 600 genes; many of these are of unknown function (Shiu and Bleecker, 2001).

Cellulose synthesis is a complex chemical and mechanical process. The proteins involved in primary and secondary cell wall synthesis are becoming clearer, for a review see (Fagard et al., 2000; Bosca et al., 2006; Desprez et al., 2007; Presson et al., 2007). There are no RLKs that have been shown to positively affect cellulose synthesis, that is until now.

The function of these genes in this large gene family was evaluated using an approach whereby a dominant negative (DN) form of the receptor was used to help elucidate the gene's subfamily function. In this process a DN-RLK transgenic plant was generated with unusually large leaves and when examined further, larger epidermal cells were identified. With further investigation into these genes, members of the Strubbelig Receptor Family (SRF) were identified.

The Strubbelig Receptor Family (SRF) contains nine subfamily members and belongs to the leucine-rich repeat (LRR) class of receptor-like kinases (Eyüboglu et al., 2007). It has been reported that SRF4 was a positive regulator of leaf size, and that the Strubbelig Receptor Family is characterized by functional diversity when reverse genetics and bioinformatic data mining was used to determine the functions of this receptor gene family (Eyüboglu et al., 2007). SRF7 can play a role in cell wall biology by the observations that DN-srf7 mutants showed an enlargement in leaf size and an increase in epidermal cell size. These observations led to independent examination the genome-wide expression data found on the Genevestigator (https:~~www.genevestigator.ethz.ch) and the ATTED-II (http:~~www.atted.bio.titech.ac.jp) websites to examine the coexpression of all genes to SRF6 and SRF7. SRF6 and SRF7 were coexpressed with many of the cellulose synthase A (CesA) genes.

The disclosure demonstrates that two members of the Strubbelig Receptor Family are not only coexpressed with cell wall synthesis genes but also have similar dark grown phenotypes to mutants affected in cellulose synthesis as well as altered CesA gene expression. Knockout mutants of SRF6 and SRF7 have shorter dark grown hypocotyls similar to the primary cell wall cellulose synthase CesA6 (prc1-1). Using FT-IR microspectroscopy and Real-Time RT-PCR there was a coordinate relationship of CesA3 and CesA4 gene expression and the amount of cellulose specific bonding. The overexpression of SRF7 demonstrated a large increase in CesA3 and CesA4 gene expression and also in cellulose composition. This may be due to the ectopic expression of secondary cell wall synthesis in epidermal cells that would under normal conditions only have primary cell walls, as the SRF7 gene is driven under the 35S constitutive promoter from the cauliflower mosaic virus (CaMV). The increase in cellulose and CesA3 or CesA4 gene expression do not alter the reproductive success or biomass of the SRF7 overexpressing lines and there are many plant species with homologs to SRF7, this makes it an exceptional candidate for increasing the cellulose content in future cellulolitic feedstock plants.

The disclosure provides methods and compositions for increasing cellulose content and biomass of a plant or cellulose producing microorganism. The method includes transforming a plant cell or host cell with a vector the increase expression of a SRF-6 and/or SRF-7 polynucleotide or homolog thereof or comprising transforming a plant or microorganism with a mutant SRF-6 or SRF-7 that encodes a truncated SRF-6 or -7 polypeptide the promotes increased expression of a cellulase synthase gene.

A cellulose promoting polypeptide of the disclosure includes SRF-6 or -7 polypeptide as well as homologs thereof (collectively referred to herein as SRF-6 or -7 polypeptides, unless the context clearly indicates otherwise). Thus, an SRF-6 or -7 polypeptide comprises any of the polypeptides of SEQ ID NOs:2 or 4. In addition, based upon the alignment of the sequence set forth FIG. 11, one of skill in the art can readily generate polypeptides having at least 1-50 (e.g., 1-40, 1-30, 1-20, or 1-10) conservative amino acid substitutions and encoding a polypeptide that promotes increase cellulosic production in a plant.

Figure 11E:
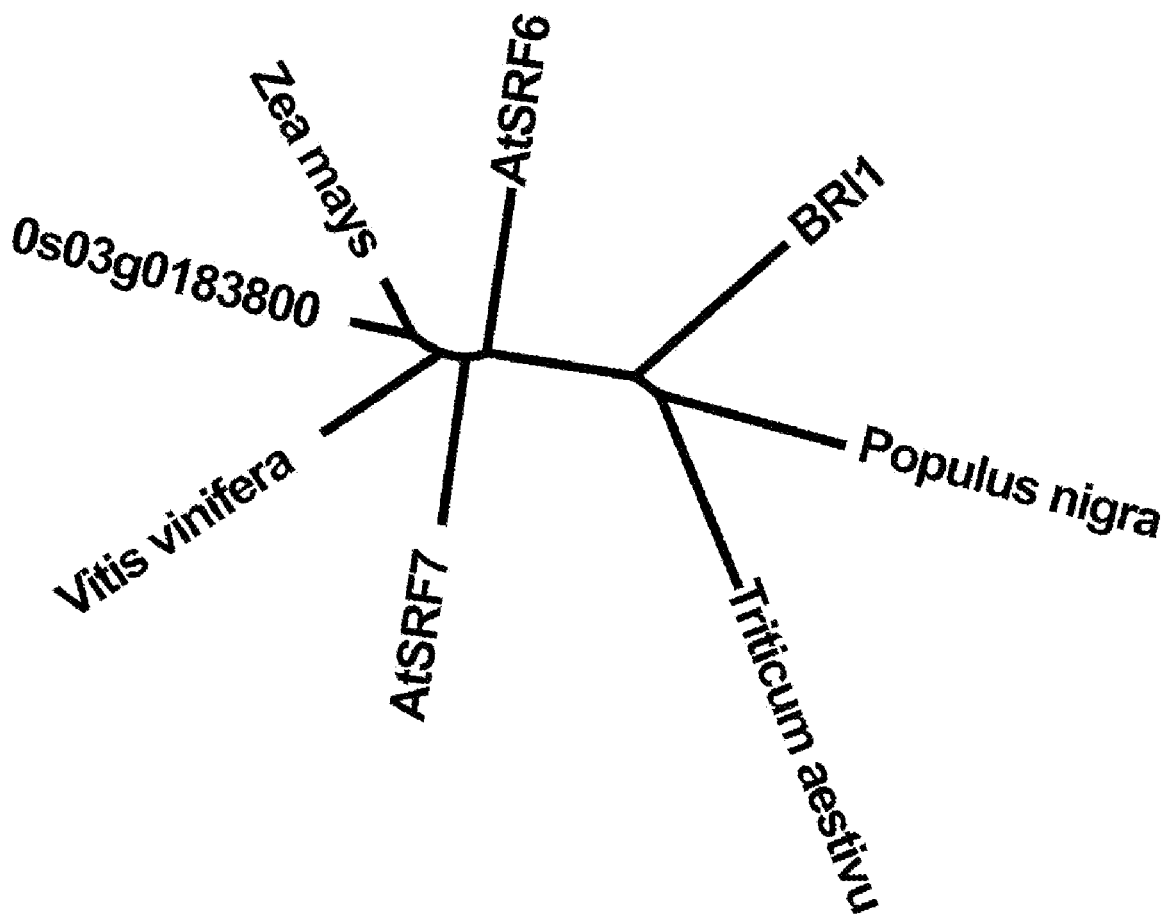

Furthermore, the disclosure provides SRF-6 or SRF-7 polypeptides having at least 58, 60, 70, 80, 90, 95, 98, or 99% identity to any of the SRF polypeptide set forth in FIG. 11 and having the ability to increase cellulosic material production in a plant. One of skill in the art can readily generate polynucleotides encoding the polypeptide of any of the foregoing using skill available in the art (e.g., molecule biology cloning strategies) and with reference to SEQ ID NO:1 and 3.

The disclosure demonstrates that Strubbelig Receptor Family (SRF) 6 and 7 (or homologs or variants thereof) control cellulose synthase A (CesA) gene expression and affects cellulose deposition and quantity.

Cellulose synthesis is a critical process in plants for both the structural integrity of the developing cell and also for the overall structure and rigidity of the plant. The disclosure shows that loss-of-function mutations of SRF6 (At1g53730) and SRF7 (At3g14350) (srf6-1 and srf7-1) reduced cellulose synthase A (CesA) gene expression, had reduced hypocotyl elongation in the dark similar to the CesA6 mutant PROCUSTE1 (prc1-1, At5g64740) and had reduced cellulose deposition as observed by Fourier Transform Infrared (FT-IR) microspectroscopy. Other insertional mutants of SRF7 (srf7-2 and srf7-3), which truncate the C-terminus, showed an increase in CesA gene expression that may be caused by the elimination of an auto-inhibitory region and thus generates a constitutively active mutant. Full-length overexpression of SRF7 (35S:SRF7) exhibited increased CesA gene expression and also had increased glycosidic bonds and carbohydrate bonds indicative of increased cellulose. This increase in cellulose production without a deleterious increase in pectin would be of great interest to bioenergy producers interested in cellulolytic ethanol production.

The SRF family of polypeptides whose sequences are set forth in the accession numbers below are incorporated herein by reference in their entirety:

| Gene | Agi Code | GenBank Accession No. |
|---|---|---|
| SUB (SRF9) | At1g11130 | AF399923 |
| SRF1A | (Col) At2g20850 | AY518286 |
| SRF1B | Col DQ914918 | |
| SRF1A | Ler DQ914919 | |
| SRF1B | Ler DQ914920 | |

-continued

| Gene | Agi Code | GenBank Accession No. |
|------|----------|----------------------|
| SRF2 | At5g06820 | AY518287 |
| SRF3 | At4g03390 | AY518288 |
| SRF4 | At3g13065 | AY518289 |
| SRF5 | At1g78980 | AY518290 |
| SRF6 | At1g53730 | AY518291 |
| SRF7 | At3g14350 | AY518292 |
| SRF8 | At4g22130 | AY518293 |

Homologs and variants of the above references sequences can be identified using available databases in the art without out due effort.

Based on the aforementioned findings, the disclosure provides DNA whose expression varies during plant cell wall component biosynthesis and wood fiber cell morphogenesis.

The disclosure provides methods and compositions for generating increased cellulose material in plants. The methods include increasing the expression of a SRF-6 or -7 polypeptide or homolog thereof or transforming a plant cell with a mutant SRF-6 or -7 lacking a C-terminal portion of the polypeptide. The disclosure also provides transgenic plants that overexpress an SRF-6 and/or SRF-7 or a homolog thereof or which express a mutant SRF-6 or SRF-7, wherein the transgenic plant produces an increased amount of cellulose compared to a wild-type plant.

The disclosure provides recombinant host cells and transgenic plants that comprise a modified expression of an SRF6 and/or SRF7 or homolog thereof wherein the host cell comprises increased expression of cellulose synthase genes and wherein the transgenic plant comprise increased cellulose content compared to a plant (e.g., a plant of the same parental species) lacking a change in SRF6, SRF7 or homolog thereof expression.

As used herein, the terms "host cells" and "recombinant host cells" are used interchangeably and refer to cells (for example, plant cells) into which the compositions of the presently disclosed subject matter (for example, an expression vector comprising an SRF6, or -7 polynucleotide or homolog thereof) can be introduced. Furthermore, the terms refer not only to the particular plant cell into which an expression construct is initially introduced, but also to the progeny or potential progeny of such a cell. Because certain modifications can occur in succeeding generations due to either mutation or environmental influences, such progeny might not, in fact, be identical to the parent cell, but are still included within the scope of the term as used herein.

An example of a useful polynucleotide for production of cellulosic material comprises an SRF-6 or -7 polynucleotide, variants, mutants and fragment thereof, wherein the variants, mutants and fragments stimulate CesA gene expression. An SRF-6 or -7 polynucleotide includes homologs and variants that are capable of hybridization under stringent conditions with a DNA consisting of a nucleotide sequence described in GenBank accession no. AY518291 or GenBank accession no. AY518292. Stringent hybridization conditions comprise allowing to stand overnight at 60° C. in 0.1×SSC solution, or conditions yielding stringencies similar to these. Useful fragments of SRF-6 or -7 includes those lacking a function C-terminal end of the wild-type polypeptide.

Also contemplated by the disclosure are transgenic plants overexpressing an SRF-6 or -7 polynucleotide present in the organisms genome wherein the SRF-6 or -7 is operably linked to a heterologous promoter (e.g., a tissue specific, constitutive or inducible promoter).

In addition, the disclosure contemplates a polynucleotide that encodes an polypeptide that induces expression of CesA polypeptides. In one embodiment, the polynucleotide encodes a polypeptide comprising at least 50% identity to an SRF-6 or -7. In another embodiment, the polynucleotide encodes a mutant SRF-6 or -7 polypeptide lacking a function C-terminal portion of SRF-6 or -7.

Homologs of an SRF-6 or -7 can be identified and isolated using techniques known in the art including, for example, hybridization reactions to isolate such DNAs under stringent conditions. Stringent hybridization conditions can include, for example, conditions such as 6 M urea, 0.4% SDS, and 0.5×SSC, and those conditions yielding similar stringencies to these. DNAs with higher homology are expected to be isolated when hybridization is performed under more stringent conditions, for example, 6 M urea, 0.4% SDS, and 0.1× SSC. DNAs thus isolated are thought to have high homology, at an amino acid level, with amino acid sequences encoded by DNAs that hybridize under stringent conditions to DNAs comprising any one of the nucleotide sequences described in Genbank accession no. AY518291 or GenBank accession no. AY518292. Herein, high homology means an identity over the entire amino acid sequence of at least 50% or above, more preferably 70% or above, even more preferably 80% or above, still more preferably 90% or above, even still more preferably 95% or above, and most preferably 98% or above. Such DNAs comprise degenerative variants of the DNAs that hybridize under stringent conditions with the DNAs an SRF-6 or -7 as set forth in Genbank accession no. AY518291 or GenBank accession no. AY518292.

Useful variants of an SRF-6 or -7 can be identified by introducing mutations by site-directed mutagenesis, directed evolution, shuffling, and the like (Kramer, W. & Fritz, H J., Methods Enzymol, 1987, 154, 350). The mutant polynucleotide can then be screened to determine if it modulates cesA expression, wherein an increase in CesA is indicative that the mutant SFR-6 or -7 can promote cellulose formation.

An SRF-6 or -7 polynucleotide or homolog thereof refers to a polynucleotide comprising SEQ ID NO:1 or 3, polynucleotide having at least 80%, 90%, 95%, 98% or 99% identity to a sequence consisting of SEQ ID NO:1 or 3, fragments of the foregoing wherein the fragments encode a polypeptide that promotes cellulase synthase expression, polynucleotide that are complementary to any of the foregoing and polynucleotides that comprise a U instead of T in their sequence.

Polynucleotides useful in the methods of the disclosure include naturally occurring polynucleotides, recombinant polynucleotides and chemically synthesized polynucleotides. There is no particular limitation on the type of polynucleotides of the disclosure so long as they are capable of encoding polypeptides useful for modulating cellulose production (e.g., through modulating expression of cesA) and include genomic DNA, cDNA, chemically synthesized DNA, and the like. Genomic DNAs may be prepared by conducting PCR (Saiki et al., Science, 1988, 239, 487) using as a template genomic DNA prepared according to a method described in literature (Rogers and Bendich, Plant Mol. Biol., 1985, 5, 69) and primers prepared based on a nucleotide sequence of a polynucleotide of the disclosure (e.g. a nucleotide sequence set forth in accession nos. AY518291 or GenBank accession no. AY518292). Furthermore, cDNA may be prepared according to the standard method (Maniatis et al., "Molecular Cloning", Cold Spring Harbor Laboratory Press), by preparing mRNA from plants, performing reverse transcription, and conducting PCR using primers similar to those described above. Genomic DNA and cDNA may also be prepared by constructing a genomic DNA library or a cDNA library according to the standard method, and screening this library using a probe, for example, one synthesized based on the a nucleotide sequence of a DNA of the disclosure. The DNA thus obtained may be easily sequenced using, for example, the "Sequencer Model 373" (ABI).

As used herein, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy for a nucleic acid molecule with its complementary sequence is sufficient to allow the relevant function of the nucleic acid to proceed, in some embodiments, ribonuclease activity. Determination of binding free energies for nucleic acid molecules is well known in the art. See e.g., Freier et al., 1986; Turner et al., 1987.

As used herein, the phrase "percent complementarity" refers to the percentage of contiguous residues in a nucleic acid molecule that can form hydrogen bonds (e.g., Watson-Crick base pairing) with a second nucleic acid sequence (e.g., 5, 6, 7, 8, 9, out of 10 being 50%, 60%, 70%, 80%, 90%, and 100% complementary). The terms "100% complementary", "fully complementary", and "perfectly complementary" indicate that all of the contiguous residues of a nucleic acid sequence can hydrogen bond with the same number of contiguous residues in a second nucleic acid sequence.

As used herein, the term "gene" refers to a nucleic acid sequence that encodes an RNA. The term "gene" also refers broadly to any segment of DNA associated with a biological function. As such, the term "gene" encompasses sequences including, but not limited to, a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation from one or more existing sequences.

As is understood in the art, a gene typically comprises a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

The phrase "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides. Additionally, processes that affect protein-protein interactions within the cell can also affect gene expression as defined herein.

The terms "heterologous gene", "heterologous DNA sequence", "heterologous nucleotide sequence", "exogenous nucleic acid molecule", "exogenous DNA segment", and "transgene" as used herein refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found. A transgenic plant or host cell can comprise, for example, a heterologous promoter the promotes transcription of an SRF-6 or -7, or homologs thereof in a desired plant cell or host cell.

As used herein, the term "isolated" refers to a molecule substantially free of other nucleic acids, proteins, lipids, carbohydrates, and/or other materials with which it is normally associated, such association being either in cellular material or in a synthesis medium. Thus, the term "isolated polynucleotide" or "isolated nucleic acid" refers to a ribonucleic acid molecule or a deoxyribonucleic acid molecule (for example, a genomic DNA, cDNA, mRNA, and the like) of natural or synthetic origin or some combination thereof, which (1) is not associated with the cell in which the "isolated polynucleotide" is found in nature, or (2) is operatively linked to a polynucleotide to which it is not linked in nature. Similarly, the term "isolated polypeptide" refers to a polypeptide, in some embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

The term "isolated", when used in the context of an "isolated cell", refers to a cell that has been removed from its natural environment, for example, as a part of an organ, tissue, or organism.

As used herein, the term "modulate" refers to an increase, decrease, or other alteration of any, or all, chemical and biological activities or properties of a biochemical entity, e.g., a wild type or mutant nucleic acid molecule. For example, the term "modulate" can refer to a change in the expression level of a gene or a level of an RNA molecule or equivalent RNA molecules encoding one or more proteins or protein subunits; or to an activity of one or more proteins or protein subunits that is upregulated or downregulated, such that expression, level, or activity is greater than or less than that observed in the absence of the modulator. For example, the term "modulate" can mean "increasing" or "promoting", but the use of the word "modulate" is not limited to this definition.

The term "naturally occurring", as applied to an object, refers to the fact that an object can be found in nature. For example, a polypeptide or polynucleotide sequence that is present in an organism (including bacteria) that can be isolated from a source in nature and which has not been intentionally modified by man in the laboratory is naturally occurring. It must be understood, however, that any manipulation by the hand of man can render a "naturally occurring" object an "isolated" object as that term is used herein.

As used herein, the terms "polynucleotide" or "nucleic acid molecule" refer to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally occurring nucleotides (such as deoxyribonucleotides and ribonucleotides), or analogs of naturally occurring nucleotides (e.g., alpha-enantiomeric forms of naturally occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term also includes so-called "peptide nucleic acids", which comprise naturally occurring or modified nucleic acid bases attached to a polyamide backbone. Nucleic acids can be either single stranded or double stranded.

The terms "operably linked" and "operatively linked" are used interchangeably. When describing the relationship between two nucleic acid regions, each term refers to a juxtaposition wherein the regions are in a relationship permitting them to function in their intended manner. For example, a control sequence "operably linked" to a coding sequence can be ligated in such a way that expression of the coding sequence is achieved under conditions compatible with the control sequences, such as when the appropriate molecules (e.g., inducers and polymerases) are bound to the control or regulatory sequence(s). Thus, in some embodiments, the phrase "operably linked" refers to a promoter connected to a coding sequence in such a way that the transcription of that coding sequence is controlled and regulated by that promoter. Techniques for operably linking a promoter to a coding sequence are well known in the art; the precise orientation and location relative to a coding sequence of interest is dependent, inter alia, upon the specific nature of the promoter.

Thus, the term "operably linked" can refer to a promoter region that is connected to a nucleic acid sequence in such a way that the transcription of that nucleic acid sequence is controlled and regulated by that promoter region. Similarly, a nucleic acid sequence is said to be under the "transcriptional control" of a promoter to which it is operably linked. Techniques for operably linking a promoter region to a nucleotide sequence are known in the art. In some embodiments, a nucleotide sequence comprises a coding sequence and/or an open reading frame. The term "operably linked" can also refer to a transcription termination sequence that is connected to a nucleotide sequence in such a way that termination of transcription of that nucleotide sequence is controlled by that transcription termination sequence. For example, the disclosure provides vectors and host cells comprising an SRF-6 and/or -7 (or homolog thereof) polynucleotide operably linked to a promoter for expression (e.g., overexpression) of the polynucleotide in the plant or cell.

In some embodiments, more than one of these elements can be operably linked in a single molecule. Thus, in some embodiments multiple terminators, coding sequences, and promoters can be operably linked together. Techniques are known to one of ordinary skill in the art that would allow for the generation of nucleic acid molecules that comprise different combinations of coding sequences and/or regulatory elements that would function to allow for the expression of one or more nucleic acid sequences in a cell.

The term "regulatory sequence" is a generic term used throughout the specification to refer to polynucleotide sequences, such as initiation signals, enhancers, regulators, promoters, and termination sequences, which are necessary or desirable to affect the expression of coding and non-coding sequences to which they are operatively linked. Exemplary regulatory sequences are described in Goeddel, 1990, and include, for example, the early and late promoters of simian virus 40 (SV40), adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. The nature and use of such control sequences can differ depending upon the host organism. In prokaryotes, such regulatory sequences generally include promoter, ribosomal binding site, and transcription termination sequences. The term "regulatory sequence" is intended to include, at a minimum, components the presence of which can influence expression, and can also include additional components the presence of which is advantageous, for example, leader sequences and fusion partner sequences.

In some embodiments, transcription of a polynucleotide sequence is under the control of a promoter sequence (or other regulatory sequence) that controls the expression of the polynucleotide in a cell-type in which expression is intended. It will also be understood that the polynucleotide can be under the control of regulatory sequences that are the same or different from those sequences which control expression of the naturally occurring form of the polynucleotide. As used herein, the phrase "functional derivative" refers to a subsequence of a promoter or other regulatory element that has substantially the same activity as the full length sequence from which it was derived. As such, a "functional derivative" of a seed-specific promoter can itself function as a seed-specific promoter.

Termination of transcription of a polynucleotide sequence is typically regulated by an operatively linked transcription termination sequence (for example, an RNA polymerase III termination sequence). In certain instances, transcriptional terminators are also responsible for correct mRNA polyadenylation. The 3' non-transcribed regulatory DNA sequence includes in some embodiments about 50 to about 1,000, and in some embodiments about 100 to about 1,000, nucleotide base pairs and contains plant transcriptional and translational termination sequences. Appropriate transcriptional terminators and those that are known to function in plants include the cauliflower mosaic virus (CaMV) 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, a gamma coixin, oleosin 3, or other terminator from the genus *Coix* can be used.

The term "promoter" or "promoter region" each refers to a nucleotide sequence within a gene that is positioned 5' to a coding sequence and functions to direct transcription of the coding sequence. The promoter region comprises a transcriptional start site, and can additionally include one or more transcriptional regulatory elements. In some embodiments, a method of the presently disclosed subject matter employs a RNA polymerase III promoter.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters are often augmented with one or more transcriptional regulatory elements to influence the transcription of an operatively linked gene. For example, cell-type-specific or tissue-specific transcriptional regulatory elements can be added to minimal promoters to create recombinant promoters that direct transcription of an operatively linked nucleotide sequence in a cell-type-specific or tissue-specific manner.

Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types (in some embodiments, in all cell types) of an organism. Exemplary constitutive promoters include the promoters for the following genes which encode certain constitutive or "housekeeping" functions: hypoxanthine phosphoribosyl transferase (HPRT), dihydrofolate reductase (DHFR; (Scharfmann et al., 1991), adenosine deaminase, phosphoglycerate kinase (PGK), pyruvate kinase, phosphoglycerate mutase, the beta-actin promoter (see e.g., Williams et al., 1993), and other constitutive promoters known to those of skill in the art. "Tissue-specific" or "cell-type-specific" promoters, on the other hand, direct transcription in some tissues or cell types of an organism but are inactive in some or all others tissues or cell types. Exemplary tissue-specific promoters include those promoters described in more detail hereinbelow, as well as other tissue-specific and cell-type specific promoters known to those of skill in the art. In some embodiments, a tissue-specific promoter is a seed-specific promoter, leaf specific, root specific promoter.

When used in the context of a promoter, the term "linked" as used herein refers to a physical proximity of promoter elements such that they function together to direct transcription of an operatively linked nucleotide sequence The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element. In some embodiments, a transcriptional regulatory sequence is a transcription termination sequence, alternatively referred to herein as a transcription termination signal.

Coding sequences intended for expression in transgenic plants can be first assembled in expression cassettes operably linked to a suitable promoter expressible in plants. The expression cassettes can also comprise any further sequences required or selected for the expression of the transgene. Such sequences include, but are not limited to, transcription terminators, extraneous sequences to enhance expression such as introns, vital sequences, and sequences intended for the targeting of the transgene-encoded product to specific organelles and cell compartments. These expression cassettes can then be easily transferred to the plant transformation vectors disclosed below. The following is a description of various components of typical expression cassettes.

The selection of the promoter used in expression cassettes can determine the spatial and temporal expression pattern of the transgene in the transgenic plant. Selected promoters can express transgenes in specific cell types (such as leaf epidermal cells, mesophyll cells, root cortex cells) or in specific tissues or organs (roots, leaves, flowers, or seeds, for example) and the selection can reflect the desired location for accumulation of the transgene. Alternatively, the selected promoter can drive expression of the gene under various inducing conditions. Promoters vary in their strength; i.e., their abilities to promote transcription. Depending upon the host cell system utilized, any one of a number of suitable promoters can be used, including the gene's native promoter. The following are non-limiting examples of promoters that can be used in expression cassettes.

Ubiquitin is a gene product known to accumulate in many cell types and its promoter has been cloned from several species for use in transgenic plants (e.g. sunflower-Binet et al., 1991; maize-Christensen & Quail, 1989; and *Arabidopsis*-Callis et al., 1990). The *Arabidopsis* ubiquitin promoter is suitable for use with the nucleotide sequences of the presently disclosed subject matter. The ubiquitin promoter is suitable for gene expression in transgenic plants, both monocotyledons and dicotyledons. Suitable vectors are derivatives of pAHC25 or any of the transformation vectors disclosed herein, modified by the introduction of the appropriate ubiquitin promoter and/or intron sequences.

Construction of the plasmid pCGN1761 is disclosed in the published patent application EP 0 392 225, which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker that includes NotI and XhoI sites in addition to the existing EcoRI site. This derivative is designated pCGN1761 ENX. pCGN1761 ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those disclosed below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that can enhance translation. This is particularly useful when overexpression is desired. For example, pCGN1761ENX can be modified by optimization of the translational initiation site as disclosed in U.S. Pat. No. 5,639,949, incorporated herein by reference.

Several isoforms of actin are known to be expressed in most cell types and consequently the actin promoter can be used as a constitutive promoter. In particular, the promoter from the rice Actl gene has been cloned and characterized (McElroy et al., 1990). A 1.3 kilobase (kb) fragment of the promoter was found to contain all the regulatory elements required for expression in rice protoplasts. Furthermore, expression vectors based on the Acti promoter have been constructed (McElroy et al., 1991). These incorporate the Actl-intron 1, Adhl 5' flanking sequence (from the maize alcohol dehydrogenase gene) and Adhl-intron 1 and sequence from the CaMV 35S promoter. Vectors showing highest expression were fusions of 35S and Actl intron or the Actl 5' flanking sequence and the Actl intron. Optimization of sequences around the initiating ATG (of the beta-glucuronidase (GUS) reporter gene) also enhanced expression.

The promoter expression cassettes disclosed in McElroy et al., 1991, can be easily modified for gene expression. For example, promoter-containing fragments are removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice Actl promoter with its first intron has also been found to direct high expression in cultured barley cells (Chibbar et al., 1993).

The double 35S promoter in pCGN1761ENX can be replaced with any other promoter of choice that will result in suitably high expression levels. By way of example, one of the chemically regulatable promoters disclosed in U.S. Pat. No. 5,614,395, such as the tobacco PR-1a promoter, can replace the double 35S promoter. Alternately, the *Arabidopsis* PR-1 promoter disclosed in Lebel et al., 1998, can be used. The promoter of choice can be excised from its source by restriction enzymes, but can alternatively be PCR-amplified using primers that carry appropriate terminal restriction sites.

A promoter inducible by certain alcohols or ketones, such as ethanol, can also be used to confer inducible expression of a coding sequence of the presently disclosed subject matter. Such a promoter is for example the alcA gene promoter from *Aspergillus nidulans* (Caddick et al., 1998). In *A. nidulans*, the alcA gene encodes alcohol dehydrogenase I, the expression of which is regulated by the AlcR transcription factors in presence of the chemical inducer. For the purposes of the presently disclosed subject matter, the CAT coding sequences in plasmid palcA:CAT comprising a alcA gene promoter sequence fused to a minimal 35S promoter (Caddick et al., 1998) are replaced by a coding sequence of the presently disclosed subject matter to form an expression cassette having the coding sequence under the control of the alcA gene promoter. This is carried out using methods known in the art.

Induction of expression of a nucleic acid sequence of the presently disclosed subject matter using systems based on steroid hormones is also provided. For example, a glucocorticoid-mediated induction system can be used and gene expression is induced by application of a glucocorticoid, for example a synthetic glucocorticoid, for example dexamethasone, at a concentration ranging in some embodiments from 0.1 mM to 1 mM, and in some embodiments from 10 mM to 100 mM.

Another pattern of gene expression is root expression. A suitable root promoter is the promoter of the maize metallothionein-like (MTL) gene disclosed in de Framond, 1991, and also in U.S. Pat. No. 5,466,785, each of which is incorporated herein by reference. This "MTL" promoter is transferred to a suitable vector such as pCGN 1761 ENX for the insertion of a selected gene and subsequent transfer of the entire promoter-gene-terminator cassette to a transformation vector of interest.

Wound-inducible promoters can also be suitable for gene expression. Numerous such promoters have been disclosed (e.g. Xu et al., 1993; Logemann et al., 1989; Rohrmeier & Lehle, 1993; Firek et al., 1993; Warner et al., 1993) and all are suitable for use with the presently disclosed subject matter. Logemann et al. describe the 5' upstream sequences of the dicotyledonous potato wunl gene. Xu et al. show that a wound-inducible promoter from the dicotyledon potato (pin2) is active in the monocotyledon rice. Further, Rohrmeier & Lehle describe the cloning of the maize Wip1 cDNA that is wound induced and which can be used to isolate the cognate promoter using standard techniques. Similarly, Firek et al. and Warner et al. have disclosed a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to the presently disclosed subject matter, and used to express these genes at the sites of plant wounding.

A maize gene encoding phosphoenol carboxylase (PEPC) has been disclosed by Hudspeth and Grula, 1989. Using standard molecular biological techniques, the promoter for this gene can be used to drive the expression of any gene in a leaf-specific manner in transgenic plants.

A variety of transcriptional terminators are available for use in expression cassettes. These are responsible for termination of transcription and correct mRNA polyadenylation. Appropriate transcriptional terminators are those that are known to function in plants and include the CaMV 35S terminator, the tml terminator, the nopaline synthase terminator, the octopine synthase terminator, and the pea rbcS E9 terminator. These can be used in both monocotyledons and dicotyledons. In addition, a gene's native transcription terminator can be used.

Numerous sequences have been found to enhance gene expression from within the transcriptional unit and these sequences can be used in conjunction with the genes of the presently disclosed subject matter to increase their expression in transgenic plants.

Various intron sequences have been shown to enhance expression, particularly in monocotyledonous cells. For example, the introns of the maize Adhl gene have been found to significantly enhance the expression of the wild type gene under its cognate promoter when introduced into maize cells. Intron 1 was found to be particularly effective and enhanced expression in fusion constructs with the chloramphenicol acetyltransferase gene (Callis et al., 1987). In the same experimental system, the intron from the maize bronze1 gene had a similar effect in enhancing expression. Intron sequences have been routinely incorporated into plant transformation vectors, typically within the non-translated leader.

Promoters for constant expression are exemplified by the 35S promoter of cauliflower mosaic virus (Odell et al., Nature, 1985, 313, 810), the actin promoter of rice (Zhang et al., Plant Cell, 1991, 3, 1155), the ubiquitin promoter of corn (Cornejo et al., Plant Mol. Biol., 1993, 23, 567), etc. Furthermore, promoters for inductive expression are exemplified by promoters that are expressed by extrinsic factors such as infection and invasion of filamentous fungi, bacteria, and viruses, low temperature, high temperature, drought, ultraviolet irradiation, spraying of particular compounds, and the like. Such promoters are exemplified by the chitinase gene promoter of rice (Xu et al., Plant Mol. Biol., 1996, 30, 387.) and tobacco PR protein gene promoter (Ohshima et al., Plant Cell, 1990, 2, 95.) expressed by the infection and invasion of filamentous fungi, bacteria and viruses, the "lip 19" gene promoter of rice induced by low temperature (Aguan et al., Mol. Gen. Genet., 1993, 240, 1.), "hsp 80" and "hsp 72" gene promotors of rice induced by high temperature (Van Breusegem et al., Planta, 1994, 193, 57.), "rab 16" gene promoter of *Arabidopsis thaliana* induced by dryness (Nundy et al., Proc. Natl. Acad. Sci. USA, 1990, 87, 1406), chalcone synthase gene promoter of parsley induced by ultraviolet irradiation (Schulze-Lefert et al., EMBO J., 1989, 8, 651.), alcohol dehydrogenase gene promoter of corn induced by anaerobic conditions (Walker et al., Proc. Natl. Acad. Sci. USA, 1987, 84, 6624) and so on. In addition, the chitinase gene promoter of rice and PR protein gene promoter of tobacco are induced also by specific compounds such as salicylic acid, and such, and the "rab 16" gene promoter is induced by the spraying of abcisic acid, a phytohormone.

A number of non-translated leader sequences derived from viruses are also known to enhance expression, and these are particularly effective in dicotyledonous cells. Specifically, leader sequences from Tobacco Mosaic Virus (TMV; the "W-sequence"), Maize Chlorotic Mottle Virus (MCMV), and Alfalfa Mosaic Virus (AMV) have been shown to be effective in enhancing expression (see e.g., Gallie et al., 1987; Skuzeski et al., 1990). Other leader sequences known in the art include, but are not limited to, picornavirus leaders, for example, EMCV (encephalomyocarditis virus) leader (5' noncoding region; see Elroy-Stein et al., 1989); potyvirus leaders, for example, from Tobacco Etch Virus (TEV; see Allison et al., 1986); Maize Dwarf Mosaic Virus (MDMV; see Kong & Steinbiss 1998); human immunoglobulin heavy-chain binding polypeptide (BiP) leader (Macejak & Sarnow, 1991); untranslated leader from the coat polypeptide mRNA of alfalfa mosaic virus (AMV; RNA 4; see Jobling & Gehrke, 1987); tobacco mosaic virus (TMV) leader (Gallie et al., 1989); and Maize Chlorotic Mottle Virus (MCMV) leader (Lommel et al., 1991). See also Della-Cioppa et al., 1987.

The term "transcription factor" generally refers to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

The phrases "percent identity" and "percent identical," in the context of two nucleic acid or protein sequences, refer to two or more sequences or subsequences that have in some embodiments at least 60%, in some embodiments at least 70%, in some embodiments at least 80%, in some embodiments at least 85%, in some embodiments at least 90%, in some embodiments at least 95%, in some embodiments at least 98%, and in some embodiments at least 99% nucleotide or amino acid residue identity, when compared and aligned for maximum correspondence, as measured using one of the following sequence comparison algorithms or by visual inspection. The percent identity exists in some embodiments over a region of the sequences that is at least about 50 residues in length, in some embodiments over a region of at least about 100 residues, and in some embodiments the percent identity exists over at least about 150 residues. In some embodiments, the percent identity exists over the entire length of a given region, such as a coding region.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

A "reference sequence" is a defined sequence used as a basis for a sequence comparison. A reference sequence can be a subset of a larger sequence, for example, as a segment of a full-length nucleotide, or amino acid sequence, or can comprise a complete sequence. Generally, when used to refer to a nucleotide sequence, a reference sequence is at least 200, 300, or 400 nucleotides in length, frequently at least 600 nucleotides in length, and often at least 800 nucleotides in length. Because two proteins can each (1) comprise a sequence (i.e., a portion of the complete protein sequence) that is similar between the two proteins, and (2) can further comprise a sequence that is divergent between the two proteins, sequence comparisons between two (or more) proteins are typically performed by comparing sequences of the two proteins over a "comparison window" (defined hereinabove) to identify and compare local regions of sequence similarity.

Optimal alignment of sequences for comparison can be conducted, for example, by the local homology algorithm described in Smith & Waterman, 1981, by the homology alignment algorithm described in Needleman & Wunsch, 1970, by the search for similarity method described in Pearson & Lipman, 1988, by computerized implementations of these algorithms (GAP, BESTFIT, FASTA, and TFASTA in the GCG WISCONSIN PACKAGE, available from Accelrys, Inc., San Diego, Calif., United States of America), or by visual inspection. See generally, Ausubel et al., 1989.

One example of an algorithm that is suitable for determining percent sequence identity and sequence similarity is the BLAST algorithm, which is described in Altschul et al., 1990. Software for performing BLAST analyses is publicly available through the National Center for Biotechnology Information via the World Wide Web. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

As used herein, the terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide", and "peptide" are used interchangeably herein when referring to a gene product. The term "polypeptide" encompasses proteins of all functions, including enzymes. Thus, exemplary polypeptides include gene products, naturally occurring proteins, homologs, orthologs, paralogs, fragments, and other equivalents, variants and analogs of the foregoing.

Modification of amino acids in proteins can include conservative and non-conservative amino acid substitutions and may further include deletions, rearrangements or additions. In one embodiment, an SRF-6 or -7 polypeptide contains from about 1-50 amino acid substitutions either all conservative substitutions or some conservative and some non-conservative substitutions.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8, or 10 amino acids long, at least 14 amino acids long, at least 20, 30, 40, or 50 amino acids long, at least 75 amino acids long, or at least 100, 150, 200, 300, 500, or more amino acids long. A fragment can retain one or more of the biological activities of the reference polypeptide. Further, fragments can include a sub-fragment of a specific region, which sub-fragment retains a function of the region from which it is derived. For example, a useful SRF-6 or -7 fragment is capable of inducing cesA expression.

As used herein, the term "primer" refers to a sequence comprising in some embodiments two or more deoxyribonucleotides or ribonucleotides, in some embodiments more than three, in some embodiments more than eight, and in some embodiments at least about 20 nucleotides of an exonic or intronic region. Such oligonucleotides are in some embodiments between ten and thirty bases in length.

The term "purified" refers to an object species that is the predominant species present (i.e., on a molar basis it is more abundant than any other individual species in the composition).

The term "transfection" refers to the introduction of a nucleic acid, e.g., an expression vector, into a recipient cell, which in certain instances involves nucleic acid-mediated gene transfer. The term "transformation" refers to a process in which a cell's genotype is changed as a result of the cellular uptake of exogenous nucleic acid. For example, a transformed cell can express a recombinant form of a polypeptide of the presently disclosed subject matter.

The transformation of a cell with an exogenous nucleic acid (for example, an expression vector) can be characterized as transient or stable. As used herein, the term "stable" refers to a state of persistence that is of a longer duration than that which would be understood in the art as "transient". These terms can be used both in the context of the transformation of cells (for example, a stable transformation), or for the expression of a transgene (for example, the stable expression of a vector-encoded nucleic acid sequence comprising a trigger sequence) in a transgenic cell. In some embodiments, a stable transformation results in the incorporation of the exogenous nucleic acid molecule (for example, an expression vector) into the genome of the transformed cell. As a result, when the cell divides, the vector DNA is replicated along with plant genome so that progeny cells also contain the exogenous DNA in their genomes.

In some embodiments, the term "stable expression" relates to expression of a nucleic acid molecule (for example, a vector-encoded nucleic acid sequence comprising a trigger sequence) over time. Thus, stable expression requires that the cell into which the exogenous DNA is introduced express the encoded nucleic acid at a consistent level over time. Additionally, stable expression can occur over the course of generations. When the expressing cell divides, at least a fraction of the resulting daughter cells can also express the encoded nucleic acid, and at about the same level. It should be understood that it is not necessary that every cell derived from the cell into which the vector was originally introduced express the nucleic acid molecule of interest. Rather, particularly in the context of a whole plant, the term "stable expression" requires only that the nucleic acid molecule of interest be stably expressed in tissue(s) and/or location(s) of the plant in which expression is desired. In some embodiments, stable expression of an exogenous nucleic acid is achieved by the integration of the nucleic acid into the genome of the host cell.

The term "vector" refers to a nucleic acid capable of transporting another nucleic acid to which it has been linked. One type of vector that can be used in accord with the presently disclosed subject matter is an *Agrobacterium* binary vector, i.e., a nucleic acid capable of integrating the nucleic acid sequence of interest into the host cell (for example, a plant cell) genome. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of plasmids. In the present specification, "plasmid" and "vector" are used interchangeably as the plasmid is the most commonly used form of vector. However, the presently disclosed subject matter is intended to include such other forms of expression vectors which serve equivalent functions and which become known in the art subsequently hereto.

The term "expression vector" as used herein refers to a DNA sequence capable of directing expression of a particular nucleotide sequence in an appropriate host cell, comprising a promoter operatively linked to the nucleotide sequence of interest which is operatively linked to transcription termination sequences. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression. The nucleotide sequence of interest, including any additional sequences designed to effect proper expression of the nucleotide sequences, can also be referred to as an "expression cassette".

Embodiments of the presently disclosed subject matter provide an expression cassette comprising one or more elements operably linked in an isolated nucleic acid. In some embodiments, the expression cassette comprises one or more operably linked promoters, coding sequences, and/or promoters.

Further encompassed within the presently disclosed subject matter are recombinant vectors comprising an expression cassette according to the embodiments of the presently disclosed subject matter. Also encompassed are plant cells comprising expression cassettes according to the present disclosure, and plants comprising these plant cells.

In some embodiments, the expression cassette is expressed in a specific location or tissue of a plant. In some embodiments, the location or tissue includes, but is not limited to, epidermis, root, vascular tissue, meristem, cambium, cortex, pith, leaf, flower, seed, and combinations thereof.

The presently disclosed subject matter further provides a method for modifying (i.e. increasing or decreasing) the concentration or composition of a polypeptide of the presently disclosed subject matter having an effect on cellulose content in a plant or part thereof. The method comprises in some embodiments introducing into a plant cell an expression cassette comprising a nucleic acid molecule of the presently disclosed subject matter as disclosed above to obtain a transformed plant cell or tissue (also referred to herein as a "transgenic" plant cell or tissue), and culturing the transformed plant cell or tissue. The nucleic acid molecule can be under the regulation of a constitutive or inducible promoter, and in some embodiments can be under the regulation of a tissue- or cell type-specific promoter.

A plant or plant part having modified expression of a nucleic acid molecule of the presently disclosed subject matter can be analyzed and selected using methods known to those skilled in the art including, but not limited to, Southern blotting, DNA sequencing, and/or PCR analysis using primers specific to the nucleic acid molecule and detecting amplicons produced therefrom. For example, a host cell transformed with a vector or polynucleotide of the disclosure can be analyzed for cellulose synthase (e.g., CesA) expression compared to a non-transformed cell. Cells that have increased cellulose synthase expression are indicative of a cell transformed with a polynucleotide of the disclosure.

In general, the presently disclosed compositions and methods can result in an increase in cesA expression or cellulose content of a plant by at least 5%, in some embodiments at least 10%, in some embodiments at least 20%, in some embodiments at least 30%, in some embodiments at least 40%, in some embodiments at least 50%, in some embodiments at least 60%, in some embodiments at least 70%, in some embodiments at least 80%, and in some embodiments at least 90% relative to a native control plant, plant part, or cell lacking the expression cassette.

Numerous transformation vectors available for plant transformation are known to those of ordinary skill in the plant transformation art, and the genes pertinent to the presently disclosed subject matter can be used in conjunction with any such vectors. The selection of vector will depend upon the selected transformation technique and the target species for transformation. For certain target species, different antibiotic or herbicide selection markers might be employed. Selection markers used routinely in transformation include the nptil gene, which confers resistance to kanamycin and related antibiotics (Messing & Vieira, 1982; Bevan et al., 1983); the bargene, which confers resistance to the herbicide phosphinothricin (White et al., 1990; Spencer et al., 1990); the hph gene, which confers resistance to the antibiotic hygromycin (Blochinger & Diggelmann, 1984); the dhfr gene, which confers resistance to methotrexate (Bourouis & Jarry, 1983); the EPSP synthase gene, which confers resistance to glyphosate (U.S. Pat. Nos. 4,940,935 and 5,188,642); and the mannose-6-phosphate isomerase gene, which provides the ability to metabolize mannose (U.S. Pat. Nos. 5,767,378 and 5,994,629).

Many vectors are available for transformation using *Agrobacterium tumefaciens*. These typically carry at least one T-DNA border sequence and include vectors such as PBIN19 (Bevan, 1984). Below, the construction of two typical vectors suitable for *Agrobacterium* transformation is disclosed.

Transformation without the use of *Agrobacterium tumefaciens* circumvents the requirement for T-DNA sequences in the chosen transformation vector, and consequently vectors lacking these sequences can be utilized in addition to other vectors that contain T-DNA sequences. Transformation techniques that do not rely on *Agrobacterium* include transformation via particle bombardment, protoplast uptake (e.g. polyethylene glycol (PEG) and electroporation), and microinjection. The choice of vector depends largely on the species being transformed.

Once a nucleic acid sequence of the presently disclosed subject matter has been cloned into an expression system, it is transformed into a plant cell. The expression cassettes of the presently disclosed subject matter can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Transformation techniques for dicotyledons are well known in the art and include *Agrobacterium*-based techniques and techniques that do not require *Agrobacterium*. Non-Agrobacterium techniques involve the uptake of exogenous genetic material directly by protoplasts or cells. This can be accomplished by PEG or electroporation-mediated uptake, particle bombardment-mediated delivery, or microinjection. Examples of these techniques are disclosed in Paszkowski et al., 1984; Potrykus et al., 1985; and Klein et al., 1987. In each case the transformed cells are regenerated to whole plants using standard techniques known in the art.

*Agrobacterium*-mediated transformation is a useful technique for transformation of dicotyledons because of its high efficiency of transformation and its broad utility with many different species. *Agrobacterium* transformation typically involves the transfer of a binary vector carrying the foreign DNA of interest to an appropriate *Agrobacterium* strain which can depend on the complement of vir genes carried by the host *Agrobacterium* strain either on a co-resident Ti plasmid or chromosomally.

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Various techniques can be used to introduce an aforementioned expression vector into host plant cells. As described above examples of these techniques include transformation of plant cells by T-DNA using *Agrobacterium tumefaciens* or *Agrobacterium rhizogenes* for the transformation factor, direct introduction into a protoplast (by a method such as electroporation in which a DNA is introduced into plant cells by treating protoplasts with an electric pulse, fusion of protoplasts with liposomes and so forth, microinjection, and the use of polyethylene glycol), and the use of a particle gun.

In addition, a desired gene can be introduced into a plant, by using a plant virus as vector. An example of a plant virus that can be used is cauliflower mosaic virus. Namely, after first preparing a recombinant by inserting the virus genome into a vector derived from *E. coli* and so forth, the desired gene is inserted into the virus genome. Such desired genes can then be introduced into a plant by cutting out the virus genome modified in this manner from the recombinant with a restriction enzyme, and inoculating into the plant (Hohn, et al. (1982), Molecular Biology of Plant Tumors (Academic Press, New York), p. 549, U.S. Pat. No. 4,407,956). The technique for introducing a vector into plant cells or a plant is not limited to these, and includes other possibilities as well.

There are no limitations on the required vector in the case of direct insertion into a protoplast. For example, a simple plasmid such as a pUC derivative can be used. Other DNA sequences may be required depending on the method used to introduce the desired gene into plant cells. For example, in the case of using a Ti or Ri plasmid to transform plant cells, at least the sequence on the right end, and typically the sequences on both ends, of the T-DNA region of Ti and Ri plasmids must be connected so as to become an adjacent region of the gene to be introduced.

When using an *Agrobacterium* species for transformation, a gene to be introduced needs to be cloned into a special plasmid, namely an intermediate vector or a binary vector. Intermediate vectors are not replicated in *Agrobacterium* species. Intermediate vectors are transferred into *Agrobacterium* species by helper plasmids or electroporation. Since intermediate vectors have a region that is homologous with the T-DNA sequence, they are incorporated within the Ti or Ri plasmid of *Agrobacterium* species by homologous recombination. It is necessary for the *Agrobacterium* species used for the host to comprise a vir region. Normally, Ti or Ri plasmids comprise a vir region, and due to its function, T-DNA can be transferred into plant cells.

On the other hand, since a binary vector can be replicated and maintained in *Agrobacterium* species, when a vector is incorporated into *Agrobacterium* species by a helper plasmid or electroporation, the T-DNA of the binary vector can be transferred into plant cells due to the action of the vir region of the host.

Furthermore, intermediate vectors or binary vectors obtained in this manner, as well as microorganisms such as *E. coli* and *Agrobacterium* species that comprise them are also included in the disclosure.

In addition, the disclosure provides transgenic plants that have been redifferentiated from the aforementioned transgenic plant cells, transgenic plants that are progenies or clones of the transgenic plants, and breeding material of the transgenic plants. Such is a useful transgenic plant in which cell wall components and cell morphogenesis have been altered. There are no particular limitations on the alteration of cell wall components in the disclosure, and include various quantitative and qualitative changes to create plants high in cellulose, low in lignin, having thick cell walls, thin cell walls, long and short fiber lengths, etc. In addition, examples of cell morphology alterations include, but are not limited to, changes in cell elongation and cell size (quantitative changes in volume).

Another approach to transforming plant cells with a gene involves propelling inert or biologically active particles at plant tissues and cells. This technique is disclosed in U.S. Pat. Nos. 4,945,050; 5,036,006; and 5,100,792; all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium, or a bacteriophage, each containing DNA sought to be introduced) can also be propelled into plant cell tissue.

There are no particular limitations on the genus or species of plants that can be used in the methods and compositions of the disclosure. Examples include useful agricultural crops such as grains, vegetables, and fruits (including feed crops), fiber raw material plants such as pulp, and plants valued for their aesthetic beauty such as foliage plants. The methods and compositions of the disclosure can be used in Eucalyptus, pine, acacia, poplar, cedar, cypress, bamboo, yew, rice, corn, wheat, barley, rye, potato, tobacco, sugar beet, sugar cane, rapeseed, soybean, sunflower, cotton, orange, grape, peach, pear, apple, tomato, Chinese cabbage, cabbage, radish, carrot, squash, cucumber, melon, parsley, orchid, chrysanthemum, lily, and saffron. In addition, some microorganisms produce various types of cellulosic material. The methods and compositions of the disclosure can be used in the generation of recombinant microorganism for the production of cellulosic material. Such microorganisms and plants may be useful for the production of biofuels and the like.

In addition, the disclosure provides transgenic plant cells into which a vector of the disclosure has been introduced. There are no particular limitations on the cells into which a vector of the disclosure is introduced, examples of which include the cells of rice, corn, wheat, barley, rye, potato, tobacco, sugar beet, sugar cane, rapeseed, soybean, sunflower, cotton, orange, grape, peach, pear, apple, tomato, Chinese cabbage, cabbage, radish, carrot, squash, cucumber, melon, parsley, orchid, chrysanthemum, lily, and saffron; however, trees such as Eucalyptus, pine, acacia, poplar, cedar, cypress, bamboo, and yew are preferable. In addition, plant cells of the disclosure comprise cultured cells, as well as cells present in a plant. In addition, protoplasts, shoot primordia, multiple shoots, and hairy roots are also included.

A transgenic plant of the disclosure is useful as a plant having a novel value such as increased plant growth as a result of increasing cell wall biosynthesis, altered fiber cell morphology, or increased amounts of useful components in agricultural crops. In addition, it is also useful as a plant having a novel value in developing new materials by controlling cell wall biosynthesis, increasing the digestion and absorption efficiencies of feed crops, changing fiber cell morphology, and the like.

In the disclosure, a "transgenic plant" refers to a plant having the aforementioned transgenic plant cells, and includes, for example, a transgenic plant regenerated from the aforementioned transgenic cells. Although the methods used to regenerate individual plants from transformed plant cells vary according to the type of plant cell, an example of a method used in rice plants is the method of Fujimura et al. (Fujimura et al., Plant Tissue Culture Lett., 2, 74, 1995), the method of Shillito et al. (Shillito et al., Bio/Technology, 7, 581, 1989) in corn plants, the method of Visser et al. (Visser et al., Theor. Appl. Genet., 78, 589, 1989) in potato plants, the method of Akama et al. (Akama et al., Plant Cell Rep., 12, 7, 1992) in *Arabidopsis thaliana*, and the method of Doi et al. (Japanese Patent Application No. Hei 11-127025) in Eucalyptus plants. Transgenic plants produced according to these methods or transgenic plants obtained from their breeding materials (such as seeds, tubers, or cuttings) are included in the disclosure.

The disclosure includes a process of producing a plant from a plant seed by introducing into a host a gene expressed by a plant during cell wall formation and/or specifically expressed during cellulose biosynthesis, a homolog thereof, or an expression vector comprising a promoter region that is contiguous with these genes to obtain transgenic cells, regenerating a transgenic plant from said transgenic cells, and obtaining a plant seed from the resulting transgenic plant.

A process of obtaining a plant seed from a transgenic plant refers to a process in which, for example, a transgenic plant is acquired from a rooting medium, replanted in a pot containing moist soil, and grown at a constant temperature to form flowers, and finally seeds. In addition, a process of producing a plant from a seed refers to a process in which, for example, once a seed formed in a transgenic plant has matured, the seed is isolated, sowed on moist soil, and then grown at a constant temperature and luminosity, to produce a plant.

The exogenously introduced DNA or nucleic acid in a transformed plant can be confirmed by known methods, such as PCR or Southern hybridization, or by analyzing the nucleotide sequence of the plant's nucleic acid. To extract DNA or nucleic acid from a transformed plant, the known method of J. Sambrook et al. may be used (Molecular Cloning, 2nd edition, Cold Spring Harbor laboratory Press, 1989).

To conduct PCR analysis of a DNA of the disclosure that exists in a plant, an amplification reaction is carried out using, as a template, nucleic acid extracted from the regenerated plant. Amplification reaction may be carried out in a reaction mixture containing, as primers, synthesized oligonucleotides comprising nucleotide sequences appropriately selected according to the nucleotide sequence of a DNA of the disclosure. An amplified DNA fragment comprising a DNA sequence of the disclosure may be obtained by repeating several dozen cycles of the denaturation, annealing, and extension steps of the DNA amplification reaction. The respective amplified DNA fragments can be separated by, for example, electrophoresing the reaction solution containing the amplified products on agarose gel. DNA fragments corresponding to a DNA of the disclosure can then be confirmed.

Having obtained a transformed plant in which a DNA of the disclosure has been inserted into the chromosomes, one can obtain the plant's offspring by sexual or non-sexual reproduction. Also, it is possible to mass-produce such plants by obtaining reproductive materials (such as seeds, fruits, cuttings, stem tubers, root tubers, shoots, calluses, and protoplasts) from the above plant, or its offspring or clones.

A stable supply of biomass, mainly cellulose, can be provided by cultivating a transgenic plant of the disclosure on a larger scale using clone planting. At present, fossil resources are used in large amounts in industrial productions as raw materials and fuel (energy). With respect to alternative energy in particular, although the direct combustion of wood biomass (for fuel) is routinely carried out in developing countries, a more effective approach would be possible by converting the biomass into a more user-friendly form (such as alcohol, and specifically ethyl alcohol). One of the objectives is to use gasoline mixed with ethanol refined from biomass. A specific example is "gasohol" (a 10% blend of ethanol in gasoline) made from corn. Thus, for example, plants having a high cellulose content, it would be possible to obtain glucose by hydrolysis or enzyme degradation (cellulase) using the resulting lignocellulose as raw material, and in turn enable large-scale production of ethanol by alcohol fermentation. Basic technology for such processes has already been established.

In addition to conventional use as raw materials, there is also a considerable potential for creating an alternative energy to petroleum through biomass conversion, as well as the development of new plastics from cellulose and hemicellulose (both being technically possible), as a result of stable and large-scale cultivation of wood biomass and the recycling of that wood biomass through afforestation as in the disclosure. Moreover, the spread of wood biomass will contribute to solving energy security problems and environmental issues, while simultaneously leading to the development of new industries, including agricultural forestry, and the creation of employment opportunities.

The following examples are provided to further illustrate but not limit the disclosure.

EXAMPLES

*Arabidopsis thaliana* ecotype Columbia-0 (Col-0) was used. Before plating seeds were surface sterilized. First, the seeds were washed in 95% ethanol for 10 minutes, which was removed then the sterilization solution was added (20% bleach, 0.05% Tween-20 (Sigma) and double distilled water) and shaken for 10 minutes. The sterilization solution was removed and the seeds were washed three times with sterile distilled water. The seeds were cold treated for 4 days at 4° C. after plating them on the plates. Two different growth media were prepared for these experiments. For the control conditions: one-half strength Murashige and Skoog (MS) salts (Sigma), 0.5% sucrose (Sigma), 0.8% phyto agar (Research Products International Corp.), $1 \times B_5$ (1,000× in double distilled water: 10% myo-inositol, 0.1% nicotinic acid and 0.1% pyroxidine HCl) and 1× Thiamin (2,000× in double distilled water: 0.2% thiamin HCl). The other growth media contained either no sucrose but all other components remained the same. Plants used in Fourier Transform Infrared (FT-IR) Microspectroscopy and hypocotyl length, were only grown on sucrose-deprived media in the dark for four days after cold treatment. For selection of mutants from the *Arabidopsis* Biological Resource Center (ARBC), they were first plated onto MS media containing 50 µg/ml Kanamycin to select for insertions containing the NTPII (Kanamycin resistance) gene. In the case this resistance is lost the seeds were also sown onto regular MS media containing no antibiotic and then transferred to soil after one week. Plants were then grown on soil for 2-3 weeks after transfer from the plates and they were examined for status of the T-DNA insertion. Only homozygous $T_3$ and $T_4$ knockout mutants were used for the following experiments.

Dominant negative construction. The Invitrogen Gateway technology was used to expedite the generation of the different RLK mutations used in this study. Generally, the RIKEN cDNA clone (pda06938, SRF7) was used as a template for polymerase chain reaction (PCR) amplification of extracellular and transmembrane portion of the receptor of SRF7. PCR product was gel eluted using Qiagen's QIAquick gel extraction kit using the manufacturer's protocol.

Primers used:
DN-SRF7 FWD(SalI):
(SEQ ID NO: 27)
5'-GGAAGTCGACCGAGAGAGATAGAGAAAGTGAGACAAGG-3';

DN-SRF7 REV(NotI):
(SEQ ID NO: 28)
5'-ATATGCGGCCGCCCTTCACCGAGAAGATTATCTACGCTG-3'.

Eluted DNA was subsequently ligated into Promega's pGEM-Teasy PCR vector. Gene fragment inserts were confirmed by DNA sequencing using the T7 and S6 sites in the pGEM-Teasy vector. Confirmed vectors were then restriction digested using the PCR introduced restriction sites (SalI and NotI). The restriction digest was run on a 1% agarose (Invitrogen) gel and the cut insert was removed using the QIAquick kit. The fragment was then ligated into a TAP tagged entry vector that was made my taking the pENTR-1A vector and introducing a 6×His and T7 epitope DNA sequence into the EcoRV restriction site in the pENTR-1A vector. This vector was designated pENTR-TAP2. The 3' ends of the PCR fragment was designed to go into frame with the TAP sequence. The pENTR-TAP2 vector containing the SRF7 extracellular and transmembrane domain was then introduced into the final destination vector that contains the 35S promoter, pGWB2 (Invitrogen, Nakagawa). This construct was introduced into *Arabidopsis* (Col-0) via the floral dip method (Bechtold et al., 1993). Subsequent generations of the seeds were selected for using 50 µg/ml Kanamycin (Sigma) in MS media (same as control media except for addition of antibiotic), until $T_3$ homozygous lines were found and these lines were used for all of the following experiments.

SRF single knockout mutant selection. The TAIR website was used to locate insertional mutants of SRF6 and SRF7. Two mutants were found for SRF6, SALK_077702 and SALK_035476, named srf6-1 and srf6-2 respectively. Three mutants were found for SRF7: SALK_039120 (srf7-1), SALK_115238 (srf7-2) and SALK_110007 (srf7-3). Each $T_4$ SALK line was examined using PCR to confirm the insertion and genotype. Only homozygous mutants were used for further experiments. Primers for insertion detection were generated using the T-DNA primer design tool (http:~~signal.salk.edu/tdnaprimers.html) at the Salk Institute Genomic Analysis Laboratory (SIGnAL).

Primers used:
SALK_077702 (srf6-1) LP:
(SEQ ID NO: 29)
5'TCGAGTTTATAACCGTCGGTG-3';

SALK_077702 (srf6-1) RP:
(SEQ ID NO: 30)
5'-TTTGAAGCAAGAGTGAAAGGC-3';

SALK_035476 (srf6-2) LP:
(SEQ ID NO: 31)
5'-AGCGCACCTGAAGTATCAATG-3';

SALK_035476 (srf6-2)
(SEQ ID NO: 32)
5'-GTGCCACTCCCAAGTATATGG-3';

SALK_039120 (srf7-1) LP:
(SEQ ID NO: 33)
5'-AAACCTTTAAAAGCGCGTAGG-3';

SALK_039120 (srf7-1) RP:
(SEQ ID NO: 34)
5'-CCCAGAAAAGAGAACAAACACAC-3';

SALK_115238 (srf7-2) LP:
(SEQ ID NO: 35)
5'-TTTCTAACTATGTAATCATCTGGTTGC-3';

SALK_115238 (srf7-2) RP:
(SEQ ID NO: 36)
5'-TTCCATGGAGGAACAAAAGAG-3';

SALK_110007 (srf7-3) LP:
(SEQ ID NO: 37)
5'GAGTGTACAATGCGTGAAGGG-3';

SALK_110007 (srf7-3) RP:
(SEQ ID NO: 38)
5'-GCATGAAGTTTGCTCACCATC-3'.

SRF overexpression construction. Construction of the overexpression of full length SRF7 also utilized Gateway technology and was constructed in a similar manner as the dominant negative SRF mutant using the pENTR TAP2 entry vector and the pGWB2 35S binary vector.

Primers used:
SRF7-TAP FWD (SalI):
(SEQ ID NO: 39)
5'-GGAAGTCGACTGTCTCATCTGGTTTCGAGAG-3';

SRF7-TAP REV(NotI):
(SEQ ID NO: 40)
5'-ATATGCGGCCGCTTTTGTTCATGTTGTCGGAATC-3'.

Combinatorial mutant construction. Two constructs were introduced into the srf7-1 mutant background, SRF7 full-length overexpression and the dominant negative (DN-srf7).

SRF double mutant. To generate a double mutant of SRF6 and SRF7 insertional mutants srf6-1 (SALK_077702) and srf7-1 (SALK_039120) homozygous lines were crossed and allowed to self fertilize until the $F_2$ generation where they were then examined using the same PCR primers used for the single insertion mutants.

RNA and Real-Time RT-PCR Analysis. RNA was collected from four-day-old dark grown seedlings using Qiagen's RNeasy Kit following the manufacture's protocol. Two hundred nanograms of total RNA was used in a reverse transcriptase (Superscript II, Invitrogen) reaction in a 20 µl reaction volume. The cDNA was subsequently diluted to a concentration of 5 ng/µl and 5 µl (25 ng cDNA) was used per each real-time reaction (25 µl total reaction volume: 0.125 µl each primer (100 pM), 12.5 µl Bio-Rad SYBR green master mix, and sterile/DEPC ddH$_2$O). Primers for real-time PCR were designed in all circumstances to span an intron and to be a final size of 300 base pairs (+/−10 base pairs).

Primers used:
ACT2 (At3g18780) FWD:
(SEQ ID NO: 41)
5'-GATGGGCAAGTCATCACGATTGG-3';

ACT2 (At3g18780) REV:
(SEQ ID NO: 42)
5'-ACCACCGATCCAGACACTGTACTTCC-3';

CESA3 (At5g05170) FWD:
(SEQ ID NO: 43)
5'-ATTGTTCCGCAGACTTGCCAG-3';

CESA3 (At5g05170) REV:
(SEQ ID NO: 44)
5'-CACGAGTAAGATGCCAACCAAGC-3';

CESA4 (At5g44030) FWD:

-continued

CESA4 (At5g44030) REV:
(SEQ ID NO: 46)
GACGGAACCAAGAGCCCATCTAAG-3';

(SEQ ID NO: 45)
5'-GGAATGTCTCCTGTGTTTATTGCGTC-3';

SRF6 (At1g53730) FWD:
(SEQ ID NO: 47)
5'-GCATTGTAGGGTTTGAGCTTAGATTC-3';

SRF6 (At1g53730) REV:
(SEQ ID NO: 48)
5'-GGAGGAAACTGATATGGTAAATCACC-3';

SRF7 (At3g14350) FWD:
(SEQ ID NO: 49)
5'-GCATTGTTGGGTTTGAGCCAAGTTTC-3';

SRF7 (At3g14350) REV:
(SEQ ID NO: 50)
5'-GGAGGAAGCTGATAAGGCAAATCGCC-3'.

The real-time PCR protocol was: 95° C. for 5 minutes, followed by 40 cycles of 95° C. for 45 seconds and 60° C. for 45 seconds with the fluorescence quantification at the end of every 60° C. step. The fold change was found using the delta delta $C_t$ method using the ACTIN2 (At3g18780) gene expression as the control for relative gene expression values.

Fourier Transform Infrared (FT-IR) Microspectroscopy Analysis and Statistics. Plant materials used for FT-IR analysis were grown on MS plates without sucrose for 4 days in the dark following a 4-day period at 4° C. A Bruker Equinox 55 IR spectrometer equipped with a Bruker A590 IR microscope was used to analyze the 4-day old dark grown hypocotyls. Before examining on the IR spectrometer the plant material was placed on a $BaF_2$ sample window and dried for 20 minutes at 37° C. The $BaF_2$ sample window containing the dried samples was immediately placed into the sample window cassette and placed on the A590 microscope stage and examined using a 25× objective with an aperture setting of 70 µm. The entire system was purged with dry nitrogen from a Whatman purge gas generator to remove any contribution of atmospheric water or carbon dioxide to the examined spectra. Spectra were recorded from 600-4,000 cm$^{-1}$ with a resolution of 2 cm$^{-1}$, because this region contains all of the wavenumbers of cellulose and pectins. Baseline normalization of data was accomplished using MATLab software (version R207a) and additional software. This program took all of the collected wavenumbers for each experiment and reduced it to one normalized set of values for each mutant and the control wild type. This data was then analyzed for statistical significance using R (Version 2.6.2).

Confocal and SEM Imaging of Mutants. Plant materials for the observations using the Leica SP2 UV confocal microscope were 7-day old light grown seedlings (16 h light 8 h dark). Plant material for the Hitachi TM-1000 scanning electron microscope (SEM) was from 4-day old dark grown seedlings. Plant material for observation on the Leica microscope was placed on a glass slide and water was added to the slide and covered with a glass coverslip. Plants were observed using the 22× water objective and digital images were captured using the Leica software. Images were analyzed using NIH ImageJ software available from the National Institute of Health (http:~~rsb.info.nih.gov/ij/). Plant material for SEM imaging by embedding the etiolated hypocotyls in tissue embedding medium in the cryostat and then sectioning away material until the approximate center of the hypocotyl is reached and then viewed at 100-1,000× on the SEM (Hitachi TM-1000).

Monosaccharide Compositional Analysis Using GC-FID/MS. For analysis of the monosaccharide composition using gas chromatography (GC) the cell wall was isolated by use of a modified protocol from Chambers and Clamp (1971) and Chaplin (1982). First, approximately 5 grams of leaf tissue was frozen in liquid nitrogen and stored or used immediately for cell wall extraction. Frozen plant tissue was then crushed under liquid nitrogen and transferred to a 50 ml glass centrifuge tube with a Teflon lined cap and 35 ml of solution A was added and stirred for at least 2 hours at room temperature. Solution A consists of 200 ml 80% (w/v) phenol and 80 ml of glacial acetic acid. The stir bar was removed and the tube was then centrifuged at 2,500 rpm (1,200 g) for ten minutes. The supernatant was discarded and the pellet was resuspended in 35 ml of solution B and stirred for at least 2 hours. Solution B consists of 175 ml 80% (w/v) phenol, 70 ml glacial acetic acid and 35 ml distilled water. The stir bar was again removed and the tube centrifuged at 2,500 rpm (1,200 g) for ten minutes. The supernatant was discarded and the resulting pellet was resuspended in 35 ml of 70% ethanol. The pellet was then washed in 70% ethanol a total of three time or until there was no longer any phenol smell. The resulting pellet was then washed three times with 35 ml of 90% dimethylsulfoxide (DMSO) with resuspension and centrifugation for 10 minutes, and supernatant discarded. The pellet was then washed three more times in 35 ml of 70% ethanol, and then resuspended in 35 ml of 2:1 $CHCl_3$-methanol solution. 2:1 $CHCl_3$-methanol solution is made using 380 ml $CHCl_3$ and 190 ml methanol. The resuspended pellet in the 2:1 $CHCl_3$-methanol solution was centrifuged for 10 minutes, the supernatant discarded and then resuspended in 2:1 $CHCl_3$-methanol solution one more time and centrifuged, discarding the supernatant. This pellet was then prepared for drying by adding 35 ml acetone and resuspending the pellet. This was centrifuged for 10 minutes and the process was repeated for a total of three washes. On the final wash the cap is removed and the vial is covered with a single layer of Kimwipe that was kept in place with a rubber band. The vial was then placed into a vacuum desiccator without desiccant and attached to a vacuum line and vacuum was applied for around 10 hours. After the initial drying the samples were moved to a vacuum desiccator with desiccant and a vacuum was applied for 24 hours.

Imidazole and sodium hydroxide extraction from cell wall material. To further extract out proteins and other non-cellulose components of the cell wall, the dried crude cell wall extract was further extracted using imidazole and sodium hydroxide. For further separation 0.2 g of the material from the previous experiment was added to a new 50 ml high strength centrifuge tube with a Teflon cap. Forty milliliters of 500 mM imidazole HCl (ph 7.0) solution was then added and stirred overnight. The sample was centrifuged for 10 minutes at 2,500 rpm and the supernatant collected and another 40 ml of 500 mM imidazole solution was added and the remaining pellet agitated and stirred overnight at room temperature. This solution was then centrifuged again for 10 minutes at 2,500 rpm. This supernatant was added to the first supernatant and filtered through Whatman GF/A filter paper and loaded into Spectrum Spectra/Por4 dialysis tubing and dialyzed against distilled water at 4° C. overnight changing the water every 3 hours. To the pellet 30 ml of 1% NaBH$_4$ in 6M NaOH was added and allowed to spin for 6 hours. This was then centrifuged for 10 minutes at 2,500 rmp and the supernatant was retained, and another 30 ml of 1% NaBH$_4$ in 6M NaOH was added and allowed to spin overnight. After centrifugation at 2,500 rpm for 10 minutes the supernatants were pooled and then titrated to pH 5.5-6.0 with glacial acetic acid. This solution was then loaded into Spectrum Spectra/Por4 dialysis tubing and dialyzed against distilled water at 4° C. overnight. The water was replaced with fresh distilled water every 3 hours during the dialysis. The pellet was then resuspended in 1-2 ml distilled water and transferred to a pre-weighed glass vial and then frozen on dry ice, and then lyophilized for 24 hours or until all liquid was removed, this constitutes the NaOH insoluble fraction. The dialysis fractions of both the imidazol and 1% NaBH4 in 6M NaOH solution were also lyophilized.

Preparation of NaOH-Insoluble Fraction for Saemann hydrolysis. For the complete breakdown of NaOH insoluble fractions into monosaccharides acid hydrolysis was required. Five micrograms of lyophilized material from the NaOH insoluble fraction were first weighed into a glass vial and 100 μl of 11M H$_2$SO$_4$ was added and stirred for 1 hour. Then 2.1 ml of water was added with rapid stirring. The samples were then autoclaved for 1 hour at 121° C. with slow exhaust. After autoclaving ~5.7 ml of Ba(OH)$_2$ was added to the sample until the sample pH is greater then 9.5. Then 300 μl of 0.18M H$_2$SO$_4$ was added drop wise until a pH between 2 and 3 was achieved. Once this pH was obtained 300 μl of BaCO$_3$ was added to each sample and stirred at full speed at 50° C. for 1.5 hours. The spin bar was removed and the samples were placed at 3° C. for 2 hours to encourage precipitation. The samples were then centrifuged for 15 minutes at 4,000 RPM at 24° C. The supernatant was poured off and measured for volume and the pellet was discarded. The supernatant was then concentrated until it reached a volume of approximately 1.5 ml. These can then be stored at −20° C. until further analysis.

Preparation of material for analysis by gas chromatography. To each sample 100 nM inositol was added as an internal standard. These samples were then dried under N$_2$ gas and warmed to 40° C. in a water bath until no liquid was visible. At this time the sugar standards were prepared. The sugar standards consist of 100 nM of each sugar with 100 nM inositol added to also act as an internal control. Then the samples and standards were removed from the N$_2$ stream and placed in a vacuum desiccator until completely dry. To each vial 400 μl of 1.5M methanolic HCl was added using a dry syringe and then 100 μl methyl acetate was added and the vial capped tightly. The vials are then placed in an 80° C. heating block for 12-14 hours. After the vials cool to room temperature the vials were then opened and a few drops of t-butanol were added and then evaporated under a N$_2$ gas stream at room temperature. If the sample contained amino sugars then 20 μl of methanol was added followed by 20 μl of pyridine and 20 μl acetic anhydride and the vials sat at room temperature for 15 minutes. The samples were then evaporated under a N$_2$ stream until dry. The to all samples 30 μl of trimethylsilylating reagent was added and allowed let to sit for 15 minutes at room temperature. Then the samples were again evaporated under N$_2$ but not for more then a few minutes as it may drive off some of the more volatile sugars like arabinose. Finally, 200-250 μl of isooctane is added to the sample and they are now ready to be injected (1 μl) into the gas chromatograph.

Analysis of monosaccharides by gas chromatography. One microliter of each sample was injected into the Hewlett Packard 5890 Series II fitted with a DB1 capillary column. The standard sugar samples are added first followed by individual experimental samples. Each standard and sample was run in duplicate or triplicate and the area under the curve for the sugars was used to calculate the relative amount of each sugar. The first Excel spreadsheet calculates the glycosyl composition (mole percent) of a specimen based on the integrated areas of the sugar peaks in the gas chromatogram of the specimen and the gas chromatogram of a mixture of standard sugars (100 nmoles each), with all peak areas referenced to the area of inositol (100 nmoles), an internal standard added to all specimens. The second Excel spreadsheet combines the glycosyl composition results from the analyses of two whole cell wall specimens, one prepared by sulfuric acid preswelling and hydrolysis prior to methanolysis, and one prepared with methanolysis alone. The resulting combined glycosyl composition shows the additional amounts of sugars detected due to the sulfuric acid cleavage. These additional sugar amounts are predominantly glucose, plus a much smaller amount of mannose, which was derived from the cleavage of cellulose and tightly associated polymers that due to the near crystalline structure of cellulose were resistant to cleavage by methanolysis alone.

Analysis of Public Microarray Database for SRF and CesA Gene Expression During Diurnal Cycle and Isoxaben Treatment. Genevestigator (https:~~iii.genevestigator.ethz.ch/at/) a public microarray database analysis tool with a collection of all the available microarray sources allows for the search of specific experiments and gene expression levels of desired genes. Using the tool called digital northern the expression levels of the RLKs BRI1 (At4g39400), SERK1 (At1g71830), SRF3 (At4g03390), SRF6 and SRF7 were analyzed. BRI1 was used as a well known diurnally expressed RLK, SERK1 was used as a control RLK that does not show a diurnal fluctuation and SRF3 is a subfamily member related to SRF6 and SRF7 that were both being examined for diurnal fluctuations. These genes were also examined for their expression levels when exposed to a primary cellulose synthesis inhibitor called isoxaben. All ten cellulose synthase A genes (CesA1-10) were also examined for gene expression during diurnal cycle and for isoxaben treatment.

SRF6 and SRF7 are co-expressed with cellulose synthesis genes and their proteins have homologues in diverse plant species. The observed phenotype of larger leaves and epidermal cells in the dominant negative mutant of SRF6 and SRF7 demonstrate that these genes play a role in cell wall formation. Using the ATTED II database, http:~~www.atted.bio.titech.ac.jp, SRF6 and SRF7 were found to be co-expressed with multiple cellulose synthase A (CesA) genes required for primary cell wall synthesis (CesAs 1, 2, 3, 5, and 6) (Table 1). Furthermore, if these genes were important for cell wall synthesis it would be logical that they would be conserved in other plant species and this was found to be true for land plants and even some algae (Table 2).

TABLE 1

Top ten genes coexpressed with SRF6 and SRF7.
Using the ATTED II website (Arabidopsis thaliana trans-factor and cis-element prediction database II, (June 2007) http:~~www.atted.bio.titech.ac.jp) genes coexpressed with SRF6 (At1g53730) and SRF7 (At3g14350) were examined. SRF7 shows coexpression with all of the primary cell wall cellulose synthases while SRF6 is coexpressed with arabinogalactan proteins, which associated with cell wall and coexpressed with ROP2, which also may be involved with cell wall organization or signaling.

| rank | correlation | locus | function |
|---|---|---|---|
| SRF6 [At1g53730] | | | |
| 1 | 0.65 | At3g60320 | DNA binding |
| 2 | 0.62 | At3g11700 | Fasciclin-like arabinogalactan |
| 3 | 0.58 | At5g65390 | Arabinogalactan-protein (AGP7) |
| 4 | 0.58 | At1g20090 | Rho-like GTP-binding protein (ROP2) |
| 5 | 0.58 | At1g19835 | Unknown |
| 6 | 0.58 | At2g33570 | Unknown |
| 7 | 0.58 | At5g05170 | Cellulose Synthase A3 (CESA3) |
| 8 | 0.58 | At3g05900 | Neurofilament protein-related |
| 9 | 0.57 | At4g12730 | Fasciclin-like arabinogalactan-protein (FLA2) |
| 10 | 0.57 | At5g15350 | Plastocyanin-like domain-containing protein |
| SRF7 [At3g14350] | | | |
| 1 | 0.65 | At5g64740 | Cellulose Synthase A6 (CESA6) |
| 2 | 0.61 | At4g32410 | Cellulose Synthase A1 (CESA1) |
| 3 | 0.60 | At5g05170 | Cellulose Synthase A3 (CESA3) |
| 4 | 0.60 | At5g60920 | COBRA, phytochelatin synthetase |
| 5 | 0.59 | At4g39350 | Cellulose Synthase A2 (CESA2) |
| 6 | 0.56 | At1g45688 | Unknown |
| 7 | 0.52 | At5g09870 | Cellulose Synthase A5 (CESA5) |
| 8 | 0.51 | At1g75680 | Glycosyl hydrolase family 9 protein |
| 9 | 0.51 | At3g25500 | FH2 domain-containing protein, actin rearrangement |
| 10 | 0.51 | At2g35860 | Fasciclin-like arabinogalactan |

TABLE 2

Many species of land plants and algae contain homologues to SRF6 and SRF7 supporting their role as important genes for cell wall development and cellulose regulation. Homologous genes to SRF7 can be found in many other land plants. There is a high amount of protein identity to *Isatis tinctoria* a member if the Brassicaceae family, a close relative to *Arabidopsis*. The lowest identity is to the more primitive land plant like the Liver Wort and the aquatic algae. Information was gathered from the TAIR database using the protein sequence of SRF7 to BLAST the protein database of green plants.

| Species | Common Name | % Identity | % Positives |
|---|---|---|---|
| SRF6 | | | |
| *Isatis tinctoria* | Woad | 81 | 85 |
| *Malus x domestica* | Apple | 77 | 87 |
| *Vitis vinifera* | Vine grape | 75 | 86 |
| *Triticum aestivum* | Common wheat | 70 | 80 |
| *Solanum chacoense* | Wild potato | 68 | 79 |
| *Zea mays* | Corn | 63 | 77 |
| *Oryza sativa* | Rice | 62 | 76 |
| *Solanum tuberosum* | Potato | 53 | 68 |
| *Closterium chrenbergii* | Algae | 40 | 60 |
| *Medicago truncatula* | Barrel medic | 39 | 61 |
| *Marchantia polymorpha* | Liver wort | 38 | 61 |
| *Nitella axillaris* | Green algae | 37 | 62 |
| SRF7 | | | |
| *Isatis tinctoria* | Woad | 78 | 84 |
| *Malus x domestica* | Apple | 77 | 87 |
| *Triticum aestivum* | Common wheat | 70 | 80 |
| *Vitis vinifera* | Vine grape | 69 | 79 |
| *Solanum chacoense* | Wild potato | 65 | 76 |
| *Oryza sativa* | Rice | 61 | 74 |
| *Zea mays* | Corn | 61 | 74 |
| *Solanum tuberosum* | Potato | 56 | 71 |
| *Medicago truncatula* | Barrel medic | 43 | 62 |
| *Closterium chrenbergii* | Algae | 42 | 63 |
| *Marchantia polymorpha* | Liver wort | 40 | 61 |
| *Nitella axillaris* | Green algae | 38 | 61 |

Mutations in SRF6 and SRF7 alter dark grown hypocotyl length. In examining other mutants that affect cell wall synthesis it has been shown that CesA mutations can affect the length of the hypocotyl in etiolated seedlings. Presumably, by a reduction in the amount of cellulose synthesis affecting the capacity of the hypocotyl to elongate in the dark. The length of the hypocotyl of the various mutants of SRF6 and SRF7 were examined.

All SRF mutants were obtained from the ARBC as pooled $T_4$ seeds. Individual plants that were homozygous for the insertion were found using gene specific primers (LP and RP) and an insertion specific primer (Lb1). FIG. 1A shows the insertion location of the SRF mutants obtained and studied in this experiment. Both srf6-1 and srf7-1 were found to be null mutations by quantitative real-time RT-PCR using gene specific primers. No expression was found for these two genes. Expression of SRF6 in srf6-2 is like that of wild type plants, as is SRF7 gene expression levels in the srf7-2 mutants.

Figure 5:
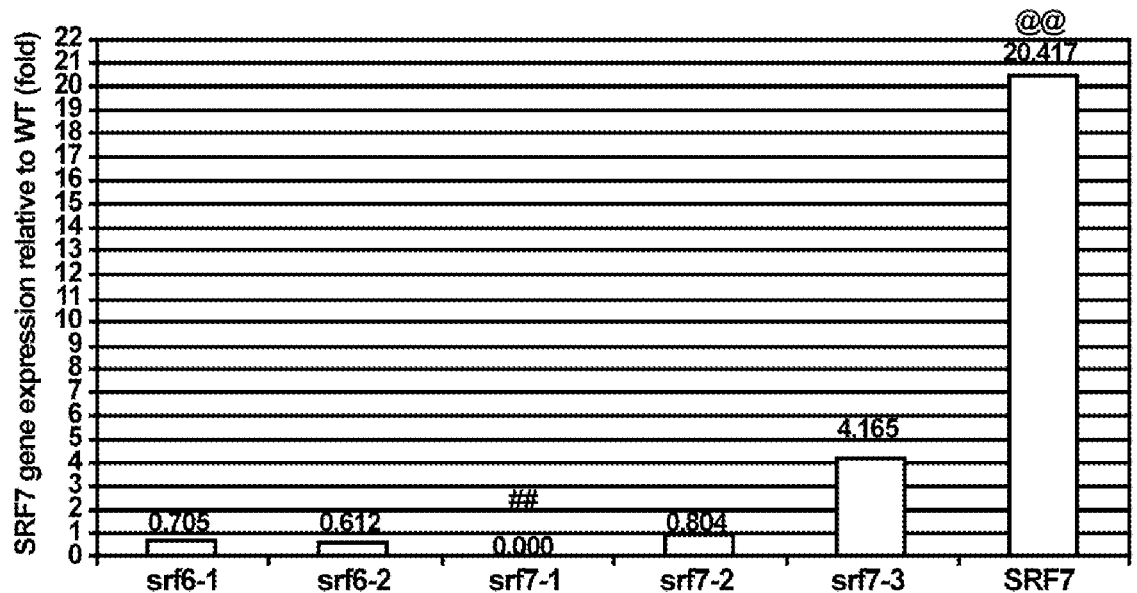
FIG. 5 shows quantitative real-time PCR analysis of gene expression levels of SRF7 for SRF mutants compared to wild type gene expression in dark treated 4-day-old seedlings grown on 0% sucrose MS media. Four-day-old dark treated plants were first cold treated (4° C.) for 4-days before harvesting and RNA isolation. This tissue was pooled from three different plates. Data analysis was done using three independent $C_t$ values for each measurement. The delta delta $C_t$ method was used for comparison of mutant SRF gene expression compared to wild type gene expression and comparison of mutant ACTIN2 gene expression compared to wild type ACTIN2 gene expression. ##=no detectible expression of SRF7. @@=p-value<0.001.

Interestingly in the srf7-3 mutant, the insertion being after the kinase domain, shows a four-fold increase in SRF7 gene expression level compared to the wild type plant (FIG. 5).

Figure 2:
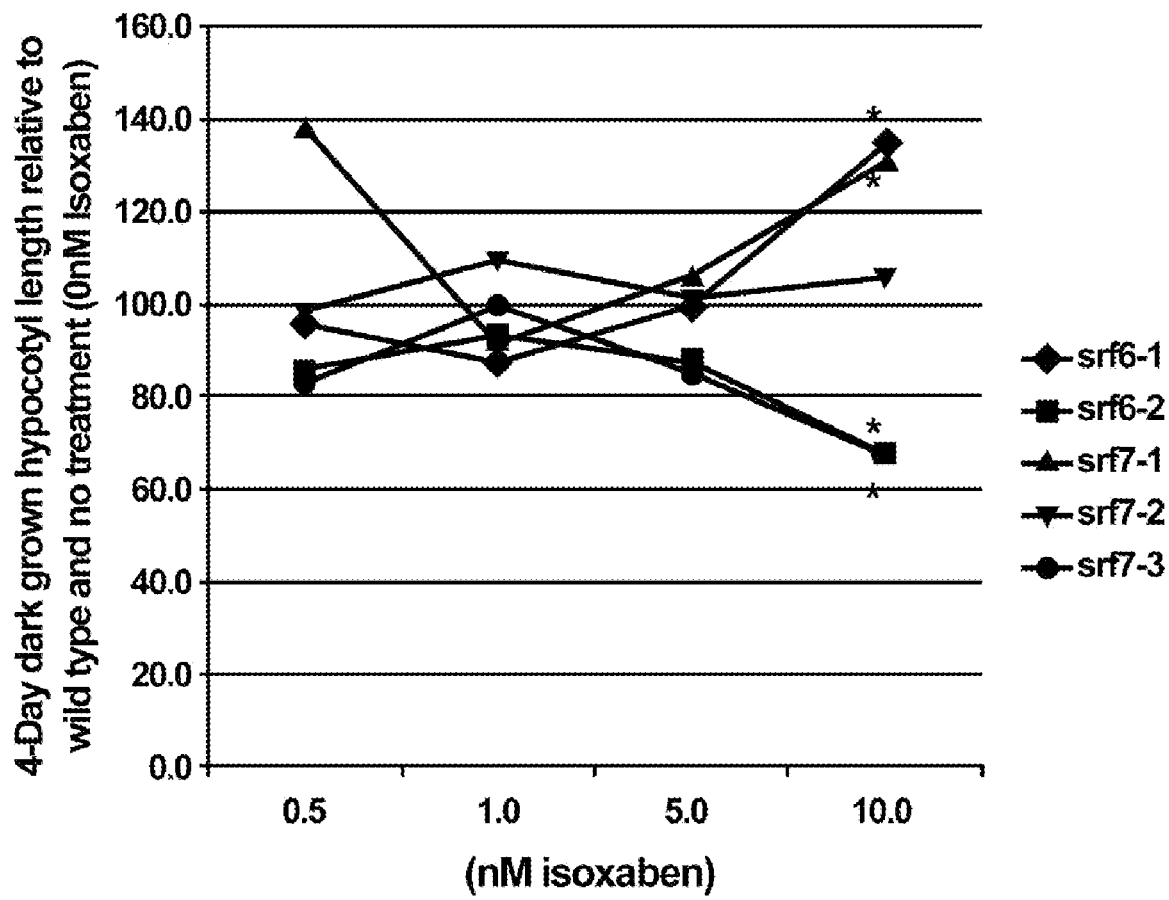
FIG. 2 shows increased resistance to isoxaben of SRF knockout mutants with insertion in the extracellular domain of the receptor-like kinase compared to insertions post transmembrane domain. Both srf6-1 and srf7-1, with insertions in the extracellular domain, show increased resistance to the increasing concentration of the cellulose synthesis inhibitor isoxaben. While, srf6-2 and srf7-3 show increased sensitivity to isoxaben and contain insertions in the c-terminal domains. srf7-2 showed no significant difference in sensitivity compared to the wild type. Data is taken from three independent experiments. Data is from hypocotyl lengths relative to wild type plants grown on the same plate and relative to mutants grown on DMSO control media. Student's t-test: $*=p<0.05$.
Figure 4:
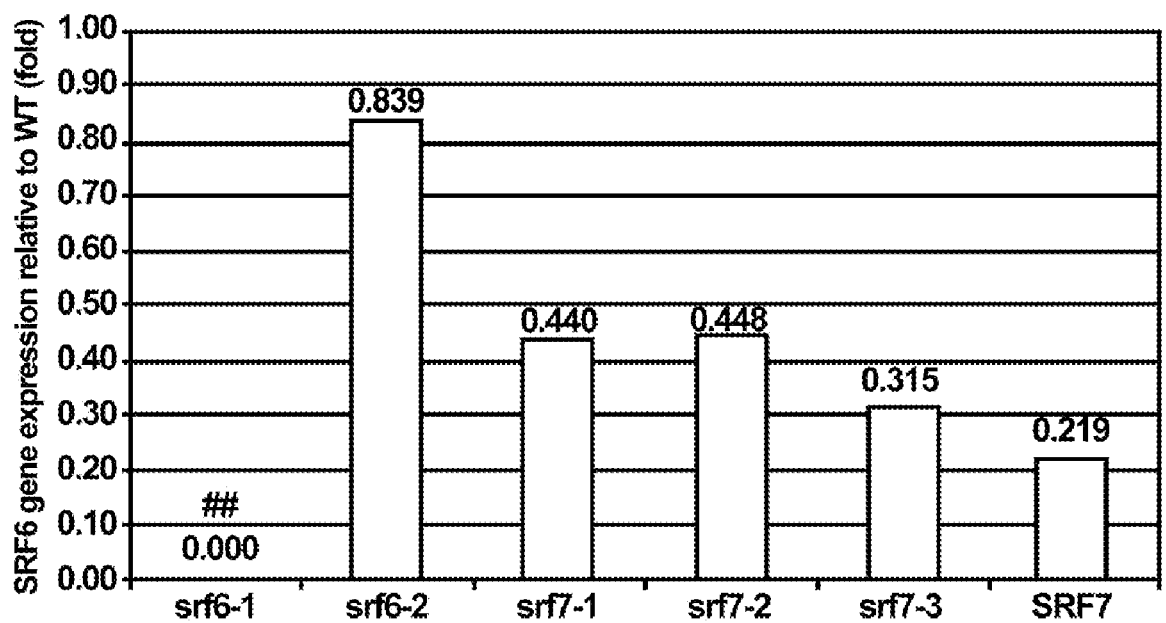
FIG. 4 shows quantitative real-time PCR analysis of gene expression levels of SRF6 for SRF mutants compared to wild type gene expression in dark treated 4-day-old seedlings grown on 0% sucrose MS media. Four-day-old dark treated plants were first cold treated (4° C.) for 4-days before harvesting and RNA isolation. This tissue was pooled from three different plates. Data analysis was done using three independent $C_t$ values for each measurement. The delta delta $C_t$ method was used for comparison of mutant SRF gene expression compared to wild type gene expression and comparison of mutant ACTIN2 gene expression compared to wild type ACTIN2 gene expression. ##=no detectible expression of SRF6.
Figure 6:
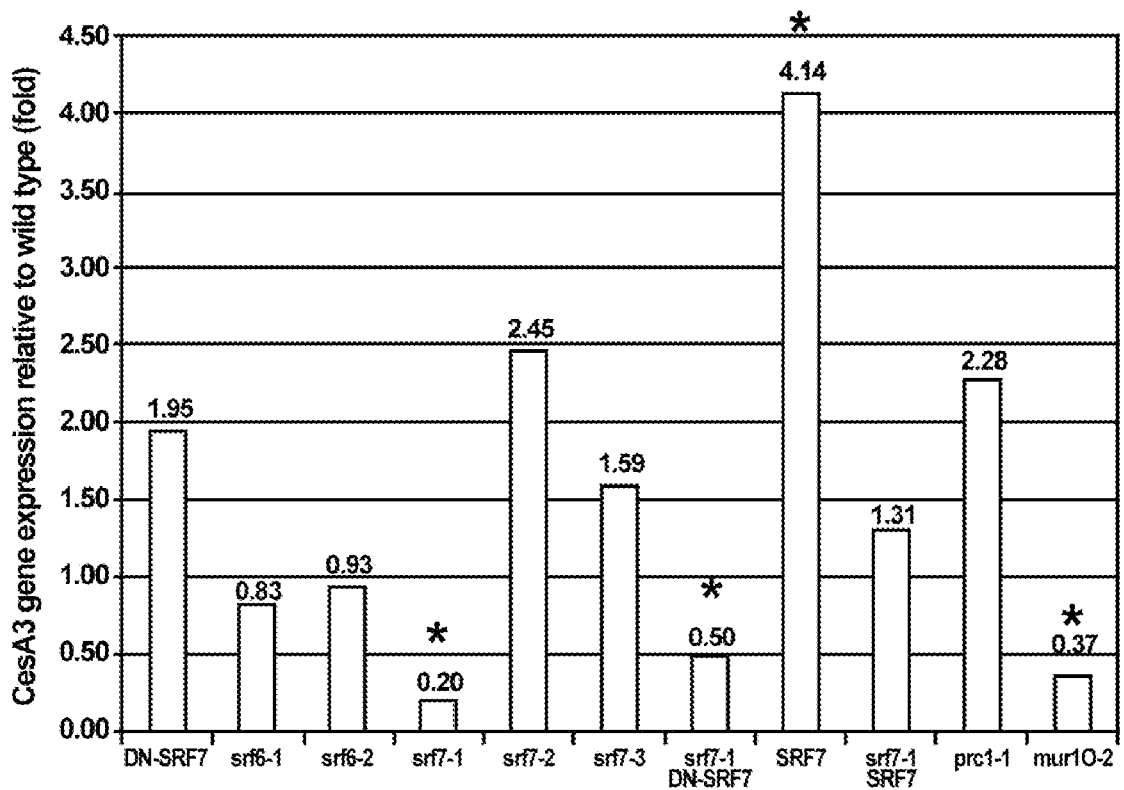
FIG. 6 shows quantitative real-time PCR analysis of gene expression levels of CesA3 for SRF mutants compared to wild type gene expression in dark treated 4-day-old seedlings grown on 0% sucrose MS media. Four-day-old dark treated plants were first cold treated (4° C.) for 4-days before harvesting and RNA isolation. This tissue was pooled from three different plates. Data analysis was done using three independent $C_t$ values for each measurement. The delta delta $C_t$ method was used for comparison of mutant CesA3 gene expression compared to wild type gene expression and comparison of mutant ACTIN2 gene expression compared to wild type ACTIN2 gene expression. *=p-value<0.05.
Figure 7:
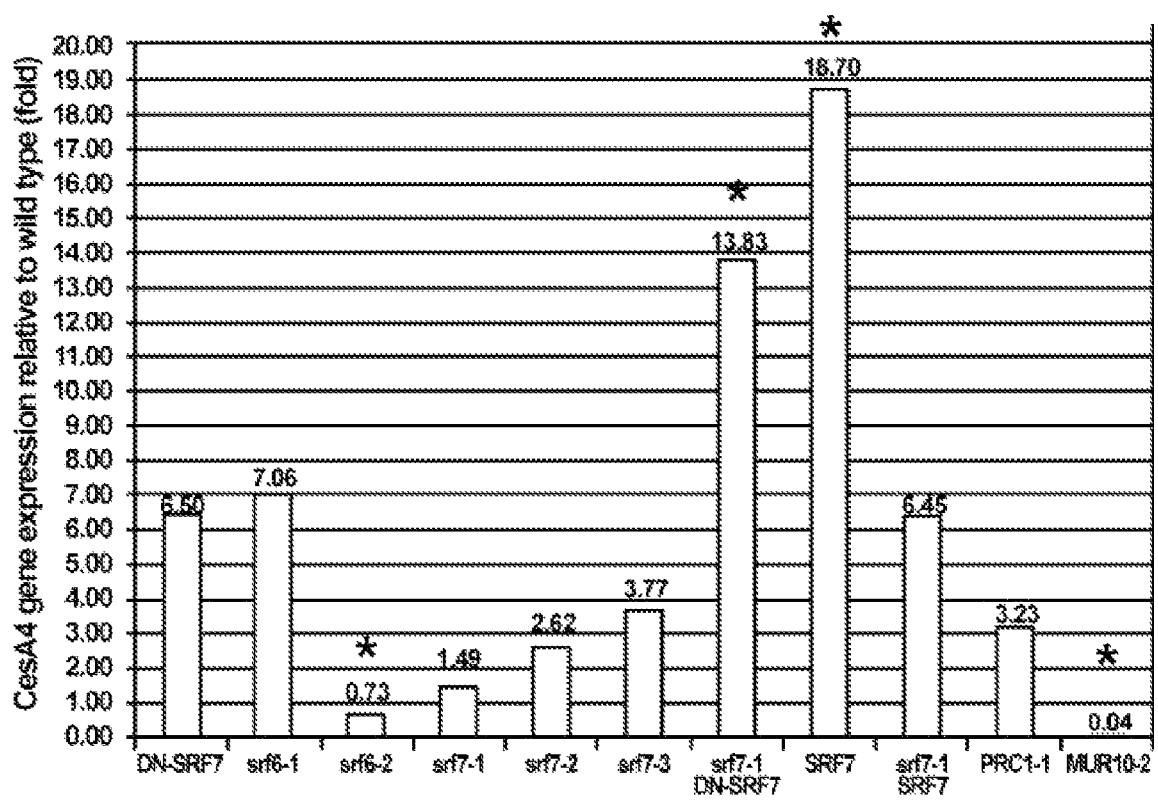
FIG. 7 shows quantitative real-time PCR analysis of gene expression levels of CesA4 for SRF mutants compared to wild type gene expression in dark treated 4-day-old seedlings grown on 0% sucrose MS media. Four-day-old dark treated plants were first cold treated (4° C.) for 4-days before harvesting and RNA isolation. This tissue was pooled from three different plates. Data analysis was done using three independent $C_t$ values for each measurement. The delta delta $C_t$ method was used for comparison of mutant CesA4 gene expression compared to wild type gene expression and comparison of mutant ACTIN2 gene expression compared to wild type ACTIN2 gene expression. *=p-value<0.05.
Figure 8:
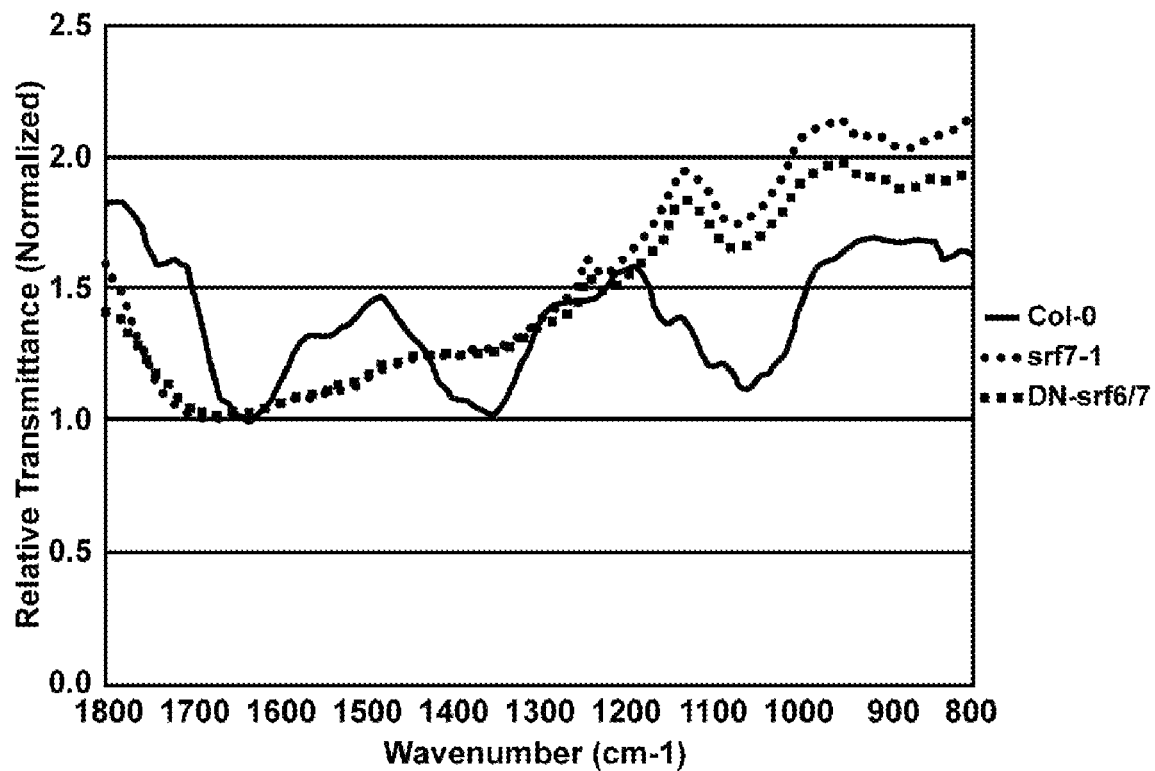
FIG. 8 shows and example of FT-IR data before and after baseline correction and normalization.

Loss-of-function null mutations (srf6-1 and srf7-1) caused reduced hypocotyl elongation when grown in the dark compared to the wild type and this was similar to procuste1-1 (CesA6 knockout), which shows an exaggerated decrease in hypocotyl length (p<0.01) (FIG. 1). The other mutations of SRF6 and SRF7 did not show a significant difference from the wild type (p>0.05), except srf7-3 that has significantly longer hypocotyls (p<0.05). The srf7-3 mutant contains an insertion after the kinase domain, which presumably truncated the C-terminal amino acid residues (FIG. 1A). The truncated srf7-3 mutant protein may act as a constitutively active mutation and gives rise to this phenotype (FIG. 1). Normal hypocotyl lengths in the srf7-1 mutation were restored by overexpressing the SRF7 gene; this shows that SRF7 being knocked out is responsible for the reduced hypocotyl length of srf7-1 (FIG. 1). The srf6-2 mutant grows to a similar length as the wild type in the dark (FIG. 1B), but shows an increase in sensitivity to isoxaben (p<0.05) (FIG. 2). srf6-2 also has no change in CesA3 or CesA4 gene expression (FIGS. 6 and 7). The srf7-2 mutant dark grown hypocotyl is similar to the wild type (FIG. 1B), and there is no difference in sensitivity to isoxaben (FIG. 2) from that of the wild type either. srf7-2 does have a two-fold increase in both CesA3 and CesA4 gene expression (FIGS. 4.6 and 4.7). The dark grown hypocotyl of srf7-3 is noteworthy because it is one and a half times the length of the wild type (FIG. 1B). srf7-3 is also more sensitive to isoxaben (p<0.05) than the wild type (FIG. 2). This mutant also had increased CesA4 gene expression compared to wild type (FIG. 7).

SRF6 and SRF7 mutants show altered responses to the cellulose synthesis inhibitor isoxaben.

Figure 3:
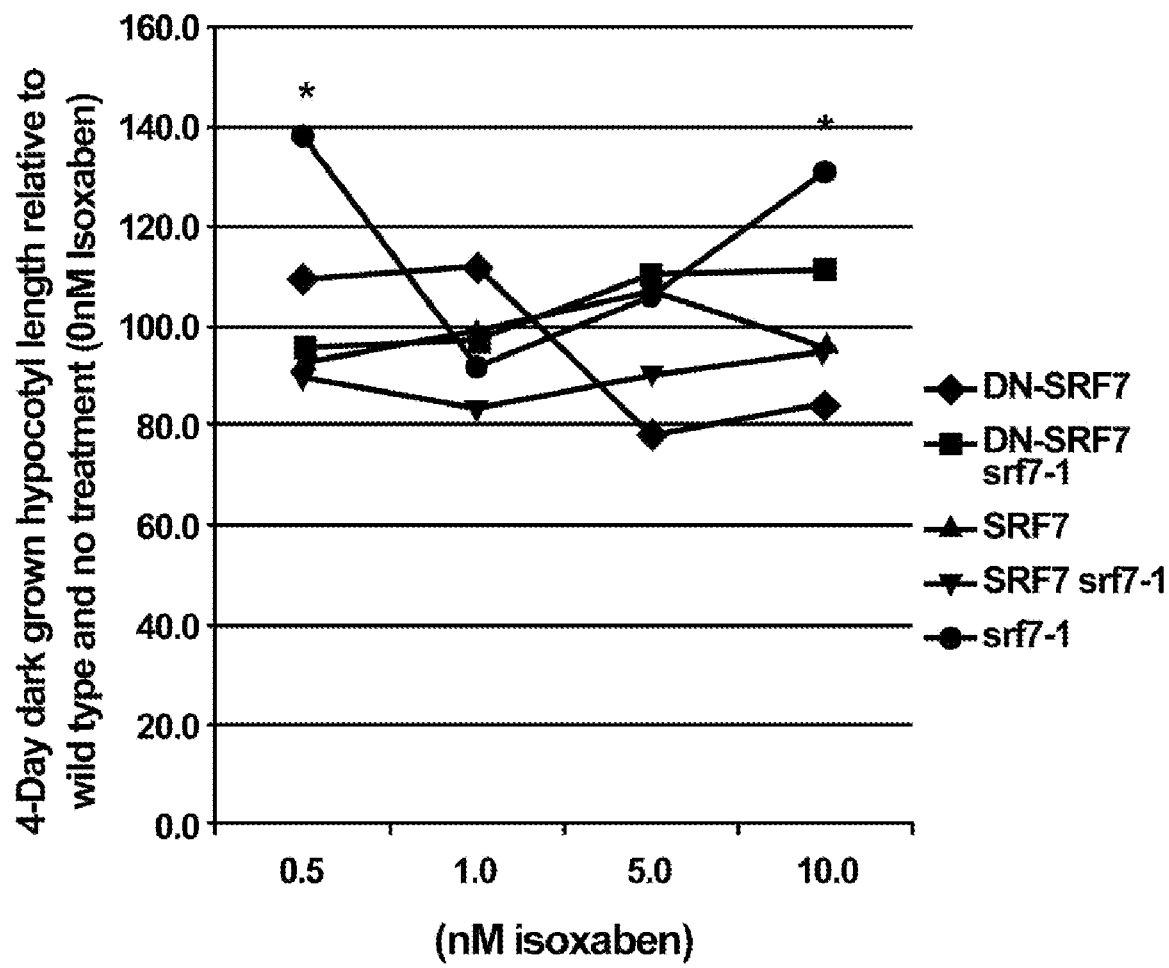
FIG. 3 shows isoxaben affects on the hypocotyls growth of combinatorial and overexpression mutants of SRF. The dominant negative of SRF7 exhibits increased resistance to low levels of isoxaben (0.5 and 1 nM) but increase sensitivity at higher levels (5 and 10 nM). Expression of DN-SRF7 in srf7-1 mutants shows some resistance to isoxaben at higher levels but is less than that of just srf7-1 alone. Overexpression of SRF7 and overexpression of SRF7 in srf7-1 do not show any change in sensitivity compared to the wild type. Data is taken from three independent experiments. Data is from hypocotyl lengths relative to wild type plants grown on the same plate and relative to mutants grown on DMSO control media. Student's t-test: *=p<0.05.

Isoxaben is a specific inhibitor of cellulose synthesis by affecting the function of the CesA proteins involved in primary cell wall synthesis, such as CesA3 and CesA6 (Scheible et al., 2001; Persson et al., 2007). Because SRF7 in particular is co-expressed with these same CesA genes the effects of isoxaben on SRF mutants was examined. The mutants with the insertion in the extracellular domain (srf6-1 (SEQ ID NO:53) and srf7-1) were significantly more resistant to isoxaben up to 10 μM (p<0.05) (FIG. 2). Mutants with insertions in the C-terminus or near the kinase domain either showed no difference in isoxaben response (srf7-2) or had increased sensitivity (srf6-2 and srf7-3) to isoxaben (FIG. 2). Overexpression of SRF7 in the srf7-1 mutant showed wild type resistance to isoxaben confirming the complementation of the srf7-1 mutant (FIG. 3). The results which are in agreement with the dark-grown hypocotyl phenotypes of the srf mutants supports the hypothesis that SRF6 and SRF7 regulate CesA-mediated synthesis of the primary cell wall Knockout mutations in SRF6 and SRF7 and the full-length overexpression of SRF7 alter cellulose synthase A (CesA) gene expression. Because SRF6 and SRF7 both seemed to be involved in cellulose synthesis as seen by the dark-grown hypocotyl and isoxaben resistance phenotypes of the mutations in the extracellular domain it was tested whether SRF6 and SRF7 regulate the expression of CesA genes. FIG. 4 and FIG. 5 show the level of SRF6 and SRF7 gene expression, respectively, in the SRF mutants. The effect of these mutations on the expression of cellulose synthases (CesAs) was examined. CesA3 and CesA4 were chosen because they are involved in either primary or secondary cell wall synthesis respectively. The primary cell wall synthesis gene, CesA3, expression for mutants of SRF6 was about the same as wild type (FIG. 6). The extracellular domain insertion of SRF7, srf7-1, showed a five-fold reduction in CesA3 gene expression (FIG. 4.6) while the other SRF7 mutations showed an increase in CesA3 gene expression: srf7-2 (2.45 fold), srf7-3 (1.59 fold) and SRF7 (4.14 fold). Overexpression of SRF7 in the srf7-1 mutant also restored CesA3 gene expression to near wild type levels (1.31 fold) (FIG. 6). The expression of the secondary cell wall synthesis gene (CesA4) was different than that of CesA3. First, srf6-1 showed an increase (7.06 fold) in CesA4 gene expression compared to wild type while srf6-2 slightly decreased CesA4 expression (0.73 fold) (FIG. 7). CesA4 gene expression was also altered by srf7 mutations with srf7-1 causing a slight increase in CesA4 gene expression (1.49 fold), and srf7-2 (2.62) and srf7-3 (3.77 fold) inducing higher CesA4 expression. SRF7 overexpression induced the greatest increase in CesA4 gene expression with an 18.70 fold change in expression (FIG. 7).

The procuste1-1 (prc1-1) mutant was used in the experiment as a primary cell wall deficient control because it is a substitution mutation in the CesA6 cellulose synthase gene that along with CesA1 and CesA3 are responsible for primary cell wall cellulose synthesis. This mutant exhibits a short thick dark grown hypocotyl that ectopically accumulates lignin (Hématy et al, 2007). The murus10-2 (mur10-2) mutant was used as secondary cell wall specific CesA control. The mur10-2 mutation is a substitution mutation in CesA7, that along with CesA4 and CesA8 are responsible for secondary cell wall cellulose synthesis (Persson et al., 2007). In this mutant there is no dark grown morphology, but biomechanical analysis has shows a significant reduction in tensile strength compared to the wild type plants (Bosca et al., 2006).

The CesA gene expression was examined in two CesA mutants, prc1-1 (CesA6) and mur10-2 (CesA7). CesA3 and CesA4 expression in mur10-2 were found to be 0.37 and 0.04 fold change respectively. These real-time PCR results are similar to the semi-quantitative RT-PCR values for mur10-2 stated in Bosca et al. (Bosca et al., 2006). For the prc1-1 mutant CesA3 gene expression increased 2.28 fold and CesA4 gene expression increased 3.23 fold.

This study was the first to show that mutations in a receptor-like kinase can have an effect on cellulose synthase gene expression, and that these mutants have similar biochemical and morphological phenotypes to known cellulose deficient mutants. Also, the overexpression of SRF7 results in increased cellulose deposition and CesA gene expression.

Figure 9:
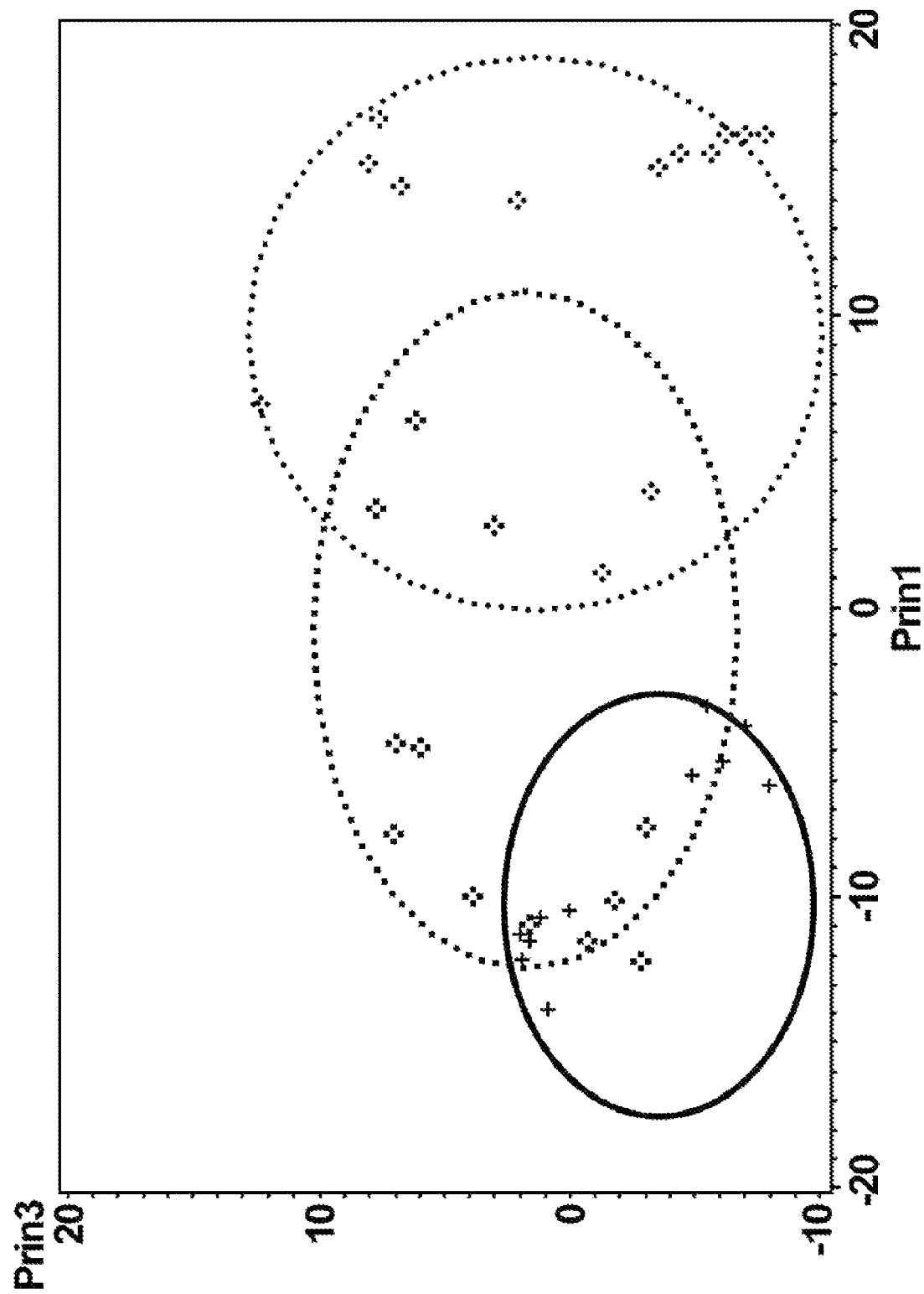
FIG. 9 shows a principal component analysis (PCA) for srf7-1, DN-srf7 and wild type. Baseline corrected and normalized data was used for the PCA, using SAS software.

Fourier-Transform Infrared (FT-IR) microspectroscopy reveals differences in cellular composition of SRF mutants. Fourier-Transform Infrared (FT-IR) microspectroscopy was used as a means to determine the relative (to wild type) amounts of the cell wall components, pectin and cellulose, in the various SRF mutants. All plant materials were grown for 4-days in darkness on MS media without sucrose. The CesA mutants prc1-1 and mur10-2 using FT-IR microspectroscopy were examined and found that mur10-2 showed no statistical difference (p>0.05) compared to the wild type while prc1-1 had increased pectic polysaccharide bonds (3.75, p<0.001 and carbohydrates (p<0.01) and reduced pectic carboxalate (−4.88, p<0.001) and amide bonds (−7.76, p<0.001) (Table 4.3). This indicates a decrease in poly-glycosidic bonds associated with the decrease in primary cell wall cellulose synthase activity in prc1-1. The lack of a difference between the wild type and the mur10-2 mutant can be explained by MUR10s function in secondary cell wall cellulose synthesis that does not affect the primary cell wall composition. In the srf6-1 and srf7-1 mutants there is a reduction in both poly-glycosidic bonds (srf6-1: −6.08, p<0.001 and srf7-1: −3.45, p<0.005) as well as in pectic polysaccharides, pectic carboxylates and pectic amide bonds (Table 3). Both srf7-2 and srf7-3 show increases in carbohydrate bonds but no increase in glycosidic bonds, while SRF7 shows a significant increase in glycosidic bonds (2.38. p<0.05) as well as an increase in carbohydrates, indicating that overexpression of SRF7 induced an increase in cellulose (Table 4.3). FIG. 4.8 shows the data collected from the FT-IR microspectrophotometer before and after normalization and baseline correction using the MATLab program generated for us by Dr. Karen Xu, UC, Riverside Statistics Department (Appendix 2). FIG. 9 shows principal component analysis (PCA) performed for DN-srf7, srf7-1 and wild type (Col-0). The PCA figure show that both the DN mutant and the knockout have much more similarity to each other then they do to the wild type. This is convincing evidence that the DN works similarly to a knock out as well as that these two mutations are significantly different in cell wall composition then the wild type and in a similar way.

Monosaccharide analysis of DN-srf7 reveals differences in cell wall components. Utilizing the dominant negative SRF7 line the monosaccharide composition of the cell wall was examined. There are three principal fractions isolated in this experiment and they are: imidizole soluble, sodium hydroxide soluble, and the sodium hydroxide insoluble fraction. These respectively contain the pectin, hemicellulose and cellulose components of the initial cell wall. Table 4 has the molar percent (mol %) of the monosaccharides determined in each fraction for both the DN and wild type plants. Because cellulose is primarily made from beta linked glucoses (glc), that would be found in the sodium hydroxide insoluble fraction it can be seen that for the DN (87.99 mol %) is less then wild type (91.17 mol %). The difference of 3.18 mol % is significant but based on the dark grown phenotype of the DN and the CesA gene expression levels, this difference is poten-

TABLE 3

Analysis of Fourier Transform-Infrared (FT-IR) Microspectroscopy of SRF7 mutants. Wavenumbers for known cell wall components: pectins, cellulose and carbohydrates were examined to determine if there was a statistically different quantity of pectin or cellulose in the SRF mutants and in known cellulose synthases prc1-1 (CesA6) and mur10-2 (CesA7). Student's t-test significance = p-value < 0.05, ns = not significant.

| Bond type | Wavenumber ($cm^{-1}$) | srf7-1 p-value | t-value | srf7-2 p-value | t-value | srf7-3 p-value | t-value | SRF-7 p-value | t-value |
|---|---|---|---|---|---|---|---|---|---|
| Pectic Polysaccharide | 1,677 | 0.001 | −3.80 | 2.4E−06 | −6.51 | 0.002 | −3.66 | ns | 0.35 |
|  | 1,639 | ns | −1.44 | ns | −0.57 | 0.019 | 2.56 | ns | 0.49 |
| Pectic Carboxylate | 1,554 | 6.5E−06 | −6.36 | 7.7E−07 | −7.84 | 0.018 | −2.61 | 9.5E−09 | −12.06 |
| Pectic Amide | 1,496 | 4.3E−06 | −6.40 | 2.1E−08 | −10.70 | 3.9E−05 | −5.27 | 2.8E−09 | −15.07 |
| Poly-glycosidic | 1,157 | 0.002 | −3.45 | ns | −0.59 | ns | 0.47 | 0.032 | 2.38 |
| Carbohydrate | 1,060 | ns | 0.68 | 1.12E−04 | 5.17 | 0.001 | 4.03 | 2.3E−08 | 11.07 |
|  | 1,049 | ns | 0.18 | 5.37E−04 | 4.41 | 0.002 | 3.73 | 3.4E−08 | 10.54 |
|  | 1,041 | ns | −0.23 | 0.002 | 3.79 | 0.003 | 3.56 | 4.3E−08 | 10.28 |

| Bond type | srf6-1 p-value | t-value | srf6-2 p-value | t-value | prc1-1 (CesA6) p-value | t-value | mur10-2 (CesA7) p-value | t-value |
|---|---|---|---|---|---|---|---|---|
| Pectic Polysaccharide | 1.87E−10 | −11.79 | ns | −1.25 | ns | −1.87 | ns | −0.12 |
|  | 3.88E−04 | −4.22 | ns | 1.71 | 8.12E−04 | 3.75 | ns | −0.44 |
| Pectic Carboxylate | 4.264E−10 | −10.98 | 0.001 | −3.63 | 7.50E−05 | −4.88 | ns | 0.77 |
| Pectic Amide | 4.055E−10 | −10.95 | 4.38E−06 | −5.56 | 1.22E−07 | −7.76 | ns | 1.13 |
| Poly-glycosidic | 8.01E−06 | −6.08 | ns | −1.05 | ns | −1.65 | ns | 0.20 |
| Carbohydrate | 0.024 | 2.46 | ns | 1.02 | 4.06E−05 | 4.66 | ns | 0.42 |
|  | ns | 1.72 | ns | 0.77 | 1.81E−04 | 4.16 | ns | 0.41 |
|  | ns | 0.96 | ns | 0.56 | 1.23E−03 | 3.50 | ns | 0.44 |

TABLE 4

Monosaccharide analysis for DN-srf7 and wild type (Col-0).

| Sugar | DN-SRF7 Imid Sol mol % | NaOH Sol mol % | NaOH Insol mol % | Col-0 Imid Sol mol % | NaOH Sol mol % | NaOH Insol mol % |
|---|---|---|---|---|---|---|
| 3-0-me Rha | 0.00 | 0.00 | 0.00 | 0.00 | 0.00 | 0.00 |
| Ara | 14.68 | 8.56 | 1.33 | 6.78 | 7.95 | 0.86 |
| Rha | 9.52 | 9.42 | 1.30 | 9.64 | 9.03 | 1.09 |
| Fuc | 3.73 | 2.87 | 0.18 | 1.79 | 2.59 | 0.18 |
| Xyl | 6.76 | 20.53 | 3.44 | 2.53 | 14.86 | 1.98 |
| GlcU | 13.22 | 2.16 | 1.10 | 8.09 | 3.00 | 0.88 |
| 4-0-me GlcU | 0.65 | 0.00 | 0.00 | 2.26 | 1.24 | 0.02 |
| GalU | 31.76 | 30.87 | 1.90 | 43.95 | 33.10 | 0.65 |
| Man | 4.08 | 5.14 | 0.90 | 1.75 | 4.22 | 1.36 |
| Gal | 11.77 | 12.84 | 1.87 | 17.83 | 14.29 | 1.80 |
| Glc | 3.83 | 7.61 | 87.99 | 5.37 | 9.72 | 91.17 | tially much greater in the knockouts of SRF6 and SRF7. There are some notable differences in the DN and wild type in the imidazole soluble fraction as well. In the imidazole, pectin, fraction the DN has much more arabinose (ara), fructose (fuc) and xylose (xyl) then the wild type. These are normal sugars that comprise the pectin portion of the cell wall along with pectic proteins. It has been shown previously that a reduction in cellulose production can increase both lignin and pectin in the cell wall as a means to counter balance the structural absence of cellulose.

Analysis of public microarray database, Genevestigator, correlates primary cell wall synthesis gene expression with SRF gene expression. In examining the gene expression of the SRF mutants it was found that there was a large difference in CesA gene expression when plants were grown in total darkness compared to when they were grown under a diurnal cycle. To examine if these genes were expressed differently in the dark than that from the light the public microarray database, Genevestigator, was used to examine gene expression.

Figure 10A:
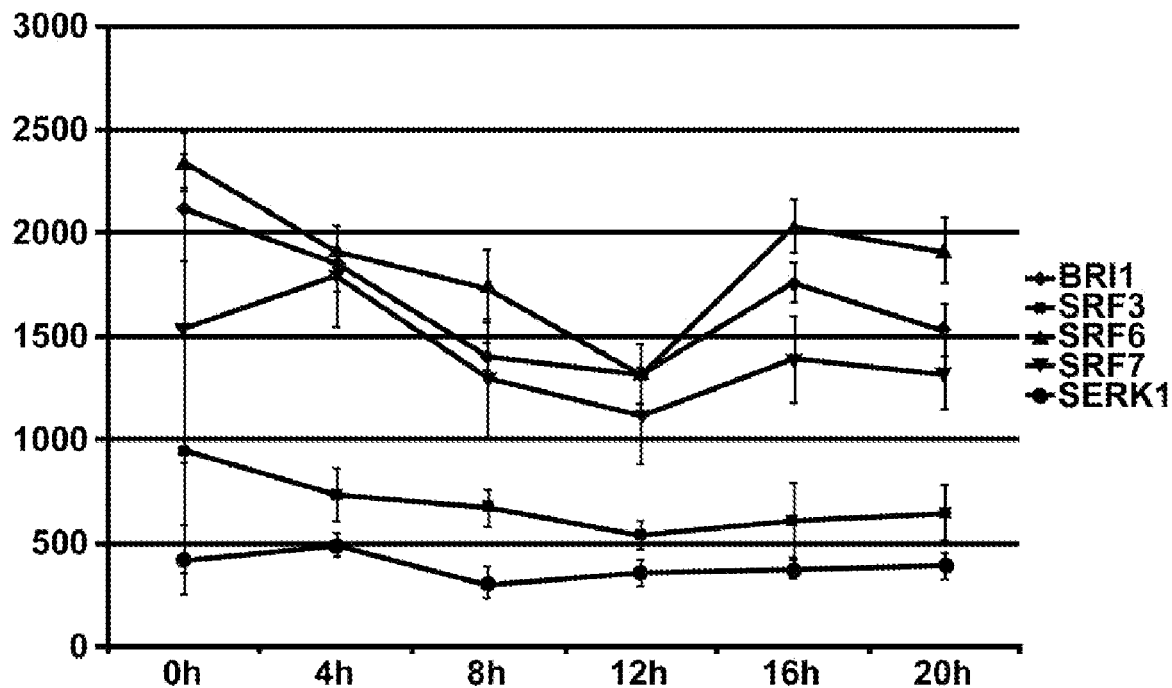
FIG. 10A-D shows gene expression data from the diurnal experiment (A and C) and isoxaben experiment (B and D), looking at either RLK (A and B) or cellulose synthase A (C and D) gene expression. Data was obtained from the Genevestigator database using the digital northern tool.
Figure 10B:
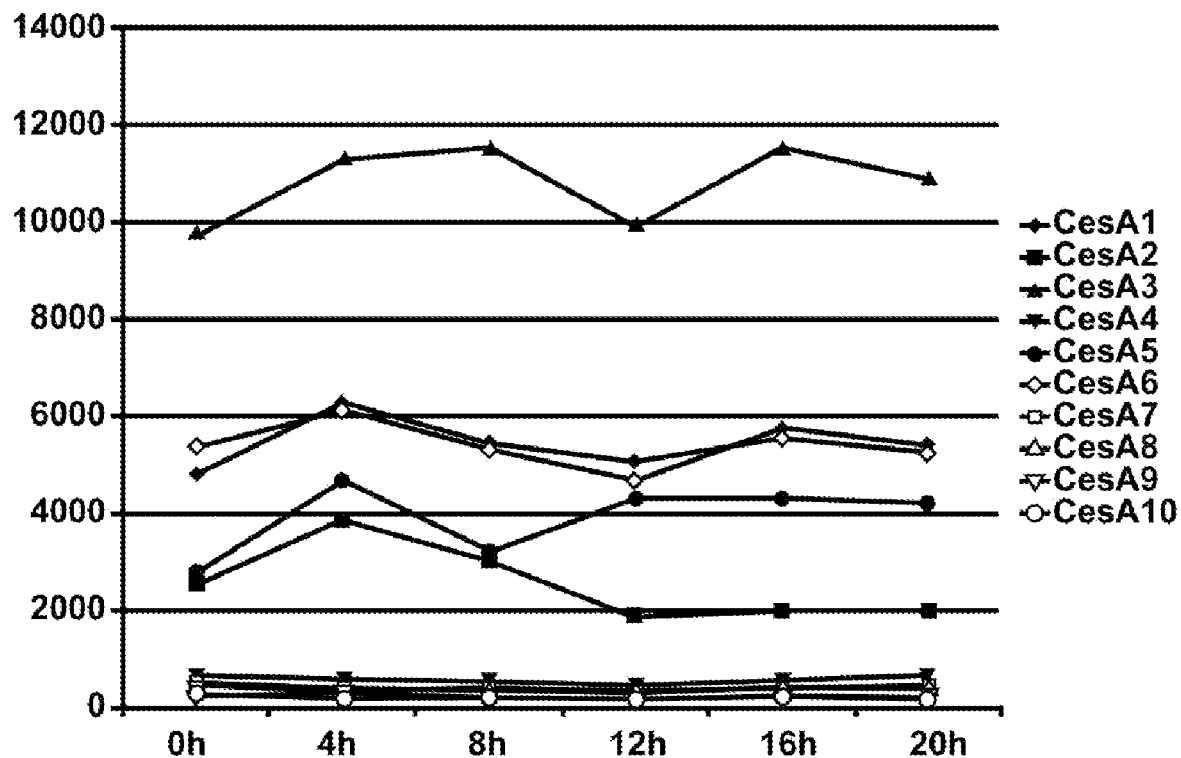
Figure 10C:
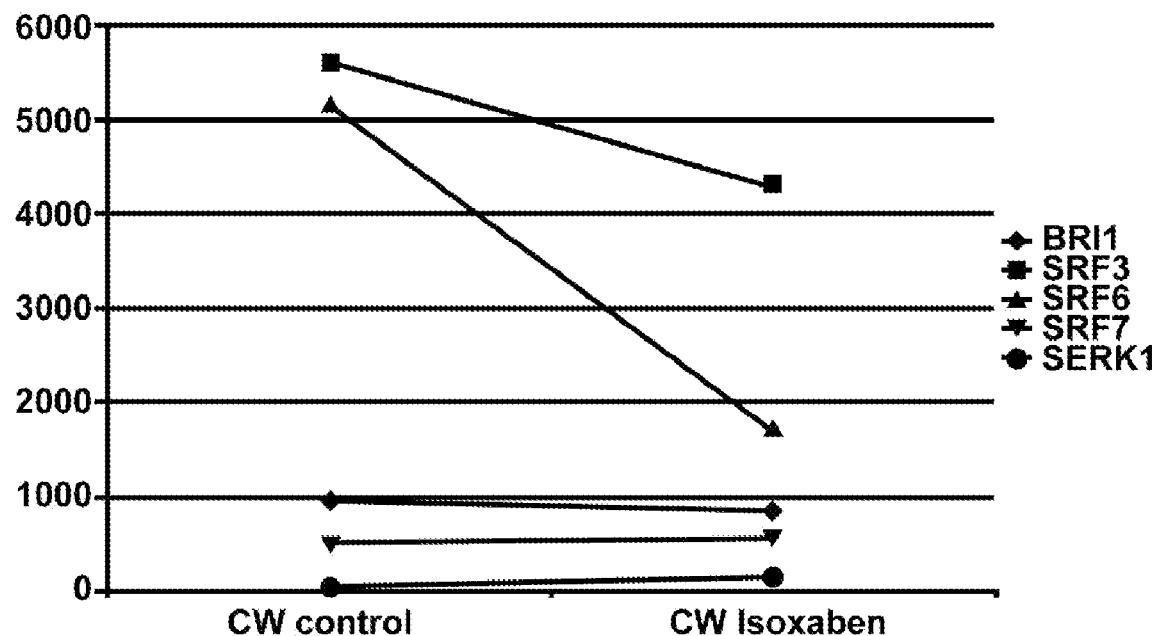
Figure 10D:
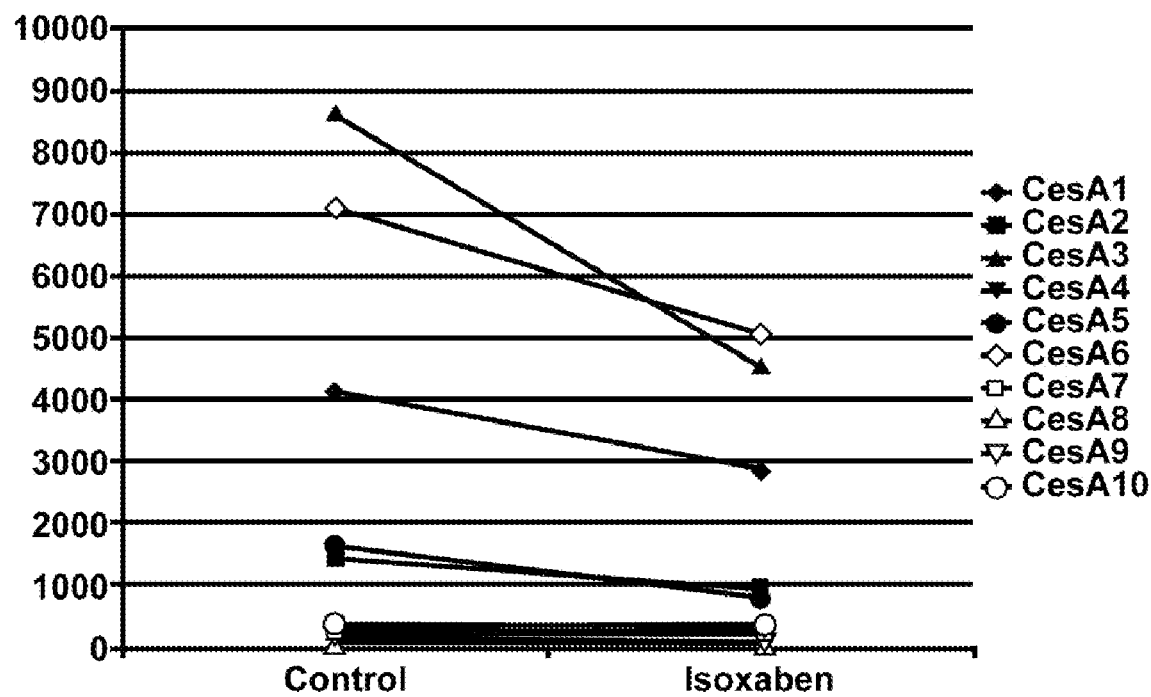

RLK and CesA gene expression levels were also examined when exposed to the primary cell wall inhibitor isoxaben. FIG. 10A shows the expression of BRI1, SRF3, SRF6, SRF7 and SERK1 under a diurnal cycle. BRI1, SRF6 and SRF7 all show a change in gene expression. The patterns are similar in that there is higher gene expression in the dark and dips drastically at the first sign of light then begin to increase again. There is no such change in gene expression in either SERK1 or the SRF gene family member SRF3. In FIG. 10C the diurnal gene expression of all 10 CesA genes can be seen. It is interesting to note that the only CesA gene that show a diurnal pattern are the genes involved in primary cell wall synthesis (CesA 1, 2, 3, 5 and 6), while those required for secondary cell wall synthesis (CesA 4, 7 and 8) have no change at all. It has been shown that the chemical isoxaben is a specific inhibitor of cellulose synthesis and that it primarily affects CesA3 and CesA6 function. It also appears that isoxaben reduces primary cell wall CesA gene expression but not the secondary cell wall CesAs (FIG. 10D). Interestingly one of the SRFs shown to be responsible in cell wall gene expression and cellulose deposition, SRF6, also has reduced gene expression upon isoxaben treatment (FIG. 10B).

A number of embodiments of the invention have been described. Nevertheless, it will be understood that various modifications may be made without departing from the spirit and scope of the invention. Accordingly, other embodiments are within the scope of the following claims.

SEQUENCE LISTING

```
<160> NUMBER OF SEQ ID NOS: 54

<210> SEQ ID NO 1
<211> LENGTH: 2163
<212> TYPE: DNA
<213> ORGANISM: Arabidopsis thaliana
<220> FEATURE:
<221> NAME/KEY: CDS
<222> LOCATION: (1)..(2163)

<400> SEQUENCE: 1 atg agg gag aat tgg gcg gtg gtg gct ctg ttt aca cta tgc att gta      48
Met Arg Glu Asn Trp Ala Val Val Ala Leu Phe Thr Leu Cys Ile Val
1               5                  10                  15 ggg ttt gag ctt aga ttc atc cat gga gct act gat gca tca gac act      96
Gly Phe Glu Leu Arg Phe Ile His Gly Ala Thr Asp Ala Ser Asp Thr
            20                  25                  30 tca gca ttg aac aca ttg ttc agt ggt atg cat tct cca gct cag cta     144
Ser Ala Leu Asn Thr Leu Phe Ser Gly Met His Ser Pro Ala Gln Leu
        35                  40                  45 aca caa tgg act gca gca gct ggt gat cct tgt ggc cag aat tgg aga     192
Thr Gln Trp Thr Ala Ala Ala Gly Asp Pro Cys Gly Gln Asn Trp Arg
    50                  55                  60 ggc gtc act tgt tcc ggc tca cga gtt act caa ata aag ttg tca ggt     240
Gly Val Thr Cys Ser Gly Ser Arg Val Thr Gln Ile Lys Leu Ser Gly
65                  70                  75                  80 ctt gag ctc tct gga act ctt gga gga tac atg ctt gat aaa ttg act     288
Leu Glu Leu Ser Gly Thr Leu Gly Gly Tyr Met Leu Asp Lys Leu Thr
                85                  90                  95 tct ctt acc gag ctt gat cta agc agc aat aat ctt gga ggt gat tta     336
Ser Leu Thr Glu Leu Asp Leu Ser Ser Asn Asn Leu Gly Gly Asp Leu
            100                 105                 110 cca tat cag ttt cct cca aat ctg caa cga ttg aac ctt gcg aat aat     384
Pro Tyr Gln Phe Pro Pro Asn Leu Gln Arg Leu Asn Leu Ala Asn Asn
        115                 120                 125 caa ttc act gga gct gct tcg tac tca ctt tct cag att aca cca ctt     432
Gln Phe Thr Gly Ala Ala Ser Tyr Ser Leu Ser Gln Ile Thr Pro Leu
    130                 135                 140 aag tat ctc aat ctt ggt cac aat cag ttt aag ggg cag ata gct atc     480
Lys Tyr Leu Asn Leu Gly His Asn Gln Phe Lys Gly Gln Ile Ala Ile
145                 150                 155                 160 gac ttc tcc aag ctc gac tct ctc aca acc ttg gac ttc tct ttc aat     528
Asp Phe Ser Lys Leu Asp Ser Leu Thr Thr Leu Asp Phe Ser Phe Asn
                165                 170                 175 tct ttc acg aac tct tta ccg gca acg ttt tcc tct cta aca agt tta     576
Ser Phe Thr Asn Ser Leu Pro Ala Thr Phe Ser Ser Leu Thr Ser Leu
            180                 185                 190
```

| | | | | | | | | | | | | | | | |
|---|---|---|---|---|---|---|---|---|---|---|---|---|---|---|---|
| aaa | tca | cta | tac | ctt | cag | aac | aat | cag | ttc | tca | ggc | aca | gtc | gat | gtc | 624 |
| Lys | Ser | Leu | Tyr | Leu | Gln | Asn | Asn | Gln | Phe | Ser | Gly | Thr | Val | Asp | Val | |
| | | | 195 | | | | | 200 | | | | | 205 | | | |

| tta | gcc | ggt | ctt | cct | ctt | gag | act | ctg | aac | att | gcg | aac | aat | gac | ttc | 672 |
|---|---|---|---|---|---|---|---|---|---|---|---|---|---|---|---|---|
| Leu | Ala | Gly | Leu | Pro | Leu | Glu | Thr | Leu | Asn | Ile | Ala | Asn | Asn | Asp | Phe | |
| 210 | | | | | 215 | | | | | 220 | | | | | | |

| acg | ggg | tgg | atc | ccc | agt | tct | tta | aag | ggc | atc | aca | tta | ata | aaa | gat | 720 |
|---|---|---|---|---|---|---|---|---|---|---|---|---|---|---|---|---|
| Thr | Gly | Trp | Ile | Pro | Ser | Ser | Leu | Lys | Gly | Ile | Thr | Leu | Ile | Lys | Asp | |
| 225 | | | | | 230 | | | | | 235 | | | | | 240 | |

| ggc | aac | tca | ttc | aat | act | gga | cct | gca | cct | cca | cca | cca | cct | ggt | aca | 768 |
|---|---|---|---|---|---|---|---|---|---|---|---|---|---|---|---|---|
| Gly | Asn | Ser | Phe | Asn | Thr | Gly | Pro | Ala | Pro | Pro | Pro | Pro | Pro | Gly | Thr | |
| | | | | 245 | | | | | 250 | | | | | 255 | | |

| cct | cct | atc | cgt | ggc | tcc | ccg | agc | cgt | aaa | tct | gga | gga | cgt | gaa | agc | 816 |
|---|---|---|---|---|---|---|---|---|---|---|---|---|---|---|---|---|
| Pro | Pro | Ile | Arg | Gly | Ser | Pro | Ser | Arg | Lys | Ser | Gly | Gly | Arg | Glu | Ser | |
| | | | 260 | | | | | 265 | | | | | 270 | | | |

| cgg | tct | agt | gat | gag | tcc | acc | aga | aat | gga | gat | tcc | aag | aaa | tca | gga | 864 |
|---|---|---|---|---|---|---|---|---|---|---|---|---|---|---|---|---|
| Arg | Ser | Ser | Asp | Glu | Ser | Thr | Arg | Asn | Gly | Asp | Ser | Lys | Lys | Ser | Gly | |
| | | 275 | | | | | 280 | | | | | 285 | | | | |

| atc | gga | gcg | ggg | gca | att | gcg | ggc | ata | atc | att | tca | ttg | tta | gta | gtt | 912 |
|---|---|---|---|---|---|---|---|---|---|---|---|---|---|---|---|---|
| Ile | Gly | Ala | Gly | Ala | Ile | Ala | Gly | Ile | Ile | Ile | Ser | Leu | Leu | Val | Val | |
| | 290 | | | | | 295 | | | | | 300 | | | | | |

| aca | gct | ctt | ctt | gtt | gct | ttc | ttc | ttg | ttc | aga | aga | aaa | aaa | tca | aag | 960 |
|---|---|---|---|---|---|---|---|---|---|---|---|---|---|---|---|---|
| Thr | Ala | Leu | Leu | Val | Ala | Phe | Phe | Leu | Phe | Arg | Arg | Lys | Lys | Ser | Lys | |
| 305 | | | | 310 | | | | | 315 | | | | | 320 | | |

| agg | tca | tca | ccc | atg | gac | att | gag | aaa | acc | gat | aac | cag | cct | ttc | act | 1008 |
|---|---|---|---|---|---|---|---|---|---|---|---|---|---|---|---|---|
| Arg | Ser | Ser | Pro | Met | Asp | Ile | Glu | Lys | Thr | Asp | Asn | Gln | Pro | Phe | Thr | |
| | | | 325 | | | | | 330 | | | | | 335 | | | |

| ctt | gct | tca | aac | gac | ttt | cac | gaa | aac | aat | tcc | att | cag | agt | tct | tca | 1056 |
|---|---|---|---|---|---|---|---|---|---|---|---|---|---|---|---|---|
| Leu | Ala | Ser | Asn | Asp | Phe | His | Glu | Asn | Asn | Ser | Ile | Gln | Ser | Ser | Ser | |
| | | | 340 | | | | | 345 | | | | | 350 | | | |

| tca | gtt | gag | aca | aag | aaa | ctg | gac | act | tca | ttg | tct | att | aat | ctt | cga | 1104 |
|---|---|---|---|---|---|---|---|---|---|---|---|---|---|---|---|---|
| Ser | Val | Glu | Thr | Lys | Lys | Leu | Asp | Thr | Ser | Leu | Ser | Ile | Asn | Leu | Arg | |
| | | 355 | | | | | 360 | | | | | 365 | | | | |

| cct | cca | cca | att | gat | aga | aac | aaa | tca | ttt | gat | gat | gaa | gat | tcg | aca | 1152 |
|---|---|---|---|---|---|---|---|---|---|---|---|---|---|---|---|---|
| Pro | Pro | Pro | Ile | Asp | Arg | Asn | Lys | Ser | Phe | Asp | Asp | Glu | Asp | Ser | Thr | |
| | 370 | | | | | 375 | | | | | 380 | | | | | |

| aga | aag | cct | att | gct | gtc | aag | aaa | tcc | aca | gtg | gtg | gtt | cct | tca | aat | 1200 |
|---|---|---|---|---|---|---|---|---|---|---|---|---|---|---|---|---|
| Arg | Lys | Pro | Ile | Ala | Val | Lys | Lys | Ser | Thr | Val | Val | Val | Pro | Ser | Asn | |
| 385 | | | | 390 | | | | | 395 | | | | | 400 | | |

| gtg | aga | ctc | tat | tca | gtt | gca | gat | ctc | caa | att | gct | act | ggc | agt | ttc | 1248 |
|---|---|---|---|---|---|---|---|---|---|---|---|---|---|---|---|---|
| Val | Arg | Leu | Tyr | Ser | Val | Ala | Asp | Leu | Gln | Ile | Ala | Thr | Gly | Ser | Phe | |
| | | | 405 | | | | | 410 | | | | | 415 | | | |

| agc | gta | gat | aat | ctt | ctt | gga | gaa | ggg | act | ttt | gga | cga | gta | tac | aga | 1296 |
|---|---|---|---|---|---|---|---|---|---|---|---|---|---|---|---|---|
| Ser | Val | Asp | Asn | Leu | Leu | Gly | Glu | Gly | Thr | Phe | Gly | Arg | Val | Tyr | Arg | |
| | | | 420 | | | | | 425 | | | | | 430 | | | |

| gct | gag | ttt | gat | gat | gga | aag | gtt | ctt | gct | gtg | aag | aaa | att | gat | tcg | 1344 |
|---|---|---|---|---|---|---|---|---|---|---|---|---|---|---|---|---|
| Ala | Glu | Phe | Asp | Asp | Gly | Lys | Val | Leu | Ala | Val | Lys | Lys | Ile | Asp | Ser | |
| | | 435 | | | | | 440 | | | | | 445 | | | | |

| tct | gct | ctc | cca | cat | ggc | atg | acc | gat | gat | ttc | att | gaa | atg | gta | tcg | 1392 |
|---|---|---|---|---|---|---|---|---|---|---|---|---|---|---|---|---|
| Ser | Ala | Leu | Pro | His | Gly | Met | Thr | Asp | Asp | Phe | Ile | Glu | Met | Val | Ser | |
| 450 | | | | 455 | | | | | 460 | | | | | | | |

| aaa | ata | gcc | aat | ttg | gat | cat | cca | aat | gtg | acc | aag | ctt | gtt | ggt | tac | 1440 |
|---|---|---|---|---|---|---|---|---|---|---|---|---|---|---|---|---|
| Lys | Ile | Ala | Asn | Leu | Asp | His | Pro | Asn | Val | Thr | Lys | Leu | Val | Gly | Tyr | |
| 465 | | | | 470 | | | | | 475 | | | | | 480 | | |

| tgt | gct | gag | cac | gga | caa | cat | ctc | gtg | gtc | tat | gaa | ttc | cac | aaa | aat | 1488 |
|---|---|---|---|---|---|---|---|---|---|---|---|---|---|---|---|---|
| Cys | Ala | Glu | His | Gly | Gln | His | Leu | Val | Val | Tyr | Glu | Phe | His | Lys | Asn | |
| | | | 485 | | | | | 490 | | | | | 495 | | | |

| gga | tca | tta | cat | gac | ttc | tta | cac | tta | tca | gaa | gag | gaa | agt | aaa | gca | 1536 |
|---|---|---|---|---|---|---|---|---|---|---|---|---|---|---|---|---|
| Gly | Ser | Leu | His | Asp | Phe | Leu | His | Leu | Ser | Glu | Glu | Glu | Ser | Lys | Ala | |
| | | 500 | | | | | 505 | | | | | 510 | | | | |

```
ttg gtg tgg aat tca cga gtc aag atc gct ctt ggg act gca cgc gca    1584
Leu Val Trp Asn Ser Arg Val Lys Ile Ala Leu Gly Thr Ala Arg Ala
        515                 520                 525 ttg gag tat ctg cat gaa gtt tgc tca ccg tct ata gtg gac aag aat    1632
Leu Glu Tyr Leu His Glu Val Cys Ser Pro Ser Ile Val Asp Lys Asn
530                 535                 540 atc aaa tca gct aat att tta ctc gat tca gag ctg aat cct cac tta    1680
Ile Lys Ser Ala Asn Ile Leu Leu Asp Ser Glu Leu Asn Pro His Leu
545                 550                 555                 560 tca gat tct ggt ctc gca agc ttc ctt ccc aca gct aat gag tta tta    1728
Ser Asp Ser Gly Leu Ala Ser Phe Leu Pro Thr Ala Asn Glu Leu Leu
                565                 570                 575 aac caa acc gat gaa ggg tat agc gca cct gaa gta tca atg tca ggc    1776
Asn Gln Thr Asp Glu Gly Tyr Ser Ala Pro Glu Val Ser Met Ser Gly
            580                 585                 590 caa tat tct ttg aag agt gac att tac agt ttt gga gta gtg atg ctt    1824
Gln Tyr Ser Leu Lys Ser Asp Ile Tyr Ser Phe Gly Val Val Met Leu
        595                 600                 605 gaa ctt tta act ggg aga aaa cca ttt gac agc agc aca agg tca aga    1872
Glu Leu Leu Thr Gly Arg Lys Pro Phe Asp Ser Ser Thr Arg Ser Arg
610                 615                 620 tct gag cag tca ctg gtt cga tgg gcg aca cca caa ctt cac gac att    1920
Ser Glu Gln Ser Leu Val Arg Trp Ala Thr Pro Gln Leu His Asp Ile
625                 630                 635                 640 gat gct tta gcc aaa atg gtt gat cca gct ctt aaa ggg ctt tat cct    1968
Asp Ala Leu Ala Lys Met Val Asp Pro Ala Leu Lys Gly Leu Tyr Pro
                645                 650                 655 gtc aaa tcc ctt tct cga ttt gca gat gtt atc gct ctc tgt gtc cag    2016
Val Lys Ser Leu Ser Arg Phe Ala Asp Val Ile Ala Leu Cys Val Gln
            660                 665                 670 ccg gag ccg gag ttt aga cca cca atg tct gaa gtt gtg cag gct cta    2064
Pro Glu Pro Glu Phe Arg Pro Pro Met Ser Glu Val Val Gln Ala Leu
        675                 680                 685 gtt gtg tta gtg cag aga gct aac atg agc aag aga act gtc gga gtt    2112
Val Val Leu Val Gln Arg Ala Asn Met Ser Lys Arg Thr Val Gly Val
690                 695                 700 gat cca tcg caa cgt gct ggt agt gcc gac acg acc agt gat tac atg    2160
Asp Pro Ser Gln Arg Ala Gly Ser Ala Asp Thr Thr Ser Asp Tyr Met
705                 710                 715                 720 taa                                                                2163
```

<210> SEQ ID NO 2
<211> LENGTH: 720
<212> TYPE: PRT
<213> ORGANISM: Arabidopsis thaliana

<400> SEQUENCE: 2

```
Met Arg Glu Asn Trp Ala Val Val Ala Leu Phe Thr Leu Cys Ile Val
1               5                   10                  15

Gly Phe Glu Leu Arg Phe Ile His Gly Ala Thr Asp Ala Ser Asp Thr
            20                  25                  30

Ser Ala Leu Asn Thr Leu Phe Ser Gly Met His Ser Pro Ala Gln Leu
        35                  40                  45

Thr Gln Trp Thr Ala Ala Ala Gly Asp Pro Cys Gly Gln Asn Trp Arg
    50                  55                  60

Gly Val Thr Cys Ser Gly Ser Arg Val Thr Gln Ile Lys Leu Ser Gly
65                  70                  75                  80

Leu Glu Leu Ser Gly Thr Leu Gly Gly Tyr Met Leu Asp Lys Leu Thr
                85                  90                  95
```

```
Ser Leu Thr Glu Leu Asp Leu Ser Ser Asn Asn Leu Gly Gly Asp Leu
            100                 105                 110

Pro Tyr Gln Phe Pro Pro Asn Leu Gln Arg Leu Asn Leu Ala Asn Asn
        115                 120                 125

Gln Phe Thr Gly Ala Ala Ser Tyr Ser Leu Ser Gln Ile Thr Pro Leu
    130                 135                 140

Lys Tyr Leu Asn Leu Gly His Asn Gln Phe Lys Gly Gln Ile Ala Ile
145                 150                 155                 160

Asp Phe Ser Lys Leu Asp Ser Leu Thr Thr Leu Asp Phe Ser Phe Asn
                165                 170                 175

Ser Phe Thr Asn Ser Leu Pro Ala Thr Phe Ser Ser Leu Thr Ser Leu
            180                 185                 190

Lys Ser Leu Tyr Leu Gln Asn Asn Gln Phe Ser Gly Thr Val Asp Val
        195                 200                 205

Leu Ala Gly Leu Pro Leu Glu Thr Leu Asn Ile Ala Asn Asn Asp Phe
    210                 215                 220

Thr Gly Trp Ile Pro Ser Ser Leu Lys Gly Ile Thr Leu Ile Lys Asp
225                 230                 235                 240

Gly Asn Ser Phe Asn Thr Gly Pro Ala Pro Pro Pro Pro Gly Thr
                245                 250                 255

Pro Pro Ile Arg Gly Ser Pro Ser Arg Lys Ser Gly Gly Arg Glu Ser
            260                 265                 270

Arg Ser Ser Asp Glu Ser Thr Arg Asn Gly Asp Ser Lys Lys Ser Gly
        275                 280                 285

Ile Gly Ala Gly Ala Ile Ala Gly Ile Ile Ile Ser Leu Leu Val Val
    290                 295                 300

Thr Ala Leu Leu Val Ala Phe Phe Leu Phe Arg Arg Lys Lys Ser Lys
305                 310                 315                 320

Arg Ser Ser Pro Met Asp Ile Glu Lys Thr Asp Asn Gln Pro Phe Thr
                325                 330                 335

Leu Ala Ser Asn Asp Phe His Glu Asn Asn Ser Ile Gln Ser Ser Ser
            340                 345                 350

Ser Val Glu Thr Lys Lys Leu Asp Thr Ser Leu Ser Ile Asn Leu Arg
        355                 360                 365

Pro Pro Pro Ile Asp Arg Asn Lys Ser Phe Asp Asp Glu Asp Ser Thr
    370                 375                 380

Arg Lys Pro Ile Ala Val Lys Lys Ser Thr Val Val Pro Ser Asn
385                 390                 395                 400

Val Arg Leu Tyr Ser Val Ala Asp Leu Gln Ile Ala Thr Gly Ser Phe
                405                 410                 415

Ser Val Asp Asn Leu Leu Gly Glu Gly Thr Phe Gly Arg Val Tyr Arg
            420                 425                 430

Ala Glu Phe Asp Asp Gly Lys Val Leu Ala Val Lys Lys Ile Asp Ser
        435                 440                 445

Ser Ala Leu Pro His Gly Met Thr Asp Asp Phe Ile Glu Met Val Ser
    450                 455                 460

Lys Ile Ala Asn Leu Asp His Pro Asn Val Thr Lys Leu Val Gly Tyr
465                 470                 475                 480

Cys Ala Glu His Gly Gln His Leu Val Val Tyr Glu Phe His Lys Asn
                485                 490                 495

Gly Ser Leu His Asp Phe Leu His Leu Ser Glu Glu Ser Lys Ala
            500                 505                 510

Leu Val Trp Asn Ser Arg Val Lys Ile Ala Leu Gly Thr Ala Arg Ala
```

```
                515                 520                 525
Leu Glu Tyr Leu His Glu Val Cys Ser Pro Ser Ile Val Asp Lys Asn
    530                 535                 540

Ile Lys Ser Ala Asn Ile Leu Leu Asp Ser Glu Leu Asn Pro His Leu
545                 550                 555                 560

Ser Asp Ser Gly Leu Ala Ser Phe Leu Pro Thr Ala Asn Glu Leu Leu
                565                 570                 575

Asn Gln Thr Asp Glu Gly Tyr Ser Ala Pro Glu Val Ser Met Ser Gly
            580                 585                 590

Gln Tyr Ser Leu Lys Ser Asp Ile Tyr Ser Phe Gly Val Val Met Leu
        595                 600                 605

Glu Leu Leu Thr Gly Arg Lys Pro Phe Asp Ser Ser Thr Arg Ser Arg
    610                 615                 620

Ser Glu Gln Ser Leu Val Arg Trp Ala Thr Pro Gln Leu His Asp Ile
625                 630                 635                 640

Asp Ala Leu Ala Lys Met Val Asp Pro Ala Leu Lys Gly Leu Tyr Pro
                645                 650                 655

Val Lys Ser Leu Ser Arg Phe Ala Asp Val Ile Ala Leu Cys Val Gln
            660                 665                 670

Pro Glu Pro Glu Phe Arg Pro Pro Met Ser Glu Val Val Gln Ala Leu
        675                 680                 685

Val Val Leu Val Gln Arg Ala Asn Met Ser Lys Arg Thr Val Gly Val
    690                 695                 700

Asp Pro Ser Gln Arg Ala Gly Ser Ala Asp Thr Thr Ser Asp Tyr Met
705                 710                 715                 720

<210> SEQ ID NO 3
<211> LENGTH: 2154
<212> TYPE: DNA
<213> ORGANISM: Arabidopsis thaliana
<220> FEATURE:
<221> NAME/KEY: CDS
<222> LOCATION: (1)..(2154)

<400> SEQUENCE: 3 atg act gag aat cgg gtg gtt ttg gct ctg ctt ata ctc tgc att gtt      48
Met Thr Glu Asn Arg Val Val Leu Ala Leu Leu Ile Leu Cys Ile Val
1               5                   10                  15 ggg ttt gag cca agt ttc atc cat gga gct acg gat tca tca gat act      96
Gly Phe Glu Pro Ser Phe Ile His Gly Ala Thr Asp Ser Ser Asp Thr
            20                  25                  30 tcg gcg tta aac atc atg ttc agc tcc atg aat tct cca gga cag ctc     144
Ser Ala Leu Asn Ile Met Phe Ser Ser Met Asn Ser Pro Gly Gln Leu
        35                  40                  45 tca caa tgg aca gca tca gga ggt gat cct tgt ggc caa aac tgg aaa     192
Ser Gln Trp Thr Ala Ser Gly Gly Asp Pro Cys Gly Gln Asn Trp Lys
    50                  55                  60 ggc ata act tgc tct ggc tct cga gtt aca caa ata aag tta cca agt     240
Gly Ile Thr Cys Ser Gly Ser Arg Val Thr Gln Ile Lys Leu Pro Ser
65                  70                  75                  80 ctt gga ctt tct gga tca ctt gga ttc atg ctt gat aaa ttg act tct     288
Leu Gly Leu Ser Gly Ser Leu Gly Phe Met Leu Asp Lys Leu Thr Ser
                85                  90                  95 gtt act gag ttt gat atg agc aac aat aac ctt gga ggc gat ttg cct     336
Val Thr Glu Phe Asp Met Ser Asn Asn Asn Leu Gly Gly Asp Leu Pro
            100                 105                 110 tat cag ctt cct cca aac ttg gag cga ttg aat ctt gct aat aac cag     384
Tyr Gln Leu Pro Pro Asn Leu Glu Arg Leu Asn Leu Ala Asn Asn Gln
        115                 120                 125
```

| | | | | | | | | | | | | | | | | |
|---|---|---|---|---|---|---|---|---|---|---|---|---|---|---|---|---|
| ttc | act | gga | tct | gct | caa | tat | tcc | att | tct | atg | atg | gct | cct | ctt | aag | 432 |
| Phe | Thr | Gly | Ser | Ala | Gln | Tyr | Ser | Ile | Ser | Met | Met | Ala | Pro | Leu | Lys | |
| | 130 | | | | | 135 | | | | 140 | | | | | | |
| tac | ctc | aac | ctt | gct | cac | aac | cag | ttg | aag | cag | cta | gct | att | gac | ttc | 480 |
| Tyr | Leu | Asn | Leu | Ala | His | Asn | Gln | Leu | Lys | Gln | Leu | Ala | Ile | Asp | Phe | |
| 145 | | | | | 150 | | | | | 155 | | | | | 160 | |
| aca | aaa | ctc | acc | tct | ctc | tct | ata | ttg | gac | ctc | tct | tcc | aat | gct | ttt | 528 |
| Thr | Lys | Leu | Thr | Ser | Leu | Ser | Ile | Leu | Asp | Leu | Ser | Ser | Asn | Ala | Phe | |
| | | | | 165 | | | | | 170 | | | | | 175 | | |
| ata | ggg | tct | ctc | cca | aac | act | tgt | agc | tct | ctt | acg | agt | gca | aaa | tca | 576 |
| Ile | Gly | Ser | Leu | Pro | Asn | Thr | Cys | Ser | Ser | Leu | Thr | Ser | Ala | Lys | Ser | |
| | | | 180 | | | | | 185 | | | | | 190 | | | |
| att | tat | ctt | cag | aac | aat | cag | ttc | tca | ggc | acc | att | gat | att | cta | gcc | 624 |
| Ile | Tyr | Leu | Gln | Asn | Asn | Gln | Phe | Ser | Gly | Thr | Ile | Asp | Ile | Leu | Ala | |
| | | | 195 | | | | | 200 | | | | | 205 | | | |
| acc | ctt | cct | ctc | gaa | aat | ctg | aat | att | gca | aac | aat | cgg | ttc | aca | ggc | 672 |
| Thr | Leu | Pro | Leu | Glu | Asn | Leu | Asn | Ile | Ala | Asn | Asn | Arg | Phe | Thr | Gly | |
| | 210 | | | | | 215 | | | | 220 | | | | | | |
| tgg | atc | cct | gat | tct | ttg | aaa | ggc | att | aac | ttg | caa | aaa | gat | ggc | aat | 720 |
| Trp | Ile | Pro | Asp | Ser | Leu | Lys | Gly | Ile | Asn | Leu | Gln | Lys | Asp | Gly | Asn | |
| 225 | | | | | 230 | | | | | 235 | | | | | 240 | |
| tta | tta | aat | tcc | ggg | cct | gca | cct | cca | cca | cct | cct | ggt | aca | cca | ccg | 768 |
| Leu | Leu | Asn | Ser | Gly | Pro | Ala | Pro | Pro | Pro | Pro | Pro | Gly | Thr | Pro | Pro | |
| | | | | 245 | | | | | 250 | | | | | 255 | | |
| atc | agt | aaa | tca | tca | cct | act | ccg | aaa | tcc | ggg | aac | cgt | gga | aac | cgt | 816 |
| Ile | Ser | Lys | Ser | Ser | Pro | Thr | Pro | Lys | Ser | Gly | Asn | Arg | Gly | Asn | Arg | |
| | | | 260 | | | | | 265 | | | | | 270 | | | |
| tcc | aat | ggt | gat | tcc | agc | aat | agc | aaa | gac | tcc | agc | aaa | tca | ggg | ctt | 864 |
| Ser | Asn | Gly | Asp | Ser | Ser | Asn | Ser | Lys | Asp | Ser | Ser | Lys | Ser | Gly | Leu | |
| | | 275 | | | | | 280 | | | | | 285 | | | | |
| gga | gct | ggt | gga | gta | gca | gga | ata | gtc | att | tct | ttg | ata | gtt | gta | aca | 912 |
| Gly | Ala | Gly | Gly | Val | Ala | Gly | Ile | Val | Ile | Ser | Leu | Ile | Val | Val | Thr | |
| | 290 | | | | | 295 | | | | | 300 | | | | | |
| gca | gtc | ata | gct | ttc | ttc | ttg | atc | aag | aga | aaa | aga | tca | aag | cgg | tca | 960 |
| Ala | Val | Ile | Ala | Phe | Phe | Leu | Ile | Lys | Arg | Lys | Arg | Ser | Lys | Arg | Ser | |
| 305 | | | | | 310 | | | | | 315 | | | | | 320 | |
| tca | tcc | acg | gac | att | gaa | aag | act | gat | aat | aac | att | aac | caa | ccc | att | 1008 |
| Ser | Ser | Thr | Asp | Ile | Glu | Lys | Thr | Asp | Asn | Asn | Ile | Asn | Gln | Pro | Ile | |
| | | | | 325 | | | | | 330 | | | | | 335 | | |
| ata | cta | gcg | tcc | aat | gac | ttt | cat | caa | gag | aat | aag | tct | gta | cag | aat | 1056 |
| Ile | Leu | Ala | Ser | Asn | Asp | Phe | His | Gln | Glu | Asn | Lys | Ser | Val | Gln | Asn | |
| | | | 340 | | | | | 345 | | | | | 350 | | | |
| cca | cca | ttg | gtt | gag | aca | aag | aaa | ctg | gat | acg | tca | ttg | tcg | atg | aat | 1104 |
| Pro | Pro | Leu | Val | Glu | Thr | Lys | Lys | Leu | Asp | Thr | Ser | Leu | Ser | Met | Asn | |
| | | 355 | | | | | 360 | | | | | 365 | | | | |
| cta | cgt | cct | cca | cca | tct | gag | cga | cat | aag | tcg | ttt | gat | gac | gat | gat | 1152 |
| Leu | Arg | Pro | Pro | Pro | Ser | Glu | Arg | His | Lys | Ser | Phe | Asp | Asp | Asp | Asp | |
| | 370 | | | | | 375 | | | | | 380 | | | | | |
| tca | aca | atg | aga | aaa | cct | att | gtt | gca | aag | aaa | gct | gct | gtt | gtt | gtt | 1200 |
| Ser | Thr | Met | Arg | Lys | Pro | Ile | Val | Ala | Lys | Lys | Ala | Ala | Val | Val | Val | |
| 385 | | | | | 390 | | | | | 395 | | | | | 400 | |
| cct | tca | aat | gtg | aac | aca | tat | acg | gtt | tca | gat | ctt | caa | gta | gct | acc | 1248 |
| Pro | Ser | Asn | Val | Asn | Thr | Tyr | Thr | Val | Ser | Asp | Leu | Gln | Val | Ala | Thr | |
| | | | | 405 | | | | | 410 | | | | | 415 | | |
| aac | agt | ttc | agc | gta | gat | aat | ctt | ctc | ggt | gaa | gga | aca | ttt | gga | aga | 1296 |
| Asn | Ser | Phe | Ser | Val | Asp | Asn | Leu | Leu | Gly | Glu | Gly | Thr | Phe | Gly | Arg | |
| | | | 420 | | | | | 425 | | | | | 430 | | | |
| gta | tac | aga | gct | cag | ttt | gaa | gat | gga | aag | gta | ctt | gct | gtg | aag | aaa | 1344 |
| Val | Tyr | Arg | Ala | Gln | Phe | Glu | Asp | Gly | Lys | Val | Leu | Ala | Val | Lys | Lys | |
| | 435 | | | | | 440 | | | | | 445 | | | | | |

```
atc gac tca tct gcg ctt ccc acg gat act gct gat gat ttt acc gaa    1392
Ile Asp Ser Ser Ala Leu Pro Thr Asp Thr Ala Asp Asp Phe Thr Glu
    450                 455                 460 att gta tcg aaa ata gcg cat ttg gat cac gaa aat gtc aca aag ctt    1440
Ile Val Ser Lys Ile Ala His Leu Asp His Glu Asn Val Thr Lys Leu
465                 470                 475                 480 gat ggt tac tgt tct gaa cac ggg caa cac ttg gtg gtc tat gag ttc    1488
Asp Gly Tyr Cys Ser Glu His Gly Gln His Leu Val Val Tyr Glu Phe
                485                 490                 495 cat aga aac ggc tca ttg cat gac ttt tta cat ctt gca gaa gag gaa    1536
His Arg Asn Gly Ser Leu His Asp Phe Leu His Leu Ala Glu Glu Glu
                500                 505                 510 agc aaa ccg ttg ata tgg aat ccc cgt gtc aag atc gct ctt ggc act    1584
Ser Lys Pro Leu Ile Trp Asn Pro Arg Val Lys Ile Ala Leu Gly Thr
            515                 520                 525 gca cgt gca ttg gag tac ttg cat gaa gtt tgc tca cca tct ata gtc    1632
Ala Arg Ala Leu Glu Tyr Leu His Glu Val Cys Ser Pro Ser Ile Val
530                 535                 540 cac aag aac att aaa tca gca aat att tta ctt gac tca gag ctg aat    1680
His Lys Asn Ile Lys Ser Ala Asn Ile Leu Leu Asp Ser Glu Leu Asn
545                 550                 555                 560 cca cac ctc tca gac tca ggt ctc gct agc ttc ctt ccc act gca aac    1728
Pro His Leu Ser Asp Ser Gly Leu Ala Ser Phe Leu Pro Thr Ala Asn
                565                 570                 575 gag cta cta aac caa aac gat gaa gga tac agc gca cca gaa act tca    1776
Glu Leu Leu Asn Gln Asn Asp Glu Gly Tyr Ser Ala Pro Glu Thr Ser
            580                 585                 590 atg tca ggc caa tac tct ttg aag agc gat gtt tac agt ttt gga gta    1824
Met Ser Gly Gln Tyr Ser Leu Lys Ser Asp Val Tyr Ser Phe Gly Val
            595                 600                 605 gtg atg ctc gag ctt tta acc gga aga aaa cca ttc gac agc aca agg    1872
Val Met Leu Glu Leu Leu Thr Gly Arg Lys Pro Phe Asp Ser Thr Arg
        610                 615                 620 tca aga tcg gaa caa tca ttg gta aga tgg gca aca cct cag ctt cac    1920
Ser Arg Ser Glu Gln Ser Leu Val Arg Trp Ala Thr Pro Gln Leu His
625                 630                 635                 640 gac att gat gct ttg ggc aaa atg gtt gat cca gct ctc aaa ggg cta    1968
Asp Ile Asp Ala Leu Gly Lys Met Val Asp Pro Ala Leu Lys Gly Leu
                645                 650                 655 tac ccg gtt aaa tcc ctc tcc cga ttt gca gat gtt atc gcc ctt tgc    2016
Tyr Pro Val Lys Ser Leu Ser Arg Phe Ala Asp Val Ile Ala Leu Cys
            660                 665                 670 gtc cag ccg gag cca gag ttt aga cca ccc atg tct gaa gtg gtg caa    2064
Val Gln Pro Glu Pro Glu Phe Arg Pro Pro Met Ser Glu Val Val Gln
        675                 680                 685 gca ttg gtt gta ttg gtg cag aga gct aac atg agc aag aga act gtt    2112
Ala Leu Val Val Leu Val Gln Arg Ala Asn Met Ser Lys Arg Thr Val
    690                 695                 700 gga gtc ggc tcc ggt agc tcc ggc gtc aat gat tac atg taa            2154
Gly Val Gly Ser Gly Ser Ser Gly Val Asn Asp Tyr Met
705                 710                 715

<210> SEQ ID NO 4
<211> LENGTH: 717
<212> TYPE: PRT
<213> ORGANISM: Arabidopsis thaliana

<400> SEQUENCE: 4

Met Thr Glu Asn Arg Val Val Leu Ala Leu Leu Ile Leu Cys Ile Val
1               5                   10                  15
```

-continued

```
Gly Phe Glu Pro Ser Phe Ile His Gly Ala Thr Asp Ser Ser Asp Thr
             20                  25                  30

Ser Ala Leu Asn Ile Met Phe Ser Met Asn Ser Pro Gly Gln Leu
         35                  40                  45

Ser Gln Trp Thr Ala Ser Gly Gly Asp Pro Cys Gly Gln Asn Trp Lys
 50                  55                  60

Gly Ile Thr Cys Ser Gly Ser Arg Val Thr Gln Ile Lys Leu Pro Ser
 65                  70                  75                  80

Leu Gly Leu Ser Gly Ser Leu Gly Phe Met Leu Asp Lys Leu Thr Ser
                 85                  90                  95

Val Thr Glu Phe Asp Met Ser Asn Asn Leu Gly Gly Asp Leu Pro
            100                 105                 110

Tyr Gln Leu Pro Pro Asn Leu Glu Arg Leu Asn Leu Ala Asn Asn Gln
            115                 120                 125

Phe Thr Gly Ser Ala Gln Tyr Ser Ile Ser Met Met Ala Pro Leu Lys
            130                 135                 140

Tyr Leu Asn Leu Ala His Asn Gln Leu Lys Gln Leu Ala Ile Asp Phe
145                 150                 155                 160

Thr Lys Leu Thr Ser Leu Ser Ile Leu Asp Leu Ser Ser Asn Ala Phe
                165                 170                 175

Ile Gly Ser Leu Pro Asn Thr Cys Ser Ser Leu Thr Ser Ala Lys Ser
            180                 185                 190

Ile Tyr Leu Gln Asn Asn Gln Phe Ser Gly Thr Ile Asp Ile Leu Ala
            195                 200                 205

Thr Leu Pro Leu Glu Asn Leu Asn Ile Ala Asn Asn Arg Phe Thr Gly
210                 215                 220

Trp Ile Pro Asp Ser Leu Lys Gly Ile Asn Leu Gln Lys Asp Gly Asn
225                 230                 235                 240

Leu Leu Asn Ser Gly Pro Ala Pro Pro Pro Pro Gly Thr Pro Pro
            245                 250                 255

Ile Ser Lys Ser Ser Pro Thr Pro Lys Ser Gly Asn Arg Gly Asn Arg
            260                 265                 270

Ser Asn Gly Asp Ser Ser Asn Ser Lys Asp Ser Ser Lys Ser Gly Leu
            275                 280                 285

Gly Ala Gly Gly Val Ala Gly Ile Val Ile Ser Leu Ile Val Val Thr
            290                 295                 300

Ala Val Ile Ala Phe Phe Leu Ile Lys Arg Lys Arg Ser Lys Arg Ser
305                 310                 315                 320

Ser Ser Thr Asp Ile Glu Lys Thr Asp Asn Asn Ile Asn Gln Pro Ile
            325                 330                 335

Ile Leu Ala Ser Asn Asp Phe His Gln Glu Asn Lys Ser Val Gln Asn
            340                 345                 350

Pro Pro Leu Val Glu Thr Lys Lys Leu Asp Thr Ser Leu Ser Met Asn
            355                 360                 365

Leu Arg Pro Pro Pro Ser Glu Arg His Lys Ser Phe Asp Asp Asp
            370                 375                 380

Ser Thr Met Arg Lys Pro Ile Val Ala Lys Ala Ala Val Val Val
385                 390                 395                 400

Pro Ser Asn Val Asn Thr Tyr Thr Val Ser Asp Leu Gln Val Ala Thr
            405                 410                 415

Asn Ser Phe Ser Val Asp Asn Leu Leu Gly Glu Gly Thr Phe Gly Arg
            420                 425                 430

Val Tyr Arg Ala Gln Phe Glu Asp Gly Lys Val Leu Ala Val Lys Lys
            435                 440                 445
```

```
Ile Asp Ser Ser Ala Leu Pro Thr Asp Thr Ala Asp Asp Phe Thr Glu
    450                 455                 460
Ile Val Ser Lys Ile Ala His Leu Asp His Glu Asn Val Thr Lys Leu
465                 470                 475                 480
Asp Gly Tyr Cys Ser Glu His Gly Gln His Leu Val Val Tyr Glu Phe
                485                 490                 495
His Arg Asn Gly Ser Leu His Asp Phe Leu His Leu Ala Glu Glu Glu
            500                 505                 510
Ser Lys Pro Leu Ile Trp Asn Pro Arg Val Lys Ile Ala Leu Gly Thr
        515                 520                 525
Ala Arg Ala Leu Glu Tyr Leu His Glu Val Cys Ser Pro Ser Ile Val
    530                 535                 540
His Lys Asn Ile Lys Ser Ala Asn Ile Leu Leu Asp Ser Glu Leu Asn
545                 550                 555                 560
Pro His Leu Ser Asp Ser Gly Leu Ala Ser Phe Leu Pro Thr Ala Asn
                565                 570                 575
Glu Leu Leu Asn Gln Asn Asp Glu Gly Tyr Ser Ala Pro Glu Thr Ser
            580                 585                 590
Met Ser Gly Gln Tyr Ser Leu Lys Ser Asp Val Tyr Ser Phe Gly Val
        595                 600                 605
Val Met Leu Glu Leu Leu Thr Gly Arg Lys Pro Phe Asp Ser Thr Arg
    610                 615                 620
Ser Arg Ser Glu Gln Ser Leu Val Arg Trp Ala Thr Pro Gln Leu His
625                 630                 635                 640
Asp Ile Asp Ala Leu Gly Lys Met Val Asp Pro Ala Leu Lys Gly Leu
                645                 650                 655
Tyr Pro Val Lys Ser Leu Ser Arg Phe Ala Asp Val Ile Ala Leu Cys
            660                 665                 670
Val Gln Pro Glu Pro Glu Phe Arg Pro Pro Met Ser Glu Val Val Gln
        675                 680                 685
Ala Leu Val Val Leu Val Gln Arg Ala Asn Met Ser Lys Arg Thr Val
    690                 695                 700
Gly Val Gly Ser Gly Ser Ser Gly Val Asn Asp Tyr Met
705                 710                 715

<210> SEQ ID NO 5
<211> LENGTH: 2328
<212> TYPE: DNA
<213> ORGANISM: Arabidopsis thaliana
<220> FEATURE:
<221> NAME/KEY: CDS
<222> LOCATION: (1)..(2328)

<400> SEQUENCE: 5 atg aga tcg atg aga tct ggg aga gac aac aac atc tgc ttc ctg ggt      48
Met Arg Ser Met Arg Ser Gly Arg Asp Asn Asn Ile Cys Phe Leu Gly
1               5                   10                  15 ttt ctg tcc ttt gcc ctt atc tcc ctt ccc tcc ttg tca ctt gct ctt      96
Phe Leu Ser Phe Ala Leu Ile Ser Leu Pro Ser Leu Ser Leu Ala Leu
            20                  25                  30 acc aat cct gac gat gtt gcg gct att aac agt ctc ttc ctt gca ctg     144
Thr Asn Pro Asp Asp Val Ala Ala Ile Asn Ser Leu Phe Leu Ala Leu
        35                  40                  45 gag tct cct ctt ctc ccc ggt tgg gtt gca tct gga ggt gac cca tgt     192
Glu Ser Pro Leu Leu Pro Gly Trp Val Ala Ser Gly Gly Asp Pro Cys
    50                  55                  60 ggg gag agt tgg caa ggt gtt cta tgt aat gct tcc caa gta gaa aca     240
```

-continued

| | | | | | | | | | | | | | | | | |
|---|---|---|---|---|---|---|---|---|---|---|---|---|---|---|---|---|
|Gly|Glu|Ser|Trp|Gln|Gly|Val|Leu|Cys|Asn|Ala|Ser|Gln|Val|Glu|Thr| |
|65| | | |70| | | |75| | | |80| | | | |

```
ata att ctc atc agt gcc aat ctt gga gga gag ctt ggt gtt ggc tta      288
Ile Ile Leu Ile Ser Ala Asn Leu Gly Gly Glu Leu Gly Val Gly Leu
                85                  90                  95 aac atg ttt acc tct ctt aaa gca atg gat ttt agc aac aat cac att      336
Asn Met Phe Thr Ser Leu Lys Ala Met Asp Phe Ser Asn Asn His Ile
        100                 105                 110 gga gga agt atc cca tcc acg tta cct gtt tca ttg cag aac ttg ttt      384
Gly Gly Ser Ile Pro Ser Thr Leu Pro Val Ser Leu Gln Asn Leu Phe
            115                 120                 125 ctt tca ggt aac aac ttt aca gga acc atc cca gaa tct ctt tcc tcc      432
Leu Ser Gly Asn Asn Phe Thr Gly Thr Ile Pro Glu Ser Leu Ser Ser
130                 135                 140 tta aaa tct ttg tct gtc atg tcc ttg aac aat aac cta ttg tct ggc      480
Leu Lys Ser Leu Ser Val Met Ser Leu Asn Asn Asn Leu Leu Ser Gly
145                 150                 155                 160 aag ata ccc gat gtc ttt caa gac ctt ggc ctt atg atc aat ata gat      528
Lys Ile Pro Asp Val Phe Gln Asp Leu Gly Leu Met Ile Asn Ile Asp
                165                 170                 175 ttg tca agc aac aat ctg agt gga cca tta cct cct tcc atg cag aat      576
Leu Ser Ser Asn Asn Leu Ser Gly Pro Leu Pro Pro Ser Met Gln Asn
        180                 185                 190 ctt tcg aat ctt aca tcc ttg ctt ttg cag aac aat cat ctt tca gga      624
Leu Ser Asn Leu Thr Ser Leu Leu Leu Gln Asn Asn His Leu Ser Gly
            195                 200                 205 gag ctt gat gtt ctt caa gat ctt ccc ctc aag gac ttg aac gtt gag      672
Glu Leu Asp Val Leu Gln Asp Leu Pro Leu Lys Asp Leu Asn Val Glu
210                 215                 220 aac aac ctc ttc aat gga cct ata cca gaa aag ttg ttg agt ata cca      720
Asn Asn Leu Phe Asn Gly Pro Ile Pro Glu Lys Leu Leu Ser Ile Pro
225                 230                 235                 240 aat ttc ata aaa ggc ggt aac ctg ttt aac gtc act att gct cca tcg      768
Asn Phe Ile Lys Gly Gly Asn Leu Phe Asn Val Thr Ile Ala Pro Ser
                245                 250                 255 cct tca cct gaa aca cct cca agt cca aca tca cct aag cgg ccg ttt      816
Pro Ser Pro Glu Thr Pro Pro Ser Pro Thr Ser Pro Lys Arg Pro Phe
        260                 265                 270 ttt gga cca cca tct ccc aat gca tca act ggt cat ggt cag gca cac      864
Phe Gly Pro Pro Ser Pro Asn Ala Ser Thr Gly His Gly Gln Ala His
            275                 280                 285 gtg aga tca ccc cct tct gat cat cac cca tcc cga cca act cct caa      912
Val Arg Ser Pro Pro Ser Asp His His Pro Ser Arg Pro Thr Pro Gln
290                 295                 300 ggg aaa gaa gac tca ttt acc agt aaa aga att att tgg ata tcc att      960
Gly Lys Glu Asp Ser Phe Thr Ser Lys Arg Ile Ile Trp Ile Ser Ile
305                 310                 315                 320 ctt ggg gct ttt tca ttt gtg gtt ttg gcc ttg gta tgt cta ctt tgt     1008
Leu Gly Ala Phe Ser Phe Val Val Leu Ala Leu Val Cys Leu Leu Cys
                325                 330                 335 ggg aga aaa tgt ctc aga aaa aga gaa gac agt gaa caa cta tcc aaa     1056
Gly Arg Lys Cys Leu Arg Lys Arg Glu Asp Ser Glu Gln Leu Ser Lys
        340                 345                 350 ccg cac cta act agt gaa tac ggg aag gca agg gag ggt tct cgc tca     1104
Pro His Leu Thr Ser Glu Tyr Gly Lys Ala Arg Glu Gly Ser Arg Ser
            355                 360                 365 aat gct tct atg ctt cct cca tcc aat aca ttc aat aaa gac aag gag     1152
Asn Ala Ser Met Leu Pro Pro Ser Asn Thr Phe Asn Lys Asp Lys Glu
370                 375                 380 gct aaa cca aaa gag aga gta gga ggt gct ttg aag ctg cag ggt ggg     1200
Ala Lys Pro Lys Glu Arg Val Gly Gly Ala Leu Lys Leu Gln Gly Gly
```

```
Ala Lys Pro Lys Glu Arg Val Gly Gly Ala Leu Lys Leu Gln Gly Gly
385                 390                 395                 400 gca aaa aga agc gta gga agt aag tca aag cag gag agt cat gag ata      1248
Ala Glu Arg Ser Val Gly Ser Lys Ser Lys Gln Glu Ser His Glu Ile
            405                 410                 415 gac atg aat gac aat gct atg gat ttg atg cat ccc tca tca att cca      1296
Asp Met Asn Asp Asn Ala Met Asp Leu Met His Pro Ser Ser Ile Pro
        420                 425                 430 cct atc aaa agg gtc atc gca aag gcg aat gaa cct gct gaa gca tct      1344
Pro Ile Lys Arg Val Ile Ala Lys Ala Asn Glu Pro Ala Glu Ala Ser
    435                 440                 445 cta aaa aag aca tcc agt aaa tcc cat ggt ccc ttg aca gct gtg aag      1392
Leu Lys Lys Thr Ser Ser Lys Ser His Gly Pro Leu Thr Ala Val Lys
450                 455                 460 cat ttc acg gtc gca tct cta caa caa cac aca aat aac ttt tcc ctc      1440
His Phe Thr Val Ala Ser Leu Gln Gln His Thr Asn Asn Phe Ser Leu
465                 470                 475                 480 gaa aac ctt att gga aca ggc atg ctt ggg agt gtc tac agg gca gag      1488
Glu Asn Leu Ile Gly Thr Gly Met Leu Gly Ser Val Tyr Arg Ala Glu
            485                 490                 495 ctt cca ggt gga aag ctc ttg gct gtg aag aag ttg gat aag aag tct      1536
Leu Pro Gly Gly Lys Leu Leu Ala Val Lys Lys Leu Asp Lys Lys Ser
        500                 505                 510 ccc aat cat gaa gaa gaa ggg aaa ttt gtg gag cta gtg aat aac ata      1584
Pro Asn His Glu Glu Glu Gly Lys Phe Val Glu Leu Val Asn Asn Ile
    515                 520                 525 gat aga atc cgg cat gcc aac att gtc caa ctc gtt ggt ttt tgt tct      1632
Asp Arg Ile Arg His Ala Asn Ile Val Gln Leu Val Gly Phe Cys Ser
530                 535                 540 gag cac agt caa agg ctt ctg atc cat gag tac tgc agg aac ggt aca      1680
Glu His Ser Gln Arg Leu Leu Ile His Glu Tyr Cys Arg Asn Gly Thr
545                 550                 555                 560 ctg cac gat ttg ctg cat act gat gac aga ttg aag att gaa cta tca      1728
Leu His Asp Leu Leu His Thr Asp Asp Arg Leu Lys Ile Glu Leu Ser
            565                 570                 575 tgg aat atc cgt gtt agg atg gca cta gaa gct gca aaa gct ctg gag      1776
Trp Asn Ile Arg Val Arg Met Ala Leu Glu Ala Ala Lys Ala Leu Glu
        580                 585                 590 tat ctg cat gag atc tgt gat cta cct agt atc cac caa aat ttc aag      1824
Tyr Leu His Glu Ile Cys Asp Leu Pro Ser Ile His Gln Asn Phe Lys
    595                 600                 605 tct gca aat att ctc ctt gat gac gat atg agg gtg cat gtc tca gac      1872
Ser Ala Asn Ile Leu Leu Asp Asp Asp Met Arg Val His Val Ser Asp
610                 615                 620 tgc ggc ttg gct cct cta atc tcc tca ggt gcc gta agt cag tta tcc      1920
Cys Gly Leu Ala Pro Leu Ile Ser Ser Gly Ala Val Ser Gln Leu Ser
625                 630                 635                 640 ggt caa ctc tta gcg gcc tac gga tat gga gct cca gag ttt gaa tat      1968
Gly Gln Leu Leu Ala Ala Tyr Gly Tyr Gly Ala Pro Glu Phe Glu Tyr
            645                 650                 655 ggg atc tat aca atg aaa tgt gat gtc tac agt ttt gga gta gtt atg      2016
Gly Ile Tyr Thr Met Lys Cys Asp Val Tyr Ser Phe Gly Val Val Met
        660                 665                 670 tta gaa ctc ttg aca ggc cgc aag tca tat gac aag aaa cgg gat aga      2064
Leu Glu Leu Leu Thr Gly Arg Lys Ser Tyr Asp Lys Lys Arg Asp Arg
    675                 680                 685 gga gag cag ttt ctg gtg aga tgg gca atc cca cag ctt cac gac att      2112
Gly Glu Gln Phe Leu Val Arg Trp Ala Ile Pro Gln Leu His Asp Ile
690                 695                 700 gat gca tta gag aag atg gtc gac cca tct ctc aag ggt gac tat cca      2160
```

-continued

```
                Asp Ala Leu Glu Lys Met Val Asp Pro Ser Leu Lys Gly Asp Tyr Pro
                705                 710                 715                 720 gcc aag tcg ctg tca cac ttt gct gat gta ata tca cgt tgt gtt cag          2208
Ala Lys Ser Leu Ser His Phe Ala Asp Val Ile Ser Arg Cys Val Gln
                725                 730                 735 tcg gaa cca gag ttc agg cca cta atg tca gaa gtg gtt caa gac ctc          2256
Ser Glu Pro Glu Phe Arg Pro Leu Met Ser Glu Val Val Gln Asp Leu
            740                 745                 750 tca gac atg atc cag aga gaa cat cgg aga aat gac tca aat ggg gat          2304
Ser Asp Met Ile Gln Arg Glu His Arg Arg Asn Asp Ser Asn Gly Asp
        755                 760                 765 aat cag tat acg aga aga aga tag                                          2328
Asn Gln Tyr Thr Arg Arg Arg
    770                 775
```

<210> SEQ ID NO 6
<211> LENGTH: 775
<212> TYPE: PRT
<213> ORGANISM: Arabidopsis thaliana

<400> SEQUENCE: 6

```
Met Arg Ser Met Arg Ser Gly Arg Asp Asn Asn Ile Cys Phe Leu Gly
1               5                   10                  15

Phe Leu Ser Phe Ala Leu Ile Ser Leu Pro Ser Leu Ser Leu Ala Leu
                20                  25                  30

Thr Asn Pro Asp Asp Val Ala Ala Ile Asn Ser Leu Phe Leu Ala Leu
            35                  40                  45

Glu Ser Pro Leu Leu Pro Gly Trp Val Ala Ser Gly Gly Asp Pro Cys
        50                  55                  60

Gly Glu Ser Trp Gln Gly Val Leu Cys Asn Ala Ser Gln Val Glu Thr
65                  70                  75                  80

Ile Ile Leu Ile Ser Ala Asn Leu Gly Gly Glu Leu Gly Val Gly Leu
                85                  90                  95

Asn Met Phe Thr Ser Leu Lys Ala Met Asp Phe Ser Asn Asn His Ile
                100                 105                 110

Gly Gly Ser Ile Pro Ser Thr Leu Pro Val Ser Leu Gln Asn Leu Phe
            115                 120                 125

Leu Ser Gly Asn Asn Phe Thr Gly Thr Ile Pro Glu Ser Leu Ser Ser
        130                 135                 140

Leu Lys Ser Leu Ser Val Met Ser Leu Asn Asn Leu Leu Ser Gly
145                 150                 155                 160

Lys Ile Pro Asp Val Phe Gln Asp Leu Gly Leu Met Ile Asn Ile Asp
                165                 170                 175

Leu Ser Ser Asn Asn Leu Ser Gly Pro Leu Pro Pro Ser Met Gln Asn
                180                 185                 190

Leu Ser Asn Leu Thr Ser Leu Leu Gln Asn Asn His Leu Ser Gly
            195                 200                 205

Glu Leu Asp Val Leu Gln Asp Leu Pro Leu Lys Asp Leu Asn Val Glu
        210                 215                 220

Asn Asn Leu Phe Asn Gly Pro Ile Pro Glu Lys Leu Leu Ser Ile Pro
225                 230                 235                 240

Asn Phe Ile Lys Gly Gly Asn Leu Phe Asn Val Thr Ile Ala Pro Ser
                245                 250                 255

Pro Ser Pro Glu Thr Pro Pro Ser Thr Ser Pro Lys Arg Pro Phe
            260                 265                 270

Phe Gly Pro Pro Ser Pro Asn Ala Ser Thr Gly His Gly Gln Ala His
        275                 280                 285
```

```
Val Arg Ser Pro Pro Ser Asp His His Pro Ser Arg Pro Thr Pro Gln
    290                 295                 300

Gly Lys Glu Asp Ser Phe Thr Ser Lys Arg Ile Ile Trp Ile Ser Ile
305                 310                 315                 320

Leu Gly Ala Phe Ser Phe Val Val Leu Ala Leu Val Cys Leu Leu Cys
                325                 330                 335

Gly Arg Lys Cys Leu Arg Lys Arg Glu Asp Ser Glu Gln Leu Ser Lys
            340                 345                 350

Pro His Leu Thr Ser Glu Tyr Gly Lys Ala Arg Glu Gly Ser Arg Ser
        355                 360                 365

Asn Ala Ser Met Leu Pro Pro Ser Asn Thr Phe Asn Lys Asp Lys Glu
    370                 375                 380

Ala Lys Pro Lys Glu Arg Val Gly Gly Ala Leu Lys Leu Gln Gly Gly
385                 390                 395                 400

Ala Glu Arg Ser Val Gly Ser Lys Ser Lys Gln Glu Ser His Glu Ile
                405                 410                 415

Asp Met Asn Asp Asn Ala Met Asp Leu Met His Pro Ser Ser Ile Pro
            420                 425                 430

Pro Ile Lys Arg Val Ile Ala Lys Ala Asn Glu Pro Ala Glu Ala Ser
        435                 440                 445

Leu Lys Lys Thr Ser Ser Lys Ser His Gly Pro Leu Thr Ala Val Lys
    450                 455                 460

His Phe Thr Val Ala Ser Leu Gln Gln His Thr Asn Asn Phe Ser Leu
465                 470                 475                 480

Glu Asn Leu Ile Gly Thr Gly Met Leu Gly Ser Val Tyr Arg Ala Glu
                485                 490                 495

Leu Pro Gly Gly Lys Leu Leu Ala Val Lys Lys Leu Asp Lys Lys Ser
            500                 505                 510

Pro Asn His Glu Glu Glu Gly Lys Phe Val Glu Leu Val Asn Asn Ile
        515                 520                 525

Asp Arg Ile Arg His Ala Asn Ile Val Gln Leu Val Gly Phe Cys Ser
    530                 535                 540

Glu His Ser Gln Arg Leu Leu Ile His Glu Tyr Cys Arg Asn Gly Thr
545                 550                 555                 560

Leu His Asp Leu Leu His Thr Asp Asp Arg Leu Lys Ile Glu Leu Ser
                565                 570                 575

Trp Asn Ile Arg Val Arg Met Ala Leu Glu Ala Ala Lys Ala Leu Glu
            580                 585                 590

Tyr Leu His Glu Ile Cys Asp Leu Pro Ser Ile His Gln Asn Phe Lys
        595                 600                 605

Ser Ala Asn Ile Leu Leu Asp Asp Asp Met Arg Val His Val Ser Asp
    610                 615                 620

Cys Gly Leu Ala Pro Leu Ile Ser Ser Gly Ala Val Ser Gln Leu Ser
625                 630                 635                 640

Gly Gln Leu Leu Ala Ala Tyr Gly Tyr Gly Ala Pro Glu Phe Glu Tyr
                645                 650                 655

Gly Ile Tyr Thr Met Lys Cys Asp Val Tyr Ser Phe Gly Val Val Met
            660                 665                 670

Leu Glu Leu Leu Thr Gly Arg Lys Ser Tyr Asp Lys Lys Arg Asp Arg
        675                 680                 685

Gly Glu Gln Phe Leu Val Arg Trp Ala Ile Pro Gln Leu His Asp Ile
    690                 695                 700

Asp Ala Leu Glu Lys Met Val Asp Pro Ser Leu Lys Gly Asp Tyr Pro
```

| | | | |
|---|---|---|---|
| Ala Lys Ser Leu Ser His Phe Ala Asp Val Ile Ser Arg Cys Val Gln | | | |
| 705 | 710 | 715 | 720 |
| Ser Glu Pro Glu Phe Arg Pro Leu Met Ser Glu Val Val Gln Asp Leu | | | |
| | 725 | 730 | 735 |
| Ser Asp Met Ile Gln Arg Glu His Arg Arg Asn Asp Ser Asn Gly Asp | | | |
| | 740 | 745 | 750 |
| Asn Gln Tyr Thr Arg Arg Arg | | | |
| | 755 | 760 | 765 |
| 770 | 775 | | |

```
<210> SEQ ID NO 7
<211> LENGTH: 2319
<212> TYPE: DNA
<213> ORGANISM: Arabidopsis thaliana
<220> FEATURE:
<221> NAME/KEY: CDS
<222> LOCATION: (1)..(2319)

<400> SEQUENCE: 7
```

| | | | | | | | | | | | | | | | | |
|---|---|---|---|---|---|---|---|---|---|---|---|---|---|---|---|---|
| atg | aga | tct | ggg | aga | gac | aac | aac | atc | tgc | ttc | ctg | ggt | ttt | ctc | tcc | 48 |
| Met | Arg | Ser | Gly | Arg | Asp | Asn | Asn | Ile | Cys | Phe | Leu | Gly | Phe | Leu | Ser | |
| 1 | | | | 5 | | | | | 10 | | | | | 15 | | |
| ttt | gcc | ctt | atc | tcc | ctt | ccc | tcc | ttg | tca | ctt | gct | ctt | acc | aat | cct | 96 |
| Phe | Ala | Leu | Ile | Ser | Leu | Pro | Ser | Leu | Ser | Leu | Ala | Leu | Thr | Asn | Pro | |
| | | | 20 | | | | | 25 | | | | | 30 | | | |
| gac | gat | gtt | gcg | gct | att | aac | agt | ctc | ttc | ctt | gca | ctg | gag | tct | cct | 144 |
| Asp | Asp | Val | Ala | Ala | Ile | Asn | Ser | Leu | Phe | Leu | Ala | Leu | Glu | Ser | Pro | |
| | | 35 | | | | | 40 | | | | | 45 | | | | |
| ctt | ctc | ccc | ggt | tgg | gtt | gca | tct | gga | ggt | gac | cca | tgt | ggt | gag | agc | 192 |
| Leu | Leu | Pro | Gly | Trp | Val | Ala | Ser | Gly | Gly | Asp | Pro | Cys | Gly | Glu | Ser | |
| | 50 | | | | | 55 | | | | | 60 | | | | | |
| tgg | caa | ggt | gtt | cta | tgt | aat | gct | tcc | caa | gta | gaa | aca | ata | att | ctc | 240 |
| Trp | Gln | Gly | Val | Leu | Cys | Asn | Ala | Ser | Gln | Val | Glu | Thr | Ile | Ile | Leu | |
| 65 | | | | | 70 | | | | | 75 | | | | | 80 | |
| atc | agt | gcc | aat | ctt | gga | gga | gag | ctt | ggt | gtt | ggc | tta | aac | atg | ttt | 288 |
| Ile | Ser | Ala | Asn | Leu | Gly | Gly | Glu | Leu | Gly | Val | Gly | Leu | Asn | Met | Phe | |
| | | | | 85 | | | | | 90 | | | | | 95 | | |
| acc | tct | ctt | aaa | gca | atg | gat | ttt | agc | aac | aat | cac | att | gga | gga | agt | 336 |
| Thr | Ser | Leu | Lys | Ala | Met | Asp | Phe | Ser | Asn | Asn | His | Ile | Gly | Gly | Ser | |
| | | | 100 | | | | | 105 | | | | | 110 | | | |
| atc | cca | tcc | acg | ttg | cct | gtt | tca | ttg | cag | aac | ttg | ttt | ctt | tca | ggt | 384 |
| Ile | Pro | Ser | Thr | Leu | Pro | Val | Ser | Leu | Gln | Asn | Leu | Phe | Leu | Ser | Gly | |
| | | 115 | | | | | 120 | | | | | 125 | | | | |
| aac | aac | ttt | aca | gga | acc | atc | cca | gaa | tct | ctt | tcc | tcc | tta | aaa | tct | 432 |
| Asn | Asn | Phe | Thr | Gly | Thr | Ile | Pro | Glu | Ser | Leu | Ser | Ser | Leu | Lys | Ser | |
| | 130 | | | | | 135 | | | | | 140 | | | | | |
| ttg | tct | gtc | atg | tcc | ttg | aac | aat | aac | ctt | ttg | tct | ggc | aag | ata | ccc | 480 |
| Leu | Ser | Val | Met | Ser | Leu | Asn | Asn | Asn | Leu | Leu | Ser | Gly | Lys | Ile | Pro | |
| 145 | | | | | 150 | | | | | 155 | | | | | 160 | |
| gat | gtc | ttt | caa | gac | ctt | ggc | ctt | atg | atc | aat | ata | gat | ttg | tct | agc | 528 |
| Asp | Val | Phe | Gln | Asp | Leu | Gly | Leu | Met | Ile | Asn | Ile | Asp | Leu | Ser | Ser | |
| | | | | 165 | | | | | 170 | | | | | 175 | | |
| aac | aat | ctg | agt | gga | cca | tta | cct | cct | tcc | atg | cag | aat | ctt | tcg | act | 576 |
| Asn | Asn | Leu | Ser | Gly | Pro | Leu | Pro | Pro | Ser | Met | Gln | Asn | Leu | Ser | Thr | |
| | | | 180 | | | | | 185 | | | | | 190 | | | |
| ctc | aca | tcc | ttg | ctt | ttg | cag | aac | aat | cat | ctt | tca | gga | gag | ctt | gat | 624 |
| Leu | Thr | Ser | Leu | Leu | Leu | Gln | Asn | Asn | His | Leu | Ser | Gly | Glu | Leu | Asp | |
| | | 195 | | | | | 200 | | | | | 205 | | | | |
| gtt | ctt | caa | gat | ctt | ccc | ctc | aag | gac | ttg | aac | gtt | gag | aac | aac | ctc | 672 |
| Val | Leu | Gln | Asp | Leu | Pro | Leu | Lys | Asp | Leu | Asn | Val | Glu | Asn | Asn | Leu | |
| | 210 | | | | | 215 | | | | | 220 | | | | | |

| | | |
|---|---|---|
| ttc aat gga cct ata cca gaa aag ttg ttg agt ata cca aat ttc ata<br>Phe Asn Gly Pro Ile Pro Glu Lys Leu Leu Ser Ile Pro Asn Phe Ile<br>225                         230                          235                        240 | 720 |
| aaa ggc ggt aat ctg ttt aac gtc act att gct cca tcg cct tca cct<br>Lys Gly Gly Asn Leu Phe Asn Val Thr Ile Ala Pro Ser Pro Ser Pro<br>                      245                          250                        255 | 768 |
| gaa aca cct cca agt cca aca tca cct aag cgg cca ttt ttt gga cca<br>Glu Thr Pro Pro Ser Pro Thr Ser Pro Lys Arg Pro Phe Phe Gly Pro<br>260                         265                         270 | 816 |
| cca tct ccc aat gca tca gct ggt cat ggt cag gca cac gtg aga tca<br>Pro Ser Pro Asn Ala Ser Ala Gly His Gly Gln Ala His Val Arg Ser<br>                      275                       280                       285 | 864 |
| ccc cct tct gat cat cac cca tcc cga cca act cct caa ggg aaa gaa<br>Pro Pro Ser Asp His His Pro Ser Arg Pro Thr Pro Gln Gly Lys Glu<br>290                         295                         300 | 912 |
| gac tca ttt acc agt aaa aga att att tgg ata tcc att ctt ggg gct<br>Asp Ser Phe Thr Ser Lys Arg Ile Ile Trp Ile Ser Ile Leu Gly Ala<br>305                         310                         315                  320 | 960 |
| ttt tca ttt gtg gtt ttg gcc ttg gta tgt cta ctt tgt ggg aga aaa<br>Phe Ser Phe Val Val Leu Ala Leu Val Cys Leu Leu Cys Gly Arg Lys<br>                      325                       330                       335 | 1008 |
| tgt ctc aga aaa aga gaa gac agt gaa caa cta tcc aaa ccg cac cta<br>Cys Leu Arg Lys Arg Glu Asp Ser Glu Gln Leu Ser Lys Pro His Leu<br>                    340                       345                     350 | 1056 |
| act agt gaa tac ggg agg gca agg gag ggt tct cgc tca aat gct tct<br>Thr Ser Glu Tyr Gly Arg Ala Arg Glu Gly Ser Arg Ser Asn Ala Ser<br>                355                       360                     365 | 1104 |
| atg ctt cct cca tcc aat aca ttc aat aaa gac aag gag gct aga cca<br>Met Leu Pro Pro Ser Asn Thr Phe Asn Lys Asp Lys Glu Ala Arg Pro<br>370                         375                         380 | 1152 |
| aaa gag aga gta gga ggt gct tcg aag ctg cat ggt ggg gca gaa aga<br>Lys Glu Arg Val Gly Gly Ala Ser Lys Leu His Gly Gly Ala Glu Arg<br>385                         390                         395                  400 | 1200 |
| agc gta gga agt gaa tca aag cag gag agt cat gag ata gac atg aat<br>Ser Val Gly Ser Glu Ser Lys Gln Glu Ser His Glu Ile Asp Met Asn<br>                      405                       410                     415 | 1248 |
| ggc aat gct atg gat ttg atg cat ccc tca tca att cca cct atc aaa<br>Gly Asn Ala Met Asp Leu Met His Pro Ser Ser Ile Pro Pro Ile Lys<br>                420                       425                     430 | 1296 |
| agg gtc atc gca aag gcg act gaa cct gct gaa gca tct cta aaa agg<br>Arg Val Ile Ala Lys Ala Thr Glu Pro Ala Glu Ala Ser Leu Lys Arg<br>                435                       440                     445 | 1344 |
| aca acc agt aaa tcc cat ggt ccc ttg aca gct gtg aag cat ttc acg<br>Thr Thr Ser Lys Ser His Gly Pro Leu Thr Ala Val Lys His Phe Thr<br>450                         455                         460 | 1392 |
| gtc gca tct cta caa caa cac aca aat agc ttt tcc cac gaa aac ctt<br>Val Ala Ser Leu Gln Gln His Thr Asn Ser Phe Ser His Glu Asn Leu<br>465                         470                         475                  480 | 1440 |
| att gga aca ggc atg ctt ggg agt gtc tac agg gca gag ctt cca ggt<br>Ile Gly Thr Gly Met Leu Gly Ser Val Tyr Arg Ala Glu Leu Pro Gly<br>                        485                       490                     495 | 1488 |
| gga aag ctc ttc gct gtg agg aag ttg gat aag aag tct ccc aat cat<br>Gly Lys Leu Phe Ala Val Arg Lys Leu Asp Lys Lys Ser Pro Asn His<br>                  500                       505                     510 | 1536 |
| gaa gaa gaa ggc aaa ttt ttg gag cta gtg aat aat ata gat aga ata<br>Glu Glu Glu Gly Lys Phe Leu Glu Leu Val Asn Asn Ile Asp Arg Ile<br>              515                       520                     525 | 1584 |
| cgg cat gcc aat att gtc caa ctc gtg ggt ttc tgt tct gag cac agt<br>Arg His Ala Asn Ile Val Gln Leu Val Gly Phe Cys Ser Glu His Ser<br>530                         535                         540 | 1632 |

| | | | | | | | | | | | | | | |
|---|---|---|---|---|---|---|---|---|---|---|---|---|---|---|
| caa | agg | ctt | ctg | atc | cat | gag | tat | tgt | agg | aac | ggt | aca | ctg | cac gat | 1680 |
| Gln | Arg | Leu | Leu | Ile | His | Glu | Tyr | Cys | Arg | Asn | Gly | Thr | Leu | His Asp |
| 545 | | | | 550 | | | | | 555 | | | | | 560 |

| | | | | | | | | | | | | | | | |
|---|---|---|---|---|---|---|---|---|---|---|---|---|---|---|---|
| ttg | ctg | cat | att | gat | gac | agg | ttg | aag | att | gaa | cta | tca | tgg | aat gtc | 1728 |
| Leu | Leu | His | Ile | Asp | Asp | Arg | Leu | Lys | Ile | Glu | Leu | Ser | Trp | Asn Val |
| | | | | 565 | | | | | 570 | | | | | 575 |

| | | | | | | | | | | | | | | | |
|---|---|---|---|---|---|---|---|---|---|---|---|---|---|---|---|
| cgt | gtt | agg | att | gca | cta | gaa | gct | gca | aaa | gct | ctg | gag | tat | ctg cat | 1776 |
| Arg | Val | Arg | Ile | Ala | Leu | Glu | Ala | Ala | Lys | Ala | Leu | Glu | Tyr | Leu His |
| | | | | 580 | | | | | 585 | | | | | 590 |

| | | | | | | | | | | | | | | | |
|---|---|---|---|---|---|---|---|---|---|---|---|---|---|---|---|
| gag | atc | tgt | gat | cca | cct | agt | atc | cac | cga | aat | ttc | aag | tct | gca aat | 1824 |
| Glu | Ile | Cys | Asp | Pro | Pro | Ser | Ile | His | Arg | Asn | Phe | Lys | Ser | Ala Asn |
| | | | | 595 | | | | | 600 | | | | | 605 |

| | | | | | | | | | | | | | | | |
|---|---|---|---|---|---|---|---|---|---|---|---|---|---|---|---|
| att | ctc | ctt | gat | gac | gat | ata | agg | gtg | cat | gtc | tca | gac | tgc | ggc ttg | 1872 |
| Ile | Leu | Leu | Asp | Asp | Asp | Ile | Arg | Val | His | Val | Ser | Asp | Cys | Gly Leu |
| | | | | 610 | | | | | 615 | | | | | 620 |

| | | | | | | | | | | | | | | | |
|---|---|---|---|---|---|---|---|---|---|---|---|---|---|---|---|
| gct | cct | cta | atc | tcc | tca | ggt | gcc | gta | agt | cag | tta | tcg | ggt | caa ctc | 1920 |
| Ala | Pro | Leu | Ile | Ser | Ser | Gly | Ala | Val | Ser | Gln | Leu | Ser | Gly | Gln Leu |
| 625 | | | | 630 | | | | | 635 | | | | | 640 |

| | | | | | | | | | | | | | | | |
|---|---|---|---|---|---|---|---|---|---|---|---|---|---|---|---|
| tta | gcg | gcc | tac | gga | tat | gga | gct | cca | gag | ttt | gaa | tat | ggg | atc tat | 1968 |
| Leu | Ala | Ala | Tyr | Gly | Tyr | Gly | Ala | Pro | Glu | Phe | Glu | Tyr | Gly | Ile Tyr |
| | | | | 645 | | | | | 650 | | | | | 655 |

| | | | | | | | | | | | | | | | |
|---|---|---|---|---|---|---|---|---|---|---|---|---|---|---|---|
| aca | atg | aaa | tgt | gat | gtc | tac | agt | ttt | gga | gta | gtt | atg | tta | gaa ctc | 2016 |
| Thr | Met | Lys | Cys | Asp | Val | Tyr | Ser | Phe | Gly | Val | Val | Met | Leu | Glu Leu |
| | | | | 660 | | | | | 665 | | | | | 670 |

| | | | | | | | | | | | | | | | |
|---|---|---|---|---|---|---|---|---|---|---|---|---|---|---|---|
| ttg | aca | ggt | cgc | aag | tca | tat | gac | aag | aaa | cgg | gat | aga | gga | gag caa | 2064 |
| Leu | Thr | Gly | Arg | Lys | Ser | Tyr | Asp | Lys | Lys | Arg | Asp | Arg | Gly | Glu Gln |
| 675 | | | | | 680 | | | | | 685 | | | | |

| | | | | | | | | | | | | | | | |
|---|---|---|---|---|---|---|---|---|---|---|---|---|---|---|---|
| ttt | ctg | gtg | aga | tgg | gca | atc | cca | cag | ctt | cac | gac | att | gat | gca tta | 2112 |
| Phe | Leu | Val | Arg | Trp | Ala | Ile | Pro | Gln | Leu | His | Asp | Ile | Asp | Ala Leu |
| 690 | | | | | 695 | | | | | 700 | | | | |

| | | | | | | | | | | | | | | | |
|---|---|---|---|---|---|---|---|---|---|---|---|---|---|---|---|
| gcg | aag | atg | gtc | gac | cca | tcc | ctc | aag | ggt | gac | tat | cca | gcc | aag tcg | 2160 |
| Ala | Lys | Met | Val | Asp | Pro | Ser | Leu | Lys | Gly | Asp | Tyr | Pro | Ala | Lys Ser |
| 705 | | | | | 710 | | | | | 715 | | | | | 720 |

| | | | | | | | | | | | | | | | |
|---|---|---|---|---|---|---|---|---|---|---|---|---|---|---|---|
| ttg | tca | cac | ttt | gct | gat | gtg | ata | tca | cgt | tgt | gtt | cag | tcg | gaa cca | 2208 |
| Leu | Ser | His | Phe | Ala | Asp | Val | Ile | Ser | Arg | Cys | Val | Gln | Ser | Glu Pro |
| | | | | 725 | | | | | 730 | | | | | 735 |

| | | | | | | | | | | | | | | | |
|---|---|---|---|---|---|---|---|---|---|---|---|---|---|---|---|
| gag | tac | agg | cca | cta | atg | tcg | gaa | gtg | gtt | caa | gac | ctc | tca | gac atg | 2256 |
| Glu | Tyr | Arg | Pro | Leu | Met | Ser | Glu | Val | Val | Gln | Asp | Leu | Ser | Asp Met |
| | | | | 740 | | | | | 745 | | | | | 750 |

| | | | | | | | | | | | | | | | |
|---|---|---|---|---|---|---|---|---|---|---|---|---|---|---|---|
| atc | cag | aga | gaa | cat | cgg | aga | aat | gac | tca | aat | ggg | gat | aat | cag tat | 2304 |
| Ile | Gln | Arg | Glu | His | Arg | Arg | Asn | Asp | Ser | Asn | Gly | Asp | Asn | Gln Tyr |
| | | | | 755 | | | | | 760 | | | | | 765 |

| | | | |
|---|---|---|---|
| acg | gga | aga | aga tag | 2319 |
| Thr | Gly | Arg | Arg |
| 770 | | | |

<210> SEQ ID NO 8
<211> LENGTH: 772
<212> TYPE: PRT
<213> ORGANISM: Arabidopsis thaliana

<400> SEQUENCE: 8

Met Arg Ser Gly Arg Asp Asn Asn Ile Cys Phe Leu Gly Phe Leu Ser
1               5                   10                  15

Phe Ala Leu Ile Ser Leu Pro Ser Leu Ser Leu Ala Leu Thr Asn Pro
            20                  25                  30

Asp Asp Val Ala Ala Ile Asn Ser Leu Phe Leu Ala Leu Glu Ser Pro
        35                  40                  45

Leu Leu Pro Gly Trp Val Ala Ser Gly Gly Asp Pro Cys Gly Glu Ser
    50                  55                  60

```
Trp Gln Gly Val Leu Cys Asn Ala Ser Gln Val Glu Thr Ile Ile Leu
 65                  70                  75                  80

Ile Ser Ala Asn Leu Gly Gly Glu Leu Gly Val Gly Leu Asn Met Phe
                 85                  90                  95

Thr Ser Leu Lys Ala Met Asp Phe Ser Asn Asn His Ile Gly Gly Ser
            100                 105                 110

Ile Pro Ser Thr Leu Pro Val Ser Leu Gln Asn Leu Phe Leu Ser Gly
        115                 120                 125

Asn Asn Phe Thr Gly Thr Ile Pro Glu Ser Leu Ser Ser Leu Lys Ser
    130                 135                 140

Leu Ser Val Met Ser Leu Asn Asn Asn Leu Leu Ser Gly Lys Ile Pro
145                 150                 155                 160

Asp Val Phe Gln Asp Leu Gly Leu Met Ile Asn Ile Asp Leu Ser Ser
                165                 170                 175

Asn Asn Leu Ser Gly Pro Leu Pro Ser Met Gln Asn Leu Ser Thr
            180                 185                 190

Leu Thr Ser Leu Leu Leu Gln Asn Asn His Leu Ser Gly Glu Leu Asp
        195                 200                 205

Val Leu Gln Asp Leu Pro Leu Lys Asp Leu Asn Val Glu Asn Asn Leu
    210                 215                 220

Phe Asn Gly Pro Ile Pro Glu Lys Leu Leu Ser Ile Pro Asn Phe Ile
225                 230                 235                 240

Lys Gly Gly Asn Leu Phe Asn Val Thr Ile Ala Pro Ser Pro Ser Pro
                245                 250                 255

Glu Thr Pro Pro Ser Pro Thr Ser Pro Lys Arg Pro Phe Phe Gly Pro
            260                 265                 270

Pro Ser Pro Asn Ala Ser Ala Gly His Gly Gln Ala His Val Arg Ser
        275                 280                 285

Pro Pro Ser Asp His His Pro Ser Arg Pro Thr Pro Gln Gly Lys Glu
    290                 295                 300

Asp Ser Phe Thr Ser Lys Arg Ile Ile Trp Ile Ser Ile Leu Gly Ala
305                 310                 315                 320

Phe Ser Phe Val Val Leu Ala Leu Val Cys Leu Leu Cys Gly Arg Lys
                325                 330                 335

Cys Leu Arg Lys Arg Glu Asp Ser Glu Gln Leu Ser Lys Pro His Leu
            340                 345                 350

Thr Ser Glu Tyr Gly Arg Ala Arg Glu Gly Ser Arg Ser Asn Ala Ser
        355                 360                 365

Met Leu Pro Pro Ser Asn Thr Phe Asn Lys Asp Lys Glu Ala Arg Pro
    370                 375                 380

Lys Glu Arg Val Gly Gly Ala Ser Lys Leu His Gly Gly Ala Glu Arg
385                 390                 395                 400

Ser Val Gly Ser Glu Ser Lys Gln Glu Ser His Glu Ile Asp Met Asn
                405                 410                 415

Gly Asn Ala Met Asp Leu Met His Pro Ser Ile Pro Pro Ile Lys
            420                 425                 430

Arg Val Ile Ala Lys Ala Thr Glu Pro Ala Glu Ala Ser Leu Lys Arg
        435                 440                 445

Thr Thr Ser Lys Ser His Gly Pro Leu Thr Ala Val Lys His Phe Thr
    450                 455                 460

Val Ala Ser Leu Gln Gln His Thr Asn Ser Phe Ser His Glu Asn Leu
465                 470                 475                 480

Ile Gly Thr Gly Met Leu Gly Ser Val Tyr Arg Ala Glu Leu Pro Gly
```

```
                        485                 490                 495
Gly Lys Leu Phe Ala Val Arg Lys Leu Asp Lys Lys Ser Pro Asn His
                500                 505                 510
Glu Glu Glu Gly Lys Phe Leu Glu Leu Val Asn Asn Ile Asp Arg Ile
            515                 520                 525
Arg His Ala Asn Ile Val Gln Leu Val Gly Phe Cys Ser Glu His Ser
        530                 535                 540
Gln Arg Leu Leu Ile His Glu Tyr Cys Arg Asn Gly Thr Leu His Asp
545                 550                 555                 560
Leu Leu His Ile Asp Asp Arg Leu Lys Ile Glu Leu Ser Trp Asn Val
                565                 570                 575
Arg Val Arg Ile Ala Leu Glu Ala Ala Lys Ala Leu Glu Tyr Leu His
            580                 585                 590
Glu Ile Cys Asp Pro Pro Ser Ile His Arg Asn Phe Lys Ser Ala Asn
        595                 600                 605
Ile Leu Leu Asp Asp Ile Arg Val His Val Ser Asp Cys Gly Leu
        610                 615                 620
Ala Pro Leu Ile Ser Ser Gly Ala Val Ser Gln Leu Ser Gly Gln Leu
625                 630                 635                 640
Leu Ala Ala Tyr Gly Tyr Gly Ala Pro Glu Phe Glu Tyr Gly Ile Tyr
                645                 650                 655
Thr Met Lys Cys Asp Val Tyr Ser Phe Gly Val Val Met Leu Glu Leu
            660                 665                 670
Leu Thr Gly Arg Lys Ser Tyr Asp Lys Lys Arg Asp Arg Gly Glu Gln
        675                 680                 685
Phe Leu Val Arg Trp Ala Ile Pro Gln Leu His Asp Ile Asp Ala Leu
        690                 695                 700
Ala Lys Met Val Asp Pro Ser Leu Lys Gly Asp Tyr Pro Ala Lys Ser
705                 710                 715                 720
Leu Ser His Phe Ala Asp Val Ile Ser Arg Cys Val Gln Ser Glu Pro
                725                 730                 735
Glu Tyr Arg Pro Leu Met Ser Glu Val Val Gln Asp Leu Ser Asp Met
            740                 745                 750
Ile Gln Arg Glu His Arg Arg Asn Asp Ser Asn Gly Asp Asn Gln Tyr
        755                 760                 765
Thr Gly Arg Arg
    770

<210> SEQ ID NO 9
<211> LENGTH: 1263
<212> TYPE: DNA
<213> ORGANISM: Arabidopsis thaliana
<220> FEATURE:
<221> NAME/KEY: CDS
<222> LOCATION: (1)..(1263)

<400> SEQUENCE: 9 atg aga tcg atg aga tct ggg aga gac aac aac atc tgc ttc ctg ggt      48
Met Arg Ser Met Arg Ser Gly Arg Asp Asn Asn Ile Cys Phe Leu Gly
1               5                   10                  15 ttt ctc tcc ttt gcc ctt atc tcc ctt ccc tcc ttg tca ctt gct ctt      96
Phe Leu Ser Phe Ala Leu Ile Ser Leu Pro Ser Leu Ser Leu Ala Leu
            20                  25                  30 acc aat cct gac gat gtt gcg gct att aac agt ctc ttc ctt gca ctg     144
Thr Asn Pro Asp Asp Val Ala Ala Ile Asn Ser Leu Phe Leu Ala Leu
        35                  40                  45 gag tct cct ctt ctc ccc ggt tgg gtt gca tct gga ggt gac cca tgt     192
```

|     |     |     |     |     |     |     |     |     |     |     |     |     |
| --- | --- | --- | --- | --- | --- | --- | --- | --- | --- | --- | --- | --- |
| Glu | Ser | Pro | Leu | Leu | Pro | Gly | Trp | Val | Ala | Ser | Gly | Gly | Asp | Pro | Cys |
|     | 50  |     |     |     | 55  |     |     |     | 60  |     |     |     |

```
ggt gag agc tgg caa ggt gtt cta tgt aat gct tcc caa gta gaa aca        240
Gly Glu Ser Trp Gln Gly Val Leu Cys Asn Ala Ser Gln Val Glu Thr
 65          70                  75                  80 ata att ctc atc agt gcc aat ctt gga gga gag ctt ggt gtt ggc tta        288
Ile Ile Leu Ile Ser Ala Asn Leu Gly Gly Glu Leu Gly Val Gly Leu
             85                  90                  95 aac atg ttt acc tct ctt aaa gca atg gat ttt agc aac aat cac att        336
Asn Met Phe Thr Ser Leu Lys Ala Met Asp Phe Ser Asn Asn His Ile
100                 105                 110 gga gga agt atc cca tcc acg ttg cct gtt tca ttg cag aac ttg ttt        384
Gly Gly Ser Ile Pro Ser Thr Leu Pro Val Ser Leu Gln Asn Leu Phe
        115                 120                 125 ctt tca ggt aac aac ttt aca gga acc atc cca gaa tct ctt tcc tcc        432
Leu Ser Gly Asn Asn Phe Thr Gly Thr Ile Pro Glu Ser Leu Ser Ser
130                 135                 140 tta aaa tct ttg tct gtc atg tcc ttg aac aat aac ctt ttg tct ggc        480
Leu Lys Ser Leu Ser Val Met Ser Leu Asn Asn Asn Leu Leu Ser Gly
145                 150                 155                 160 aag ata ccc gat gtc ttt caa gac ctt ggc ctt atg atc aat ata gat        528
Lys Ile Pro Asp Val Phe Gln Asp Leu Gly Leu Met Ile Asn Ile Asp
                165                 170                 175 ttg tct agc aac aat ctg agt gga cca tta cct cct tcc atg cag aat        576
Leu Ser Ser Asn Asn Leu Ser Gly Pro Leu Pro Pro Ser Met Gln Asn
            180                 185                 190 ctt tcg act ctc aca tcc ttg ctt ttg cag aac aat cat ctt tca gga        624
Leu Ser Thr Leu Thr Ser Leu Leu Leu Gln Asn Asn His Leu Ser Gly
        195                 200                 205 gag ctt gat gtt ctt caa gat ctt ccc ctc aag gac ttg aac gtt gag        672
Glu Leu Asp Val Leu Gln Asp Leu Pro Leu Lys Asp Leu Asn Val Glu
210                 215                 220 aac aac ctc ttc aat gga cct ata cca gaa aag ttg ttg agt ata cca        720
Asn Asn Leu Phe Asn Gly Pro Ile Pro Glu Lys Leu Leu Ser Ile Pro
225                 230                 235                 240 aat ttc ata aaa ggc ggt aat ctg ttt aac gtc act att gct cca tcg        768
Asn Phe Ile Lys Gly Gly Asn Leu Phe Asn Val Thr Ile Ala Pro Ser
                245                 250                 255 cct tca cct gaa aca cct cca agt cca aca tca cct aag cgg cca ttt        816
Pro Ser Pro Glu Thr Pro Pro Ser Pro Thr Ser Pro Lys Arg Pro Phe
            260                 265                 270 ttt gga cca cca tct ccc aat gca tca gct ggt cat ggt cag gca cac        864
Phe Gly Pro Pro Ser Pro Asn Ala Ser Ala Gly His Gly Gln Ala His
        275                 280                 285 gtg aga tca ccc cct tct gat cat cac cca tcc cga cca act cct caa        912
Val Arg Ser Pro Pro Ser Asp His His Pro Ser Arg Pro Thr Pro Gln
290                 295                 300 ggg aaa gaa gac tca ttt acc agt aaa aga att att tgg ata tcc att        960
Gly Lys Glu Asp Ser Phe Thr Ser Lys Arg Ile Ile Trp Ile Ser Ile
305                 310                 315                 320 ctt ggg gct ttt tca ttt gtg gtt ttg gcc ttg gta tgt cta ctt tgt       1008
Leu Gly Ala Phe Ser Phe Val Val Leu Ala Leu Val Cys Leu Leu Cys
                325                 330                 335 ggg aga aaa tgt ctc aga aaa aga gaa gac agt gaa caa cta tcc aaa       1056
Gly Arg Lys Cys Leu Arg Lys Arg Glu Asp Ser Glu Gln Leu Ser Lys
            340                 345                 350 ccg cac cta act agt gaa tac ggg agg gca agg gag ggt tct cgc tca       1104
Pro His Leu Thr Ser Glu Tyr Gly Arg Ala Arg Glu Gly Ser Arg Ser
        355                 360                 365 aat gct tct atg ctt cct cca tcc aat aca ttc aat aaa ggt gaa atc       1152
Asn Ala Ser Met Leu Pro Pro Ser Asn Thr Phe Asn Lys Gly Glu Ile
```

-continued

| | | | | | | | | | | | | |
|---|---|---|---|---|---|---|---|---|---|---|---|---|
| Asn | Ala | Ser | Met | Leu | Pro | Pro | Ser | Asn | Thr | Phe | Asn | Lys | Gly | Glu | Ile |
| | 370 | | | | 375 | | | | 380 | | | |

```
tca tat ctt gat ttc ttc act ttt aga ttt caa gaa agt cac atg ttt    1200
Ser Tyr Leu Asp Phe Phe Thr Phe Arg Phe Gln Glu Ser His Met Phe
385             390                 395                 400 gtt ttc tct tct tca atg aaa ttc aaa caa aag aca agg agg cta gac    1248
Val Phe Ser Ser Ser Met Lys Phe Lys Gln Lys Thr Arg Arg Leu Asp
                405                 410                 415 caa aag aga gag tag                                                 1263
Gln Lys Arg Glu
            420

<210> SEQ ID NO 10
<211> LENGTH: 420
<212> TYPE: PRT
<213> ORGANISM: Arabidopsis thaliana

<400> SEQUENCE: 10
```

Met Arg Ser Met Arg Ser Gly Arg Asp Asn Asn Ile Cys Phe Leu Gly
1               5                   10                  15

Phe Leu Ser Phe Ala Leu Ile Ser Leu Pro Ser Leu Ser Leu Ala Leu
                20                  25                  30

Thr Asn Pro Asp Asp Val Ala Ala Ile Asn Ser Leu Phe Leu Ala Leu
            35                  40                  45

Glu Ser Pro Leu Leu Pro Gly Trp Val Ala Ser Gly Gly Asp Pro Cys
50              55                  60

Gly Glu Ser Trp Gln Gly Val Leu Cys Asn Ala Ser Gln Val Glu Thr
65                  70                  75                  80

Ile Ile Leu Ile Ser Ala Asn Leu Gly Gly Glu Leu Gly Val Gly Leu
                85                  90                  95

Asn Met Phe Thr Ser Leu Lys Ala Met Asp Phe Ser Asn Asn His Ile
                100                 105                 110

Gly Gly Ser Ile Pro Ser Thr Leu Pro Val Ser Leu Gln Asn Leu Phe
            115                 120                 125

Leu Ser Gly Asn Asn Phe Thr Gly Thr Ile Pro Glu Ser Leu Ser Ser
130                 135                 140

Leu Lys Ser Leu Ser Val Met Ser Leu Asn Asn Asn Leu Leu Ser Gly
145                 150                 155                 160

Lys Ile Pro Asp Val Phe Gln Asp Leu Gly Leu Met Ile Asn Ile Asp
                165                 170                 175

Leu Ser Ser Asn Asn Leu Ser Gly Pro Leu Pro Pro Ser Met Gln Asn
            180                 185                 190

Leu Ser Thr Leu Thr Ser Leu Leu Leu Gln Asn Asn His Leu Ser Gly
        195                 200                 205

Glu Leu Asp Val Leu Gln Asp Leu Pro Leu Lys Asp Leu Asn Val Glu
210                 215                 220

Asn Asn Leu Phe Asn Gly Pro Ile Pro Gly Lys Leu Leu Ser Ile Pro
225                 230                 235                 240

Asn Phe Ile Lys Gly Gly Asn Leu Phe Asn Val Thr Ile Ala Pro Ser
                245                 250                 255

Pro Ser Pro Glu Thr Pro Pro Ser Pro Thr Ser Pro Lys Arg Pro Phe
            260                 265                 270

Phe Gly Pro Pro Ser Pro Asn Ala Ser Ala Gly His Gly Gln Ala His
        275                 280                 285

Val Arg Ser Pro Pro Ser Asp His His Pro Ser Arg Pro Thr Pro Gln
290                 295                 300

```
Gly Lys Glu Asp Ser Phe Thr Ser Lys Arg Ile Ile Trp Ile Ser Ile
305                 310                 315                 320

Leu Gly Ala Phe Ser Phe Val Val Leu Ala Leu Val Cys Leu Leu Cys
            325                 330                 335

Gly Arg Lys Cys Leu Arg Lys Arg Glu Asp Ser Glu Gln Leu Ser Lys
        340                 345                 350

Pro His Leu Thr Ser Glu Tyr Gly Arg Ala Arg Glu Gly Ser Arg Ser
    355                 360                 365

Asn Ala Ser Met Leu Pro Pro Ser Asn Thr Phe Asn Lys Gly Glu Ile
370                 375                 380

Ser Tyr Leu Asp Phe Phe Thr Phe Arg Phe Gln Glu Ser His Met Phe
385                 390                 395                 400

Val Phe Ser Ser Ser Met Lys Phe Lys Gln Lys Thr Arg Arg Leu Asp
            405                 410                 415

Gln Lys Arg Glu
            420

<210> SEQ ID NO 11
<211> LENGTH: 1263
<212> TYPE: DNA
<213> ORGANISM: Arabidopsis thaliana
<220> FEATURE:
<221> NAME/KEY: CDS
<222> LOCATION: (1)..(1263)

<400> SEQUENCE: 11 atg aga tcg atg aga tct ggg aga gac aac aac atc tgc ttc ctg ggt      48
Met Arg Ser Met Arg Ser Gly Arg Asp Asn Asn Ile Cys Phe Leu Gly
1               5                   10                  15 ttt ctg tcc ttt gcc ctt atc tcc ctt ccc tcc ttg tca ctt gct ctt      96
Phe Leu Ser Phe Ala Leu Ile Ser Leu Pro Ser Leu Ser Leu Ala Leu
                20                  25                  30 acc aat cct gac gat gtt gcg gct att aac agt ctc ttc ctt gca ctg     144
Thr Asn Pro Asp Asp Val Ala Ala Ile Asn Ser Leu Phe Leu Ala Leu
            35                  40                  45 gag tct cct ctt ctc ccc ggt tgg gtt gca tct gga ggt gac cca tgt     192
Glu Ser Pro Leu Leu Pro Gly Trp Val Ala Ser Gly Gly Asp Pro Cys
        50                  55                  60 ggg gag agt tgg caa ggt gtt cta tgt aat gct tcc caa gta gaa aca     240
Gly Glu Ser Trp Gln Gly Val Leu Cys Asn Ala Ser Gln Val Glu Thr
65                  70                  75                  80 ata att ctc atc agt gcc aat ctt gga gga gag ctt ggt gtt ggc tta     288
Ile Ile Leu Ile Ser Ala Asn Leu Gly Gly Glu Leu Gly Val Gly Leu
                85                  90                  95 aac atg ttt acc tct ctt aaa gca atg gat ttt agc aac aat cac att     336
Asn Met Phe Thr Ser Leu Lys Ala Met Asp Phe Ser Asn Asn His Ile
                100                 105                 110 gga gga agt atc cca tcc acg tta cct gtt tca ttg cag aac ttg ttt     384
Gly Gly Ser Ile Pro Ser Thr Leu Pro Val Ser Leu Gln Asn Leu Phe
            115                 120                 125 ctt tca ggt aac aac ttt aca gga acc atc cca gaa tct ctt tcc tcc     432
Leu Ser Gly Asn Asn Phe Thr Gly Thr Ile Pro Glu Ser Leu Ser Ser
        130                 135                 140 tta aaa tct ttg tct gtc atg tcc ttg aac aat aac cta ttg tct ggc     480
Leu Lys Ser Leu Ser Val Met Ser Leu Asn Asn Asn Leu Leu Ser Gly
145                 150                 155                 160 aag ata ccc gat gtc ttt caa gac ctt ggc ctt atg atc aat ata gat     528
Lys Ile Pro Asp Val Phe Gln Asp Leu Gly Leu Met Ile Asn Ile Asp
                165                 170                 175 ttg tca agc aac aat ctg agt gga cca tta cct cct tcc atg cag aat     576
```

```
Leu Ser Ser Asn Asn Leu Ser Gly Pro Leu Pro Ser Met Gln Asn
            180                 185                 190 ctt tcg aat ctt aca tcc ttg ctt ttg cag aac aat cat ctt tca gga        624
Leu Ser Asn Leu Thr Ser Leu Leu Leu Gln Asn Asn His Leu Ser Gly
        195                 200                 205 gag ctt gat gtt ctt caa gat ctt ccc ctc aag gac ttg aac gtt gag        672
Glu Leu Asp Val Leu Gln Asp Leu Pro Leu Lys Asp Leu Asn Val Glu
    210                 215                 220 aac aac ctc ttc aat gga cct ata cca gaa aag ttg ttg agt ata cca        720
Asn Asn Leu Phe Asn Gly Pro Ile Pro Glu Lys Leu Leu Ser Ile Pro
225                 230                 235                 240 aat ttc ata aaa ggc ggt aac ctg ttt aac gtc act att gct cca tcg        768
Asn Phe Ile Lys Gly Gly Asn Leu Phe Asn Val Thr Ile Ala Pro Ser
                245                 250                 255 cct tca cct gaa aca cct cca agt cca aca tca cct aag cgg ccg ttt        816
Pro Ser Pro Glu Thr Pro Pro Ser Pro Thr Ser Pro Lys Arg Pro Phe
            260                 265                 270 ttt gga cca cca tct ccc aat gca tca act ggt cat ggt cag gca cac        864
Phe Gly Pro Pro Ser Pro Asn Ala Ser Thr Gly His Gly Gln Ala His
        275                 280                 285 gtg aga tca ccc cct tct gat cat cac cca tcc cga cca act cct caa        912
Val Arg Ser Pro Pro Ser Asp His His Pro Ser Arg Pro Thr Pro Gln
    290                 295                 300 ggg aaa gaa gac tca ttt acc agt aaa aga att att tgg ata tcc att        960
Gly Lys Glu Asp Ser Phe Thr Ser Lys Arg Ile Ile Trp Ile Ser Ile
305                 310                 315                 320 ctt ggg gct ttt tca ttt gtg gtt ttg gcc ttg gta tgt cta ctt tgt        1008
Leu Gly Ala Phe Ser Phe Val Val Leu Ala Leu Val Cys Leu Leu Cys
                325                 330                 335 ggg aga aaa tgt ctc aga aaa aga gaa gac agt gaa caa cta tcc aaa        1056
Gly Arg Lys Cys Leu Arg Lys Arg Glu Asp Ser Glu Gln Leu Ser Lys
            340                 345                 350 ccg cac cta act agt gaa tac ggg aag gca agg gag ggt tct cgc tca        1104
Pro His Leu Thr Ser Glu Tyr Gly Lys Ala Arg Glu Gly Ser Arg Ser
        355                 360                 365 aat gct tct atg ctt cct cca tcc aat aca ttc aat aaa ggt gaa atc        1152
Asn Ala Ser Met Leu Pro Pro Ser Asn Thr Phe Asn Lys Gly Glu Ile
    370                 375                 380 tca tat ctt gat ttc ttc act ttt aga ttt caa gaa aat cac atg ttt        1200
Ser Tyr Leu Asp Phe Phe Thr Phe Arg Phe Gln Glu Asn His Met Phe
385                 390                 395                 400 gtt ttc tct cct tca atg aaa ttc aaa caa aag aca agg agg cta aac        1248
Val Phe Ser Pro Ser Met Lys Phe Lys Gln Lys Thr Arg Arg Leu Asn
                405                 410                 415 caa aag aga gag tag                                                    1263
Gln Lys Arg Glu
        420

<210> SEQ ID NO 12
<211> LENGTH: 420
<212> TYPE: PRT
<213> ORGANISM: Arabidopsis thaliana

<400> SEQUENCE: 12

Met Arg Ser Met Arg Ser Gly Arg Asp Asn Asn Ile Cys Phe Leu Gly
1               5                   10                  15

Phe Leu Ser Phe Ala Leu Ile Ser Leu Pro Ser Leu Ser Leu Ala Leu
            20                  25                  30

Thr Asn Pro Asp Asp Val Ala Ala Ile Asn Ser Leu Phe Leu Ala Leu
        35                  40                  45
```

Glu Ser Pro Leu Leu Pro Gly Trp Val Ala Ser Gly Gly Asp Pro Cys
 50                  55                  60

Gly Glu Ser Trp Gln Gly Val Leu Cys Asn Ala Ser Gln Val Glu Thr
 65                  70                  75                  80

Ile Ile Leu Ile Ser Ala Asn Leu Gly Gly Glu Leu Gly Val Gly Leu
                 85                  90                  95

Asn Met Phe Thr Ser Leu Lys Ala Met Asp Phe Ser Asn Asn His Ile
                100                 105                 110

Gly Gly Ser Ile Pro Ser Thr Leu Pro Val Ser Leu Gln Asn Leu Phe
            115                 120                 125

Leu Ser Gly Asn Asn Phe Thr Gly Thr Ile Pro Glu Ser Leu Ser Ser
130                 135                 140

Leu Lys Ser Leu Ser Val Met Ser Leu Asn Asn Asn Leu Leu Ser Gly
145                 150                 155                 160

Lys Ile Pro Asp Val Phe Gln Asp Leu Gly Leu Met Ile Asn Ile Asp
                165                 170                 175

Leu Ser Ser Asn Asn Leu Ser Gly Pro Leu Pro Pro Ser Met Gln Asn
                180                 185                 190

Leu Ser Asn Leu Thr Ser Leu Leu Leu Gln Asn Asn His Leu Ser Gly
            195                 200                 205

Glu Leu Asp Val Leu Gln Asp Leu Pro Leu Lys Asp Leu Asn Val Glu
210                 215                 220

Asn Asn Leu Phe Asn Gly Pro Ile Pro Glu Lys Leu Leu Ser Ile Pro
225                 230                 235                 240

Asn Phe Ile Lys Gly Gly Asn Leu Phe Asn Val Thr Ile Ala Pro Ser
                245                 250                 255

Pro Ser Pro Glu Thr Pro Pro Ser Pro Thr Ser Pro Lys Arg Pro Phe
                260                 265                 270

Phe Gly Pro Pro Ser Pro Asn Ala Ser Thr Gly His Gly Gln Ala His
            275                 280                 285

Val Arg Ser Pro Pro Ser Asp His His Pro Ser Arg Pro Thr Pro Gln
290                 295                 300

Gly Lys Glu Asp Ser Phe Thr Ser Lys Arg Ile Ile Trp Ile Ser Ile
305                 310                 315                 320

Leu Gly Ala Phe Ser Phe Val Val Leu Ala Leu Val Cys Leu Leu Cys
                325                 330                 335

Gly Arg Lys Cys Leu Arg Lys Arg Glu Asp Ser Glu Gln Leu Ser Lys
                340                 345                 350

Pro His Leu Thr Ser Glu Tyr Gly Lys Ala Arg Glu Gly Ser Arg Ser
            355                 360                 365

Asn Ala Ser Met Leu Pro Pro Ser Asn Thr Phe Asn Lys Gly Glu Ile
370                 375                 380

Ser Tyr Leu Asp Phe Pro Thr Phe Arg Phe Gln Glu Asn His Met Phe
385                 390                 395                 400

Val Phe Ser Pro Ser Met Lys Phe Lys Gln Lys Thr Arg Arg Leu Asn
                405                 410                 415

Gln Lys Arg Glu
            420

<210> SEQ ID NO 13
<211> LENGTH: 2208
<212> TYPE: DNA
<213> ORGANISM: Arabidopsis thaliana
<220> FEATURE:
<221> NAME/KEY: CDS
<222> LOCATION: (1)..(2208)

<400> SEQUENCE: 13

```
atg aaa acc aaa cag caa ttg cga ttc ctc gct aca att ctg ctc acg       48
Met Lys Thr Lys Gln Gln Leu Arg Phe Leu Ala Thr Ile Leu Leu Thr
1               5                   10                  15 acg att cta ttt gtt ctg gcg aag act gat act gat ccg ctt gaa gtt       96
Thr Ile Leu Phe Val Leu Ala Lys Thr Asp Thr Asp Pro Leu Glu Val
                20                  25                  30 ttg gct ctt caa gat ctc tac aag tct ctg aga aat cca gaa cag ctg      144
Leu Ala Leu Gln Asp Leu Tyr Lys Ser Leu Arg Asn Pro Glu Gln Leu
            35                  40                  45 aga gga tgg aga tta gag ggt gga gat cca tgc gga gaa gcc tgg ctg      192
Arg Gly Trp Arg Leu Glu Gly Gly Asp Pro Cys Gly Glu Ala Trp Leu
        50                  55                  60 gga att tct tgt tct ggt tct tct ata gta gac cta caa ctg cga gag      240
Gly Ile Ser Cys Ser Gly Ser Ser Ile Val Asp Leu Gln Leu Arg Glu
65                  70                  75                  80 tta aag ctt ttg ggc agc ctt gga aac cag ctt caa cat ctc cac aat      288
Leu Lys Leu Leu Gly Ser Leu Gly Asn Gln Leu Gln His Leu His Asn
                85                  90                  95 ttg aag att ctg gat gta agc ttc aat aac ctt gag ggt gaa att ccg      336
Leu Lys Ile Leu Asp Val Ser Phe Asn Asn Leu Glu Gly Glu Ile Pro
            100                 105                 110 ttt ggc ttg cct cct aac gct act cat ata aac atg gct tac aac aat      384
Phe Gly Leu Pro Pro Asn Ala Thr His Ile Asn Met Ala Tyr Asn Asn
        115                 120                 125 ctg acc caa agt atc cct ttt tcc tta cct ctt atg aca tct ctt cag      432
Leu Thr Gln Ser Ile Pro Phe Ser Leu Pro Leu Met Thr Ser Leu Gln
    130                 135                 140 tct tta aat ttg agc cat aat tca tta tct gga cct ctt gga aat gtg      480
Ser Leu Asn Leu Ser His Asn Ser Leu Ser Gly Pro Leu Gly Asn Val
145                 150                 155                 160 ttc tct ggg tta cag att aaa gaa atg gat ctg tca ttc aat aac ctg      528
Phe Ser Gly Leu Gln Ile Lys Glu Met Asp Leu Ser Phe Asn Asn Leu
                165                 170                 175 acg gga gat cta ccg agc tct ttt ggg act cta atg aat ctg act tca      576
Thr Gly Asp Leu Pro Ser Ser Phe Gly Thr Leu Met Asn Leu Thr Ser
            180                 185                 190 ctg tac ctc cag aac aac aga tta aca gga tca gtc ata tat ctc gcg      624
Leu Tyr Leu Gln Asn Asn Arg Leu Thr Gly Ser Val Ile Tyr Leu Ala
        195                 200                 205 gat ctt cct tta gct gac ctg aac atc gaa gat aac cag ttc agt ggt      672
Asp Leu Pro Leu Ala Asp Leu Asn Ile Glu Asp Asn Gln Phe Ser Gly
    210                 215                 220 att atc cca agt cat ttt cag tcc att cct cat ctg tgg att tgg gga      720
Ile Ile Pro Ser His Phe Gln Ser Ile Pro His Leu Trp Ile Trp Gly
225                 230                 235                 240 aac aag ttc cat gta gag ccc aac tat aaa ccg tgg aag ttc cca ttg      768
Asn Lys Phe His Val Glu Pro Asn Tyr Lys Pro Trp Lys Phe Pro Leu
                245                 250                 255 gac gtc aga cca ctg ata caa aat gat act ggc tat cca aca aca gag      816
Asp Val Arg Pro Leu Ile Gln Asn Asp Thr Gly Tyr Pro Thr Thr Glu
            260                 265                 270 tca agt gcc att atg aat ttt ccc aga cct gag act cag aag gtc aaa      864
Ser Ser Ala Ile Met Asn Phe Pro Arg Pro Glu Thr Gln Lys Val Lys
        275                 280                 285 aag aag aag aaa ggc ata gga gca gga agt acc ttt tta ctg gtt ggt      912
Lys Lys Lys Lys Gly Ile Gly Ala Gly Ser Thr Phe Leu Leu Val Gly
    290                 295                 300 ggg tta gct ttg ctg gga act ttc ttt gca ctt ttc gca gtt cgc atg      960
```

-continued

| | | | | | | | | | | | | | | | |
|---|---|---|---|---|---|---|---|---|---|---|---|---|---|---|---|
| Gly | Leu | Ala | Leu | Leu | Gly | Thr | Phe | Phe | Ala | Leu | Phe | Ala | Val | Arg | Met |
| 305 | | | | 310 | | | | | 315 | | | | | 320 | |

| aat | cat | cga | cgt | gca | caa | aac | ctt | gct | gct | att | cac | aga | agc | aac | aat | 1008 |
|---|---|---|---|---|---|---|---|---|---|---|---|---|---|---|---|---|
| Asn | His | Arg | Arg | Ala | Gln | Asn | Leu | Ala | Ala | Ile | His | Arg | Ser | Asn | Asn | |
| | | | 325 | | | | | 330 | | | | | 335 | | | |

| agc | ata | gca | tac | tct | ctt | cca | gtc | agt | aca | ggc | cga | gaa | tat | cct | gtt | 1056 |
|---|---|---|---|---|---|---|---|---|---|---|---|---|---|---|---|---|
| Ser | Ile | Ala | Tyr | Ser | Leu | Pro | Val | Ser | Thr | Gly | Arg | Glu | Tyr | Pro | Val | |
| | | | 340 | | | | | 345 | | | | | 350 | | | |

| gca | act | gaa | gat | aac | cca | cag | att | aaa | agg | ttc | cag | cca | cca | cca | gct | 1104 |
|---|---|---|---|---|---|---|---|---|---|---|---|---|---|---|---|---|
| Ala | Thr | Glu | Asp | Asn | Pro | Gln | Ile | Lys | Arg | Phe | Gln | Pro | Pro | Pro | Ala | |
| | | | 355 | | | | | 360 | | | | | 365 | | | |

| ccc | caa | ctc | aga | cat | tta | cct | tct | cca | cct | gtc | aga | atc | gat | aaa | tct | 1152 |
|---|---|---|---|---|---|---|---|---|---|---|---|---|---|---|---|---|
| Pro | Gln | Leu | Arg | His | Leu | Pro | Ser | Pro | Pro | Val | Arg | Ile | Asp | Lys | Ser | |
| 370 | | | | | 375 | | | | | 380 | | | | | | |

| gca | aga | aga | aag | agc | ttc | tct | gca | aca | tgt | caa | tat | cca | tcg | ttc | gct | 1200 |
|---|---|---|---|---|---|---|---|---|---|---|---|---|---|---|---|---|
| Ala | Arg | Arg | Lys | Ser | Phe | Ser | Ala | Thr | Cys | Gln | Tyr | Pro | Ser | Phe | Ala | |
| 385 | | | | | 390 | | | | | 395 | | | | | 400 | |

| aag | ctt | ttc | tca | gct | gca | gag | ctt | caa | ctg | gca | act | aac | tgt | ttc | agt | 1248 |
|---|---|---|---|---|---|---|---|---|---|---|---|---|---|---|---|---|
| Lys | Leu | Phe | Ser | Ala | Ala | Glu | Leu | Gln | Leu | Ala | Thr | Asn | Cys | Phe | Ser | |
| | | | | 405 | | | | | 410 | | | | | 415 | | |

| gag | gaa | aat | cta | ctc | gga | gag | ggt | cct | ctt | ggt | tct | gtt | tac | aga | gca | 1296 |
|---|---|---|---|---|---|---|---|---|---|---|---|---|---|---|---|---|
| Glu | Glu | Asn | Leu | Leu | Gly | Glu | Gly | Pro | Leu | Gly | Ser | Val | Tyr | Arg | Ala | |
| | | | 420 | | | | | 425 | | | | | 430 | | | |

| aag | ttg | cct | gat | ggt | cag | ttt | gcc | gtc | gtc | aga | aac | atc | cca | atg | tct | 1344 |
|---|---|---|---|---|---|---|---|---|---|---|---|---|---|---|---|---|
| Lys | Leu | Pro | Asp | Gly | Gln | Phe | Ala | Val | Val | Arg | Asn | Ile | Pro | Met | Ser | |
| | | | 435 | | | | | 440 | | | | | 445 | | | |

| tcg | cta | tct | tta | cat | gaa | gag | gaa | cag | ttt | act | gaa | gtg | ctt | cag | aca | 1392 |
|---|---|---|---|---|---|---|---|---|---|---|---|---|---|---|---|---|
| Ser | Leu | Ser | Leu | His | Glu | Glu | Glu | Gln | Phe | Thr | Glu | Val | Leu | Gln | Thr | |
| | | | 450 | | | | | 455 | | | | | 460 | | | |

| gcc | tcc | aaa | cta | aga | cac | cca | aac | att | gtt | aca | ctt | ctc | ggt | ttc | tgc | 1440 |
|---|---|---|---|---|---|---|---|---|---|---|---|---|---|---|---|---|
| Ala | Ser | Lys | Leu | Arg | His | Pro | Asn | Ile | Val | Thr | Leu | Leu | Gly | Phe | Cys | |
| 465 | | | | | 470 | | | | | 475 | | | | | 480 | |

| att | gag | aat | gga | gag | cat | ctt | ctt | gtc | tat | gag | tat | gtt | ggc | cat | ttg | 1488 |
|---|---|---|---|---|---|---|---|---|---|---|---|---|---|---|---|---|
| Ile | Glu | Asn | Gly | Glu | His | Leu | Leu | Val | Tyr | Glu | Tyr | Val | Gly | His | Leu | |
| | | | | 485 | | | | | 490 | | | | | 495 | | |

| tcg | ttg | tac | aat | gct | atg | cat | gat | gag | gta | tac | aag | cca | ctt | tct | tgg | 1536 |
|---|---|---|---|---|---|---|---|---|---|---|---|---|---|---|---|---|
| Ser | Leu | Tyr | Asn | Ala | Met | His | Asp | Glu | Val | Tyr | Lys | Pro | Leu | Ser | Trp | |
| | | | 500 | | | | | 505 | | | | | 510 | | | |

| ggc | ttg | cgt | ctc | cgc | att | gct | att | gga | gtt | gcc | cga | gct | ctg | gac | tat | 1584 |
|---|---|---|---|---|---|---|---|---|---|---|---|---|---|---|---|---|
| Gly | Leu | Arg | Leu | Arg | Ile | Ala | Ile | Gly | Val | Ala | Arg | Ala | Leu | Asp | Tyr | |
| | | 515 | | | | | 520 | | | | | 525 | | | | |

| ttg | cac | tcg | tcg | ttt | tgc | cct | cct | ata | gcc | cat | agc | gat | ctg | aaa | gca | 1632 |
|---|---|---|---|---|---|---|---|---|---|---|---|---|---|---|---|---|
| Leu | His | Ser | Ser | Phe | Cys | Pro | Pro | Ile | Ala | His | Ser | Asp | Leu | Lys | Ala | |
| | | 530 | | | | | 535 | | | | | 540 | | | | |

| aca | aac | atc | tta | cta | gac | gaa | gaa | ctt | aca | cct | cgt | att | gct | gac | tgt | 1680 |
|---|---|---|---|---|---|---|---|---|---|---|---|---|---|---|---|---|
| Thr | Asn | Ile | Leu | Leu | Asp | Glu | Glu | Leu | Thr | Pro | Arg | Ile | Ala | Asp | Cys | |
| 545 | | | | | 550 | | | | | 555 | | | | | 560 | |

| ggg | ctt | gct | agt | tta | agg | cca | ctt | aca | agc | aac | agt | gtt | aaa | ctt | cgg | 1728 |
|---|---|---|---|---|---|---|---|---|---|---|---|---|---|---|---|---|
| Gly | Leu | Ala | Ser | Leu | Arg | Pro | Leu | Thr | Ser | Asn | Ser | Val | Lys | Leu | Arg | |
| | | | | 565 | | | | | 570 | | | | | 575 | | |

| gct | tca | gaa | ata | gcg | ata | caa | aac | act | ggc | tac | ata | gca | cca | gaa | cat | 1776 |
|---|---|---|---|---|---|---|---|---|---|---|---|---|---|---|---|---|
| Ala | Ser | Glu | Ile | Ala | Ile | Gln | Asn | Thr | Gly | Tyr | Ile | Ala | Pro | Glu | His | |
| | | | 580 | | | | | 585 | | | | | 590 | | | |

| gga | cag | cca | gga | agc | agt | ggc | aca | aag | agt | gac | act | tat | gca | ctg | ggt | 1824 |
|---|---|---|---|---|---|---|---|---|---|---|---|---|---|---|---|---|
| Gly | Gln | Pro | Gly | Ser | Ser | Gly | Thr | Lys | Ser | Asp | Thr | Tyr | Ala | Leu | Gly | |
| | | | 595 | | | | | 600 | | | | | 605 | | | |

| gtg | cta | ctc | tta | gaa | ctg | tta | aca | gga | agg | aaa | gca | ttt | gac | agc | tca | 1872 |
|---|---|---|---|---|---|---|---|---|---|---|---|---|---|---|---|---|
| Val | Leu | Leu | Leu | Glu | Leu | Leu | Thr | Gly | Arg | Lys | Ala | Phe | Asp | Ser | Ser | |
| 610 | | | | | 615 | | | | | 620 | | | | | | |

| cga | ccc | cga | gga | gaa | cag | cta | ctg | gtg | aaa | tgg | gca | tca | acc | aga | ctt | 1920 |

```
Arg Pro Arg Gly Glu Gln Leu Leu Val Lys Trp Ala Ser Thr Arg Leu
625                 630                 635                 640 cat gac agg cga agc tta gaa cag atg att gat gga ggc ata gcc ggc    1968
His Asp Arg Arg Ser Leu Glu Gln Met Ile Asp Gly Gly Ile Ala Gly
                645                 650                 655 aca ttc tcc tca aga gtc gcc tca caa tac gca gac att atc tcc cta    2016
Thr Phe Ser Ser Arg Val Ala Ser Gln Tyr Ala Asp Ile Ile Ser Leu
            660                 665                 670 tgc act cag gca gag aag gag ttc aga cca ccg gtt tca gaa ata gtg    2064
Cys Thr Gln Ala Glu Lys Glu Phe Arg Pro Pro Val Ser Glu Ile Val
        675                 680                 685 gaa gcc ctc act gcg ctg ata cag aaa cag aac aag gaa gca agc agt    2112
Glu Ala Leu Thr Ala Leu Ile Gln Lys Gln Asn Lys Glu Ala Ser Ser
    690                 695                 700 agt gta gca gac aag acc gac cct ttt agt aaa tct ttc tgc tca aca    2160
Ser Val Ala Asp Lys Thr Asp Pro Phe Ser Lys Ser Phe Cys Ser Thr
705                 710                 715                 720 cgc aca cgc ttc atc tcc tca cct acc ttc agc tac ctc tcc tct tga    2208
Arg Thr Arg Phe Ile Ser Ser Pro Thr Phe Ser Tyr Leu Ser Ser
                725                 730                 735
```

<210> SEQ ID NO 14
<211> LENGTH: 735
<212> TYPE: PRT
<213> ORGANISM: Arabidopsis thaliana

<400> SEQUENCE: 14

```
Met Lys Thr Lys Gln Gln Leu Arg Phe Leu Ala Thr Ile Leu Leu Thr
1               5                   10                  15

Thr Ile Leu Phe Val Leu Ala Lys Thr Asp Thr Asp Pro Leu Glu Val
            20                  25                  30

Leu Ala Leu Gln Asp Leu Tyr Lys Ser Leu Arg Asn Pro Glu Gln Leu
        35                  40                  45

Arg Gly Trp Arg Leu Glu Gly Gly Asp Pro Cys Gly Glu Ala Trp Leu
    50                  55                  60

Gly Ile Ser Cys Ser Gly Ser Ser Ile Val Asp Leu Gln Leu Arg Glu
65                  70                  75                  80

Leu Lys Leu Leu Gly Ser Leu Gly Asn Gln Leu Gln His Leu His Asn
                85                  90                  95

Leu Lys Ile Leu Asp Val Ser Phe Asn Asn Leu Glu Gly Glu Ile Pro
            100                 105                 110

Phe Gly Leu Pro Pro Asn Ala Thr His Ile Asn Met Ala Tyr Asn Asn
        115                 120                 125

Leu Thr Gln Ser Ile Pro Phe Ser Leu Pro Leu Met Thr Ser Leu Gln
    130                 135                 140

Ser Leu Asn Leu Ser His Asn Ser Leu Ser Gly Pro Leu Gly Asn Val
145                 150                 155                 160

Phe Ser Gly Leu Gln Ile Lys Glu Met Asp Leu Ser Phe Asn Asn Leu
                165                 170                 175

Thr Gly Asp Leu Pro Ser Ser Phe Gly Thr Leu Met Asn Leu Thr Ser
            180                 185                 190

Leu Tyr Leu Gln Asn Asn Arg Leu Thr Gly Ser Val Ile Tyr Leu Ala
        195                 200                 205

Asp Leu Pro Leu Ala Asp Leu Asn Ile Glu Asp Asn Gln Phe Ser Gly
    210                 215                 220

Ile Ile Pro Ser His Phe Gln Ser Ile Pro His Leu Trp Ile Trp Gly
225                 230                 235                 240
```

```
Asn Lys Phe His Val Glu Pro Asn Tyr Lys Pro Trp Lys Phe Pro Leu
            245                 250                 255

Asp Val Arg Pro Leu Ile Gln Asn Asp Thr Gly Tyr Pro Thr Thr Glu
                260                 265                 270

Ser Ser Ala Ile Met Asn Phe Pro Arg Pro Glu Thr Gln Lys Val Lys
        275                 280                 285

Lys Lys Lys Lys Gly Ile Gly Ala Gly Ser Thr Phe Leu Leu Val Gly
    290                 295                 300

Gly Leu Ala Leu Leu Gly Thr Phe Phe Ala Leu Phe Ala Val Arg Met
305                 310                 315                 320

Asn His Arg Arg Ala Gln Asn Leu Ala Ala Ile His Arg Ser Asn Asn
                325                 330                 335

Ser Ile Ala Tyr Ser Leu Pro Val Ser Thr Gly Arg Glu Tyr Pro Val
            340                 345                 350

Ala Thr Glu Asp Asn Pro Gln Ile Lys Arg Phe Gln Pro Pro Pro Ala
                355                 360                 365

Pro Gln Leu Arg His Leu Pro Ser Pro Val Arg Ile Asp Lys Ser
    370                 375                 380

Ala Arg Arg Lys Ser Phe Ser Ala Thr Cys Gln Tyr Pro Ser Phe Ala
385                 390                 395                 400

Lys Leu Phe Ser Ala Ala Glu Leu Gln Leu Ala Thr Asn Cys Phe Ser
                405                 410                 415

Glu Glu Asn Leu Leu Gly Glu Gly Pro Leu Gly Ser Val Tyr Arg Ala
            420                 425                 430

Lys Leu Pro Asp Gly Gln Phe Ala Val Val Arg Asn Ile Pro Met Ser
                435                 440                 445

Ser Leu Ser Leu His Glu Glu Glu Gln Phe Thr Glu Val Leu Gln Thr
        450                 455                 460

Ala Ser Lys Leu Arg His Pro Asn Ile Val Thr Leu Leu Gly Phe Cys
465                 470                 475                 480

Ile Glu Asn Gly Glu His Leu Leu Val Tyr Glu Tyr Val Gly His Leu
                485                 490                 495

Ser Leu Tyr Asn Ala Met His Asp Glu Val Tyr Lys Pro Leu Ser Trp
            500                 505                 510

Gly Leu Arg Leu Arg Ile Ala Ile Gly Val Ala Arg Ala Leu Asp Tyr
        515                 520                 525

Leu His Ser Ser Phe Cys Pro Pro Ile Ala His Ser Asp Leu Lys Ala
    530                 535                 540

Thr Asn Ile Leu Leu Asp Glu Glu Leu Thr Pro Arg Ile Ala Asp Cys
545                 550                 555                 560

Gly Leu Ala Ser Leu Arg Pro Leu Thr Ser Asn Ser Val Lys Leu Arg
                565                 570                 575

Ala Ser Glu Ile Ala Ile Gln Asn Thr Gly Tyr Ile Ala Pro Glu His
            580                 585                 590

Gly Gln Pro Gly Ser Ser Gly Thr Lys Ser Asp Thr Tyr Ala Leu Gly
        595                 600                 605

Val Leu Leu Leu Glu Leu Leu Thr Gly Arg Lys Ala Phe Asp Ser Ser
    610                 615                 620

Arg Pro Arg Gly Glu Gln Leu Leu Val Lys Trp Ala Ser Thr Arg Leu
625                 630                 635                 640

His Asp Arg Arg Ser Leu Glu Gln Met Ile Asp Gly Gly Ile Ala Gly
                645                 650                 655

Thr Phe Ser Ser Arg Val Ala Ser Gln Tyr Ala Asp Ile Ile Ser Leu
            660                 665                 670
```

| | | | | | | | | | | | |
|---|---|---|---|---|---|---|---|---|---|---|---|
| Cys | Thr | Gln | Ala | Glu | Lys | Glu | Phe | Arg | Pro | Pro | Val | Ser | Glu | Ile | Val |
| | | 675 | | | | 680 | | | | 685 | |
| Glu | Ala | Leu | Thr | Ala | Leu | Ile | Gln | Lys | Gln | Asn | Lys | Glu | Ala | Ser | Ser |
| | 690 | | | | | 695 | | | | 700 | | | | | |
| Ser | Val | Ala | Asp | Lys | Thr | Asp | Pro | Phe | Ser | Lys | Ser | Phe | Cys | Ser | Thr |
| 705 | | | | | 710 | | | | | 715 | | | | | 720 |
| Arg | Thr | Arg | Phe | Ile | Ser | Ser | Pro | Thr | Phe | Ser | Tyr | Leu | Ser | Ser | |
| | | | | 725 | | | | | 730 | | | | | 735 | |

```
<210> SEQ ID NO 15
<211> LENGTH: 2331
<212> TYPE: DNA
<213> ORGANISM: Arabidopsis thaliana
<220> FEATURE:
<221> NAME/KEY: CDS
<222> LOCATION: (1)..(2331)

<400> SEQUENCE: 15
```

| | | | | | | | | | | | | | | | | |
|---|---|---|---|---|---|---|---|---|---|---|---|---|---|---|---|---|
| atg | gct | gct | aag | aga | tct | atc | tac | tgt | ctt | ctt | ctt | ctt | cct | ctg | ctc | 48 |
| Met | Ala | Ala | Lys | Arg | Ser | Ile | Tyr | Cys | Leu | Leu | Leu | Leu | Pro | Leu | Leu | |
| 1 | | | | 5 | | | | | 10 | | | | | 15 | | |
| ttg | tct | tta | ctg | atc | tgg | att | cct | tcg | atc | tcc | tta | gct | gct | act | aac | 96 |
| Leu | Ser | Leu | Leu | Ile | Trp | Ile | Pro | Ser | Ile | Ser | Leu | Ala | Ala | Thr | Asn | |
| | | | 20 | | | | | 25 | | | | | 30 | | | |
| cct | gat | gat | gtt | gct | gca | att | aac | gga | tta | ttc | gct | gca | ctt | gga | gca | 144 |
| Pro | Asp | Asp | Val | Ala | Ala | Ile | Asn | Gly | Leu | Phe | Ala | Ala | Leu | Gly | Ala | |
| | | 35 | | | | | 40 | | | | | 45 | | | | |
| cct | gtt | ctt | cct | ggt | tgg | att | gct | tct | ggt | gga | gat | cca | tgt | ggt | gaa | 192 |
| Pro | Val | Leu | Pro | Gly | Trp | Ile | Ala | Ser | Gly | Gly | Asp | Pro | Cys | Gly | Glu | |
| | 50 | | | | | 55 | | | | | 60 | | | | | |
| gct | tgg | caa | ggc | att | atc | tgc | aat | gtt | tca | gat | att | ata | agc | ata | act | 240 |
| Ala | Trp | Gln | Gly | Ile | Ile | Cys | Asn | Val | Ser | Asp | Ile | Ile | Ser | Ile | Thr | |
| 65 | | | | | 70 | | | | | 75 | | | | | 80 | |
| gta | aat | gct | gca | aat | ttg | caa | gga | gag | ctt | ggt | gac | aac | tta | gct | aag | 288 |
| Val | Asn | Ala | Ala | Asn | Leu | Gln | Gly | Glu | Leu | Gly | Asp | Asn | Leu | Ala | Lys | |
| | | | | 85 | | | | | 90 | | | | | 95 | | |
| ttc | act | tct | atc | agg | gga | ata | gat | ttc | agc | aac | aat | cgc | att | gga | gga | 336 |
| Phe | Thr | Ser | Ile | Arg | Gly | Ile | Asp | Phe | Ser | Asn | Asn | Arg | Ile | Gly | Gly | |
| | | | 100 | | | | | 105 | | | | | 110 | | | |
| agc | ata | cct | tct | act | ttg | ccg | gtt | aca | ttg | cag | cat | ttt | ttt | ctt | tca | 384 |
| Ser | Ile | Pro | Ser | Thr | Leu | Pro | Val | Thr | Leu | Gln | His | Phe | Phe | Leu | Ser | |
| | | 115 | | | | | 120 | | | | | 125 | | | | |
| gct | aat | cag | ttc | acc | gga | agc | atc | ccg | gaa | tct | cta | gga | aca | ttg | agt | 432 |
| Ala | Asn | Gln | Phe | Thr | Gly | Ser | Ile | Pro | Glu | Ser | Leu | Gly | Thr | Leu | Ser | |
| | 130 | | | | | 135 | | | | | 140 | | | | | |
| ttt | ctg | aat | gac | atg | tct | ttg | aac | gat | aac | ctt | ctc | tct | gga | gag | cta | 480 |
| Phe | Leu | Asn | Asp | Met | Ser | Leu | Asn | Asp | Asn | Leu | Leu | Ser | Gly | Glu | Leu | |
| 145 | | | | | 150 | | | | | 155 | | | | | 160 | |
| ccc | gac | gtg | ttt | caa | aac | ctt | gtc | ggg | ctg | att | aat | ctt | gat | ata | tca | 528 |
| Pro | Asp | Val | Phe | Gln | Asn | Leu | Val | Gly | Leu | Ile | Asn | Leu | Asp | Ile | Ser | |
| | | | | 165 | | | | | 170 | | | | | 175 | | |
| tct | aac | aat | ata | agc | ggc | aca | ttg | cct | cct | tct | atg | gag | aat | tta | tta | 576 |
| Ser | Asn | Asn | Ile | Ser | Gly | Thr | Leu | Pro | Pro | Ser | Met | Glu | Asn | Leu | Leu | |
| | | | 180 | | | | | 185 | | | | | 190 | | | |
| act | ctt | aca | aca | tta | cgt | gtt | cag | aac | aat | cag | ctc | tca | gga | act | ctg | 624 |
| Thr | Leu | Thr | Thr | Leu | Arg | Val | Gln | Asn | Asn | Gln | Leu | Ser | Gly | Thr | Leu | |
| | | 195 | | | | | 200 | | | | | 205 | | | | |
| gac | gtt | ctt | caa | ggc | ctt | cct | ctt | caa | gac | tta | aac | ata | gag | aat | aac | 672 |
| Asp | Val | Leu | Gln | Gly | Leu | Pro | Leu | Gln | Asp | Leu | Asn | Ile | Glu | Asn | Asn | |
| | 210 | | | | | 215 | | | | | 220 | | | | | |

```
                                                           -continued ctc ttc tct gga ccc ata ccg gac aaa tta cta agc att ccg aaa ttc    720
Leu Phe Ser Gly Pro Ile Pro Asp Lys Leu Leu Ser Ile Pro Lys Phe
225                 230                 235                 240 cta cat gaa gga aac ccg ttc aat gcc aca atg atc aat tcc acc tcg    768
Leu His Glu Gly Asn Pro Phe Asn Ala Thr Met Ile Asn Ser Thr Ser
            245                 250                 255 act gca cca tca ttg tct ccg tct cta tct cca aca aaa cca gct cca    816
Thr Ala Pro Ser Leu Ser Pro Ser Leu Ser Pro Thr Lys Pro Ala Pro
        260                 265                 270 acg cga cca ttt tct gga gtt cca cct cct cca aat gag agg aat cga    864
Thr Arg Pro Phe Ser Gly Val Pro Pro Pro Pro Asn Glu Arg Asn Arg
    275                 280                 285 ggg aaa gtt gct gat gga cct tct gat tca gaa gga tcg agc tct gag    912
Gly Lys Val Ala Asp Gly Pro Ser Asp Ser Glu Gly Ser Ser Ser Glu
290                 295                 300 aat tca aag gga aag aac tct tca cat act aaa aag ata atc ctt att    960
Asn Ser Lys Gly Lys Asn Ser Ser His Thr Lys Lys Ile Ile Leu Ile
305                 310                 315                 320 gca ttc gct ggc gtc ctc gtc ttc ata att ctg gtt ttg gca ata ctc   1008
Ala Phe Ala Gly Val Leu Val Phe Ile Ile Leu Val Leu Ala Ile Leu
            325                 330                 335 ttg ctg ttg cca aaa tgt gca aga cgt aga gaa cat gct aac aga gtt   1056
Leu Leu Leu Pro Lys Cys Ala Arg Arg Arg Glu His Ala Asn Arg Val
        340                 345                 350 ttc aaa ccg cat caa gtt ggc gct gat aga gga agc aga gag aat gct   1104
Phe Lys Pro His Gln Val Gly Ala Asp Arg Gly Ser Arg Glu Asn Ala
    355                 360                 365 ctg gaa aac ggg act ccg gta ctg cca cca cct ggt cga tct gaa aaa   1152
Leu Glu Asn Gly Thr Pro Val Leu Pro Pro Pro Gly Arg Ser Glu Lys
370                 375                 380 gtt caa aga gaa ccc ttc aag aaa gct gga gag gaa cca aag gtc tta   1200
Val Gln Arg Glu Pro Phe Lys Lys Ala Gly Glu Glu Pro Lys Val Leu
385                 390                 395                 400 cat gac ctt gag agg ctg cgg aga cct gca cct ata tca aga cag gaa   1248
His Asp Leu Glu Arg Leu Arg Arg Pro Ala Pro Ile Ser Arg Gln Glu
            405                 410                 415 agt caa gat att gac ttt tca atg ttg atg cct cct cct cca cca cct   1296
Ser Gln Asp Ile Asp Phe Ser Met Leu Met Pro Pro Pro Pro Pro Pro
        420                 425                 430 cca cca cca cca cca cct cct cct ttg gat gag aag gtc acg gtt atg   1344
Pro Pro Pro Pro Pro Pro Pro Pro Leu Asp Glu Lys Val Thr Val Met
    435                 440                 445 cca atc ata tca ccc gaa aga ccc gtt aag aaa act tcc cct aaa cgc   1392
Pro Ile Ile Ser Pro Glu Arg Pro Val Lys Lys Thr Ser Pro Lys Arg
450                 455                 460 tta ccc tta act tct gtg aag cac tat tct att gct tct ctt caa caa   1440
Leu Pro Leu Thr Ser Val Lys His Tyr Ser Ile Ala Ser Leu Gln Gln
465                 470                 475                 480 tac acg gaa agc ttc gct cag gaa aat ctc att ggc tca ggc atg ctc   1488
Tyr Thr Glu Ser Phe Ala Gln Glu Asn Leu Ile Gly Ser Gly Met Leu
            485                 490                 495 ggt agt gtt tat agg gcc cgg ctt ccc aat gga aag ttg ttt gct gtc   1536
Gly Ser Val Tyr Arg Ala Arg Leu Pro Asn Gly Lys Leu Phe Ala Val
        500                 505                 510 aag aag ttg gac aag agg gct tct gaa caa caa cag gat cac gaa ttt   1584
Lys Lys Leu Asp Lys Arg Ala Ser Glu Gln Gln Gln Asp His Glu Phe
    515                 520                 525 atc gaa cta gtg aac aat ata gat atg att cgc cac tcc aat atc gtt   1632
Ile Glu Leu Val Asn Asn Ile Asp Met Ile Arg His Ser Asn Ile Val
530                 535                 540
```

```
gaa ctt gtg ggt tac tgt gct gag cac gat caa aga cta ttg gtc tac    1680
Glu Leu Val Gly Tyr Cys Ala Glu His Asp Gln Arg Leu Leu Val Tyr
545                 550                 555                 560 gaa tat tgc agt aac ggt acg tta caa gac ggg ttg cat tca gac gat    1728
Glu Tyr Cys Ser Asn Gly Thr Leu Gln Asp Gly Leu His Ser Asp Asp
                565                 570                 575 gaa ttc aag aag aaa ctt tcg tgg aat acc cgt gtc agt atg gca ctt    1776
Glu Phe Lys Lys Lys Leu Ser Trp Asn Thr Arg Val Ser Met Ala Leu
            580                 585                 590 gga gct gct aga gcc ctt gag tac ttg cat gag gtg tgt gaa cca cct    1824
Gly Ala Ala Arg Ala Leu Glu Tyr Leu His Glu Val Cys Glu Pro Pro
        595                 600                 605 atc ata cac aga aac ttc aaa tca gcc aat gtt cta ctc gac gat gac    1872
Ile Ile His Arg Asn Phe Lys Ser Ala Asn Val Leu Leu Asp Asp Asp
    610                 615                 620 ctg agt gtt ctt gtc tca gat tgt ggt ttg gcc cca cta ata tca tca    1920
Leu Ser Val Leu Val Ser Asp Cys Gly Leu Ala Pro Leu Ile Ser Ser
625                 630                 635                 640 ggc tct gtg agt cag tta tca ggg caa ttg cta gcc gct tac gga tat    1968
Gly Ser Val Ser Gln Leu Ser Gly Gln Leu Leu Ala Ala Tyr Gly Tyr
                645                 650                 655 gga gct cca gag ttc gac tct gga atc tat aca tgg cag agt gat gta    2016
Gly Ala Pro Glu Phe Asp Ser Gly Ile Tyr Thr Trp Gln Ser Asp Val
            660                 665                 670 tat agt ttt ggt gtt gtt atg tta gaa cta ttg acg ggt aga atg tcc    2064
Tyr Ser Phe Gly Val Val Met Leu Glu Leu Leu Thr Gly Arg Met Ser
        675                 680                 685 tac gat agg gac cgg agt aga gga gag cag ttc ttg gtg agg tgg gca    2112
Tyr Asp Arg Asp Arg Ser Arg Gly Glu Gln Phe Leu Val Arg Trp Ala
    690                 695                 700 atc cca cag ctt cat gat atc gat gca ttg ggc aaa atg gtt gat cca    2160
Ile Pro Gln Leu His Asp Ile Asp Ala Leu Gly Lys Met Val Asp Pro
705                 710                 715                 720 tct ctt aat gga caa tac cct gca aag tca ttg tca cac ttt gct gat    2208
Ser Leu Asn Gly Gln Tyr Pro Ala Lys Ser Leu Ser His Phe Ala Asp
                725                 730                 735 ata ata tcc cgg tgt gtt cag tct gaa cca gaa ttt aga cca ctg atg    2256
Ile Ile Ser Arg Cys Val Gln Ser Glu Pro Glu Phe Arg Pro Leu Met
            740                 745                 750 tca gaa gtt gtt caa gat cta cta gat atg atc aga aga gag cgt cat    2304
Ser Glu Val Val Gln Asp Leu Leu Asp Met Ile Arg Arg Glu Arg His
        755                 760                 765 ggt tcg ggt gat tct acc gcg gac tag                                2331
Gly Ser Gly Asp Ser Thr Ala Asp
    770                 775

<210> SEQ ID NO 16
<211> LENGTH: 776
<212> TYPE: PRT
<213> ORGANISM: Arabidopsis thaliana

<400> SEQUENCE: 16

Met Ala Ala Lys Arg Ser Ile Tyr Cys Leu Leu Leu Pro Leu Leu
1               5                   10                  15

Leu Ser Leu Leu Ile Trp Ile Pro Ser Ile Ser Leu Ala Ala Thr Asn
                20                  25                  30

Pro Asp Asp Val Ala Ala Ile Asn Gly Leu Phe Ala Ala Leu Gly Ala
            35                  40                  45

Pro Val Leu Pro Gly Trp Ile Ala Ser Gly Gly Asp Pro Cys Gly Glu
        50                  55                  60
```

-continued

```
Ala Trp Gln Gly Ile Ile Cys Asn Val Ser Asp Ile Ser Ile Thr
 65                  70                  75                  80

Val Asn Ala Ala Asn Leu Gln Gly Glu Leu Gly Asp Asn Leu Ala Lys
                 85                  90                  95

Phe Thr Ser Ile Arg Gly Ile Asp Phe Ser Asn Asn Arg Ile Gly Gly
            100                 105                 110

Ser Ile Pro Ser Thr Leu Pro Val Thr Leu Gln His Phe Phe Leu Ser
            115                 120                 125

Ala Asn Gln Phe Thr Gly Ser Ile Pro Glu Ser Leu Gly Thr Leu Ser
            130                 135                 140

Phe Leu Asn Asp Met Ser Leu Asn Asp Asn Leu Leu Ser Gly Glu Leu
145                 150                 155                 160

Pro Asp Val Phe Gln Asn Leu Val Gly Leu Ile Asn Leu Asp Ile Ser
                165                 170                 175

Ser Asn Asn Ile Ser Gly Thr Leu Pro Pro Ser Met Glu Asn Leu Leu
            180                 185                 190

Thr Leu Thr Thr Leu Arg Val Gln Asn Asn Gln Leu Ser Gly Thr Leu
            195                 200                 205

Asp Val Leu Gln Gly Leu Pro Leu Gln Asp Leu Asn Ile Glu Asn Asn
210                 215                 220

Leu Phe Ser Gly Pro Ile Pro Asp Lys Leu Leu Ser Ile Pro Lys Phe
225                 230                 235                 240

Leu His Glu Gly Asn Pro Phe Asn Ala Thr Met Ile Asn Ser Thr Ser
                245                 250                 255

Thr Ala Pro Ser Leu Ser Pro Ser Leu Ser Pro Thr Lys Pro Ala Pro
            260                 265                 270

Thr Arg Pro Phe Ser Gly Val Pro Pro Pro Asn Glu Arg Asn Arg
            275                 280                 285

Gly Lys Val Ala Asp Gly Pro Ser Asp Ser Glu Gly Ser Ser Ser Glu
            290                 295                 300

Asn Ser Lys Gly Lys Asn Ser Ser His Thr Lys Lys Ile Ile Leu Ile
305                 310                 315                 320

Ala Phe Ala Gly Val Leu Val Phe Ile Ile Leu Val Leu Ala Ile Leu
                325                 330                 335

Leu Leu Leu Pro Lys Cys Ala Arg Arg Arg Glu His Ala Asn Arg Val
            340                 345                 350

Phe Lys Pro His Gln Val Gly Ala Asp Arg Gly Ser Arg Glu Asn Ala
            355                 360                 365

Leu Glu Asn Gly Thr Pro Val Leu Pro Pro Gly Arg Ser Glu Lys
            370                 375                 380

Val Gln Arg Glu Pro Phe Lys Lys Ala Gly Glu Pro Lys Val Leu
385                 390                 395                 400

His Asp Leu Glu Arg Leu Arg Arg Pro Ala Pro Ile Ser Arg Gln Glu
                405                 410                 415

Ser Gln Asp Ile Asp Phe Ser Met Leu Met Pro Pro Pro Pro Pro
            420                 425                 430

Pro Pro Pro Pro Pro Pro Pro Leu Asp Glu Lys Val Thr Val Met
            435                 440                 445

Pro Ile Ile Ser Pro Glu Arg Pro Val Lys Lys Thr Ser Pro Lys Arg
            450                 455                 460

Leu Pro Leu Thr Ser Val Lys His Tyr Ser Ile Ala Ser Leu Gln Gln
465                 470                 475                 480

Tyr Thr Glu Ser Phe Ala Gln Glu Asn Leu Ile Gly Ser Gly Met Leu
                485                 490                 495
```

```
Gly Ser Val Tyr Arg Ala Arg Leu Pro Asn Gly Lys Leu Phe Ala Val
            500                 505                 510
Lys Lys Leu Asp Lys Arg Ala Ser Glu Gln Gln Gln Asp His Glu Phe
        515                 520                 525
Ile Glu Leu Val Asn Asn Ile Asp Met Ile Arg His Ser Asn Ile Val
    530                 535                 540
Glu Leu Val Gly Tyr Cys Ala Glu His Asp Gln Arg Leu Leu Val Tyr
545                 550                 555                 560
Glu Tyr Cys Ser Asn Gly Thr Leu Gln Asp Gly Leu His Ser Asp Asp
                565                 570                 575
Glu Phe Lys Lys Lys Leu Ser Trp Asn Thr Arg Val Ser Met Ala Leu
            580                 585                 590
Gly Ala Ala Arg Ala Leu Glu Tyr Leu His Glu Val Cys Glu Pro Pro
        595                 600                 605
Ile Ile His Arg Asn Phe Lys Ser Ala Asn Val Leu Leu Asp Asp Asp
    610                 615                 620
Leu Ser Val Leu Val Ser Asp Cys Gly Leu Ala Pro Leu Ile Ser Ser
625                 630                 635                 640
Gly Ser Val Ser Gln Leu Ser Gly Gln Leu Leu Ala Ala Tyr Gly Tyr
                645                 650                 655
Gly Ala Pro Glu Phe Asp Ser Gly Ile Tyr Thr Trp Gln Ser Asp Val
            660                 665                 670
Tyr Ser Phe Gly Val Val Met Leu Glu Leu Thr Gly Arg Met Ser
        675                 680                 685
Tyr Asp Arg Asp Arg Ser Arg Gly Glu Gln Phe Leu Val Arg Trp Ala
    690                 695                 700
Ile Pro Gln Leu His Asp Ile Asp Ala Leu Gly Lys Met Val Asp Pro
705                 710                 715                 720
Ser Leu Asn Gly Gln Tyr Pro Ala Lys Ser Leu Ser His Phe Ala Asp
                725                 730                 735
Ile Ile Ser Arg Cys Val Gln Ser Glu Pro Glu Phe Arg Pro Leu Met
            740                 745                 750
Ser Glu Val Val Gln Asp Leu Leu Asp Met Ile Arg Arg Glu Arg His
        755                 760                 765
Gly Ser Gly Asp Ser Thr Ala Asp
    770                 775

<210> SEQ ID NO 17
<211> LENGTH: 2064
<212> TYPE: DNA
<213> ORGANISM: Arabidopsis thaliana
<220> FEATURE:
<221> NAME/KEY: CDS
<222> LOCATION: (1)..(2064)

<400> SEQUENCE: 17 atg gga cca aat ctg cag cga atc gta ctt gtc ttc att gca tgt ttc    48
Met Gly Pro Asn Leu Gln Arg Ile Val Leu Val Phe Ile Ala Cys Phe
1               5                   10                  15 gga atc ttc acc tcc gtt gtt ctt gca aaa acc gat agc caa gac gta    96
Gly Ile Phe Thr Ser Val Val Leu Ala Lys Thr Asp Ser Gln Asp Val
            20                  25                  30 tct gct ctt aat gac gct tat aag agc atg aac tct cca tca aaa ctc    144
Ser Ala Leu Asn Asp Ala Tyr Lys Ser Met Asn Ser Pro Ser Lys Leu
        35                  40                  45 aaa ggc tgg tct tca agc gga ggc gat cct tgt ggc gat tcg tgg gat    192
Lys Gly Trp Ser Ser Ser Gly Gly Asp Pro Cys Gly Asp Ser Trp Asp
    50                  55                  60
```

```
                   50                   55                    60
ggc att act tgc aaa ggc tct tct gtt act gaa ata aaa gta tct gga        240
Gly Ile Thr Cys Lys Gly Ser Ser Val Thr Glu Ile Lys Val Ser Gly
 65              70                  75                   80 cgt gga ctc agt gga tct tta ggt tac cag ctt gga aac ttg aaa tcg        288
Arg Gly Leu Ser Gly Ser Leu Gly Tyr Gln Leu Gly Asn Leu Lys Ser
                 85                  90                   95 ctc act tac ctt gat gta agc aag aac aat ctt aac gga aac tta ccc        336
Leu Thr Tyr Leu Asp Val Ser Lys Asn Asn Leu Asn Gly Asn Leu Pro
             100                 105                 110 tac cag ctt cct gac aag ctt act tat cta gat ggc tct gag aat gac        384
Tyr Gln Leu Pro Asp Lys Leu Thr Tyr Leu Asp Gly Ser Glu Asn Asp
             115                 120                 125 ttc aac ggt aat gtg cca tat tcg gtg tct ctc atg aac gac ctc agt        432
Phe Asn Gly Asn Val Pro Tyr Ser Val Ser Leu Met Asn Asp Leu Ser
         130                 135                 140 tac cta aac ctt ggc cgt aac aac ctc aat ggt gaa ctc agt gac atg        480
Tyr Leu Asn Leu Gly Arg Asn Asn Leu Asn Gly Glu Leu Ser Asp Met
145                 150                 155                 160 ttt caa aag ctt cca aaa ctt gaa aca att gat ctt tct tcc aat caa        528
Phe Gln Lys Leu Pro Lys Leu Glu Thr Ile Asp Leu Ser Ser Asn Gln
                 165                 170                 175 ctc acg gga aaa cta ccg cag agt ttt gcc aat cta aca ggt ctt aaa        576
Leu Thr Gly Lys Leu Pro Gln Ser Phe Ala Asn Leu Thr Gly Leu Lys
             180                 185                 190 aca ctg cat ttg caa gaa aac caa ttc aaa ggc tct ata aat gct ctc        624
Thr Leu His Leu Gln Glu Asn Gln Phe Lys Gly Ser Ile Asn Ala Leu
             195                 200                 205 agg gac ctc cct cag att gat gat gta aac gta gca aac aat caa ttt        672
Arg Asp Leu Pro Gln Ile Asp Asp Val Asn Val Ala Asn Asn Gln Phe
         210                 215                 220 act ggt tgg atc cca aac gag ttg aag aat att gga aac ctt gaa act        720
Thr Gly Trp Ile Pro Asn Glu Leu Lys Asn Ile Gly Asn Leu Glu Thr
225                 230                 235                 240 gga gga aac aag tgg tca agc ggt aga gct cct tca cca cct ccg gga        768
Gly Gly Asn Lys Trp Ser Ser Gly Arg Ala Pro Ser Pro Pro Pro Gly
                 245                 250                 255 acc cgt cac ata gac aga aac tca tca gga ggc ggt gga gga agc agc        816
Thr Arg His Ile Asp Arg Asn Ser Ser Gly Gly Gly Gly Gly Ser Ser
             260                 265                 270 aag gct ctg aca cta gga gtt ata ata gcg gtg tct tct ata ggt gga        864
Lys Ala Leu Thr Leu Gly Val Ile Ile Ala Val Ser Ser Ile Gly Gly
             275                 280                 285 ctc att tta ttt gca ggg ttg att gca ttg att tct cga aga aag aac        912
Leu Ile Leu Phe Ala Gly Leu Ile Ala Leu Ile Ser Arg Arg Lys Asn
         290                 295                 300 tct aat gat tct tct cac ttt ttc gac gac gag aaa gga acc aac cga        960
Ser Asn Asp Ser Ser His Phe Phe Asp Asp Glu Lys Gly Thr Asn Arg
305                 310                 315                 320 agc aag cca ctc ttc aca cca caa tcc tct cag atg ctt caa ttc gat       1008
Ser Lys Pro Leu Phe Thr Pro Gln Ser Ser Gln Met Leu Gln Phe Asp
                 325                 330                 335 aat atg gaa gaa ttc aaa aac cag aag aca gtt gat tct aat act tca       1056
Asn Met Glu Glu Phe Lys Asn Gln Lys Thr Val Asp Ser Asn Thr Ser
             340                 345                 350 ctt gaa aca aag cct tct gtt aaa aga act tct tct gtc agt ttc aag       1104
Leu Glu Thr Lys Pro Ser Val Lys Arg Thr Ser Ser Val Ser Phe Lys
             355                 360                 365 aac tct cct act ttt cat ctc ata cct tct acc caa gtg gct gct acc       1152
Asn Ser Pro Thr Phe His Leu Ile Pro Ser Thr Gln Val Ala Ala Thr
```

```
                370                    375                    380
cct gac cgt tcc tcc acc tcc caa gac tct cct gat aca cgc ggt gtg      1200
Pro Asp Arg Ser Ser Thr Ser Gln Asp Ser Pro Asp Thr Arg Gly Val
385                    390                    395                400 aaa gcg ttt tca cta gcg gat ttg cag aat acc gcg tct tgt ttc tcg      1248
Lys Ala Phe Ser Leu Ala Asp Leu Gln Asn Thr Ala Ser Cys Phe Ser
                405                    410                    415 ccg aat cgc ctt ctt ggt gaa gga acc att gga cgt gtt tat aaa gct      1296
Pro Asn Arg Leu Leu Gly Glu Gly Thr Ile Gly Arg Val Tyr Lys Ala
            420                    425                    430 aaa ttt cag gat gga agg aaa ttt gca gtc aaa gag att gat tct tct      1344
Lys Phe Gln Asp Gly Arg Lys Phe Ala Val Lys Glu Ile Asp Ser Ser
        435                    440                    445 ctg tta gga aaa ggc aat ccg gaa gag ttt tca cac ata gtg tcg agt      1392
Leu Leu Gly Lys Gly Asn Pro Glu Glu Phe Ser His Ile Val Ser Ser
    450                    455                    460 atc tcg agt att cac cac aag aat atg gca gaa ctc gtg ggt tat tgt      1440
Ile Ser Ser Ile His His Lys Asn Met Ala Glu Leu Val Gly Tyr Cys
465                    470                    475                480 tca gaa caa gga aga aat atg ctt gtt tat gag tat ttc aca agt gga      1488
Ser Glu Gln Gly Arg Asn Met Leu Val Tyr Glu Tyr Phe Thr Ser Gly
                485                    490                    495 tca ctt cac aga ttt ctt cac ctg tct gat gat ttc agc aaa cca ttg      1536
Ser Leu His Arg Phe Leu His Leu Ser Asp Asp Phe Ser Lys Pro Leu
            500                    505                    510 acg tgg aac acc aga atc cga atc gct ctc gga act gct aaa gct ata      1584
Thr Trp Asn Thr Arg Ile Arg Ile Ala Leu Gly Thr Ala Lys Ala Ile
        515                    520                    525 gag tac ctt cat gaa aca tgt tcg cct ccg cta gtt cac aag aac atc      1632
Glu Tyr Leu His Glu Thr Cys Ser Pro Pro Leu Val His Lys Asn Ile
    530                    535                    540 aag tca tca aac att tta ctt gat aat gag cta aat ccc cgc ctc tca      1680
Lys Ser Ser Asn Ile Leu Leu Asp Asn Glu Leu Asn Pro Arg Leu Ser
545                    550                    555                560 gac tat ggc ttg gca aac ttt cac cac cgc aca agt cag aat ctt gga      1728
Asp Tyr Gly Leu Ala Asn Phe His His Arg Thr Ser Gln Asn Leu Gly
                565                    570                    575 gtt gga tac aat gcc cca gaa tgc aca gat ccc tcc gct tac aca caa      1776
Val Gly Tyr Asn Ala Pro Glu Cys Thr Asp Pro Ser Ala Tyr Thr Gln
            580                    585                    590 aag agc gac gtg tac agc ttt ggt gtg gtg atg ctt gag ctg cta act      1824
Lys Ser Asp Val Tyr Ser Phe Gly Val Val Met Leu Glu Leu Leu Thr
        595                    600                    605 ggt cga aag cct tat gac agt ggg agg cca aaa gca gaa cag tct tta      1872
Gly Arg Lys Pro Tyr Asp Ser Gly Arg Pro Lys Ala Glu Gln Ser Leu
    610                    615                    620 gtt cgt tgg gca aag ccg cag ctt aaa gac atg gat act ctg gat gaa      1920
Val Arg Trp Ala Lys Pro Gln Leu Lys Asp Met Asp Thr Leu Asp Glu
625                    630                    635                640 atg gtg gat ccc gcg ttg tgc gga ctc tac gct cca gaa tct gta tca      1968
Met Val Asp Pro Ala Leu Cys Gly Leu Tyr Ala Pro Glu Ser Val Ser
                645                    650                    655 tca ttc gcg gat ata gtt tcc atc tgc gta atg acg gag cct gga ctt      2016
Ser Phe Ala Asp Ile Val Ser Ile Cys Val Met Thr Glu Pro Gly Leu
            660                    665                    670 agg cct cca gtg tca aat gtg gtg gag gca ttg aag agg cta gtg tag      2064
Arg Pro Pro Val Ser Asn Val Val Glu Ala Leu Lys Arg Leu Val
        675                    680                    685
```

<210> SEQ ID NO 18

```
<211> LENGTH: 687
<212> TYPE: PRT
<213> ORGANISM: Arabidopsis thaliana

<400> SEQUENCE: 18

Met Gly Pro Asn Leu Gln Arg Ile Val Leu Val Phe Ile Ala Cys Phe
1               5                   10                  15

Gly Ile Phe Thr Ser Val Val Leu Ala Lys Thr Asp Ser Gln Asp Val
            20                  25                  30

Ser Ala Leu Asn Asp Ala Tyr Lys Ser Met Asn Ser Pro Ser Lys Leu
        35                  40                  45

Lys Gly Trp Ser Ser Gly Gly Asp Pro Cys Gly Asp Ser Trp Asp
    50                  55                  60

Gly Ile Thr Cys Lys Gly Ser Ser Val Thr Glu Ile Lys Val Ser Gly
65                  70                  75                  80

Arg Gly Leu Ser Gly Ser Leu Gly Tyr Gln Leu Gly Asn Leu Lys Ser
                85                  90                  95

Leu Thr Tyr Leu Asp Val Ser Lys Asn Asn Leu Asn Gly Asn Leu Pro
            100                 105                 110

Tyr Gln Leu Pro Asp Lys Leu Thr Tyr Leu Asp Gly Ser Glu Asn Asp
        115                 120                 125

Phe Asn Gly Asn Val Pro Tyr Ser Val Ser Leu Met Asn Asp Leu Ser
130                 135                 140

Tyr Leu Asn Leu Gly Arg Asn Asn Leu Asn Gly Glu Leu Ser Asp Met
145                 150                 155                 160

Phe Gln Lys Leu Pro Lys Leu Glu Thr Ile Asp Leu Ser Asn Gln
                165                 170                 175

Leu Thr Gly Lys Leu Pro Gln Ser Phe Ala Asn Leu Thr Gly Leu Lys
            180                 185                 190

Thr Leu His Leu Gln Glu Asn Gln Phe Lys Gly Ser Ile Asn Ala Leu
        195                 200                 205

Arg Asp Leu Pro Gln Ile Asp Asp Val Asn Val Ala Asn Asn Gln Phe
    210                 215                 220

Thr Gly Trp Ile Pro Asn Glu Leu Lys Asn Ile Gly Asn Leu Glu Thr
225                 230                 235                 240

Gly Gly Asn Lys Trp Ser Ser Gly Arg Ala Pro Ser Pro Pro Gly
                245                 250                 255

Thr Arg His Ile Asp Arg Asn Ser Ser Gly Gly Gly Ser Ser
            260                 265                 270

Lys Ala Leu Thr Leu Gly Val Ile Ile Ala Val Ser Ser Ile Gly Gly
        275                 280                 285

Leu Ile Leu Phe Ala Gly Leu Ile Ala Leu Ile Ser Arg Arg Lys Asn
    290                 295                 300

Ser Asn Asp Ser Ser His Phe Phe Asp Glu Lys Gly Thr Asn Arg
305                 310                 315                 320

Ser Lys Pro Leu Phe Thr Pro Gln Ser Ser Gln Met Leu Gln Phe Asp
                325                 330                 335

Asn Met Glu Glu Phe Lys Asn Gln Lys Thr Val Asp Ser Asn Thr Ser
            340                 345                 350

Leu Glu Thr Lys Pro Ser Val Lys Arg Thr Ser Ser Val Ser Phe Lys
        355                 360                 365

Asn Ser Pro Thr Phe His Leu Ile Pro Ser Thr Gln Val Ala Ala Thr
    370                 375                 380

Pro Asp Arg Ser Ser Thr Ser Gln Asp Ser Pro Asp Thr Arg Gly Val
385                 390                 395                 400
```

```
Lys Ala Phe Ser Leu Ala Asp Leu Gln Asn Thr Ala Ser Cys Phe Ser
                405                 410                 415

Pro Asn Arg Leu Leu Gly Glu Gly Thr Ile Gly Arg Val Tyr Lys Ala
            420                 425                 430

Lys Phe Gln Asp Gly Arg Lys Phe Ala Val Lys Glu Ile Asp Ser Ser
        435                 440                 445

Leu Leu Gly Lys Gly Asn Pro Glu Glu Phe Ser His Ile Val Ser Ser
    450                 455                 460

Ile Ser Ser Ile His His Lys Asn Met Ala Glu Leu Val Gly Tyr Cys
465                 470                 475                 480

Ser Glu Gln Gly Arg Asn Met Leu Val Tyr Glu Tyr Phe Thr Ser Gly
                485                 490                 495

Ser Leu His Arg Phe Leu His Leu Ser Asp Asp Phe Ser Lys Pro Leu
            500                 505                 510

Thr Trp Asn Thr Arg Ile Arg Ile Ala Leu Gly Thr Ala Lys Ala Ile
        515                 520                 525

Glu Tyr Leu His Glu Thr Cys Ser Pro Pro Leu Val His Lys Asn Ile
    530                 535                 540

Lys Ser Ser Asn Ile Leu Leu Asp Asn Glu Leu Asn Pro Arg Leu Ser
545                 550                 555                 560

Asp Tyr Gly Leu Ala Asn Phe His His Arg Thr Ser Gln Asn Leu Gly
                565                 570                 575

Val Gly Tyr Asn Ala Pro Glu Cys Thr Asp Pro Ser Ala Tyr Thr Gln
            580                 585                 590

Lys Ser Asp Val Tyr Ser Phe Gly Val Val Met Leu Glu Leu Leu Thr
        595                 600                 605

Gly Arg Lys Pro Tyr Asp Ser Gly Arg Pro Lys Ala Glu Gln Ser Leu
    610                 615                 620

Val Arg Trp Ala Lys Pro Gln Leu Lys Asp Met Asp Thr Leu Asp Glu
625                 630                 635                 640

Met Val Asp Pro Ala Leu Cys Gly Leu Tyr Ala Pro Glu Ser Val Ser
                645                 650                 655

Ser Phe Ala Asp Ile Val Ser Ile Cys Val Met Thr Glu Pro Gly Leu
            660                 665                 670

Arg Pro Pro Val Ser Asn Val Val Glu Ala Leu Lys Arg Leu Val
        675                 680                 685

<210> SEQ ID NO 19
<211> LENGTH: 2100
<212> TYPE: DNA
<213> ORGANISM: Arabidopsis thaliana
<220> FEATURE:
<221> NAME/KEY: CDS
<222> LOCATION: (1)..(2100)

<400> SEQUENCE: 19 atg acg cag aag ctc gta cgc ctt gtg atc gtc tct ctg gct att act       48
Met Thr Gln Lys Leu Val Arg Leu Val Ile Val Ser Leu Ala Ile Thr
1               5                   10                  15 gtc act tta ctt caa gca aaa acc gat aac caa gaa gtc tcc gcg ttg       96
Val Thr Leu Leu Gln Ala Lys Thr Asp Asn Gln Glu Val Ser Ala Leu
            20                  25                  30 aac gta atg ttc acg agc tta aat tcg ccg tcg aaa ctc aaa ggt tgg      144
Asn Val Met Phe Thr Ser Leu Asn Ser Pro Ser Lys Leu Lys Gly Trp
        35                  40                  45 aaa gct aac gga ggt gat ccc tgc gaa gat tct tgg gaa ggc gtc aaa      192
Lys Ala Asn Gly Gly Asp Pro Cys Glu Asp Ser Trp Glu Gly Val Lys
```

```
              50                  55                  60
tgc aaa ggc tct tcg gtc act gaa tta cag tta tca ggc ttt gag cta       240
Cys Lys Gly Ser Ser Val Thr Glu Leu Gln Leu Ser Gly Phe Glu Leu
 65                  70                  75                  80 ggt gga tct cgc ggt tat cta cta agc aac ctc aaa tct ctc aca act       288
Gly Gly Ser Arg Gly Tyr Leu Leu Ser Asn Leu Lys Ser Leu Thr Thr
                     85                  90                  95 ttt gat ctc agc aaa aac aat ctc aaa gga aac ata cct tat caa ctc       336
Phe Asp Leu Ser Lys Asn Asn Leu Lys Gly Asn Ile Pro Tyr Gln Leu
                100                 105                 110 cca ccc aac att gcc aat cta gac ttt tct gaa aac gaa ctc gat gga       384
Pro Pro Asn Ile Ala Asn Leu Asp Phe Ser Glu Asn Glu Leu Asp Gly
            115                 120                 125 aac gtg ccc tac tcg tta tct caa atg aaa aat ctc caa agc att aat       432
Asn Val Pro Tyr Ser Leu Ser Gln Met Lys Asn Leu Gln Ser Ile Asn
        130                 135                 140 ctt gga caa aac aag ctc aat gga gaa cta cca gat atg ttt cag aaa       480
Leu Gly Gln Asn Lys Leu Asn Gly Glu Leu Pro Asp Met Phe Gln Lys
145                 150                 155                 160 ctg tcc aaa ctc gaa act ctg gac ttt tcg ttg aat aaa ctc tct ggg       528
Leu Ser Lys Leu Glu Thr Leu Asp Phe Ser Leu Asn Lys Leu Ser Gly
                    165                 170                 175 aaa tta cct cag agt ttt gct aat ctc aca agc ctc aaa aaa cta cac       576
Lys Leu Pro Gln Ser Phe Ala Asn Leu Thr Ser Leu Lys Lys Leu His
                180                 185                 190 ttg cag gat aat cga ttc aca ggc gac ata aac gtt ctc agg aac ctt       624
Leu Gln Asp Asn Arg Phe Thr Gly Asp Ile Asn Val Leu Arg Asn Leu
            195                 200                 205 gcc atc gat gac ttg aac gtc gaa gac aac cag ttt gaa gga tgg ata       672
Ala Ile Asp Asp Leu Asn Val Glu Asp Asn Gln Phe Glu Gly Trp Ile
        210                 215                 220 cct aat gag ctt aag gac ata gac agt tta ctg act gga ggt aac gac       720
Pro Asn Glu Leu Lys Asp Ile Asp Ser Leu Leu Thr Gly Gly Asn Asp
225                 230                 235                 240 tgg tca act gaa act gcc cca cca cca ccg ggt gtt aaa tat ggc           768
Trp Ser Thr Glu Thr Ala Pro Pro Pro Pro Gly Val Lys Tyr Gly
                    245                 250                 255 cga aaa tct tcg ggt tcg aaa gac gga gga ggt ata acc gcc gga act       816
Arg Lys Ser Ser Gly Ser Lys Asp Gly Gly Gly Ile Thr Ala Gly Thr
                260                 265                 270 gga atg gtg atc gct gga gca tgt tta ggc gtt ctt gtg ttg atc att       864
Gly Met Val Ile Ala Gly Ala Cys Leu Gly Val Leu Val Leu Ile Ile
            275                 280                 285 gtt tta att gcg ctc gtt tcc aag aaa aaa tca tct ctc tca cct cat       912
Val Leu Ile Ala Leu Val Ser Lys Lys Lys Ser Ser Leu Ser Pro His
        290                 295                 300 ttc atc gac gaa gat aac agt cat cac acc cca aag ttc aaa tct ctc       960
Phe Ile Asp Glu Asp Asn Ser His His Thr Pro Lys Phe Lys Ser Leu
305                 310                 315                 320 acc tcg cat gga tct gcg caa gag ctt cgt gtt gat ttc ggc aac gat      1008
Thr Ser His Gly Ser Ala Gln Glu Leu Arg Val Asp Phe Gly Asn Asp
                    325                 330                 335 tac aaa gat ggg aaa tct gga gat tcg ggt gat gaa aat atc cat agg      1056
Tyr Lys Asp Gly Lys Ser Gly Asp Ser Gly Asp Glu Asn Ile His Arg
                340                 345                 350 ata gga tca aag gga cta aaa cat tat gtt tcg tcg cgt gtg atg tct      1104
Ile Gly Ser Lys Gly Leu Lys His Tyr Val Ser Ser Arg Val Met Ser
            355                 360                 365 ttc act gat acc gaa ttt gcg aac aag ctc aat gca aaa cga acc act      1152
Phe Thr Asp Thr Glu Phe Ala Asn Lys Leu Asn Ala Lys Arg Thr Thr
```

|                                                                                    |      |
|------------------------------------------------------------------------------------|------|
| 370                   375                    380                                   |      |
| tca act cgt tcc gct gtg gaa ttc gag ctc tct gat ttg caa agc gca                    | 1200 |
| Ser Thr Arg Ser Ala Val Glu Phe Glu Leu Ser Asp Leu Gln Ser Ala                    |      |
| 385                   390                    395                    400            |      |
| aca gcc aat ttc tca cct gga aat cta cta ggg gaa ggc tca atc gga                    | 1248 |
| Thr Ala Asn Phe Ser Pro Gly Asn Leu Leu Gly Glu Gly Ser Ile Gly                    |      |
|         405                    410                    415                          |      |
| cgt gtt tac aga gcc aaa tat tcc gac gga cgt act ttg gcg gtt aag                    | 1296 |
| Arg Val Tyr Arg Ala Lys Tyr Ser Asp Gly Arg Thr Leu Ala Val Lys                    |      |
|         420                    425                    430                          |      |
| aag atc gat tca acg ttg ttt gat tcg ggt aaa tca gaa gga ata acg                    | 1344 |
| Lys Ile Asp Ser Thr Leu Phe Asp Ser Gly Lys Ser Glu Gly Ile Thr                    |      |
|         435                    440                    445                          |      |
| ccg att gta atg agc ctc tca aag att agg cat caa aat ata gca gag                    | 1392 |
| Pro Ile Val Met Ser Leu Ser Lys Ile Arg His Gln Asn Ile Ala Glu                    |      |
|         450                    455                    460                          |      |
| ctc gta ggc tat tgc tca gag caa ggt cac aac atg tta gtc tac gaa                    | 1440 |
| Leu Val Gly Tyr Cys Ser Glu Gln Gly His Asn Met Leu Val Tyr Glu                    |      |
| 465                   470                    475                    480            |      |
| tac ttc agg aat ggc tca ctc cat gag ttc ctt cat ttg tca gat tgc                    | 1488 |
| Tyr Phe Arg Asn Gly Ser Leu His Glu Phe Leu His Leu Ser Asp Cys                    |      |
|         485                    490                    495                          |      |
| ttc agt aaa ccc ttg act tgg aac aca aga gtc aga atc gcc ttg gga                    | 1536 |
| Phe Ser Lys Pro Leu Thr Trp Asn Thr Arg Val Arg Ile Ala Leu Gly                    |      |
|         500                    505                    510                          |      |
| acc gct cga gcc gtt gag tac ctg cac gag gca tgt tca cct tct gtg                    | 1584 |
| Thr Ala Arg Ala Val Glu Tyr Leu His Glu Ala Cys Ser Pro Ser Val                    |      |
|         515                    520                    525                          |      |
| atg cat aag aat atc aag tct tct aac att ttg cta gac gca gat ctc                    | 1632 |
| Met His Lys Asn Ile Lys Ser Ser Asn Ile Leu Leu Asp Ala Asp Leu                    |      |
|         530                    535                    540                          |      |
| aac cct cgt ctc tca gat tac ggc ctc tca aaa ttc tac ctt aga acg                    | 1680 |
| Asn Pro Arg Leu Ser Asp Tyr Gly Leu Ser Lys Phe Tyr Leu Arg Thr                    |      |
| 545                   550                    555                    560            |      |
| agt caa aat cta gga gaa gga tac aat gca cca gaa gcc agg gac cct                    | 1728 |
| Ser Gln Asn Leu Gly Glu Gly Tyr Asn Ala Pro Glu Ala Arg Asp Pro                    |      |
|         565                    570                    575                          |      |
| tct gct tat aca cca aag agt gac gtc tac agc ttt ggc gtc gtc atg                    | 1776 |
| Ser Ala Tyr Thr Pro Lys Ser Asp Val Tyr Ser Phe Gly Val Val Met                    |      |
|         580                    585                    590                          |      |
| tta gag ctt ctc acc ggt cga gtt cca ttt gac gga gag aag cca agg                    | 1824 |
| Leu Glu Leu Leu Thr Gly Arg Val Pro Phe Asp Gly Glu Lys Pro Arg                    |      |
|         595                    600                    605                          |      |
| ccg gag aga tcg ttg gta cgg tgg gcg aca cca caa ctt cac gac ata                    | 1872 |
| Pro Glu Arg Ser Leu Val Arg Trp Ala Thr Pro Gln Leu His Asp Ile                    |      |
|         610                    615                    620                          |      |
| gat gca ttg tcg aat ata gcg gat cca gct ctg cac gga ctt tac cca                    | 1920 |
| Asp Ala Leu Ser Asn Ile Ala Asp Pro Ala Leu His Gly Leu Tyr Pro                    |      |
| 625                   630                    635                    640            |      |
| cca aaa tca ttg tca aga ttc gcc gac att atc gca tta tgt gtt cag                    | 1968 |
| Pro Lys Ser Leu Ser Arg Phe Ala Asp Ile Ile Ala Leu Cys Val Gln                    |      |
|         645                    650                    655                          |      |
| gtg gaa ccg gag ttc cga cca ccg atg tca gaa gtt gtg gag gcg ctt                    | 2016 |
| Val Glu Pro Glu Phe Arg Pro Pro Met Ser Glu Val Val Glu Ala Leu                    |      |
|         660                    665                    670                          |      |
| gta cgg atg gtt caa cgg tca agt atg aag ctt aaa gat gat ctt tca                    | 2064 |
| Val Arg Met Val Gln Arg Ser Ser Met Lys Leu Lys Asp Asp Leu Ser                    |      |
|         675                    680                    685                          |      |
| tcg tct tat cga gcc cac gac gat tat gat tac tag                                    | 2100 |
| Ser Ser Tyr Arg Ala His Asp Asp Tyr Asp Tyr                                        |      |

```
                690                 695

<210> SEQ ID NO 20
<211> LENGTH: 699
<212> TYPE: PRT
<213> ORGANISM: Arabidopsis thaliana

<400> SEQUENCE: 20

Met Thr Gln Lys Leu Val Arg Leu Val Ile Val Ser Leu Ala Ile Thr
1               5                   10                  15

Val Thr Leu Leu Gln Ala Lys Thr Asp Asn Gln Glu Val Ser Ala Leu
            20                  25                  30

Asn Val Met Phe Thr Ser Leu Asn Ser Pro Ser Lys Leu Lys Gly Trp
        35                  40                  45

Lys Ala Asn Gly Gly Asp Pro Cys Glu Asp Ser Trp Glu Gly Val Lys
    50                  55                  60

Cys Lys Gly Ser Ser Val Thr Glu Leu Gln Leu Ser Gly Phe Glu Leu
65                  70                  75                  80

Gly Gly Ser Arg Gly Tyr Leu Leu Ser Asn Leu Lys Ser Leu Thr Thr
                85                  90                  95

Phe Asp Leu Ser Lys Asn Asn Leu Lys Gly Asn Ile Pro Tyr Gln Leu
            100                 105                 110

Pro Pro Asn Ile Ala Asn Leu Asp Phe Ser Glu Asn Glu Leu Asp Gly
        115                 120                 125

Asn Val Pro Tyr Ser Leu Ser Gln Met Lys Asn Leu Gln Ser Ile Asn
    130                 135                 140

Leu Gly Gln Asn Lys Leu Asn Gly Glu Leu Pro Asp Met Phe Gln Lys
145                 150                 155                 160

Leu Ser Lys Leu Glu Thr Leu Asp Phe Ser Leu Asn Lys Leu Ser Gly
                165                 170                 175

Lys Leu Pro Gln Ser Phe Ala Asn Leu Thr Ser Leu Lys Lys Leu His
            180                 185                 190

Leu Gln Asp Asn Arg Phe Thr Gly Asp Ile Asn Val Leu Arg Asn Leu
        195                 200                 205

Ala Ile Asp Asp Leu Asn Val Glu Asp Asn Gln Phe Glu Gly Trp Ile
    210                 215                 220

Pro Asn Glu Leu Lys Asp Ile Asp Ser Leu Leu Thr Gly Gly Asn Asp
225                 230                 235                 240

Trp Ser Thr Glu Thr Ala Pro Pro Pro Pro Gly Val Lys Tyr Gly
                245                 250                 255

Arg Lys Ser Ser Gly Ser Lys Asp Gly Gly Ile Thr Ala Gly Thr
            260                 265                 270

Gly Met Val Ile Ala Gly Ala Cys Leu Gly Val Leu Val Ile Ile
        275                 280                 285

Val Leu Ile Ala Leu Val Ser Lys Lys Ser Ser Leu Ser Pro His
    290                 295                 300

Phe Ile Asp Glu Asp Asn Ser His His Thr Pro Lys Phe Lys Ser Leu
305                 310                 315                 320

Thr Ser His Gly Ser Ala Gln Glu Leu Arg Val Asp Phe Gly Asn Asp
                325                 330                 335

Tyr Lys Asp Gly Lys Ser Gly Asp Ser Gly Asp Glu Asn Ile His Arg
            340                 345                 350

Ile Gly Ser Lys Gly Leu Lys His Tyr Val Ser Ser Arg Val Met Ser
        355                 360                 365

Phe Thr Asp Thr Glu Phe Ala Asn Lys Leu Asn Ala Lys Arg Thr Thr
```

```
                    370              375              380
Ser Thr Arg Ser Ala Val Glu Phe Glu Leu Ser Asp Leu Gln Ser Ala
385                 390                  395                 400

Thr Ala Asn Phe Ser Pro Gly Asn Leu Leu Gly Glu Gly Ser Ile Gly
                405                  410                 415

Arg Val Tyr Arg Ala Lys Tyr Ser Asp Gly Arg Thr Leu Ala Val Lys
            420                  425                 430

Lys Ile Asp Ser Thr Leu Phe Asp Ser Gly Lys Ser Glu Gly Ile Thr
            435                  440                 445

Pro Ile Val Met Ser Leu Ser Lys Ile Arg His Gln Asn Ile Ala Glu
        450                  455                 460

Leu Val Gly Tyr Cys Ser Glu Gln Gly His Asn Met Leu Val Tyr Glu
465                 470                  475                 480

Tyr Phe Arg Asn Gly Ser Leu His Glu Phe His Leu Ser Asp Cys
                485                  490                 495

Phe Ser Lys Pro Leu Thr Trp Asn Thr Arg Val Arg Ile Ala Leu Gly
                500                  505                 510

Thr Ala Arg Ala Val Glu Tyr Leu His Glu Ala Cys Ser Pro Ser Val
            515                  520                 525

Met His Lys Asn Ile Lys Ser Ser Asn Ile Leu Leu Asp Ala Asp Leu
        530                  535                 540

Asn Pro Arg Leu Ser Asp Tyr Gly Leu Ser Lys Phe Tyr Leu Arg Thr
545                 550                  555                 560

Ser Gln Asn Leu Gly Glu Gly Tyr Asn Ala Pro Glu Ala Arg Asp Pro
                565                  570                 575

Ser Ala Tyr Thr Pro Lys Ser Asp Val Tyr Ser Phe Gly Val Val Met
            580                  585                 590

Leu Glu Leu Leu Thr Gly Arg Val Pro Phe Asp Gly Glu Lys Pro Arg
        595                  600                 605

Pro Glu Arg Ser Leu Val Arg Trp Ala Thr Pro Gln Leu His Asp Ile
    610                  615                 620

Asp Ala Leu Ser Asn Ile Ala Asp Pro Ala Leu His Gly Leu Tyr Pro
625                 630                  635                 640

Pro Lys Ser Leu Ser Arg Phe Ala Asp Ile Ile Ala Leu Cys Val Gln
                645                  650                 655

Val Glu Pro Glu Phe Arg Pro Pro Met Ser Glu Val Val Glu Ala Leu
            660                  665                 670

Val Arg Met Val Gln Arg Ser Ser Met Lys Leu Lys Asp Asp Leu Ser
        675                  680                 685

Ser Ser Tyr Arg Ala His Asp Asp Tyr Asp Tyr
690                 695

<210> SEQ ID NO 21
<211> LENGTH: 2160
<212> TYPE: DNA
<213> ORGANISM: Arabidopsis thaliana
<220> FEATURE:
<221> NAME/KEY: CDS
<222> LOCATION: (1)..(2160)

<400> SEQUENCE: 21 atg agg gag aat tgg gcg gtg gtg gct ctg ttt aca cta tgc att gta      48
Met Arg Glu Asn Trp Ala Val Val Ala Leu Phe Thr Leu Cys Ile Val
1               5                   10                  15 ggg ttt gag ctt aga ttc atc cat gga gct act gat gca tca gac act      96
Gly Phe Glu Leu Arg Phe Ile His Gly Ala Thr Asp Ala Ser Asp Thr
            20                  25                  30
```

| | | | | | | | | | | | | | | |
|---|---|---|---|---|---|---|---|---|---|---|---|---|---|---|
| tca | gca | ttg | aac | aca | ttg | ttc | agt | ggt | atg | cat | tct | cca | gct | cag | cta | 144 |
| Ser | Ala | Leu | Asn | Thr | Leu | Phe | Ser | Gly | Met | His | Ser | Pro | Ala | Gln | Leu |
| | | 35 | | | | 40 | | | | 45 | | | |

| aca | caa | tgg | act | gca | gca | gct | ggt | gat | cct | tgt | ggc | cag | aat | tgg | aga | 192 |
| Thr | Gln | Trp | Thr | Ala | Ala | Ala | Gly | Asp | Pro | Cys | Gly | Gln | Asn | Trp | Arg |
| 50 | | | | | 55 | | | | | 60 | | | |

| ggc | gtc | act | tgt | tcc | ggc | tca | cga | gtt | act | caa | ata | aag | ttg | tca | ggt | 240 |
| Gly | Val | Thr | Cys | Ser | Gly | Ser | Arg | Val | Thr | Gln | Ile | Lys | Leu | Ser | Gly |
| 65 | | | | | 70 | | | | | 75 | | | | | 80 |

| ctt | gag | ctc | tct | gga | act | ctt | gga | gga | tac | atg | ctt | gat | aaa | ttg | act | 288 |
| Leu | Glu | Leu | Ser | Gly | Thr | Leu | Gly | Gly | Tyr | Met | Leu | Asp | Lys | Leu | Thr |
| | | | | 85 | | | | | 90 | | | | | 95 |

| tct | ctt | acc | gag | ctt | gat | cta | agc | agc | aat | aat | ctt | gga | ggt | gat | tta | 336 |
| Ser | Leu | Thr | Glu | Leu | Asp | Leu | Ser | Ser | Asn | Asn | Leu | Gly | Gly | Asp | Leu |
| | | | 100 | | | | | 105 | | | | | 110 |

| cca | tat | cag | ttt | cct | cca | aat | ctg | caa | cga | ttg | aac | ctt | gcg | aat | aat | 384 |
| Pro | Tyr | Gln | Phe | Pro | Pro | Asn | Leu | Gln | Arg | Leu | Asn | Leu | Ala | Asn | Asn |
| | 115 | | | | | 120 | | | | | 125 |

| caa | ttc | act | gga | gct | gct | tcg | tac | tca | ctt | tct | cag | att | aca | cca | ctt | 432 |
| Gln | Phe | Thr | Gly | Ala | Ala | Ser | Tyr | Ser | Leu | Ser | Gln | Ile | Thr | Pro | Leu |
| 130 | | | | | 135 | | | | | 140 |

| aag | tat | ctc | aat | ctt | ggt | cac | aat | cag | ttt | aag | ggg | cag | ata | gct | atc | 480 |
| Lys | Tyr | Leu | Asn | Leu | Gly | His | Asn | Gln | Phe | Lys | Gly | Gln | Ile | Ala | Ile |
| 145 | | | | | 150 | | | | | 155 | | | | | 160 |

| gac | ttc | tcc | aag | ctc | gac | tct | ctc | aca | acc | ttg | gac | ttc | tct | ttc | aat | 528 |
| Asp | Phe | Ser | Lys | Leu | Asp | Ser | Leu | Thr | Thr | Leu | Asp | Phe | Ser | Phe | Asn |
| | | | | 165 | | | | | 170 | | | | | 175 |

| tct | ttc | acg | aac | tct | tta | ccg | gca | acg | ttt | tcc | tct | cta | aca | agt | tta | 576 |
| Ser | Phe | Thr | Asn | Ser | Leu | Pro | Ala | Thr | Phe | Ser | Ser | Leu | Thr | Ser | Leu |
| | | | 180 | | | | | 185 | | | | | 190 |

| aaa | tca | cta | tac | ctt | cag | aac | aat | cag | ttc | tca | ggc | aca | gtc | gat | gtc | 624 |
| Lys | Ser | Leu | Tyr | Leu | Gln | Asn | Asn | Gln | Phe | Ser | Gly | Thr | Val | Asp | Val |
| | 195 | | | | | 200 | | | | | 205 |

| tta | gcc | ggt | ctt | cct | ctt | gag | act | ctg | aac | att | gcg | aac | aat | gac | ttc | 672 |
| Leu | Ala | Gly | Leu | Pro | Leu | Glu | Thr | Leu | Asn | Ile | Ala | Asn | Asn | Asp | Phe |
| 210 | | | | | 215 | | | | | 220 |

| acg | ggg | tgg | atc | ccc | agt | tct | tta | aag | ggc | atc | aca | tta | ata | aaa | gat | 720 |
| Thr | Gly | Trp | Ile | Pro | Ser | Ser | Leu | Lys | Gly | Ile | Thr | Leu | Ile | Lys | Asp |
| 225 | | | | | 230 | | | | | 235 | | | | | 240 |

| ggc | aac | tca | ttc | aat | act | gga | cct | gca | cct | cca | cca | cca | cct | ggt | aca | 768 |
| Gly | Asn | Ser | Phe | Asn | Thr | Gly | Pro | Ala | Pro | Pro | Pro | Pro | Pro | Gly | Thr |
| | | | 245 | | | | | 250 | | | | | 255 |

| cct | cct | atc | cgt | ggc | tcc | ccg | agc | cgt | aaa | tct | gga | gga | cgt | gaa | agc | 816 |
| Pro | Pro | Ile | Arg | Gly | Ser | Pro | Ser | Arg | Lys | Ser | Gly | Gly | Arg | Glu | Ser |
| | | 260 | | | | | 265 | | | | | 270 |

| cgg | tct | agt | gat | gag | tcc | acc | aga | aat | gga | gat | tcc | aag | aaa | tca | gga | 864 |
| Arg | Ser | Ser | Asp | Glu | Ser | Thr | Arg | Asn | Gly | Asp | Ser | Lys | Lys | Ser | Gly |
| | 275 | | | | | 280 | | | | | 285 |

| atc | gga | gcg | ggg | gca | att | gcg | ggc | ata | atc | att | tca | ttg | tta | gta | gtt | 912 |
| Ile | Gly | Ala | Gly | Ala | Ile | Ala | Gly | Ile | Ile | Ile | Ser | Leu | Leu | Val | Val |
| 290 | | | | | 295 | | | | | 300 |

| aca | gct | ctt | ctt | gtt | gct | ttc | ttc | ttg | ttc | aga | aga | aaa | aaa | tca | aag | 960 |
| Thr | Ala | Leu | Leu | Val | Ala | Phe | Phe | Leu | Phe | Arg | Arg | Lys | Lys | Ser | Lys |
| 305 | | | | | 310 | | | | | 315 | | | | | 320 |

| agg | tca | tca | ccc | atg | gac | att | gag | aaa | acc | gat | aac | cag | cct | ttc | act | 1008 |
| Arg | Ser | Ser | Pro | Met | Asp | Ile | Glu | Lys | Thr | Asp | Asn | Gln | Pro | Phe | Thr |
| | | | | 325 | | | | | 330 | | | | | 335 |

| ctt | gct | tca | aac | gac | ttt | cac | gaa | aac | aat | tcc | att | cag | agt | tct | tca | 1056 |
| Leu | Ala | Ser | Asn | Asp | Phe | His | Glu | Asn | Asn | Ser | Ile | Gln | Ser | Ser | Ser |
| | | 340 | | | | | 345 | | | | | 350 |

```
tca gtt gag aca aag aaa ctg gac act tca ttg tct att aat ctt cga   1104
Ser Val Glu Thr Lys Lys Leu Asp Thr Ser Leu Ser Ile Asn Leu Arg
    355                 360                 365 cct cca cca att gat aga aac aaa tca ttt gat gat gaa gat tcg aca   1152
Pro Pro Pro Ile Asp Arg Asn Lys Ser Phe Asp Asp Glu Asp Ser Thr
370                 375                 380 aga aag cct att gct gtc aag aaa tcc aca gtg gtg gtt cct tca aat   1200
Arg Lys Pro Ile Ala Val Lys Lys Ser Thr Val Val Val Pro Ser Asn
385                 390                 395                 400 gtg aga ctc tat tca gtt gca gat ctc caa att gct act ggc agt ttc   1248
Val Arg Leu Tyr Ser Val Ala Asp Leu Gln Ile Ala Thr Gly Ser Phe
            405                 410                 415 agc gta gat aat ctt ctt gga gaa ggg act ttt ggg cga gta tac aga   1296
Ser Val Asp Asn Leu Leu Gly Glu Gly Thr Phe Gly Arg Val Tyr Arg
        420                 425                 430 gct gag ttt gat gat gga aag gtt ctt gct gtg aag aaa att gat tcg   1344
Ala Glu Phe Asp Asp Gly Lys Val Leu Ala Val Lys Lys Ile Asp Ser
435                 440                 445 tct gct ctc cca cat ggc atg acc gat gat ttc att gaa atg gta tcg   1392
Ser Ala Leu Pro His Gly Met Thr Asp Asp Phe Ile Glu Met Val Ser
450                 455                 460 aaa ata gcc aat ttg gat cat cca aat gtg acc aag ctt gtt ggt tac   1440
Lys Ile Ala Asn Leu Asp His Pro Asn Val Thr Lys Leu Val Gly Tyr
465                 470                 475                 480 tgt gct gag cac gga caa cat ctc gtg gtc tat gaa ttc cac aaa aat   1488
Cys Ala Glu His Gly Gln His Leu Val Val Tyr Glu Phe His Lys Asn
            485                 490                 495 gga tca tta cat gac ttc tta cac tta tca gaa gag gaa agt aaa gca   1536
Gly Ser Leu His Asp Phe Leu His Leu Ser Glu Glu Glu Ser Lys Ala
        500                 505                 510 ttg gtg tgg aat tca cga gtc aag atc gct ctt ggg act gca cgc gca   1584
Leu Val Trp Asn Ser Arg Val Lys Ile Ala Leu Gly Thr Ala Arg Ala
    515                 520                 525 ttg gag tat ctg cat gaa gtt tgc tca ccg tct ata gtg gac aag aat   1632
Leu Glu Tyr Leu His Glu Val Cys Ser Pro Ser Ile Val Asp Lys Asn
530                 535                 540 atc aaa tca gct aat att tta ctc gat tca gag ctg aat cct cac tta   1680
Ile Lys Ser Ala Asn Ile Leu Leu Asp Ser Glu Leu Asn Pro His Leu
545                 550                 555                 560 tca gat tct ggt ctc gca agc ttc ctt ccc aca gct aat gag tta tta   1728
Ser Asp Ser Gly Leu Ala Ser Phe Leu Pro Thr Ala Asn Glu Leu Leu
            565                 570                 575 aac caa acc gat gaa ggg tat agc gca cct gaa gta tca atg tca ggc   1776
Asn Gln Thr Asp Glu Gly Tyr Ser Ala Pro Glu Val Ser Met Ser Gly
        580                 585                 590 caa tat tct ttg aag agt gac att tac agt ttt gga gta gtg atg ctt   1824
Gln Tyr Ser Leu Lys Ser Asp Ile Tyr Ser Phe Gly Val Val Met Leu
    595                 600                 605 gaa ctt tta act ggg aga aaa cca ttt gac agc aca agg tca aga tct   1872
Glu Leu Leu Thr Gly Arg Lys Pro Phe Asp Ser Thr Arg Ser Arg Ser
610                 615                 620 gag cag tca ctg gtt cga tgg gcg aca cca caa ctt cac gac att gat   1920
Glu Gln Ser Leu Val Arg Trp Ala Thr Pro Gln Leu His Asp Ile Asp
625                 630                 635                 640 gct tta gcc aaa atg gtt gat cca gct ctt aaa ggg ctt tat cct gtc   1968
Ala Leu Ala Lys Met Val Asp Pro Ala Leu Lys Gly Leu Tyr Pro Val
            645                 650                 655 aaa tcc ctt tct cga ttt gca gat gtt atc gct ctc tgt gtc cag ccg   2016
Lys Ser Leu Ser Arg Phe Ala Asp Val Ile Ala Leu Cys Val Gln Pro
        660                 665                 670
```

-continued

```
gag ccg gag ttt aga cca cca atg tct gaa gtt gtg cag gct cta gtt    2064
Glu Pro Glu Phe Arg Pro Pro Met Ser Glu Val Val Gln Ala Leu Val
        675                 680                 685 gtg tta gtg cag aga gct aac atg agc aag aga act gtc gga gtt gac    2112
Val Leu Val Gln Arg Ala Asn Met Ser Lys Arg Thr Val Gly Val Asp
690                 695                 700 cca tcg caa cgt gct ggt agt gcc gac acg acc agt gat tac atg taa    2160
Pro Ser Gln Arg Ala Gly Ser Ala Asp Thr Thr Ser Asp Tyr Met
705                 710                 715
```

<210> SEQ ID NO 22
<211> LENGTH: 719
<212> TYPE: PRT
<213> ORGANISM: Arabidopsis thaliana

<400> SEQUENCE: 22

```
Met Arg Glu Asn Trp Ala Val Val Ala Leu Phe Thr Leu Cys Ile Val
1               5                   10                  15

Gly Phe Glu Leu Arg Phe Ile His Gly Ala Thr Ala Ser Asp Thr
            20                  25                  30

Ser Ala Leu Asn Thr Leu Phe Ser Gly Met His Ser Pro Ala Gln Leu
        35                  40                  45

Thr Gln Trp Thr Ala Ala Ala Gly Asp Pro Cys Gly Gln Asn Trp Arg
    50                  55                  60

Gly Val Thr Cys Ser Gly Ser Arg Val Thr Gln Ile Lys Leu Ser Gly
65                  70                  75                  80

Leu Glu Leu Ser Gly Thr Leu Gly Gly Tyr Met Leu Asp Lys Leu Thr
                85                  90                  95

Ser Leu Thr Glu Leu Asp Leu Ser Ser Asn Asn Leu Gly Gly Asp Leu
            100                 105                 110

Pro Tyr Gln Phe Pro Pro Asn Leu Gln Arg Leu Asn Leu Ala Asn Asn
        115                 120                 125

Gln Phe Thr Gly Ala Ala Ser Tyr Ser Leu Ser Gln Ile Thr Pro Leu
    130                 135                 140

Lys Tyr Leu Asn Leu Gly His Asn Gln Phe Lys Gly Gln Ile Ala Ile
145                 150                 155                 160

Asp Phe Ser Lys Leu Asp Ser Leu Thr Thr Leu Asp Phe Ser Phe Asn
                165                 170                 175

Ser Phe Thr Asn Ser Leu Pro Ala Thr Phe Ser Ser Leu Thr Ser Leu
            180                 185                 190

Lys Ser Leu Tyr Leu Gln Asn Asn Gln Phe Ser Gly Thr Val Asp Val
        195                 200                 205

Leu Ala Gly Leu Pro Leu Glu Thr Leu Asn Ile Ala Asn Asn Asp Phe
    210                 215                 220

Thr Gly Trp Ile Pro Ser Ser Leu Lys Gly Ile Thr Leu Ile Lys Asp
225                 230                 235                 240

Gly Asn Ser Phe Asn Thr Gly Pro Ala Pro Pro Pro Pro Gly Thr
                245                 250                 255

Pro Pro Ile Arg Gly Ser Pro Arg Lys Ser Gly Arg Glu Ser
            260                 265                 270

Arg Ser Ser Asp Glu Ser Thr Arg Asn Gly Asp Ser Lys Lys Ser Gly
        275                 280                 285

Ile Gly Ala Gly Ala Ile Ala Gly Ile Ile Ile Ser Leu Leu Val Val
    290                 295                 300

Thr Ala Leu Leu Val Ala Phe Phe Leu Phe Arg Arg Lys Lys Ser Lys
305                 310                 315                 320
```

```
Arg Ser Ser Pro Met Asp Ile Glu Lys Thr Asp Asn Gln Pro Phe Thr
                325                 330                 335

Leu Ala Ser Asn Asp Phe His Glu Asn Asn Ser Ile Gln Ser Ser Ser
            340                 345                 350

Ser Val Glu Thr Lys Lys Leu Asp Thr Ser Leu Ser Ile Asn Leu Arg
        355                 360                 365

Pro Pro Pro Ile Asp Arg Asn Lys Ser Phe Asp Glu Asp Ser Thr
370                 375                 380

Arg Lys Pro Ile Ala Val Lys Lys Ser Thr Val Val Pro Ser Asn
385                 390                 395                 400

Val Arg Leu Tyr Ser Val Ala Asp Leu Gln Ile Ala Thr Gly Ser Phe
                405                 410                 415

Ser Val Asp Asn Leu Leu Gly Glu Gly Thr Phe Gly Arg Val Tyr Arg
            420                 425                 430

Ala Glu Phe Asp Asp Gly Lys Val Leu Ala Val Lys Lys Ile Asp Ser
        435                 440                 445

Ser Ala Leu Pro His Gly Met Thr Asp Asp Phe Ile Glu Met Val Ser
450                 455                 460

Lys Ile Ala Asn Leu Asp His Pro Asn Val Thr Lys Leu Val Gly Tyr
465                 470                 475                 480

Cys Ala Glu His Gly Gln His Leu Val Val Tyr Glu Phe His Lys Asn
                485                 490                 495

Gly Ser Leu His Asp Phe Leu His Leu Ser Glu Glu Ser Lys Ala
            500                 505                 510

Leu Val Trp Asn Ser Arg Val Lys Ile Ala Leu Gly Thr Ala Arg Ala
        515                 520                 525

Leu Glu Tyr Leu His Glu Val Cys Ser Pro Ser Ile Val Asp Lys Asn
530                 535                 540

Ile Lys Ser Ala Asn Ile Leu Leu Asp Ser Glu Leu Asn Pro His Leu
545                 550                 555                 560

Ser Asp Ser Gly Leu Ala Ser Phe Leu Pro Thr Ala Asn Glu Leu Leu
                565                 570                 575

Asn Gln Thr Asp Glu Gly Tyr Ser Ala Pro Glu Val Ser Met Ser Gly
            580                 585                 590

Gln Tyr Ser Leu Lys Ser Asp Ile Tyr Ser Phe Gly Val Val Met Leu
        595                 600                 605

Glu Leu Leu Thr Gly Arg Lys Pro Phe Asp Ser Thr Arg Ser Arg Ser
610                 615                 620

Glu Gln Ser Leu Val Arg Trp Ala Thr Pro Gln Leu His Asp Ile Asp
625                 630                 635                 640

Ala Leu Ala Lys Met Val Asp Pro Ala Leu Lys Gly Leu Tyr Pro Val
                645                 650                 655

Lys Ser Leu Ser Arg Phe Ala Asp Val Ile Ala Leu Cys Val Gln Pro
            660                 665                 670

Glu Pro Glu Phe Arg Pro Pro Met Ser Glu Val Val Gln Ala Leu Val
        675                 680                 685

Val Leu Val Gln Arg Ala Asn Met Ser Lys Arg Thr Val Gly Val Asp
690                 695                 700

Pro Ser Gln Arg Ala Gly Ser Ala Asp Thr Thr Ser Asp Tyr Met
705                 710                 715

<210> SEQ ID NO 23
<211> LENGTH: 2154
<212> TYPE: DNA
```

<213> ORGANISM: Arabidopsis thaliana
<220> FEATURE:
<221> NAME/KEY: CDS
<222> LOCATION: (1)..(2154)

<400> SEQUENCE: 23

| | | | | | | | | | | | | | | | | |
|---|---|---|---|---|---|---|---|---|---|---|---|---|---|---|---|---|
| atg | act | gag | aat | cgg | gtg | gtt | ttg | gct | ctg | ctt | ata | ctc | tgc | att | gtt | 48 |
| Met | Thr | Glu | Asn | Arg | Val | Val | Leu | Ala | Leu | Leu | Ile | Leu | Cys | Ile | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggg | ttt | gag | cca | agt | ttc | atc | cat | gga | gct | acg | gat | tca | tca | gat | act | 96 |
| Gly | Phe | Glu | Pro | Ser | Phe | Ile | His | Gly | Ala | Thr | Asp | Ser | Ser | Asp | Thr | |
| | | | 20 | | | | | 25 | | | | | 30 | | | |

| | | | | | | | | | | | | | | | | |
|---|---|---|---|---|---|---|---|---|---|---|---|---|---|---|---|---|
| tcg | gcg | tta | aac | atc | atg | ttc | agc | tcc | atg | aat | tct | cca | gga | cag | ctc | 144 |
| Ser | Ala | Leu | Asn | Ile | Met | Phe | Ser | Ser | Met | Asn | Ser | Pro | Gly | Gln | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| tca | caa | tgg | aca | gca | tca | gga | ggt | gat | cct | tgt | ggc | caa | aac | tgg | aaa | 192 |
| Ser | Gln | Trp | Thr | Ala | Ser | Gly | Gly | Asp | Pro | Cys | Gly | Gln | Asn | Trp | Lys | |
| | 50 | | | | | 55 | | | | | 60 | | | | | |

| | | | | | | | | | | | | | | | | |
|---|---|---|---|---|---|---|---|---|---|---|---|---|---|---|---|---|
| ggc | ata | act | tgc | tct | ggc | tct | cga | gtt | aca | caa | ata | aag | tta | cca | agt | 240 |
| Gly | Ile | Thr | Cys | Ser | Gly | Ser | Arg | Val | Thr | Gln | Ile | Lys | Leu | Pro | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctt | gga | ctt | tct | gga | tca | ctt | gga | ttc | atg | ctt | gat | aaa | ttg | act | tct | 288 |
| Leu | Gly | Leu | Ser | Gly | Ser | Leu | Gly | Phe | Met | Leu | Asp | Lys | Leu | Thr | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| gtt | act | gag | ttt | gat | atg | agc | aac | aat | aac | ctt | gga | ggc | gat | ttg | cct | 336 |
| Val | Thr | Glu | Phe | Asp | Met | Ser | Asn | Asn | Asn | Leu | Gly | Gly | Asp | Leu | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| tat | cag | ctt | cct | cca | aac | ttg | gag | cga | ttg | aat | ctt | gct | aat | aac | cag | 384 |
| Tyr | Gln | Leu | Pro | Pro | Asn | Leu | Glu | Arg | Leu | Asn | Leu | Ala | Asn | Asn | Gln | |
| | | 115 | | | | | 120 | | | | | 125 | | | | |

| | | | | | | | | | | | | | | | | |
|---|---|---|---|---|---|---|---|---|---|---|---|---|---|---|---|---|
| ttc | act | gga | tct | gct | caa | tat | tcc | att | tct | atg | atg | gct | cct | ctt | aag | 432 |
| Phe | Thr | Gly | Ser | Ala | Gln | Tyr | Ser | Ile | Ser | Met | Met | Ala | Pro | Leu | Lys | |
| | 130 | | | | | 135 | | | | | 140 | | | | | |

| | | | | | | | | | | | | | | | | |
|---|---|---|---|---|---|---|---|---|---|---|---|---|---|---|---|---|
| tac | ctc | aac | ctt | gct | cac | aac | cag | ttg | aag | cag | cta | gct | att | gac | ttc | 480 |
| Tyr | Leu | Asn | Leu | Ala | His | Asn | Gln | Leu | Lys | Gln | Leu | Ala | Ile | Asp | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aca | aaa | ctc | acc | tct | ctc | tct | ata | ttg | gac | ctc | tct | tcc | aat | gct | ttt | 528 |
| Thr | Lys | Leu | Thr | Ser | Leu | Ser | Ile | Leu | Asp | Leu | Ser | Ser | Asn | Ala | Phe | |
| | | | | 165 | | | | | 170 | | | | | 175 | | |

| | | | | | | | | | | | | | | | | |
|---|---|---|---|---|---|---|---|---|---|---|---|---|---|---|---|---|
| ata | ggg | tct | ctc | cca | aac | act | tgt | agc | tct | ctt | acg | agt | gca | aaa | tca | 576 |
| Ile | Gly | Ser | Leu | Pro | Asn | Thr | Cys | Ser | Ser | Leu | Thr | Ser | Ala | Lys | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| att | tat | ctt | cag | aac | aat | cag | ttc | tca | ggc | acc | att | gat | att | cta | gcc | 624 |
| Ile | Tyr | Leu | Gln | Asn | Asn | Gln | Phe | Ser | Gly | Thr | Ile | Asp | Ile | Leu | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| acc | ctt | cct | ctc | gaa | aat | ctg | aat | att | gca | aac | aat | cgg | ttc | aca | ggc | 672 |
| Thr | Leu | Pro | Leu | Glu | Asn | Leu | Asn | Ile | Ala | Asn | Asn | Arg | Phe | Thr | Gly | |
| | 210 | | | | | 215 | | | | | 220 | | | | | |

| | | | | | | | | | | | | | | | | |
|---|---|---|---|---|---|---|---|---|---|---|---|---|---|---|---|---|
| tgg | atc | cct | gat | tct | ttg | aaa | ggc | att | aac | ttg | caa | aaa | gat | ggc | aat | 720 |
| Trp | Ile | Pro | Asp | Ser | Leu | Lys | Gly | Ile | Asn | Leu | Gln | Lys | Asp | Gly | Asn | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tta | tta | aat | tcc | ggg | cct | gca | cct | cca | cca | cct | cct | ggt | aca | cca | ccg | 768 |
| Leu | Leu | Asn | Ser | Gly | Pro | Ala | Pro | Pro | Pro | Pro | Pro | Gly | Thr | Pro | Pro | |
| | | | | 245 | | | | | 250 | | | | | 255 | | |

| | | | | | | | | | | | | | | | | |
|---|---|---|---|---|---|---|---|---|---|---|---|---|---|---|---|---|
| atc | agt | aaa | tca | tca | cct | act | ccg | aaa | tcc | ggg | aac | cgt | gga | aac | cgt | 816 |
| Ile | Ser | Lys | Ser | Ser | Pro | Thr | Pro | Lys | Ser | Gly | Asn | Arg | Gly | Asn | Arg | |
| | | | 260 | | | | | 265 | | | | | 270 | | | |

| | | | | | | | | | | | | | | | | |
|---|---|---|---|---|---|---|---|---|---|---|---|---|---|---|---|---|
| tcc | aat | ggt | gat | tcc | agc | aat | agc | aaa | gac | tcc | agc | aaa | tca | ggg | ctt | 864 |
| Ser | Asn | Gly | Asp | Ser | Ser | Asn | Ser | Lys | Asp | Ser | Ser | Lys | Ser | Gly | Leu | |
| | | 275 | | | | | 280 | | | | | 285 | | | | |

| | | | | | | | | | | | | | | | | |
|---|---|---|---|---|---|---|---|---|---|---|---|---|---|---|---|---|
| gga | gct | ggt | gga | gta | gca | gga | ata | gtc | att | tct | ttg | ata | gtt | gta | aca | 912 |

-continued

```
Gly Ala Gly Gly Val Ala Gly Ile Val Ile Ser Leu Ile Val Val Thr
290                 295                 300 gca gtc ata gct ttc ttc ttg atc aag aga aaa aga tca aag cgg tca      960
Ala Val Ile Ala Phe Phe Leu Ile Lys Arg Lys Arg Ser Lys Arg Ser
305                 310                 315                 320 tca tcc acg gac att gaa aag act gat aat aac att aac caa ccc att     1008
Ser Ser Thr Asp Ile Glu Lys Thr Asp Asn Asn Ile Asn Gln Pro Ile
                325                 330                 335 ata cta gcg tcc aat gac ttt cat caa gag aat aag tct gta cag aat     1056
Ile Leu Ala Ser Asn Asp Phe His Gln Glu Asn Lys Ser Val Gln Asn
            340                 345                 350 cca cca ttg gtt gag aca aag aaa ctg gat acg tca ttg tcg atg aat     1104
Pro Pro Leu Val Glu Thr Lys Lys Leu Asp Thr Ser Leu Ser Met Asn
        355                 360                 365 cta cgt cct cca cca tct gag cga cat aag tcg ttt gat gac gat gat     1152
Leu Arg Pro Pro Pro Ser Glu Arg His Lys Ser Phe Asp Asp Asp Asp
    370                 375                 380 tca aca atg aga aaa cct att gtt gca aag aaa gct gct gtt gtt gtt     1200
Ser Thr Met Arg Lys Pro Ile Val Ala Lys Lys Ala Ala Val Val Val
385                 390                 395                 400 cct tca aat gtg aac aca tat acg gtt tca gat ctt caa gta gct acc     1248
Pro Ser Asn Val Asn Thr Tyr Thr Val Ser Asp Leu Gln Val Ala Thr
                405                 410                 415 aac agt ttc agc gta gat aat ctt ctc ggt gaa gga aca ttt gga aga     1296
Asn Ser Phe Ser Val Asp Asn Leu Leu Gly Glu Gly Thr Phe Gly Arg
            420                 425                 430 gta tac aga gct cag ttt gaa gat gga aag gta ctt gct gtg aag aaa     1344
Val Tyr Arg Ala Gln Phe Glu Asp Gly Lys Val Leu Ala Val Lys Lys
        435                 440                 445 atc gac tca tct gcg ctt ccc acg gat act gct gat gat ttt acc gaa     1392
Ile Asp Ser Ser Ala Leu Pro Thr Asp Thr Ala Asp Asp Phe Thr Glu
    450                 455                 460 att gta tcg aaa ata gcg cat ttg gat cac gaa aat gtc aca aag ctt     1440
Ile Val Ser Lys Ile Ala His Leu Asp His Glu Asn Val Thr Lys Leu
465                 470                 475                 480 gat ggt tac tgt tct gaa cac ggg caa cac ttg gtg gtc tat gag ttc     1488
Asp Gly Tyr Cys Ser Glu His Gly Gln His Leu Val Val Tyr Glu Phe
                485                 490                 495 cat aga aac ggc tca ttg cat gac ttt tta cat ctt gca gaa gag gaa     1536
His Arg Asn Gly Ser Leu His Asp Phe Leu His Leu Ala Glu Glu Glu
            500                 505                 510 agc aaa ccg ttg ata tgg aat ccc cgt gtc aag atc gct ctt ggc act     1584
Ser Lys Pro Leu Ile Trp Asn Pro Arg Val Lys Ile Ala Leu Gly Thr
        515                 520                 525 gca cgt gca ttg gag tac ttg cat gaa gtt tgc tca cca tct ata gtc     1632
Ala Arg Ala Leu Glu Tyr Leu His Glu Val Cys Ser Pro Ser Ile Val
    530                 535                 540 cac aag aac att aaa tca gca aat att tta ctt gac tca gag ctg aat     1680
His Lys Asn Ile Lys Ser Ala Asn Ile Leu Leu Asp Ser Glu Leu Asn
545                 550                 555                 560 cca cac ctc tca gac tca ggt ctc gct agc ttc ctt ccc act gca aac     1728
Pro His Leu Ser Asp Ser Gly Leu Ala Ser Phe Leu Pro Thr Ala Asn
                565                 570                 575 gag cta cta aac caa aac gat gaa gga tac agc gca cca gaa act tca     1776
Glu Leu Leu Asn Gln Asn Asp Glu Gly Tyr Ser Ala Pro Glu Thr Ser
            580                 585                 590 atg tca ggc caa tac tct ttg aag agc gat gtt tac agt ttt gga gta     1824
Met Ser Gly Gln Tyr Ser Leu Lys Ser Asp Val Tyr Ser Phe Gly Val
        595                 600                 605 gtg atg ctc gag ctt tta acc gga aga aaa cca ttc gac agc aca agg     1872
```

```
Val Met Leu Glu Leu Leu Thr Gly Arg Lys Pro Phe Asp Ser Thr Arg
        610                 615                 620 tca aga tcg gaa caa tca ttg gta aga tgg gca aca cct cag ctt cac      1920
Ser Arg Ser Glu Gln Ser Leu Val Arg Trp Ala Thr Pro Gln Leu His
625                 630                 635                 640 gac att gat gct ttg ggc aaa atg gtt gat cca gct ctc aaa ggg cta      1968
Asp Ile Asp Ala Leu Gly Lys Met Val Asp Pro Ala Leu Lys Gly Leu
        645                 650                 655 tac ccg gtt aaa tcc ctc tcc cga ttt gca gat gtt atc gcc ctt tgc      2016
Tyr Pro Val Lys Ser Leu Ser Arg Phe Ala Asp Val Ile Ala Leu Cys
            660                 665                 670 gtc cag ccg gag cca gag ttt aga cca ccc atg tct gaa gtg gtg caa      2064
Val Gln Pro Glu Pro Glu Phe Arg Pro Pro Met Ser Glu Val Val Gln
                675                 680                 685 gca ttg gtt gta ttg gtg cag aga gct aac atg agc aag aga act gtt      2112
Ala Leu Val Val Leu Val Gln Arg Ala Asn Met Ser Lys Arg Thr Val
690                 695                 700 gga gtc ggc tcc ggt agc tcc ggc gtc aat gat tac atg taa              2154
Gly Val Gly Ser Gly Ser Ser Gly Val Asn Asp Tyr Met
705                 710                 715

<210> SEQ ID NO 24
<211> LENGTH: 717
<212> TYPE: PRT
<213> ORGANISM: Arabidopsis thaliana

<400> SEQUENCE: 24

Met Thr Glu Asn Arg Val Val Leu Ala Leu Leu Ile Leu Cys Ile Val
1               5                   10                  15

Gly Phe Glu Pro Ser Phe Ile His Gly Ala Thr Asp Ser Ser Asp Thr
            20                  25                  30

Ser Ala Leu Asn Ile Met Phe Ser Met Asn Ser Pro Gly Gln Leu
        35                  40                  45

Ser Gln Trp Thr Ala Ser Gly Gly Asp Pro Cys Gly Gln Asn Trp Lys
    50                  55                  60

Gly Ile Thr Cys Ser Gly Ser Arg Val Thr Gln Ile Lys Leu Pro Ser
65                  70                  75                  80

Leu Gly Leu Ser Gly Ser Leu Gly Phe Met Leu Asp Lys Leu Thr Ser
                85                  90                  95

Val Thr Glu Phe Asp Met Ser Asn Asn Asn Leu Gly Gly Asp Leu Pro
            100                 105                 110

Tyr Gln Leu Pro Pro Asn Leu Glu Arg Leu Asn Leu Ala Asn Asn Gln
        115                 120                 125

Phe Thr Gly Ser Ala Gln Tyr Ser Ile Ser Met Met Ala Pro Leu Lys
    130                 135                 140

Tyr Leu Asn Leu Ala His Asn Gln Leu Lys Gln Leu Ala Ile Asp Phe
145                 150                 155                 160

Thr Lys Leu Thr Ser Leu Ser Ile Leu Asp Leu Ser Ser Asn Ala Phe
                165                 170                 175

Ile Gly Ser Leu Pro Asn Thr Cys Ser Ser Leu Thr Ser Ala Lys Ser
            180                 185                 190

Ile Tyr Leu Gln Asn Asn Gln Phe Ser Gly Thr Ile Asp Ile Leu Ala
        195                 200                 205

Thr Leu Pro Leu Glu Asn Leu Asn Ile Ala Asn Asn Arg Phe Thr Gly
    210                 215                 220

Trp Ile Pro Asp Ser Leu Lys Gly Ile Asn Leu Gln Lys Asp Gly Asn
225                 230                 235                 240
```

-continued

```
Leu Leu Asn Ser Gly Pro Ala Pro Pro Pro Gly Thr Pro Pro
                245                 250                 255

Ile Ser Lys Ser Ser Pro Thr Pro Lys Ser Gly Asn Arg Gly Asn Arg
                260                 265                 270

Ser Asn Gly Asp Ser Ser Asn Ser Lys Asp Ser Ser Lys Ser Gly Leu
                275                 280                 285

Gly Ala Gly Gly Val Ala Gly Ile Val Ile Ser Leu Ile Val Val Thr
                290                 295                 300

Ala Val Ile Ala Phe Phe Leu Ile Lys Arg Lys Arg Ser Lys Arg Ser
305                 310                 315                 320

Ser Ser Thr Asp Ile Glu Lys Thr Asp Asn Asn Ile Asn Gln Pro Ile
                325                 330                 335

Ile Leu Ala Ser Asn Asp Phe His Gln Glu Asn Lys Ser Val Gln Asn
                340                 345                 350

Pro Pro Leu Val Glu Thr Lys Lys Leu Asp Thr Ser Leu Ser Met Asn
                355                 360                 365

Leu Arg Pro Pro Ser Glu Arg His Lys Ser Phe Asp Asp Asp
                370                 375                 380

Ser Thr Met Arg Lys Pro Ile Val Ala Lys Lys Ala Ala Val Val Val
385                 390                 395                 400

Pro Ser Asn Val Asn Thr Tyr Thr Val Ser Asp Leu Gln Val Ala Thr
                405                 410                 415

Asn Ser Phe Ser Val Asp Asn Leu Leu Gly Glu Gly Thr Phe Gly Arg
                420                 425                 430

Val Tyr Arg Ala Gln Phe Glu Asp Gly Lys Val Leu Ala Val Lys Lys
                435                 440                 445

Ile Asp Ser Ser Ala Leu Pro Thr Asp Thr Ala Asp Asp Phe Thr Glu
450                 455                 460

Ile Val Ser Lys Ile Ala His Leu Asp His Glu Asn Val Thr Lys Leu
465                 470                 475                 480

Asp Gly Tyr Cys Ser Glu His Gly Gln His Leu Val Val Tyr Glu Phe
                485                 490                 495

His Arg Asn Gly Ser Leu His Asp Phe Leu His Leu Ala Glu Glu Glu
                500                 505                 510

Ser Lys Pro Leu Ile Trp Asn Pro Arg Val Lys Ile Ala Leu Gly Thr
                515                 520                 525

Ala Arg Ala Leu Glu Tyr Leu His Glu Val Cys Ser Pro Ser Ile Val
                530                 535                 540

His Lys Asn Ile Lys Ser Ala Asn Ile Leu Leu Asp Ser Glu Leu Asn
545                 550                 555                 560

Pro His Leu Ser Asp Ser Gly Leu Ala Ser Phe Leu Pro Thr Ala Asn
                565                 570                 575

Glu Leu Leu Asn Gln Asn Asp Glu Gly Tyr Ser Ala Pro Glu Thr Ser
                580                 585                 590

Met Ser Gly Gln Tyr Ser Leu Lys Ser Asp Val Tyr Ser Phe Gly Val
                595                 600                 605

Val Met Leu Glu Leu Leu Thr Gly Arg Lys Pro Phe Asp Ser Thr Arg
                610                 615                 620

Ser Arg Ser Glu Gln Ser Leu Val Arg Trp Ala Thr Pro Gln Leu His
625                 630                 635                 640

Asp Ile Asp Ala Leu Gly Lys Met Val Asp Pro Ala Leu Lys Gly Leu
                645                 650                 655

Tyr Pro Val Lys Ser Leu Ser Arg Phe Ala Asp Val Ile Ala Leu Cys
                660                 665                 670
```

-continued

```
Val Gln Pro Glu Pro Glu Phe Arg Pro Pro Met Ser Glu Val Val Gln
            675                 680                 685

Ala Leu Val Val Leu Val Gln Arg Ala Asn Met Ser Lys Arg Thr Val
        690                 695                 700

Gly Val Gly Ser Gly Ser Ser Gly Val Asn Asp Tyr Met
705                 710                 715

<210> SEQ ID NO 25
<211> LENGTH: 2112
<212> TYPE: DNA
<213> ORGANISM: Arabidopsis thaliana
<220> FEATURE:
<221> NAME/KEY: CDS
<222> LOCATION: (1)..(2112)

<400> SEQUENCE: 25 atg gct att gga gat aga gct atg ttt act gtt ttg ctt cta ttc att        48
Met Ala Ile Gly Asp Arg Ala Met Phe Thr Val Leu Leu Leu Phe Ile
1               5                   10                  15 gct tcg atc tct gga ttc tct gtt gtt cgt tgt gtt act gat cca tct        96
Ala Ser Ile Ser Gly Phe Ser Val Val Arg Cys Val Thr Asp Pro Ser
                20                  25                  30 gat gtt caa gcc ctt caa gtt ttg tat act tca cta aat agt cct tca       144
Asp Val Gln Ala Leu Gln Val Leu Tyr Thr Ser Leu Asn Ser Pro Ser
            35                  40                  45 cag cta acc aat tgg aaa aat ggt ggt ggt gat cca tgt gga gag tca       192
Gln Leu Thr Asn Trp Lys Asn Gly Gly Gly Asp Pro Cys Gly Glu Ser
        50                  55                  60 tgg aaa ggg att act tgt gag ggc tct gca gtt gtc act ata gat ata       240
Trp Lys Gly Ile Thr Cys Glu Gly Ser Ala Val Val Thr Ile Asp Ile
65                  70                  75                  80 tcg gat tta gga gtc tct ggc act ctt gga tac ttg ctc tca gac ctt       288
Ser Asp Leu Gly Val Ser Gly Thr Leu Gly Tyr Leu Leu Ser Asp Leu
                85                  90                  95 aag tca ctc aga aaa ttg gat gtt agt ggt aac agc atc cat gat aca       336
Lys Ser Leu Arg Lys Leu Asp Val Ser Gly Asn Ser Ile His Asp Thr
                100                 105                 110 ctt cca tat cag ttg cca ccg aat ctc aca agc cta aat ctt gcg aga       384
Leu Pro Tyr Gln Leu Pro Pro Asn Leu Thr Ser Leu Asn Leu Ala Arg
            115                 120                 125 aac aac cta agt ggt aac ctt cca tac tcc ata tcc gcc atg ggt tct       432
Asn Asn Leu Ser Gly Asn Leu Pro Tyr Ser Ile Ser Ala Met Gly Ser
        130                 135                 140 ctt tcg tat atg aat gta agt ggt aat tca ctt aca atg tca ata gga       480
Leu Ser Tyr Met Asn Val Ser Gly Asn Ser Leu Thr Met Ser Ile Gly
145                 150                 155                 160 gat atc ttt gct gat cat aag tca ctg gca acc ttg gac ctt tct cat       528
Asp Ile Phe Ala Asp His Lys Ser Leu Ala Thr Leu Asp Leu Ser His
                165                 170                 175 aac aac ttc agt ggc gat ctt cct agt tcc tta agc aca gtg tcc aca       576
Asn Asn Phe Ser Gly Asp Leu Pro Ser Ser Leu Ser Thr Val Ser Thr
            180                 185                 190 ctt tcc gtt ctt tat gtt cag aac aat caa ttg aca ggt tcc atc gat       624
Leu Ser Val Leu Tyr Val Gln Asn Asn Gln Leu Thr Gly Ser Ile Asp
        195                 200                 205 gtt ctc tcg ggg ttg cct ttg aaa act tta aat gtt gca aac aat cat       672
Val Leu Ser Gly Leu Pro Leu Lys Thr Leu Asn Val Ala Asn Asn His
    210                 215                 220 ttc aat gga tcc ata cct aag gag ctt agt tct att cag acc tta ata       720
Phe Asn Gly Ser Ile Pro Lys Glu Leu Ser Ser Ile Gln Thr Leu Ile
225                 230                 235                 240
```

| | | |
|---|---|---|
| tat gat ggt aat tcc ttt gat aac gtc cct gcc tct cct cag cca gaa<br>Tyr Asp Gly Asn Ser Phe Asp Asn Val Pro Ala Ser Pro Gln Pro Glu<br>245 250 255 | | 768 |
| aga cct ggc aaa aaa gag aca cct tct ggt tct aag aaa ccc aaa att<br>Arg Pro Gly Lys Lys Glu Thr Pro Ser Gly Ser Lys Lys Pro Lys Ile<br>260 265 270 | | 816 |
| ggt tct gaa gag aaa tct tca gac tct ggc aag ggt ttg tct ggt gga<br>Gly Ser Glu Glu Lys Ser Ser Asp Ser Gly Lys Gly Leu Ser Gly Gly<br>275 280 285 | | 864 |
| gta gtc act ggt ata gtg ttc ggt tct cta ttt gtt gct ggt att ata<br>Val Val Thr Gly Ile Val Phe Gly Ser Leu Phe Val Ala Gly Ile Ile<br>290 295 300 | | 912 |
| gca ctt gtt ctt tac ttg tgc ctt cac aag aaa aaa cgg aaa gtt aga<br>Ala Leu Val Leu Tyr Leu Cys Leu His Lys Lys Lys Arg Lys Val Arg<br>305 310 315 320 | | 960 |
| gga agt aca aga gct tcc caa aga agt ctt ccg ctt agt gga aca cct<br>Gly Ser Thr Arg Ala Ser Gln Arg Ser Leu Pro Leu Ser Gly Thr Pro<br>325 330 335 | | 1008 |
| gag gtg cag gag cag agg gta aaa agt gta gca tcc gtt gca gac ttg<br>Glu Val Gln Glu Gln Arg Val Lys Ser Val Ala Ser Val Ala Asp Leu<br>340 345 350 | | 1056 |
| aag tct tca cct gca gaa aaa gta acg gtt gat cgc gtt atg aag aac<br>Lys Ser Ser Pro Ala Glu Lys Val Thr Val Asp Arg Val Met Lys Asn<br>355 360 365 | | 1104 |
| ggc tct ata agt aga ata aga tct cct atc act gct tca caa tac act<br>Gly Ser Ile Ser Arg Ile Arg Ser Pro Ile Thr Ala Ser Gln Tyr Thr<br>370 375 380 | | 1152 |
| gtt tcc tct ctg caa gtt gca aca aac agc ttt agt caa gaa aac atc<br>Val Ser Ser Leu Gln Val Ala Thr Asn Ser Phe Ser Gln Glu Asn Ile<br>385 390 395 400 | | 1200 |
| att ggt gaa ggt tct cta ggc cgt gtc tat aga gca gag ttc ccc aat<br>Ile Gly Glu Gly Ser Leu Gly Arg Val Tyr Arg Ala Glu Phe Pro Asn<br>405 410 415 | | 1248 |
| gga aag ata atg gcg att aag aag att gat aat gca gca ctt tca tta<br>Gly Lys Ile Met Ala Ile Lys Lys Ile Asp Asn Ala Ala Leu Ser Leu<br>420 425 430 | | 1296 |
| caa gaa gaa gat aat ttc tta gaa gcc gtt tca aat atg tcg cgg ttg<br>Gln Glu Glu Asp Asn Phe Leu Glu Ala Val Ser Asn Met Ser Arg Leu<br>435 440 445 | | 1344 |
| agg cat cca aac att gtt ccc ttg gct gga tac tgc acc gag cat ggt<br>Arg His Pro Asn Ile Val Pro Leu Ala Gly Tyr Cys Thr Glu His Gly<br>450 455 460 | | 1392 |
| caa cgt ctt cta gtg tat gaa tat gta gga aat ggg aat cta gat gat<br>Gln Arg Leu Leu Val Tyr Glu Tyr Val Gly Asn Gly Asn Leu Asp Asp<br>465 470 475 480 | | 1440 |
| acg ctt cac acg aat gat gat aga agc atg aat ctg act tgg aat gcg<br>Thr Leu His Thr Asn Asp Asp Arg Ser Met Asn Leu Thr Trp Asn Ala<br>485 490 495 | | 1488 |
| cgt gtt aaa gtg gct ctt gga act gcc aag gct tta gag tac ttg cac<br>Arg Val Lys Val Ala Leu Gly Thr Ala Lys Ala Leu Glu Tyr Leu His<br>500 505 510 | | 1536 |
| gaa gtt tgc ttg cct tca att gtc cat aga aac ttc aaa tca gcg aat<br>Glu Val Cys Leu Pro Ser Ile Val His Arg Asn Phe Lys Ser Ala Asn<br>515 520 525 | | 1584 |
| ata ttg cta gac gaa gaa ctt aat cct cac cta tca gac agt ggt tta<br>Ile Leu Leu Asp Glu Glu Leu Asn Pro His Leu Ser Asp Ser Gly Leu<br>530 535 540 | | 1632 |
| gct gct ttg aca cct aac act gag aga cag gtt tca act caa gtg gta<br>Ala Ala Leu Thr Pro Asn Thr Glu Arg Gln Val Ser Thr Gln Val Val<br>545 550 555 560 | | 1680 |

| | | |
|---|---|---|
| ggt tca ttt gga tac agc gct cca gag ttt gca ctg tcg gga att tac<br>Gly Ser Phe Gly Tyr Ser Ala Pro Glu Phe Ala Leu Ser Gly Ile Tyr<br>                   565                     570                  575 | | 1728 |
| aca gtg aaa agt gat gta tac act ttt gga gta gtc atg ctt gag ctc<br>Thr Val Lys Ser Asp Val Tyr Thr Phe Gly Val Val Met Leu Glu Leu<br>        580                         585                     590 | | 1776 |
| tta act ggt cgg aag cct ctt gac agc tcg agg acg aga gca gag caa<br>Leu Thr Gly Arg Lys Pro Leu Asp Ser Ser Arg Thr Arg Ala Glu Gln<br>             595                      600                   605 | | 1824 |
| tca cta gtg aga tgg gca aca ccg cag ctt cac gat ata gat gct ttg<br>Ser Leu Val Arg Trp Ala Thr Pro Gln Leu His Asp Ile Asp Ala Leu<br>        610                       615                  620 | | 1872 |
| tct aaa atg gtt gat cct tct ctt aat ggc atg tat cca gct aag tca<br>Ser Lys Met Val Asp Pro Ser Leu Asn Gly Met Tyr Pro Ala Lys Ser<br>625                       630                     635                  640 | | 1920 |
| ctg tct cgt ttt gcg gac atc att gct ctc tgt att cag ccg gaa cca<br>Leu Ser Arg Phe Ala Asp Ile Ile Ala Leu Cys Ile Gln Pro Glu Pro<br>                         645                     650                     655 | | 1968 |
| gag ttc agg cct cca atg tca gag gtg gtg caa cag cta gta aga tta<br>Glu Phe Arg Pro Pro Met Ser Glu Val Val Gln Gln Leu Val Arg Leu<br>             660                      665                   670 | | 2016 |
| gtt caa agg gca agt gtt gtc aaa cga aga tca agt gat gac act gga<br>Val Gln Arg Ala Ser Val Val Lys Arg Arg Ser Ser Asp Asp Thr Gly<br>        675                       680                     685 | | 2064 |
| ttt tca tac agg aca cct gaa cac gag cac gtc gat atc tca ttc tga<br>Phe Ser Tyr Arg Thr Pro Glu His Glu His Val Asp Ile Ser Phe<br>             690                      695                  700 | | 2112 |

<210> SEQ ID NO 26
<211> LENGTH: 703
<212> TYPE: PRT
<213> ORGANISM: Arabidopsis thaliana

<400> SEQUENCE: 26

Met Ala Ile Gly Asp Arg Ala Met Phe Thr Val Leu Leu Leu Phe Ile
1               5                   10                  15

Ala Ser Ile Ser Gly Phe Ser Val Val Arg Cys Val Thr Asp Pro Ser
            20                  25                  30

Asp Val Gln Ala Leu Gln Val Leu Tyr Thr Ser Leu Asn Ser Pro Ser
        35                  40                  45

Gln Leu Thr Asn Trp Lys Asn Gly Gly Asp Pro Cys Gly Glu Ser
    50                  55                  60

Trp Lys Gly Ile Thr Cys Glu Gly Ser Ala Val Val Thr Ile Asp Ile
65                  70                  75                  80

Ser Asp Leu Gly Val Ser Gly Thr Leu Gly Tyr Leu Leu Ser Asp Leu
                85                  90                  95

Lys Ser Leu Arg Lys Leu Asp Val Ser Gly Asn Ser Ile His Asp Thr
            100                 105                 110

Leu Pro Tyr Gln Leu Pro Pro Asn Leu Thr Ser Leu Asn Leu Ala Arg
        115                 120                 125

Asn Asn Leu Ser Gly Asn Leu Pro Tyr Ser Ile Ser Ala Met Gly Ser
    130                 135                 140

Leu Ser Tyr Met Asn Val Ser Gly Asn Ser Leu Thr Met Ser Ile Gly
145                 150                 155                 160

Asp Ile Phe Ala Asp His Lys Ser Leu Ala Thr Leu Asp Leu Ser His
                165                 170                 175

Asn Asn Phe Ser Gly Asp Leu Pro Ser Ser Leu Ser Thr Val Ser Thr
            180                 185                 190

```
Leu Ser Val Leu Tyr Val Gln Asn Asn Gln Leu Thr Gly Ser Ile Asp
        195                 200                 205

Val Leu Ser Gly Leu Pro Leu Lys Thr Leu Asn Val Ala Asn Asn His
    210                 215                 220

Phe Asn Gly Ser Ile Pro Lys Glu Leu Ser Ile Gln Thr Leu Ile
225                 230                 235                 240

Tyr Asp Gly Asn Ser Phe Asp Asn Val Pro Ala Ser Pro Gln Pro Glu
                245                 250                 255

Arg Pro Gly Lys Lys Glu Thr Pro Ser Gly Ser Lys Lys Pro Lys Ile
            260                 265                 270

Gly Ser Glu Glu Lys Ser Ser Asp Ser Gly Lys Gly Leu Ser Gly Gly
        275                 280                 285

Val Val Thr Gly Ile Val Phe Gly Ser Leu Phe Val Ala Gly Ile Ile
    290                 295                 300

Ala Leu Val Leu Tyr Leu Cys Leu His Lys Lys Arg Lys Val Arg
305                 310                 315                 320

Gly Ser Thr Arg Ala Ser Gln Arg Ser Leu Pro Leu Ser Gly Thr Pro
            325                 330                 335

Glu Val Gln Glu Gln Arg Val Lys Ser Val Ala Ser Val Ala Asp Leu
        340                 345                 350

Lys Ser Ser Pro Ala Glu Lys Val Thr Val Asp Arg Val Met Lys Asn
    355                 360                 365

Gly Ser Ile Ser Arg Ile Arg Ser Pro Ile Thr Ala Ser Gln Tyr Thr
    370                 375                 380

Val Ser Ser Leu Gln Val Ala Thr Asn Ser Phe Ser Gln Glu Asn Ile
385                 390                 395                 400

Ile Gly Glu Gly Ser Leu Gly Arg Val Tyr Arg Ala Glu Phe Pro Asn
                405                 410                 415

Gly Lys Ile Met Ala Ile Lys Lys Ile Asp Asn Ala Ala Leu Ser Leu
            420                 425                 430

Gln Glu Glu Asp Asn Phe Leu Glu Ala Val Ser Asn Met Ser Arg Leu
        435                 440                 445

Arg His Pro Asn Ile Val Pro Leu Ala Gly Tyr Cys Thr Glu His Gly
    450                 455                 460

Gln Arg Leu Leu Val Tyr Glu Tyr Val Gly Asn Gly Asn Leu Asp Asp
465                 470                 475                 480

Thr Leu His Thr Asn Asp Asp Arg Ser Met Asn Leu Thr Trp Asn Ala
            485                 490                 495

Arg Val Lys Val Ala Leu Gly Thr Ala Lys Ala Leu Glu Tyr Leu His
        500                 505                 510

Glu Val Cys Leu Pro Ser Ile Val His Arg Asn Phe Lys Ser Ala Asn
    515                 520                 525

Ile Leu Leu Asp Glu Glu Leu Asn Pro His Leu Ser Asp Ser Gly Leu
    530                 535                 540

Ala Ala Leu Thr Pro Asn Thr Glu Arg Gln Val Ser Thr Gln Val Val
545                 550                 555                 560

Gly Ser Phe Gly Tyr Ser Ala Pro Glu Phe Ala Leu Ser Gly Ile Tyr
                565                 570                 575

Thr Val Lys Ser Asp Val Tyr Thr Phe Gly Val Val Met Leu Glu Leu
            580                 585                 590

Leu Thr Gly Arg Lys Pro Leu Asp Ser Arg Thr Arg Ala Glu Gln
        595                 600                 605

Ser Leu Val Arg Trp Ala Thr Pro Gln Leu His Asp Ile Asp Ala Leu
```

```
                610             615             620
Ser Lys Met Val Asp Pro Ser Leu Asn Gly Met Tyr Pro Ala Lys Ser
625                 630                 635                 640

Leu Ser Arg Phe Ala Asp Ile Ile Ala Leu Cys Ile Gln Pro Glu Pro
                645                 650                 655

Glu Phe Arg Pro Pro Met Ser Glu Val Val Gln Gln Leu Val Arg Leu
                660                 665                 670

Val Gln Arg Ala Ser Val Val Lys Arg Arg Ser Ser Asp Asp Thr Gly
                675                 680                 685

Phe Ser Tyr Arg Thr Pro Glu His Glu His Val Asp Ile Ser Phe
                690                 695                 700

<210> SEQ ID NO 27
<211> LENGTH: 38
<212> TYPE: DNA
<213> ORGANISM: Artificial Sequence
<220> FEATURE:
<223> OTHER INFORMATION: DN-SRF7 primer

<400> SEQUENCE: 27
ggaagtcgac cgagagagat agagaaagtg agacaagg                          38

<210> SEQ ID NO 28
<211> LENGTH: 39
<212> TYPE: DNA
<213> ORGANISM: Artificial Sequence
<220> FEATURE:
<223> OTHER INFORMATION: DN-SRF7 primer

<400> SEQUENCE: 28
atatgcggcc gcccttcacc gagaagatta tctacgctg                         39

<210> SEQ ID NO 29
<211> LENGTH: 21
<212> TYPE: DNA
<213> ORGANISM: Artificial Sequence
<220> FEATURE:
<223> OTHER INFORMATION: srf6-1 primer

<400> SEQUENCE: 29
tcgagtttat aaccgtcggt g                                            21

<210> SEQ ID NO 30
<211> LENGTH: 21
<212> TYPE: DNA
<213> ORGANISM: Artificial Sequence
<220> FEATURE:
<223> OTHER INFORMATION: srf6-1 primer

<400> SEQUENCE: 30
tttgaagcaa gagtgaaagg c                                            21

<210> SEQ ID NO 31
<211> LENGTH: 21
<212> TYPE: DNA
<213> ORGANISM: Artificial Sequence
<220> FEATURE:
<223> OTHER INFORMATION: srf6-2 primer

<400> SEQUENCE: 31
agcgcacctg aagtatcaat g                                            21

<210> SEQ ID NO 32
<211> LENGTH: 21
```

```
<212> TYPE: DNA
<213> ORGANISM: Artificial Sequence
<220> FEATURE:
<223> OTHER INFORMATION: srf6-2 primer

<400> SEQUENCE: 32
gtgccactcc caagtatatg g                                              21

<210> SEQ ID NO 33
<211> LENGTH: 21
<212> TYPE: DNA
<213> ORGANISM: Artificial Sequence
<220> FEATURE:
<223> OTHER INFORMATION: srf7-1 primer

<400> SEQUENCE: 33
aaacctttaa aagcgcgtag g                                              21

<210> SEQ ID NO 34
<211> LENGTH: 23
<212> TYPE: DNA
<213> ORGANISM: Artificial Sequence
<220> FEATURE:
<223> OTHER INFORMATION: srf7-1 primer

<400> SEQUENCE: 34
cccagaaaag agaacaaaca cac                                            23

<210> SEQ ID NO 35
<211> LENGTH: 27
<212> TYPE: DNA
<213> ORGANISM: Artificial Sequence
<220> FEATURE:
<223> OTHER INFORMATION: srf7-2 primer

<400> SEQUENCE: 35
tttctaacta tgtaatcatc tggttgc                                        27

<210> SEQ ID NO 36
<211> LENGTH: 21
<212> TYPE: DNA
<213> ORGANISM: Artificial Sequence
<220> FEATURE:
<223> OTHER INFORMATION: srf7-2 primer

<400> SEQUENCE: 36
ttccatggag gaacaaaaga g                                              21

<210> SEQ ID NO 37
<211> LENGTH: 21
<212> TYPE: DNA
<213> ORGANISM: Artificial Sequence
<220> FEATURE:
<223> OTHER INFORMATION: srf7-3 primer

<400> SEQUENCE: 37
gagtgtacaa tgcgtgaagg g                                              21

<210> SEQ ID NO 38
<211> LENGTH: 21
<212> TYPE: DNA
<213> ORGANISM: Artificial Sequence
<220> FEATURE:
<223> OTHER INFORMATION: srf7-3 primer

<400> SEQUENCE: 38
gcatgaagtt tgctcaccat c                                              21
```

<210> SEQ ID NO 39
<211> LENGTH: 31
<212> TYPE: DNA
<213> ORGANISM: Artificial Sequence
<220> FEATURE:
<223> OTHER INFORMATION: srf7-3 primer

<400> SEQUENCE: 39
ggaagtcgac tgtctcatct ggtttcgaga g                                31

<210> SEQ ID NO 40
<211> LENGTH: 34
<212> TYPE: DNA
<213> ORGANISM: Artificial Sequence
<220> FEATURE:
<223> OTHER INFORMATION: srf7-TAP primer

<400> SEQUENCE: 40
atatgcggcc gcttttgttc atgttgtcgg aatc                             34

<210> SEQ ID NO 41
<211> LENGTH: 23
<212> TYPE: DNA
<213> ORGANISM: Artificial Sequence
<220> FEATURE:
<223> OTHER INFORMATION: ACT2 primer

<400> SEQUENCE: 41
gatgggcaag tcatcacgat tgg                                         23

<210> SEQ ID NO 42
<211> LENGTH: 26
<212> TYPE: DNA
<213> ORGANISM: Artificial Sequence
<220> FEATURE:
<223> OTHER INFORMATION: ACT2 primer

<400> SEQUENCE: 42
accaccgatc cagacactgt acttcc                                      26

<210> SEQ ID NO 43
<211> LENGTH: 21
<212> TYPE: DNA
<213> ORGANISM: Artificial Sequence
<220> FEATURE:
<223> OTHER INFORMATION: CESA3 primer

<400> SEQUENCE: 43
attgttccgc agacttgcca g                                           21

<210> SEQ ID NO 44
<211> LENGTH: 23
<212> TYPE: DNA
<213> ORGANISM: Artificial Sequence
<220> FEATURE:
<223> OTHER INFORMATION: CESA3 primer

<400> SEQUENCE: 44
cacgagtaag atgccaacca agc                                         23

<210> SEQ ID NO 45
<211> LENGTH: 26
<212> TYPE: DNA
<213> ORGANISM: Artificial Sequence
<220> FEATURE:
<223> OTHER INFORMATION: CESA4 primer

```
<400> SEQUENCE: 45
ggaatgtctc ctgtgtttat tgcgtc                                              26

<210> SEQ ID NO 46
<211> LENGTH: 24
<212> TYPE: DNA
<213> ORGANISM: Artificial Sequence
<220> FEATURE:
<223> OTHER INFORMATION: CESA4 primer

<400> SEQUENCE: 46
gacggaacca agagcccatc taag                                                24

<210> SEQ ID NO 47
<211> LENGTH: 26
<212> TYPE: DNA
<213> ORGANISM: Artificial Sequence
<220> FEATURE:
<223> OTHER INFORMATION: SRF6 primer

<400> SEQUENCE: 47
gcattgtagg gtttgagctt agattc                                              26

<210> SEQ ID NO 48
<211> LENGTH: 26
<212> TYPE: DNA
<213> ORGANISM: Artificial Sequence
<220> FEATURE:
<223> OTHER INFORMATION: SRF6 primer

<400> SEQUENCE: 48
ggaggaaact gatatggtaa atcacc                                              26

<210> SEQ ID NO 49
<211> LENGTH: 26
<212> TYPE: DNA
<213> ORGANISM: Artificial Sequence
<220> FEATURE:
<223> OTHER INFORMATION: SRF7 primer

<400> SEQUENCE: 49
gcattgttgg gtttgagcca agtttc                                              26

<210> SEQ ID NO 50
<211> LENGTH: 26
<212> TYPE: DNA
<213> ORGANISM: Artificial Sequence
<220> FEATURE:
<223> OTHER INFORMATION: SRF7 primer

<400> SEQUENCE: 50
ggaggaagct gataaggcaa atcgcc                                              26

<210> SEQ ID NO 51
<211> LENGTH: 2307
<212> TYPE: DNA
<213> ORGANISM: Arabidopsis thaliana
<220> FEATURE:
<221> NAME/KEY: CDS
<222> LOCATION: (1)..(2307)

<400> SEQUENCE: 51 atg agc ttt aca aga tgg gaa gtg ttc ttt ggt ctc tct gtt tta gcc          48
Met Ser Phe Thr Arg Trp Glu Val Phe Phe Gly Leu Ser Val Leu Ala
1               5                   10                  15
```

```
ttg aca atg cct ttc tca gct gga gtt act aat cta cga gat gtt tcg    96
Leu Thr Met Pro Phe Ser Ala Gly Val Thr Asn Leu Arg Asp Val Ser
        20                  25                  30 gcg att aat aac ttg tat atc act ttg gga gca cca tct cta cat cat   144
Ala Ile Asn Asn Leu Tyr Ile Thr Leu Gly Ala Pro Ser Leu His His
            35                  40                  45 tgg ctt gct ttt gga gga gac cct tgt gga gaa aag tgg caa ggt gtg   192
Trp Leu Ala Phe Gly Gly Asp Pro Cys Gly Glu Lys Trp Gln Gly Val
50                  55                  60 gtg tgt gac tcc tca aac atc aca gaa ata agg ata cct ggc atg aag   240
Val Cys Asp Ser Ser Asn Ile Thr Glu Ile Arg Ile Pro Gly Met Lys
65                  70                  75                  80 gta ggt gga ggc tta agt gat act ctg gct gat ttt tca tct atc caa   288
Val Gly Gly Gly Leu Ser Asp Thr Leu Ala Asp Phe Ser Ser Ile Gln
                85                  90                  95 gtc atg gac ttc agt agc aat cat att tca ggg aca att ccg cag gct   336
Val Met Asp Phe Ser Ser Asn His Ile Ser Gly Thr Ile Pro Gln Ala
            100                 105                 110 ttg cct tct tcc atc cga aac cta tct ctc tca agc aat cgc ttc act   384
Leu Pro Ser Ser Ile Arg Asn Leu Ser Leu Ser Ser Asn Arg Phe Thr
        115                 120                 125 ggg aac att ccc ttt aca ttg tcc ttt cta tcc gat ttg tct gaa ctg   432
Gly Asn Ile Pro Phe Thr Leu Ser Phe Leu Ser Asp Leu Ser Glu Leu
130                 135                 140 tca ttg gga agc aat ctt cta tca gga gag ata cca gat tac ttt cag   480
Ser Leu Gly Ser Asn Leu Leu Ser Gly Glu Ile Pro Asp Tyr Phe Gln
145                 150                 155                 160 cag cta tca aaa ctg aca aaa ctg gac tta tcg tct aac ata ctg gag   528
Gln Leu Ser Lys Leu Thr Lys Leu Asp Leu Ser Ser Asn Ile Leu Glu
                165                 170                 175 ggg cat tta cct tct tcc atg gga gac tta gct tct ctt aag ata ttg   576
Gly His Leu Pro Ser Ser Met Gly Asp Leu Ala Ser Leu Lys Ile Leu
            180                 185                 190 tat ttg cag gac aac aag ctc aca gga aca ctt gat gtt ata gag gat   624
Tyr Leu Gln Asp Asn Lys Leu Thr Gly Thr Leu Asp Val Ile Glu Asp
        195                 200                 205 ctt ttc tta acc gat ttg aat gta gaa aac aac tta ttc tcg gga cct   672
Leu Phe Leu Thr Asp Leu Asn Val Glu Asn Asn Leu Phe Ser Gly Pro
210                 215                 220 ata ccg cca aat cta ttg aaa att cca aac ttc aaa aaa gat gga act   720
Ile Pro Pro Asn Leu Leu Lys Ile Pro Asn Phe Lys Lys Asp Gly Thr
225                 230                 235                 240 ccg ttc aat aca tcg att ata aca cca ccg cct ccg cct gtg gtt gat   768
Pro Phe Asn Thr Ser Ile Ile Thr Pro Pro Pro Pro Pro Val Val Asp
                245                 250                 255 cct cct ccc gct act cac cgt gct cct cct gtt ccc cgt atc cct cct   816
Pro Pro Pro Ala Thr His Arg Ala Pro Pro Val Pro Arg Ile Pro Pro
            260                 265                 270 gtt tct ggt gtt ccc cca gca cct ttt gct cct ttt gct cca ctg caa   864
Val Ser Gly Val Pro Pro Ala Pro Phe Ala Pro Phe Ala Pro Leu Gln
        275                 280                 285 cca caa caa cat cca cca cca tca cca cct ctg gtc tgg tca cca cct   912
Pro Gln Gln His Pro Pro Pro Ser Pro Pro Leu Val Trp Ser Pro Pro
290                 295                 300 tct tct gat aat gga gga gga gat ccc tgg aac tct gtg tca ggg caa   960
Ser Ser Asp Asn Gly Gly Gly Asp Pro Trp Asn Ser Val Ser Gly Gln
305                 310                 315                 320 cct acc ttg caa ata tca cct cct tca ggt tca gga tca gga aaa ttc  1008
Pro Thr Leu Gln Ile Ser Pro Pro Ser Gly Ser Gly Ser Gly Lys Phe
                325                 330                 335
```

```
tgg tcc act caa aga atc att cta gta gtt tct tca gtg gcc ata att      1056
Trp Ser Thr Gln Arg Ile Ile Leu Val Val Ser Ser Val Ala Ile Ile
            340                 345                 350 gtt ctt gta tcc ggt ttg tgt gtt aca ctt tgg aga tgt tgc aga agt      1104
Val Leu Val Ser Gly Leu Cys Val Thr Leu Trp Arg Cys Cys Arg Ser
            355                 360                 365 aaa ata tat aac cga tat tac agt gga gct cgt aaa gat tta caa cga      1152
Lys Ile Tyr Asn Arg Tyr Tyr Ser Gly Ala Arg Lys Asp Leu Gln Arg
            370                 375                 380 cca tac ttc aat aag cct cca tct caa cca acc ccc act atg gga aaa      1200
Pro Tyr Phe Asn Lys Pro Pro Ser Gln Pro Thr Pro Thr Met Gly Lys
385                 390                 395                 400 gtt tct cgg gag cct atg gtt aag cct ttc gat gga tat gga gct gga      1248
Val Ser Arg Glu Pro Met Val Lys Pro Phe Asp Gly Tyr Gly Ala Gly
                405                 410                 415 gac agg aaa tat ggg tat cca atg cca cag cgg gct gaa gag agc cgg      1296
Asp Arg Lys Tyr Gly Tyr Pro Met Pro Gln Arg Ala Glu Glu Ser Arg
                420                 425                 430 aga gca atg cct cct act tca tat tat aat aag gat gtt aat aca cct      1344
Arg Ala Met Pro Pro Thr Ser Tyr Tyr Asn Lys Asp Val Asn Thr Pro
                435                 440                 445 caa aag ccg ctg caa caa cca ccg agg cag ttc cag tcc aat gat act      1392
Gln Lys Pro Leu Gln Gln Pro Pro Arg Gln Phe Gln Ser Asn Asp Thr
            450                 455                 460 gct tca aag aga gcg gct cat ttc ccc ccg ggc ttg aat tcc tca tct      1440
Ala Ser Lys Arg Ala Ala His Phe Pro Pro Gly Leu Asn Ser Ser Ser
465                 470                 475                 480 tct gct act gtt ttc acc att gct tca ctt cag caa tac aca aat aat      1488
Ser Ala Thr Val Phe Thr Ile Ala Ser Leu Gln Gln Tyr Thr Asn Asn
                485                 490                 495 ttc tca gaa gag aat ata atc ggg gaa ggg tcg att ggt aat gtc tac      1536
Phe Ser Glu Glu Asn Ile Ile Gly Glu Gly Ser Ile Gly Asn Val Tyr
                500                 505                 510 aga gct gag ctt cgt cat gga aag ttt ctt gcg gtg aag aag ctg agc      1584
Arg Ala Glu Leu Arg His Gly Lys Phe Leu Ala Val Lys Lys Leu Ser
            515                 520                 525 aat acc atc aac aga aca cag agt gac ggc gaa ttc ctc aat cta gtc      1632
Asn Thr Ile Asn Arg Thr Gln Ser Asp Gly Glu Phe Leu Asn Leu Val
530                 535                 540 tcc aat gtg ttg aag ctt aaa cgc ggt cat ata ttg gag ctt ctt ggt      1680
Ser Asn Val Leu Lys Leu Lys Arg Gly His Ile Leu Glu Leu Leu Gly
545                 550                 555                 560 tac tgt aac gag ttt ggt caa agg tta ctt gtg tat gag tac tgt cct      1728
Tyr Cys Asn Glu Phe Gly Gln Arg Leu Leu Val Tyr Glu Tyr Cys Pro
                565                 570                 575 aat gga tca ctt caa gat gca cta cat ttg gat cgc aag ttg cac aag      1776
Asn Gly Ser Leu Gln Asp Ala Leu His Leu Asp Arg Lys Leu His Lys
                580                 585                 590 aag ctc act tgg aat gta cgt ata aat att gca tta gga gct tca aag      1824
Lys Leu Thr Trp Asn Val Arg Ile Asn Ile Ala Leu Gly Ala Ser Lys
                595                 600                 605 gca ttg cag ttt ctt cat gag gta tgt caa ccg ccg gtt gtt cac cag      1872
Ala Leu Gln Phe Leu His Glu Val Cys Gln Pro Pro Val Val His Gln
            610                 615                 620 aat ttc aag tct tcc aag gtt ctt ctt gat gga aag ctc tca gta cgt      1920
Asn Phe Lys Ser Ser Lys Val Leu Leu Asp Gly Lys Leu Ser Val Arg
625                 630                 635                 640 gtt gca gac agc ggt ttg gct tat atg tta cca cca cgc cca acg agt      1968
Val Ala Asp Ser Gly Leu Ala Tyr Met Leu Pro Pro Arg Pro Thr Ser
                645                 650                 655
```

```
cag atg gcg ggt tat gcc gct cct gag gtt gag tat gga agc tac act    2016
Gln Met Ala Gly Tyr Ala Ala Pro Glu Val Glu Tyr Gly Ser Tyr Thr
        660                 665                 670 tgt cag agc gac gta ttt agc ctt ggg gtt gta atg tta gaa ctg ctc    2064
Cys Gln Ser Asp Val Phe Ser Leu Gly Val Val Met Leu Glu Leu Leu
    675                 680                 685 act gga cgc aga cca ttt gac agg aca agg ccg agg gga cat caa aca    2112
Thr Gly Arg Arg Pro Phe Asp Arg Thr Arg Pro Arg Gly His Gln Thr
690                 695                 700 cta gct cag tgg gcg att cct cgg ctt cat gac atc gat gcg ttg aca    2160
Leu Ala Gln Trp Ala Ile Pro Arg Leu His Asp Ile Asp Ala Leu Thr
705                 710                 715                 720 aga atg gtt gat ccg tca tta cac gga gcg tat cca atg aaa tca ttg    2208
Arg Met Val Asp Pro Ser Leu His Gly Ala Tyr Pro Met Lys Ser Leu
            725                 730                 735 tca cgt ttt gca gat atc ata tca cgt tca ctg cag atg gaa cca gga    2256
Ser Arg Phe Ala Asp Ile Ile Ser Arg Ser Leu Gln Met Glu Pro Gly
        740                 745                 750 ttt aga ccg ccg ata tca gaa ata gtc caa gat ctt caa cat atg atc    2304
Phe Arg Pro Pro Ile Ser Glu Ile Val Gln Asp Leu Gln His Met Ile
    755                 760                 765 taa                                                                2307
```

<210> SEQ ID NO 52
<211> LENGTH: 768
<212> TYPE: PRT
<213> ORGANISM: Arabidopsis thaliana

<400> SEQUENCE: 52

Met Ser Phe Thr Arg Trp Glu Val Phe Phe Gly Leu Ser Val Leu Ala
1               5                   10                  15

Leu Thr Met Pro Phe Ser Ala Gly Val Thr Asn Leu Arg Asp Val Ser
            20                  25                  30

Ala Ile Asn Asn Leu Tyr Ile Thr Leu Gly Ala Pro Ser Leu His His
        35                  40                  45

Trp Leu Ala Phe Gly Gly Asp Pro Cys Gly Glu Lys Trp Gln Gly Val
    50                  55                  60

Val Cys Asp Ser Ser Asn Ile Thr Glu Ile Arg Ile Pro Gly Met Lys
65                  70                  75                  80

Val Gly Gly Gly Leu Ser Asp Thr Leu Ala Asp Phe Ser Ser Ile Gln
                85                  90                  95

Val Met Asp Phe Ser Ser Asn His Ile Ser Gly Thr Ile Pro Gln Ala
            100                 105                 110

Leu Pro Ser Ser Ile Arg Asn Leu Ser Leu Ser Ser Asn Arg Phe Thr
        115                 120                 125

Gly Asn Ile Pro Phe Thr Leu Ser Phe Leu Ser Asp Leu Ser Glu Leu
    130                 135                 140

Ser Leu Gly Ser Asn Leu Leu Ser Gly Glu Ile Pro Asp Tyr Phe Gln
145                 150                 155                 160

Gln Leu Ser Lys Leu Thr Lys Leu Asp Leu Ser Ser Asn Ile Leu Glu
                165                 170                 175

Gly His Leu Pro Ser Ser Met Gly Asp Leu Ala Ser Leu Lys Ile Leu
            180                 185                 190

Tyr Leu Gln Asp Asn Lys Leu Thr Gly Thr Leu Asp Val Ile Glu Asp
        195                 200                 205

Leu Phe Leu Thr Asp Leu Asn Val Glu Asn Asn Leu Phe Ser Gly Pro
    210                 215                 220

-continued

```
Ile Pro Pro Asn Leu Leu Lys Ile Pro Asn Phe Lys Lys Asp Gly Thr
225                 230                 235                 240

Pro Phe Asn Thr Ser Ile Ile Thr Pro Pro Pro Pro Val Val Asp
            245                 250                 255

Pro Pro Pro Ala Thr His Arg Ala Pro Pro Val Pro Arg Ile Pro Pro
            260                 265                 270

Val Ser Gly Val Pro Pro Ala Pro Phe Ala Pro Phe Ala Pro Leu Gln
            275                 280                 285

Pro Gln Gln His Pro Pro Ser Pro Pro Leu Val Trp Ser Pro Pro
290                 295                 300

Ser Ser Asp Asn Gly Gly Asp Pro Trp Asn Ser Val Ser Gly Gln
305                 310                 315                 320

Pro Thr Leu Gln Ile Ser Pro Pro Ser Gly Ser Gly Ser Gly Lys Phe
            325                 330                 335

Trp Ser Thr Gln Arg Ile Ile Leu Val Val Ser Ser Val Ala Ile Ile
            340                 345                 350

Val Leu Val Ser Gly Leu Cys Val Thr Leu Trp Arg Cys Cys Arg Ser
            355                 360                 365

Lys Ile Tyr Asn Arg Tyr Tyr Ser Gly Ala Arg Lys Asp Leu Gln Arg
            370                 375                 380

Pro Tyr Phe Asn Lys Pro Pro Ser Gln Pro Thr Pro Thr Met Gly Lys
385                 390                 395                 400

Val Ser Arg Glu Pro Met Val Lys Pro Phe Asp Gly Tyr Gly Ala Gly
            405                 410                 415

Asp Arg Lys Tyr Gly Tyr Pro Met Pro Gln Arg Ala Glu Glu Ser Arg
            420                 425                 430

Arg Ala Met Pro Pro Thr Ser Tyr Tyr Asn Lys Asp Val Asn Thr Pro
            435                 440                 445

Gln Lys Pro Leu Gln Gln Pro Pro Arg Gln Phe Gln Ser Asn Asp Thr
            450                 455                 460

Ala Ser Lys Arg Ala Ala His Phe Pro Pro Gly Leu Asn Ser Ser Ser
465                 470                 475                 480

Ser Ala Thr Val Phe Thr Ile Ala Ser Leu Gln Gln Tyr Thr Asn Asn
            485                 490                 495

Phe Ser Glu Glu Asn Ile Ile Gly Glu Gly Ser Ile Gly Asn Val Tyr
            500                 505                 510

Arg Ala Glu Leu Arg His Gly Lys Phe Leu Ala Val Lys Lys Leu Ser
            515                 520                 525

Asn Thr Ile Asn Arg Thr Gln Ser Asp Gly Glu Phe Leu Asn Leu Val
            530                 535                 540

Ser Asn Val Leu Lys Leu Lys Arg Gly His Ile Leu Glu Leu Leu Gly
545                 550                 555                 560

Tyr Cys Asn Glu Phe Gly Gln Arg Leu Leu Val Tyr Glu Tyr Cys Pro
            565                 570                 575

Asn Gly Ser Leu Gln Asp Ala Leu His Leu Asp Arg Lys Leu His Lys
            580                 585                 590

Lys Leu Thr Trp Asn Val Arg Ile Asn Ile Ala Leu Gly Ala Ser Lys
            595                 600                 605

Ala Leu Gln Phe Leu His Glu Val Cys Gln Pro Pro Val Val His Gln
            610                 615                 620

Asn Phe Lys Ser Ser Lys Val Leu Leu Asp Gly Lys Leu Ser Val Arg
625                 630                 635                 640

Val Ala Asp Ser Gly Leu Ala Tyr Met Leu Pro Pro Arg Pro Thr Ser
            645                 650                 655
```

```
Gln Met Ala Gly Tyr Ala Ala Pro Glu Val Glu Tyr Gly Ser Tyr Thr
            660                 665                 670
Cys Gln Ser Asp Val Phe Ser Leu Gly Val Val Met Leu Glu Leu Leu
            675                 680                 685
Thr Gly Arg Arg Pro Phe Asp Arg Thr Arg Pro Arg Gly His Gln Thr
            690                 695                 700
Leu Ala Gln Trp Ala Ile Pro Arg Leu His Asp Ile Asp Ala Leu Thr
705                 710                 715                 720
Arg Met Val Asp Pro Ser Leu His Gly Ala Tyr Pro Met Lys Ser Leu
            725                 730                 735
Ser Arg Phe Ala Asp Ile Ile Ser Arg Ser Leu Gln Met Glu Pro Gly
            740                 745                 750
Phe Arg Pro Pro Ile Ser Glu Ile Val Gln Asp Leu Gln His Met Ile
            755                 760                 765

<210> SEQ ID NO 53
<211> LENGTH: 736
<212> TYPE: DNA
<213> ORGANISM: Artificial Sequence
<220> FEATURE:
<223> OTHER INFORMATION: Truncated SRF6

<400> SEQUENCE: 53
atgagggaga attgggcggt ggtggctctg tttacactat gcattgtagg gtttgagctt      60
agattcatcc atggagctac tgatgcatca gacacttcag cattgaacac attgttcagt     120
ggtatgcatt ctccagctca gctaacacaa tggactgcag cagctggtga tccttgtggc     180
cagaattgga gaggcgtcac ttgttccggc tcacgagtta ctcaaataaa gttgtcaggt     240
cttgagctct ctggaactct tggaggatac atgcttgata aattgacttc tcttaccgag     300
cttgatctaa gcagcaataa tcttggaggt gatttaccat atcagtttcc tccaaatctg     360
caacgattga accttgcgaa taatcaattc actggagctg cttcgtactc actttctcag     420
attacaccac ttaagtatct caatcttggt cacaatcagt ttaagggggca gatagctatc     480
gacttctcca agctcgactc tctcacaacc ttggacttct ctttcaattc tttcacgaac     540
tctttaccgg caacgttttc ctctctaaca agtttaaaat cactatacct tcagaacaat     600
cagttctcag gcacagtcga tgtcttagcc ggtcttcctc ttgagactct gaacattgcg     660
aacaatgact tcacggggtg gatccccagt tctttaaagg gcatcacatt aataaaagat     720
ggcaactcat tcaata                                                     736

<210> SEQ ID NO 54
<211> LENGTH: 89
<212> TYPE: DNA
<213> ORGANISM: Artificial Sequence
<220> FEATURE:
<223> OTHER INFORMATION: truncated SRF7

<400> SEQUENCE: 54
atgactgaga atcgggtggt tttggctctg cttatactct gcattgttgg gtttgagcca      60
agtttcatcc atggagctac ggattcatc                                        89
```

What is claimed is:

1. An isolated polynucleotide encoding a polypeptide lacking all or a fragment of the extracellular domain of an SRF-6 polypeptide, wherein the SRF-6 lacking all or a fragment of the extracellular domain is resistant to inhibition by isoxaben, and wherein the truncated polypeptide induces increased CesA4 expression relative to the full length endogenous SRF-6 polypeptide, wherein the SRF-6 polypeptide comprises at least 95% identity to SEQ ID NO: 2.

2. The isolated polynucleotide of claim 1, wherein the polynucleotide comprises at least 95% sequence identity to SEQ ID NO: 53.

3. An isolated polynucleotide encoding a polypeptide lacking all or a fragment of the extracellular domain of an SRF-7 polypeptide, wherein the SRF-7 lacking all or a fragment of the extracellular domain is resistant to inhibition by isoxaben and wherein the truncated polypeptide induces increased CesA4 expression relative to the full length endogenous SRF-7 polypeptide, wherein the SRF 7 comprises at least 95% identity to SEQ ID NO: 4.

4. The polynucleotide of claim 1, lacking all or a fragment of the C-terminal domain of the SRF-6 polypeptide.

5. The polynucleotide of claim 3, lacking all or a fragment of the C-terminal domain of the SRF-7 polypeptide.

6. A polypeptide encoded by the polynucleotides of any one of claims 1-3.

7. A vector comprising the polynucleotide of any one of claims 1-3.

8. A host cell transformed with the polynucleotide of any one of claims 1-3.

9. A host cell transformed with a vector of claim 7.

10. The host cell of claim 8, wherein the host cell is a plant cell.

11. The host cell of claim 9, wherein the host cell is a plant cell.

12. A transgenic plant comprising homozygous expression of the polynucleotide of any one of claims 1-3, wherein the transgenic plant comprises increased cellulose production compared to a wild-type plant.

* * * * *